United States Patent
Hartwell et al.

(10) Patent No.: US 11,103,385 B2
(45) Date of Patent: *Aug. 31, 2021

(54) WOUND TREATMENT APPARATUSES

(71) Applicant: Smith & Nephew PLC, Watford (GB)

(72) Inventors: Edward Yerbury Hartwell, Hull (GB); Mark Richardson, Grimsby (GB); Carl Saxby, Brough (GB)

(73) Assignee: Smith & Nephew PLC, Watford (GB)

(*) Notice: Subject to any disclaimer, the term of this patent is extended or adjusted under 35 U.S.C. 154(b) by 272 days.

This patent is subject to a terminal disclaimer.

(21) Appl. No.: 16/240,380

(22) Filed: Jan. 4, 2019

(65) Prior Publication Data

US 2019/0209383 A1    Jul. 11, 2019

Related U.S. Application Data

(63) Continuation of application No. 15/113,403, filed as application No. PCT/EP2015/050959 on Jan. 20, 2015, now Pat. No. 10,179,073.

(Continued)

(51) Int. Cl.
*A61M 35/00* (2006.01)
*A61M 1/00* (2006.01)
*A61F 13/00* (2006.01)
*A61M 3/00* (2006.01)
*A61M 31/00* (2006.01)
(Continued)

(52) U.S. Cl.
CPC .. *A61F 13/00068* (2013.01); *A61F 13/00017* (2013.01); *A61F 13/00034* (2013.01); *A61F 13/00987* (2013.01); *A61M 1/90* (2021.05); *A61F 2013/00174* (2013.01);
(Continued)

(58) Field of Classification Search
CPC .......... A61M 35/00; A61M 1/00; A61M 3/00; A61M 31/00; A61F 13/00; A61F 13/02; A61F 8/44
See application file for complete search history.

(56) References Cited

U.S. PATENT DOCUMENTS

| 3,194,239 A | 7/1965 | Sullivan |
| 3,789,851 A | 2/1974 | Leveen |

(Continued)

FOREIGN PATENT DOCUMENTS

| AU | 2012261793 B2 | 11/2014 |
| AU | 2013206230 B2 | 5/2016 |

(Continued)

OTHER PUBLICATIONS

American Heritage® Dictionary of the English Language, Fifth Edition (Year: 2003).*

(Continued)

*Primary Examiner* — Tatyana Zalukaeva
*Assistant Examiner* — Ilya Y Treyger
(74) *Attorney, Agent, or Firm* — Knobbe, Martens, Olson & Bear LLP

(57) ABSTRACT

Methods and apparatuses are disclosed relating to the creation and use of bespoke wound fillers and other wound treatment apparatuses. Some embodiments provide for the creation of bespoke wound fillers based on characteristics of a wound. Certain embodiments also include the use of bespoke wound fillers in combination with negative pressure to treat a wound.

15 Claims, 114 Drawing Sheets

Related U.S. Application Data

(60) Provisional application No. 61/929,864, filed on Jan. 21, 2014.

(51) Int. Cl.
  *A61F 13/02* (2006.01)
  *B32B 3/12* (2006.01)

(52) U.S. Cl.
  CPC .............. *A61F 2013/00536* (2013.01); *A61F 2013/00578* (2013.01); *B32B 3/12* (2013.01)

(56) References Cited

U.S. PATENT DOCUMENTS

| | | |
|---|---|---|
| 4,467,805 A | 8/1984 | Fukuda |
| 4,608,041 A | 8/1986 | Nielsen |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 6,176,868 B1 | 1/2001 | Detour |
| 6,503,208 B1 | 1/2003 | Skovlund |
| 6,548,727 B1 | 4/2003 | Swenson |
| 6,566,575 B1 | 5/2003 | Stickels et al. |
| 6,685,681 B2 | 2/2004 | Lockwood et al. |
| 6,770,794 B2 | 8/2004 | Fleischmann |
| 6,787,682 B2 | 9/2004 | Gilman |
| 6,977,323 B1 | 12/2005 | Swenson |
| 7,004,915 B2 | 2/2006 | Boynton et al. |
| 7,144,390 B1 | 12/2006 | Hannigan et al. |
| 7,315,183 B2 | 1/2008 | Hinterscher |
| 7,351,250 B2 | 4/2008 | Zamierowski |
| 7,361,184 B2 | 4/2008 | Joshi |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,683,667 B2 | 3/2010 | Kim et al. |
| 7,700,819 B2 | 4/2010 | Ambrosio et al. |
| 7,754,937 B2 | 7/2010 | Boehringer et al. |
| 7,779,625 B2 | 8/2010 | Joshi et al. |
| 7,799,004 B2 | 9/2010 | Tumey |
| 7,815,616 B2 | 10/2010 | Boehringer et al. |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston et al. |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,114,126 B2 | 2/2012 | Heaton et al. |
| 8,123,781 B2 | 2/2012 | Zamierowski |
| 8,142,419 B2 | 3/2012 | Heaton et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,298,200 B2 * | 10/2012 | Vess .................... A61M 1/0086 604/313 |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann |
| 8,430,867 B2 | 4/2013 | Robinson et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,535,296 B2 | 9/2013 | Blott et al. |
| 8,588,893 B2 | 11/2013 | Jaeb et al. |
| 8,608,776 B2 | 12/2013 | Coward et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,945,030 B2 | 2/2015 | Weston et al. |
| 9,044,579 B2 | 6/2015 | Blott et al. |
| 9,061,095 B2 | 6/2015 | Adie et al. |
| 9,180,231 B2 | 11/2015 | Greener |
| 9,220,822 B2 | 12/2015 | Hartwell |
| 9,301,880 B2 | 4/2016 | Lina et al. |
| 9,408,755 B2 | 8/2016 | Larsson et al. |
| 9,421,132 B2 | 8/2016 | Dunn et al. |
| 9,655,807 B2 | 5/2017 | Locke et al. |
| 9,849,023 B2 | 12/2017 | Hall et al. |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0162512 A1 | 8/2004 | Liedtke et al. |
| 2004/0267312 A1 | 12/2004 | Kanner et al. |
| 2005/0142331 A1 | 6/2005 | Anderson et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0069357 A1 | 3/2006 | Marasco |
| 2006/0217795 A1 | 9/2006 | Besselink et al. |
| 2006/0271018 A1 | 11/2006 | Korf |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman et al. |
| 2008/0275409 A1 | 11/2008 | Kane et al. |
| 2008/0316209 A1 | 12/2008 | Wen |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0326429 A1 | 12/2009 | Siniaguine |
| 2010/0022990 A1 | 1/2010 | Karpowicz et al. |

(56) References Cited

U.S. PATENT DOCUMENTS

| | | |
|---|---|---|
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0191196 A1 | 7/2010 | Heagle |
| 2010/0198128 A1 | 8/2010 | Turnlund et al. |
| 2010/0241447 A1 | 9/2010 | Siniaguine et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn et al. |
| 2012/0253302 A1 | 10/2012 | Corley |
| 2012/0321878 A1 | 12/2012 | Landon et al. |
| 2013/0150813 A1 | 6/2013 | Gordon et al. |
| 2013/0197457 A1 | 8/2013 | Kazala, Jr. et al. |
| 2013/0204213 A1 | 8/2013 | Heagle et al. |
| 2013/0211349 A1 | 8/2013 | Stokes et al. |
| 2013/0245527 A1 | 9/2013 | Croizat et al. |
| 2013/0310781 A1 | 11/2013 | Phillips et al. |
| 2013/0325142 A1 | 12/2013 | Hunter et al. |
| 2013/0331757 A1 | 12/2013 | Belson |
| 2013/0338437 A1 | 12/2013 | Abuzaina |
| 2014/0088402 A1 | 3/2014 | Xu |
| 2014/0094730 A1 | 4/2014 | Greener et al. |
| 2014/0163415 A1 | 6/2014 | Zaiken et al. |
| 2014/0228786 A1 | 8/2014 | Croizat et al. |
| 2014/0249495 A1 | 9/2014 | Mumby et al. |
| 2014/0350496 A1 | 11/2014 | Riesinger |
| 2015/0065968 A1 | 3/2015 | Sealy et al. |
| 2015/0119837 A1 | 4/2015 | Thompson, Jr. et al. |
| 2015/0139960 A1 | 5/2015 | Tumey et al. |
| 2015/0140058 A1 | 5/2015 | Tumey et al. |
| 2015/0157758 A1 | 6/2015 | Blücher et al. |
| 2015/0159066 A1 | 6/2015 | Hartwell et al. |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2016/0346444 A1 | 12/2016 | Zamierowski |
| 2017/0065751 A1 | 3/2017 | Toth et al. |

FOREIGN PATENT DOCUMENTS

| | | |
|---|---|---|
| CN | 1453749 A | 11/2003 |
| CN | 101112326 A | 1/2008 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2366721 A1 | 9/2011 |
| EP | 2567717 A1 | 3/2013 |
| EP | 2601984 A2 | 6/2013 |
| GB | 2389794 A | 12/2003 |
| GB | 2423019 A | 8/2006 |
| GB | WO 2010/092334 A1 * | 2/2009 |
| GB | 2489947 A | 10/2012 |
| GB | 2496310 A | 5/2013 |
| JP | 2011-505871 A | 3/2011 |
| JP | 2011-513003 A | 4/2011 |
| JP | 2012-105840 A | 6/2012 |
| RU | 62504 U1 | 4/2007 |
| RU | 2435520 C2 | 12/2011 |
| SU | 1818103 A1 | 5/1993 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 2005/046761 A1 | 5/2005 |
| WO | WO 2005/105174 A1 | 11/2005 |
| WO | WO 2006/046060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2010/075180 * | 12/2008 |
| WO | WO 2009/016605 A2 | 2/2009 |
| WO | WO 2009/071928 A1 | 6/2009 |
| WO | WO 2009/112062 A1 | 9/2009 |
| WO | WO 2009/149250 A1 | 12/2009 |
| WO | WO 2010/033725 A2 | 3/2010 |
| WO | WO 2010/097570 A1 | 9/2010 |
| WO | WO 2011/023384 A1 | 3/2011 |
| WO | WO 2012/082716 A2 | 6/2012 |
| WO | WO 2012/082876 A1 | 6/2012 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2015/110409 A1 | 7/2015 |
| WO | WO 2015/110410 A1 | 7/2015 |
| WO | WO-2015109359 A1 | 7/2015 |
| WO | WO-2015169637 A1 | 11/2015 |
| WO | WO-2016018448 A1 | 2/2016 |

OTHER PUBLICATIONS

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

International Preliminary Report on Patentability for Application No. PCT/EP2015/050959, dated Jul. 26, 2016, 6 pages.

(56) References Cited

OTHER PUBLICATIONS

International Search Report and Written Opinion for Application No. PCT/EP2015/050959, dated May 8, 2015, 8 pages.
Kapischke M., et al., "Self-Fixating Mesh for the Lichtenstein Procedure—a Prestudy," Langenbecks Arch Surg, 2010, vol. 395, pp. 317-322.

* cited by examiner

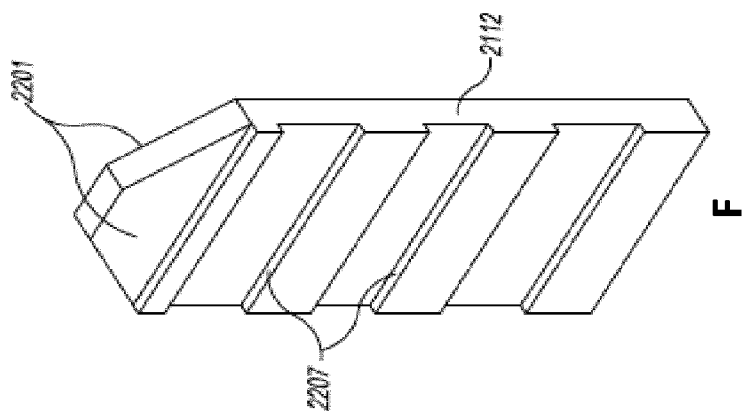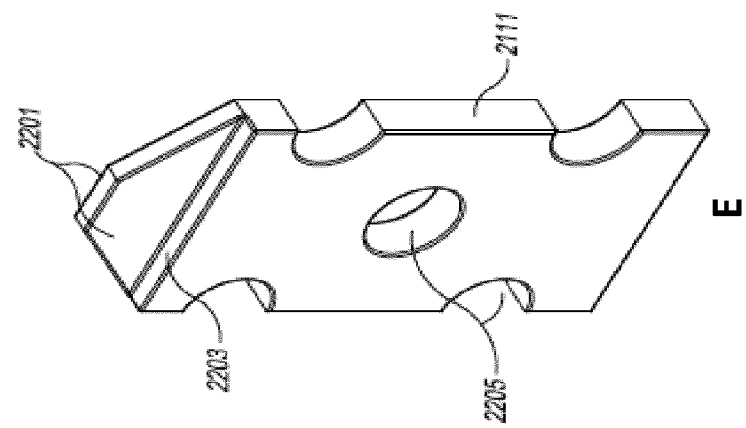
FIG. 25

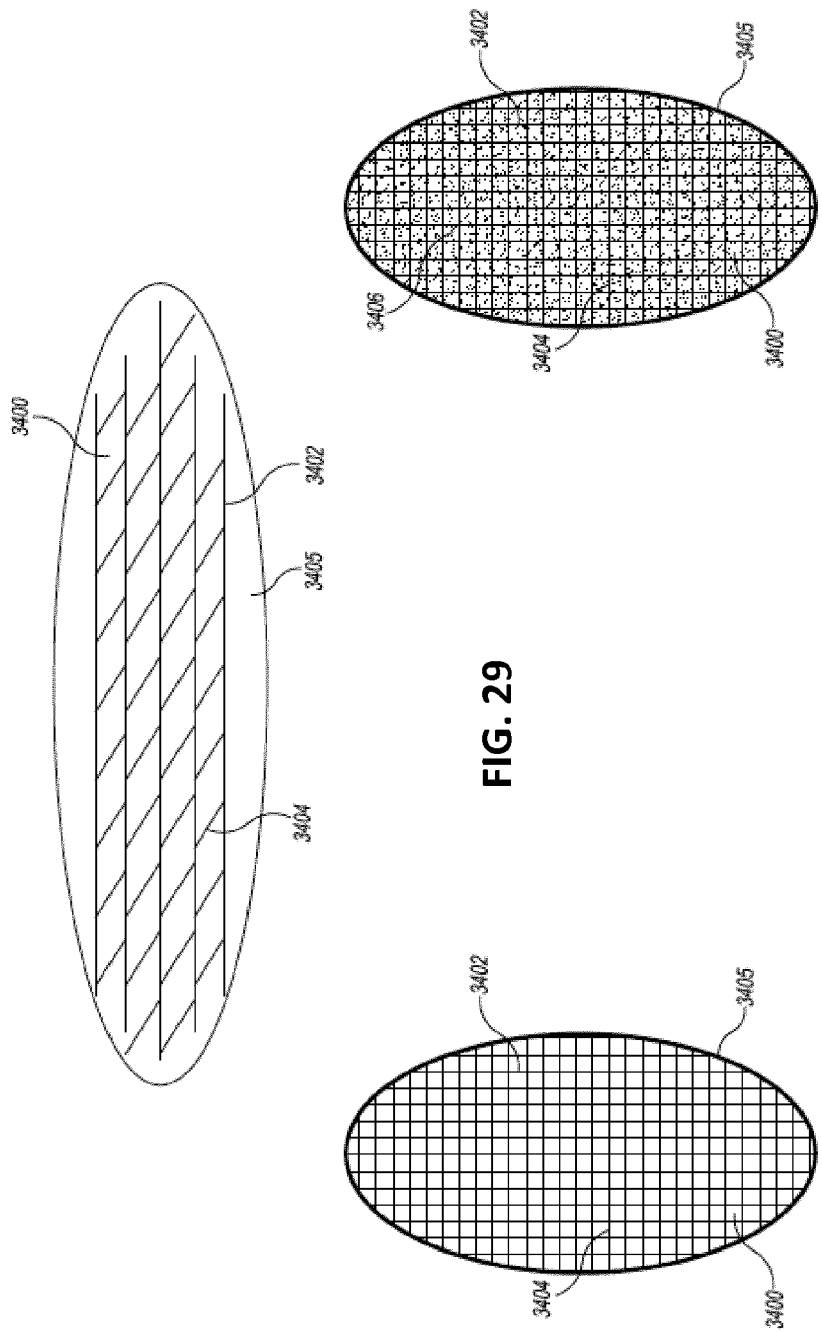

WOUND TREATMENT APPARATUSES

CROSS-REFERENCE TO RELATED APPLICATIONS

This application is a continuation of U.S. application Ser. No. 15/113,403, filed Jul. 21, 2016, which is a U.S. National Phase Application of PCT International Application Number PCT/EP2015/050959, filed on Jul. 20, 2015, designating the U.S., and published in English as WO 2015/110409 A1 on Jul. 30, 2015, which claims the benefit of U.S. Provisional Application No. 61/929,864, filed Jan. 21, 2014, and entitled BESPOKE WOUND TREATMENT APPARATUSES AND METHODS FOR USE IN NEGATIVE PRESSURE WOUND THERAPY. The content of the aforementioned application is hereby incorporated by reference in its entirety as if fully set forth herein. The benefit of priority to the foregoing application is claimed under the appropriate legal basis, including, without limitation, under 35 U.S.C. § 119(e).

BACKGROUND OF THE INVENTION

Field of the Invention

Embodiments described herein relate to wound fillers, in particular wound fillers for use with negative pressure wound therapy, and that may be fabricated or created in a bespoke or custom manner for use in wound treatment.

Description of the Related Art

Wound fillers, especially for use in negative pressure therapy, play a critical role in wound treatment. Nevertheless, sizing wound fillers for use in a wound can be difficult, time consuming, and imperfect, especially for irregularly-shaped wounds.

SUMMARY OF THE INVENTION

Accordingly, embodiments described herein relate to devices, methods, and systems for providing bespoke or customized wound fillers for the treatment of a wound. In certain embodiments, a bespoke wound filler is fabricated and optimized for use with negative pressure wound therapy. Preferably, a bespoke wound filler may be created by obtaining a three-dimensional scan or model of a wound, and manufacturing a bespoke wound filler configured to be used with the wound.

In certain embodiments, a method of manufacturing a wound filler for use in negative pressure wound therapy may comprise:

creating a three-dimensional model of a wound filler based on a three-dimensional model of a wound space to be treated with negative pressure wound therapy; and fabricating a bespoke wound filler based on the created three-dimensional model of the wound filler, wherein the bespoke wound filler comprises at least a first plurality of identical repeating cells configured to collapse in a manner determined by the three-dimensional model to account for attributes of the wound and for a negative pressure wound therapy treatment modality.

In some embodiments, an apparatus for treating a wound with negative pressure therapy may comprise a bespoke wound filler comprising at least a first plurality of identical repeating cells configured to collapse in a manner determined by a three-dimensional model created based on a scan of the wound to account for attributes of the wound and for a negative pressure wound therapy treatment modality, the wound filler having a shape and configuration constructed to custom fit into the wound.

BRIEF DESCRIPTION OF THE DRAWINGS

Other features and advantages of the present invention will be apparent from the following detailed description of the invention, taken in conjunction with the accompanying drawings of which:

FIG. 29 schematically illustrates an embodiment of a stabilizing structure.

FIG. 30A illustrates a top view of an embodiment of an oval shaped stabilizing structure.

FIG. 30B illustrates a top view of an embodiment of an oval shaped stabilizing structure with foam.

DETAILED DESCRIPTION OF THE PREFERRED EMBODIMENTS

Figure 1:
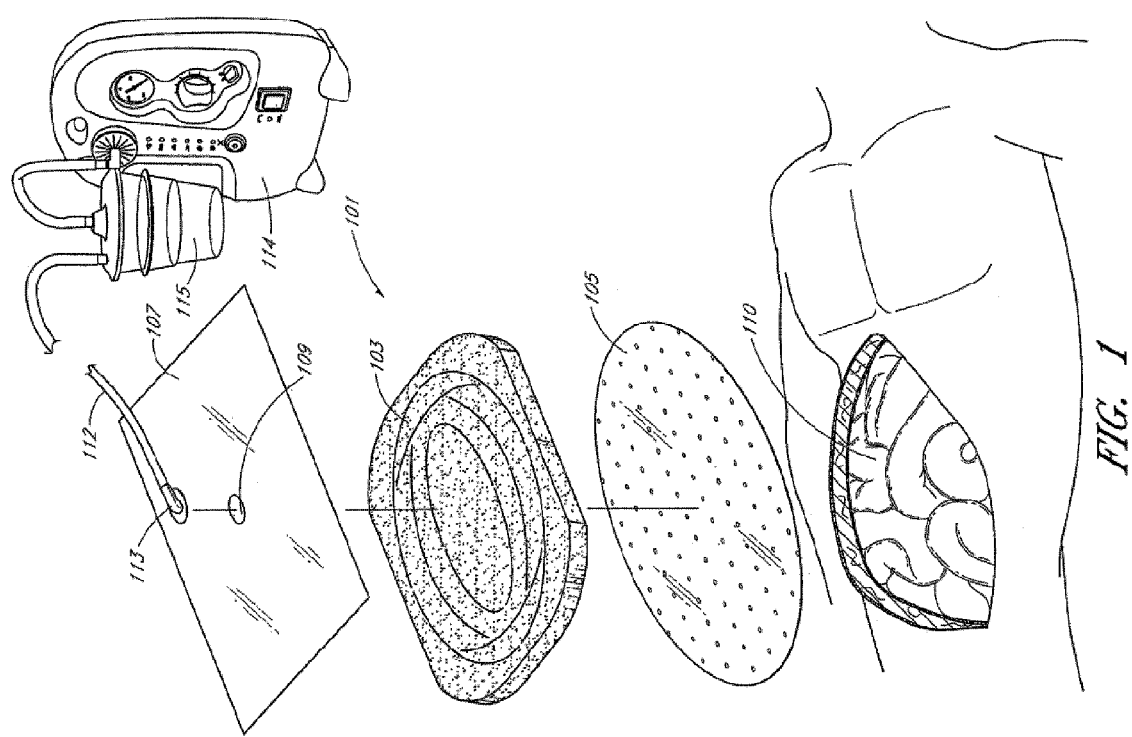
FIG. 1 is a schematic illustration of a negative pressure system.

Embodiments disclosed herein relate to apparatuses and methods of treating a wound, especially with reduced pressure. Embodiments for use with negative pressure include pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used herein, reduced or negative pressure levels, such as $-X$ mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of $(760-X)$ mmHg. In addition, negative pressure that is "less" or "smaller" than X mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg).

The negative pressure range for some embodiments of the present disclosure can be approximately $-80$ mmHg, or between about $-20$ mmHg and $-200$ mmHg. Note that these pressures are relative to normal ambient atmospheric pressure. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even 150 mmHg, can be supplied by the negative pressure apparatus. In some embodiments, the negative pressure range can be as small as about $-20$ mmHg or about $-25$ mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "WOUND TREATMENT APPARATUS AND METHOD," filed Oct. 26, 2007, published as US 2009/0306609; and U.S. Pat. No. 7,753, 894, titled "WOUND CLEANSING APPARATUS WITH STRESS," issued Jul. 13, 2010. Both applications are hereby incorporated by reference in their entirety.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. However, many different types of wounds may be treated by such a method, and the abdominal wound illustrated here is merely one particular example. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive responses to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for a wound contact layer 105 to be placed over the wound site 110. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 110 or the transmittal of negative pressure to the wound site 110. Additional embodiments of the wound contact layer 105 are described in further detail below.

Certain embodiments of the negative pressure treatment system 101 may also use a wound filler 103, which may be a bespoke wound filler as will be described in much greater detail below and which can be disposed over the wound contact layer 105 or into direct contact with the wound. The wound filler 103 shown in FIG. 1 is merely illustrative of one configuration of a wound filler that may be utilized, wherein portions of the wound filler may be torn away to appropriately size the wound filler. In some embodiments, the bespoke wound fillers described in greater detail below eliminate the need to provide a wound filler that needs to be cut or sized by the clinician before applying the wound filler into the wound. In certain embodiments, the wound filler of any of the embodiments described herein this section or elsewhere in the specification is applied directly to the wound with or without a wound contact layer 105 and/or a drape 107. This filler 103 can be constructed from a porous material, for example foam, that is soft, resiliently flexible, and generally conformable to the wound site 110. Such a foam can include an open-celled and reticulated foam made, for example, of a polymer. Suitable foams include foams composed of, for example, polyurethane, silicone, and polyvinyl alcohol. In certain embodiments, this filler 103 can channel wound exudate and other fluids through itself when negative pressure is applied to the wound. Some fillers 103 may include preformed channels or openings for such purposes. Other embodiments of wound fillers that may be used in place of or in addition to the filler 103 are discussed in further detail below.

In some embodiments, a drape 107 is used to seal the wound site 110. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and Op Site® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling of the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. application Ser. No. 10/533,275, filed Oct. 28, 2003, titled "APPARATUS FOR ASPIRATING, IRRIGATING, AND CLEANSING WOUNDS," issued as U.S. Pat. No. 7,524,315 discloses other similar aspects of negative pressure systems and is hereby incorporated by reference in its entirety. All references in this application that are incorporated in their entireties should be considered as if fully set forth herein.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister. In further embodiments, the aforementioned wound treatment system may be combined with a fluid source to allow for irrigation of the wound.

In other embodiments, a negative pressure wound therapy apparatus may utilize a canister-less system, such as the PICO system available from Smith & Nephew. In some embodiments, a wound dressing may be provided comprising an absorbent layer such as a superabsorbing material configured to store wound exudate therein. The absorbent layer may be contained between a wound cover or backing layer and an optional wound contact layer, and the entire dressing may include a port configured to be connected to a source of negative pressure. Such dressings may include multiple layers configured to facilitate transmission of negative pressure to a wound site and also to promote flow of fluid into the absorbent layer. Further details regarding wound treatment apparatuses and methods incorporating absorbent materials, transmission layers and other components are found in U.S. application Ser. No. 10/575,871, filed Jan. 29, 2007, titled "WOUND CLEANSING APPARATUS IN-SITU," issued as U.S. Pat. No. 7,964,766; U.S. application Ser. No. 12/744,055, filed May 20, 2010, titled "VACUUM ASSISTED WOUND DRESSING," published as US2011/0009838; U.S. application Ser. No. 12/744,277, filed Sep. 20, 2010, titled "WOUND DRESSING," published as US2011/0028918; U.S. application Ser. No. 12/744,218, filed Sep. 20, 2010, titled "WOUND DRESSING," published as US2011/0054421; U.S. application Ser. No. 13/092,042, filed Apr. 21, 2011, titled "WOUND DRESSING AND METHOD OF USE," published as US2011/0282309; U.S. application Ser. No. 11/432,855, filed May 11, 2006, titled "DEVICE AND METHOD FOR WOUND THERAPY," issued as U.S. Pat. No. 7,615,036; U.S. application Ser. No. 11/610,458, filed Dec. 13, 2006, titled "DEVICE AND METHOD FOR WOUND THERAPY," issued as U.S. Pat. No. 7,779,625; U.S. application Ser. No. 12/592,049, filed Nov. 18, 2009, titled "DEVICE AND METHOD FOR WOUND THERAPY," issued as U.S. Pat. No. 8,460,255; PCT Application No. PCT/US13/53075, filed Jul. 31, 2013, titled "WOUND DRESSING AND METHOD OF TREATMENT"; U.S. application Ser. No. 11/517,210, filed Sep. 6, 2006, titled "SELF CONTAINED WOUND DRESSING WITH MICROPUMP," issued as U.S. Pat. No. 7,569,742; U.S. application Ser. No. 11/516,925, filed Sep. 6, 2006, titled "WOUND DRESSING WITH VACUUM RESERVOIR," issued as U.S. Pat. No. 7,699,823; U.S. application Ser. No. 11/516,216, filed Sep. 6, 2006, titled "SELF-CONTAINED WOUND DRESSING APPARATUS," published as US2007/0055209; the entireties of each of which are hereby incorporated by reference.

Figure 2:
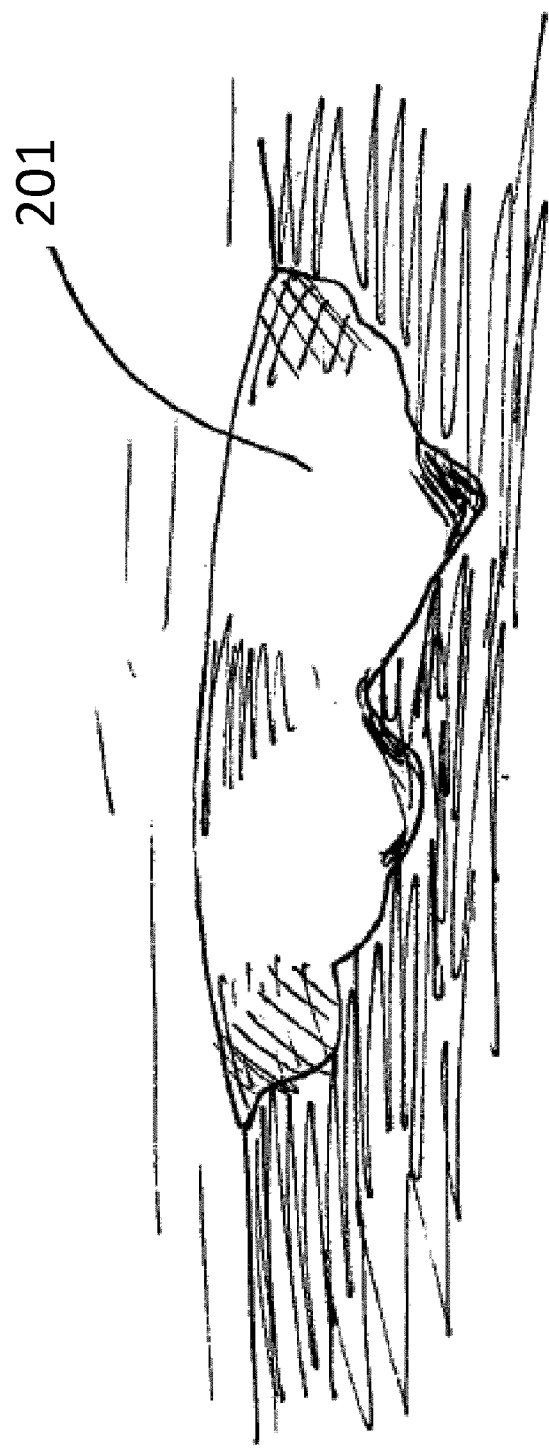
FIG. 2 is a schematic illustration of a wound with irregular margins.

FIG. 2 illustrates a wound 201 that may require filling with a bespoke wound filler so as to appropriately treat and heal the wound. Preferably, the wound 201 will be treated with negative pressure. The margins and contours of the wound 201 as illustrated are irregular, rendering it difficult to fill the wound with conventional fillers.

Figure 3:
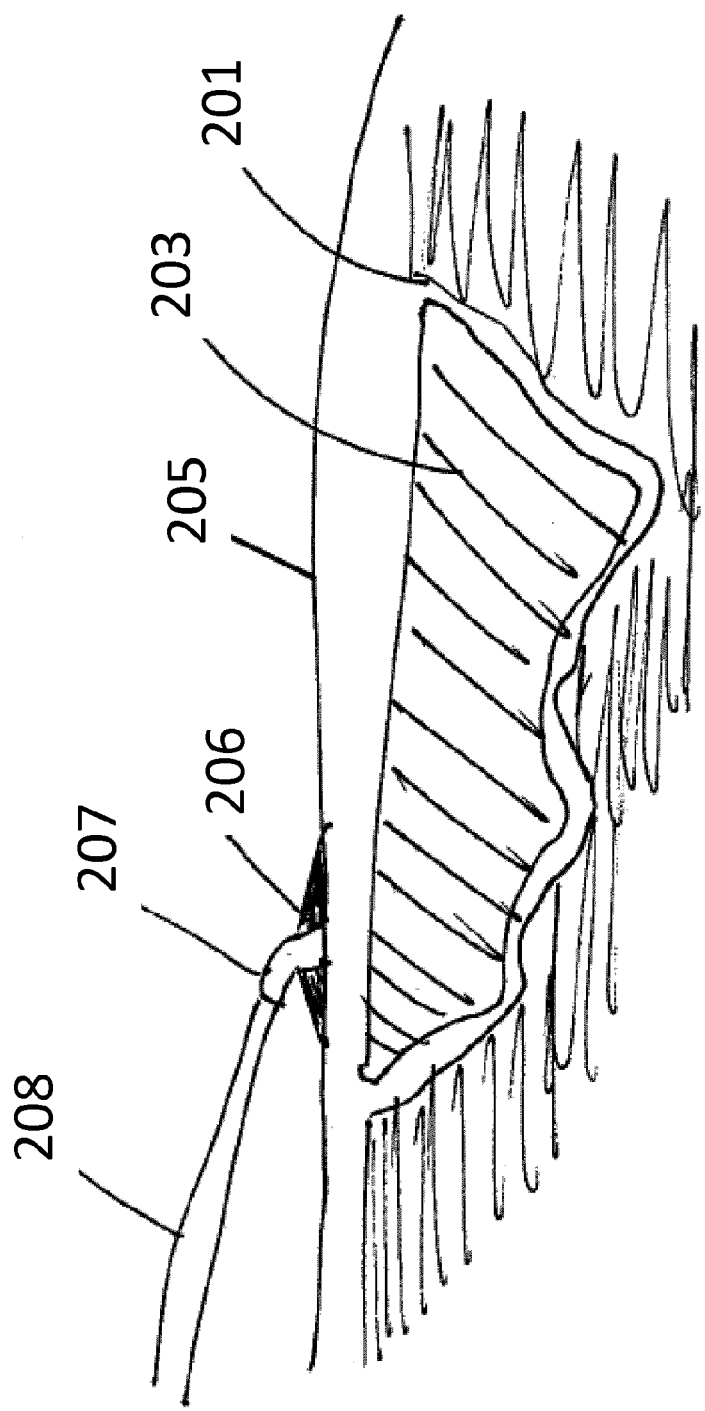
FIG. 3 is a schematic illustration of the wound from FIG. 1 filled with an embodiment of a bespoke wound filler and used in conjunction with a negative pressure treatment system.

FIG. 3 illustrates the wound 201 having a bespoke filler 203 inserted therein. Preferably, a liquid-impermeable drape 205 is placed over the wound and sealed against skin proximate the wound margins, for example with an adhesive. An aperture 206 may be made into the drape 205 so as to provide a fluidic connection to a source of negative pressure (not illustrated) such as a vacuum pump. Preferably, the aperture 206 communicates with a fluidic connector or port 207, which may be attached to the source of negative pressure via a conduit 208. Further details regarding negative pressure systems, apparatuses and methods that may be utilized with the systems, apparatuses and methods described herein are found in U.S. application Ser. No. 13/381,885, filed Dec. 30, 2011, titled "APPARATUSES AND METHODS FOR NEGATIVE PRESSURE WOUND THERAPY," published as US2012/0116334; U.S. application Ser. No. 12/886,088, filed Sep. 20, 2010, titled "SYSTEMS AND METHODS FOR USING NEGATIVE PRESSURE WOUND THERAPY TO MANAGE OPEN ABDOMINAL WOUNDS," published as US2011/0213287; U.S. application Ser. No. 13/092,042, filed Apr. 21, 2011, titled "WOUND DRESSING AND METHOD OF USE," published as US2011/0282309; the entireties of each of which are hereby incorporated by reference.

Figure 4:
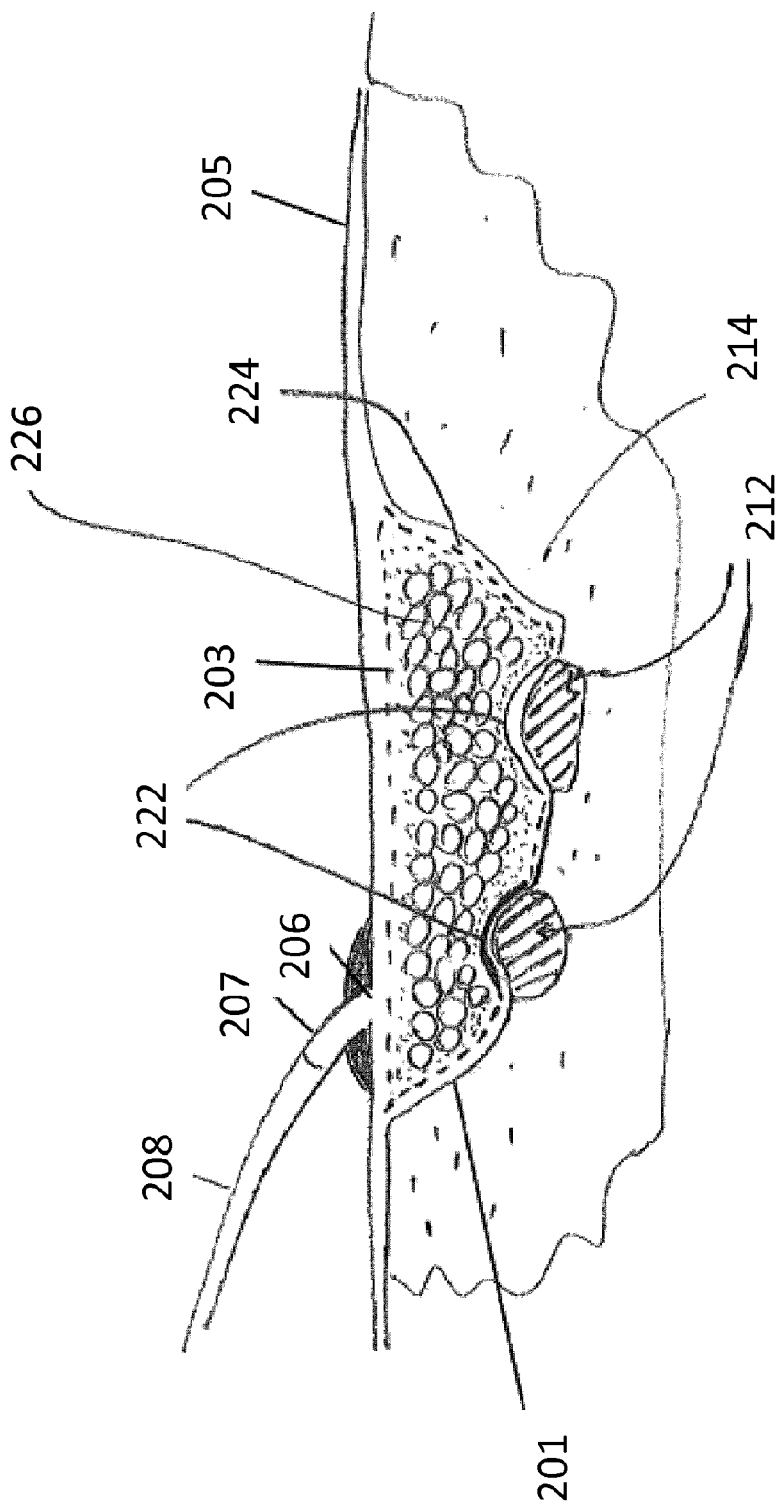
FIG. 4 is a schematic illustration of a wound comprising multiple tissue types being treated with an embodiment of a bespoke wound filler used in conjunction with a negative pressure treatment system.

FIG. 4 illustrates an example of a bespoke wound filler 203 used in conjunction with a wound 201. A drape 205 is placed over the wound 201 and sealed (e.g., using an adhesive) against the surrounding skin near the wound margins. Preferably, an aperture 206 through the drape 205 communicates with a source of negative pressure (not illustrated), and a port 207 may be used as a fluidic connector between the wound and the source of negative pressure. A conduit 208 may communicate with the source of negative pressure and the wound. Unlike FIG. 3, the wound 201 in FIG. 4 comprises different tissue anatomy, including exposed bone areas 212, in addition to soft tissue areas 214. Of course, other tissue types may be present, including for example muscles, nerves, ligaments, tendons, or any other tissue that may become exposed within a wound. According to some embodiments described herein this section and in greater detail below, the bespoke wound filler 203 is customized to the size and environment of the wound 201. The wound filler 203 illustrated here therefore comprises a first contacting area 222 configured to contact the exposed bone areas 212 and a second contacting area 224 configured to contact the soft tissue areas 214. In some embodiments, the first contacting area 222 may be occlusive, substantially fluid-impermeable, or have few to no pores, so as to limit the amount of fluid removed from and negative pressure applied to, the exposed bone area 212. In some embodiments, conversely, the second contacting area 224, when configured to contact the soft tissue areas 214, may be configured to be porous so as to enhance fluid removal and granulation tissue growth upon application of negative pressure. In some embodiments, the interior body 226 of the bespoke wound filler 203 may be of a different porosity than other areas; preferably, it comprises a material with greater porosity or larger pores than the wound-contacting surfaces. Such configurations may be preferable to enhance fluid removal, because, since the larger pores are not in contact with the wound 101, granulation tissue from the wound 101 will not grow into the larger pores.

In certain embodiments, it may be desirable to limit granulation tissue formation while still allowing fluid to be drawn away via very fine holes or slits. For example, holes or slits may have a diameter of at most about 0.1 µm, 0.5 µm, 1 µm, 2 µm, 5 µm, 10 µm, 15 µm, 20 µm, 30 µm, 40 µm, 50 µm, 75 µm, 100 µm, 125 µm, 150 µm, 175 µm, or 200 µm. Suitable materials for contacting tissue and maintaining porosity may include Elastollan (from BASF) or other materials as described herein this section or elsewhere in the specification. Further suitable materials include thermoplastic polyurethanes that are generally non-toxic and suitable for wound fillers.

Generally, the bespoke filler 203 may be constructed so as to provide a bespoke or custom fit into a wound 201. As will be described in greater detail below, various attributes of the bespoke filler may be modified, including its dimensions, density, material characteristics (including the use of multiple materials), physical characteristics, chemical characteristics, molecular delivery mechanisms, structural characteristics, and other attributes. In some embodiments, portions of the bespoke wound filler may have characteristics favorable to the application of negative pressure. In certain embodiments, the bespoke wound filler may have characteristics that are favorable to the application of irrigation.

Generating a 3D Scan of a Wound

The general shape and configuration of the bespoke filler 203 is preferably determined in relation to the shape and volume of the wound 201. The shape and volume of the wound 201 may be determined by any suitable method, but is preferably done by creating a three-dimensional (3D) scan of the wound 201. Although reference to 3D scans and/or 3D modeling is made herein this section and throughout the specification, 2D scanning or 2D modeling may also be used in place of the 3D scans and/or 3D models.

Preferably, a device capable of obtaining a 3D scan of the wound 201 is used that does not make contact with the wound. Such devices include laser scanners (particularly laser scanners employing triangulation techniques), stereo-optical scanners, or cameras with depth sensors such as those used in the Microsoft XBOX Kinect®. Other suitable devices include 3D Systems' ZScanner® 800. Preferably, the 3D scan device is capable of scanning a wound to an accuracy of at least about: 1 µm, 5 µm, 10 µm, 20 µm, 30 µm, 40 µm, 50 µm, 60 µm, 70 µm, 80 µm, 80 µm, or 100 µm. In some embodiments, other methods of obtaining a scan may be used such as deriving a scan from an analog or digital image of the wound.

3D scans may also be generated via CT or MRI images, for example by "stacking" multiple images together to form a 3D model. In certain embodiments, devices that contact the wound (e.g., via a pressure sensitive stylus), may also be used. In other embodiments, physical molds of the wound may be used to create a 3D scan. These physical molds may be fabricated from any suitable material such as Jeltrate or other alginate or silicone based materials often used for taking dental impressions.

In some embodiments, the tissue is stained with various markers that can be used to generate a more accurate 3D model. For example, the wound may be stained with markers that identify particular cell types that may be present at the wound site such as the various host cells of the patient or bacterial cells. Cell markers may give an improved overall understanding of the wound by indicating the different stages of healing of various areas of the wound or by providing information relating to infection. Additional markers may be used to stain extra-cellular matrix proteins, thus providing information about the surrounding structure and state of healing in the wound. Stained tissue can be imaged and analyzed via any suitable imaging technique, such as fluorescence microscopy or other techniques. However, imaging of a stained wound is not limited to microscopic techniques and may be performed via any suitable technique. Preferably, the characteristics data collected from staining the wound may be incorporated in the 3D model of the wound, matching particular stained areas to particular regions of the model.

Assorted hardware and software necessary to interpret and generate a 3D scan, and that is usually provided with the devices, may also be used. Such hardware and software may preferably be configured to interface with a personal computer. Some embodiments may also provide for a miniaturized and/or self-contained 3D scanning device that comprises integrated software and/or hardware.

In some embodiments, the 3D scanning device may be configured to interface with a telephone or tablet computer. Some embodiments may also provide for a patient to generate a 3D scan themselves (e.g., by using a Kinect® sensor), sending or uploading the 3D scan or model to a service provider, and having the service provider create and send a bespoke wound filler 203 customized to the patient's particular wound.

Generation of a 3D Model of the Wound Filler

The 3D scanning device will preferably generate a 3D wound model of the volume of the wound space using appropriate software. Such a 3D wound model is then modified to include a 3D model of the appropriate wound filler. Suitable software includes Solidworks, Solid Edge, and other 3D CAD programs. In certain embodiments, such 3D data sets of the wound surface volume are generated by subtracting the data set for the wound scan away from a volume larger in overall dimensions than the wound volume dimensions. Some embodiments may provide for the generation of an inverse of the scan surface volume. The data files generated may be in STL, STEP, IGES file formats, other 3D model file types, plain text files, or any suitable file format. The words "3D model" may be generally used throughout the specification to describe a 3D model of the wound alone, a 3D model of the filler alone, a 3D model of the wound with filler, or a 3D surface model of the wound surface. In some embodiments, 3D models may include polygonal mesh, voxel, solid body files, or any other suitable 3D modelling file. The models may be interchangeable between various formats. For example, when using CT scan data generated as a DICOM (Digital imaging and Communications in Medicine) data set, the tissue structures that form the wound may first be selected using a contrast threshold or through manual selection of particular tissue structures. In embodiments, the selected tissue may then be exported into a Mesh file, e.g. STL format. Following tissue selection and exportation, the data may be further filtered and modified to, for example: remove/add holes/folds, add/remove surface texturing, smooth the data set, or provide any other suitable modification. A solid body model may then be generated from this initial modified data mesh. In certain embodiments, this solid body may then be used to subtract from a solid body slightly larger than the wound in dimensions to create an exact solid body of the wound void. The use of any of the above-mentioned types of models is applicable to any of the embodiments described herein this section and elsewhere in the specification.

Preferably, the software program will modify and/or normalize the 3D wound model obtained from the 3D scanning device so as to make it usable in 3D printing devices (as described below). For example, the software program may modify the 3D model to make the mesh manifold, remove inverted normals, and optimize detail sizes, wall thicknesses, and orientations for use in the 3D printing device. Additionally, the software will preferably make the top of the 3D model flush with the surrounding skin, although in some embodiments, it may be preferable for the bespoke filler (and consequently, the 3D filler model) to extend above the skin at least in part.

At this stage, attributes of the 3D model may also be modified to account for various factors in the wound environment or to account for particular treatment modalities. A wound will typically contain multiple regions that may be in different stages of healing. For example, a wound may have areas that: are exudating heavily, are infected, are bleeding, contain dead/dying tissue, are drying, are inflamed, or in various other states. Further, the different areas of the wound may comprise different types of tissue, such as bone, cartilage, blood vessels, skin, fat, or any other organs or tissues. To effectively treat these variable tissue types and conditions may require different types of fillers with different physical and chemical characteristics as will be described in greater detail below.

The use of negative pressure in combination with various wound fillers has been demonstrated to effectively improve wound healing. However, such a combination is most effective when the wound filler is tailored to most effectively apply negative pressure to a particular type of wound. For example, as is described herein this section and elsewhere in the specification, a filler with a desired porosity may allow for an increased volume of fluid to be drawn from a wound at a greater rate. Additionally, as will be described in greater detail below, wound fillers may be tailored to more effectively deliver irrigant fluid to a wound. The fillers may also be tailored to collapse under negative pressure in a manner consistent with the direction of closure of the wound. Further details regarding the collapse of wound fillers under negative pressure will be described in greater detail below, particularly in relation to wound closure devices and stabilizing structures of FIGS. 6A-44B. In some embodiments, the wound fillers described above may collapse in any manner described with respect to the closure devices and stabilizing structures of FIGS. 6A-44B.

In some embodiments, as described elsewhere in the specification, internal manifolds may be 3D printed within the filler to deliver fluid to the wound bed. For example, a port may be printed on the exterior of the wound filler configured to connect to bot a suction tube and an irrigant tube. The port may in turn be connected to internal manifolding that connects the port to the various surfaces of the wound filler, such as the surface in contact with tissue. For example, the internal manifold may connect the port to the bottom surface and or the side surfaces. In certain embodiments, the fluid manifold may encompass at least about 10% of the total volume of the bespoke wound filler, at least about 20%, at least about 30%, at least about 40%, at least about 50%, at least about 60%, at least about 70%, at least about 80%, at least about 90%, or about 100%.

For example, and as described in further detail below, attributes of the 3D model may be modified to account for different tissue types in the wound, such as exposed bone or tendon, and which may require that the wound filler be different from wound filler to be used in the treatment of epidermal, sub-epidermal, or muscle tissue. FIG. 4, as described above, describes such an embodiment.

In some embodiments, a human may assist in the creation of a 3D model, leading to the construction of a bespoke wound filler, by identifying the properties of the various regions of the wound. Hereinafter the word "clinician" will be used to describe any human involved in the creation of the filler, however "clinician" is not limited to only medical practitioners, but could be a home user, general caregiver, or patient.

The clinician may contribute to the creation of a 3D model for a desired wound filler by identifying the characteristics of the various regions of a wound which may be treated with the wound filler, for example while under negative pressure. For instance, a clinician may identify areas as highly exudating, drying, infected, or having any other condition described herein this section or elsewhere in the specification. A clinician may further identify the tissue type of the various regions of the 3D model. The clinician can identify and define characteristics of the wound such as the shape of the wound, severity of the wound, expected closure of the wound, or any other relevant characteristic of the wound. The clinician may further identify the fluid modality of a particular area of a wound, such as by identifying the level of fluid release from such a portion of the wound. Additionally, the clinician can further identify areas of the wound that would be best served by the application of various levels of negative pressure. Further, the clinician may identify areas that would be best served by irrigation and/or the delivery of various molecules. In addition to the characteristics already described, a clinician may identify any other key characteristics that may influence the healing and closure of a wound or impact the health of a patient.

Identification of the characteristics of a wound can be performed in a variety of ways as described herein this section and elsewhere in the specification. In some embodiments, the wound is assessed by visual inspection of the wound via computer or human recognition. In certain embodiments, the assessment of the wound is completed using chemical, physical, auditory, or energy-based assays or imaging techniques. In further embodiments, any suitable identification techniques may be used.

In further embodiments, the clinician may also assess additional health-related factors of the patient and incorporate those factors into the 3D wound model. For example, the clinician could identify a diabetic patient, and recognize that their circulation may be compromised. Thus, the wound model could be altered to account for poor circulation. In other embodiments, a clinician could recognize that a patient may be immune compromised or have other relevant health conditions that may affect wound therapy treatment. The clinician may use these health-related factors to modify the 3D model in any suitable manner. In other embodiments, instead of or in additional to the clinician's contribution to the model, the scanning software can automatically generate a 3D model of the wound by automatically identifying the properties of the various regions of the wound as any of the tissue types or characteristics described herein. Additionally, the 3D model may be modified automatically by a computer algorithm based on the general health characteristics of the patient. Generally, any task described herein this section or throughout the specification as to be performed by a clinician may also be automated to be performed via a computing or generally automated process.

In some embodiments, the characteristics of the wound can be translated into data points that correspond to spatial points within the 3D model. Thus, spatial points of the 3D wound model may have corresponding wound characteristic data. Such wound characteristic data then may be used as a basis to modify the wound model to build in a corresponding wound filler model or to create a separate, independent wound filler model.

As described herein this section and elsewhere in the specification, a 3D wound filler model suitable for 3D printing or other custom means of fabrication can be generated from the 3D model of the wound. However, the 3D model of a wound filler need not be generated from a 3D model of a wound. Instead the 3D model of the wound filler can be designed manually by a clinician with assigned characteristics as needed. The clinician may use their assessment of the wound to identify and define particular regions of the wound filler to correspond with characteristics of the wound. In preferred embodiments, the wound filler is designed to facilitate the application of negative pressure to the wound and/or to irrigate the wound. In certain embodiments, the clinician may consider the long term closure of the wound in designating the characteristics of the wound filler. For example, the clinician may construct the 3D model with the direction of closure in mind, such as by aligning the closure along the Langer lines or along a shorter axis of the wound.

As is described herein this section and elsewhere in the specification, the 3D wound filler model is comprised of various regions that may have variable physical, chemical, and structural characteristics as is desired to treat the wound. The physical, chemical, and structural characteristics of the wound filler model can be determined from the corresponding characteristics of the 3D wound model or via any process as described herein this section or elsewhere in the specification. In some embodiments, the physical, chemical, and structural characteristics of the wound filler model can also be assigned. The different regions may have significant structural differences or utilize different materials as is appropriate for treatment of a wound. The different regions may have various chemical properties as is desired for proper treatment of a wound. In preferred embodiments, the different regions of the wound filler are tailored for the application of negative pressure as is desired for wound healing. In some embodiments, the 3D wound filler model is generated automatically based on characteristics of the wound, while in other embodiments the 3D wound filler information is input manually.

In certain embodiments, a 3D model of the wound filler is created merely from the spatial data contained within the 3D wound model. Such an embodiment may generate a wound filler that accommodates the width, length, and appropriate depth of a wound and could be desirable for the treatment of an irregularly shaped wound as described above. In preferred embodiments, the 3D model of the wound filler is created from multiple different wound characteristics that were incorporated into the 3D model of the wound. The 3D model of the wound filler may also be further determined by the general health-related characteristics of the patient.

As described above, in some embodiments, the characteristics of the various regions of the wound filler may be determined by the anatomical location of the wound and the surrounding tissues. For example, a wound filler used for the treatment of an abdominal wound may comprise a slit structure. In another example, a region of a wound filler associated with a bone or tendon could be constructed from a hydrophilic material with a reasonably closed cell structure so as to maintain moisture in the surrounding tissue. In some embodiments, a fine pore size in the range of about 10-350 μm may be used to maintain moisture. Such a pore size may range from at least about 1 μm, 5 μm, 10 μm, 15 μm, 20 μm, 30 μm, 40 μm, 50 μm, 75 μm, 100 μm, 125 μm, 150 μm, 200 μm, 300 μm, 400 μm, 500 μm, or more than 500 μm. In still another example, the wound filler region in the area of a pressure ulcer or highly exudating tissue may incorporate an open structure such as a reticulated foam so as to better remove liquid from the tissue. In some embodiments, a larger pore size in the range of about 350-900 μm may be used to aid in liquid removal. Such a pore size may range widely, for example from at least about 10 μm, 50 μm, 100 μm, 200 μm, 300 μm, 400 μm, 500 μm, 1000 μm, 2000 μm, 3000 μm, 4000 μm, or 5000 μm. In some embodiments, any of the pore sizes disclosed in PCT Application No. PCT/GB2012/000489, titled "WOUND CONTACTING MEMBERS AND METHODS," filed Jun. 7, 2012, and hereby incorporated by reference in its entirety. Open structures may also be used in areas of the wound where granulation tissue is desired. For example, in areas where granulation tissue is desired, the pore size may range from at least about 10 μm, 50 μm, 100 μm, 200 μm, 300 μm, 400 μm, 500 μm, 1000 μm, 2000 μm, 3000 μm, 4000 μm, or 5000 μm.

In certain embodiments, as described above, characteristics of the various regions of the wound filler may be determined automatically based on the 3D wound model or could be assigned. In some embodiments, the characteristics may include water/vapor permeability, gas permeability, absorption capacity, thickness, material type, material structure (such as number of layers), thickness/size, presence of pharmacological additives, color, hydrophobicity/hydrophilicity, or any other suitable characteristic.

The various regions of the wound filler such as determined by the 3D wound model may comprise different materials or have different structural characteristics. In non-limiting embodiments, regions of the wound filler may be comprised of: various rigid, semi-rigid, or soft foams; various hydrophilic and/or hydrophobic foams; soft, conformable, and preferably resiliently flexible materials such as polymers, including thermoplastics; various biodegradable materials; cellulose materials, superabsorbers, or other suitable materials. Suitable polymers include ABS synthetic rubbers, various silicones such as Integra, polyurethanes such as the Elastollan series Thermoplastic polyurethane elastomers (TPUs) from BASF and specifically the Elastollan series hydrophilic TPU, ethylene vinyl acetate, nylons for example Nylon 618 from Taulman 3D Missouri, polyamides, and polyethylenes. The Tangoplus family of resins, e.g. Tangoplus FC930, from Stratsys have varying levels of hardness so that structures with different degrees of flexibility and compression can be fabricated. Further examples of possible materials include 3D knit spacer fabrics such as those manufactured by Gehring Textiles. In further embodiments, the material may comprise polylactic acid (PLA), polyglycolic acid, or any other material disclosed herein this section or elsewhere in the specification. The wound filler may also include anistropic materials such as the coil-like materials found in U.S. patent Ser. No. 10/981,119, filed Nov. 4, 2011, titled "WOUND PACKING MATERIAL FOR USE WITH SUCTION," issued as U.S. Pat. No. 7,754,937 and hereby incorporated by reference in its entirety and hereinafter referred to as the '937 patent. The potential repeating of individual sections of this material is described in greater detail in the fabrication section below.

As described herein this section and elsewhere in the specification, in some embodiments, the wound filler may have varied structural characteristics such as porosity. In a preferred embodiment, the 3D printer (described further below) may control the porosity of the resulting material, either in the bespoke filler as a whole or by varying the porosity through different sections of the device. For example, a wound filler with smaller pores may be preferable to minimize tissue growth or adhesion, while larger pores may be useful to promote removal of wound exudate from the wound. Such a configuration may thus comprise, for example, a material with smaller pores in contact with the wound which encapsulates or is placed underneath a material with larger pores. As described above and elsewhere in the specification, the pore size may vary considerably, such as between about 0.1 to 200 µm. Preferably, smaller pores may measure between about 20 to 150 µm, while larger pores may measure between 400-3000 µm or greater. Still other pores may measure less than about 20 µm, less than about 1 µm, less than about 0.5 µm, or between about 150 to 400 µm. In another example, porosity may be reduced in applications where scar tissue (resulting from excess granulation tissue) should be minimized. In some cases, the number of pores per unit area may be reduced, for example, some embodiments may provide for a wound contacting layer of the bespoke wound filler having an open area of approximately 20%, and 1 mm diameter pore sizes. In certain embodiments, other structural characteristics may be varied within the material, such as to make the material open-celled with interconnected cavities within the material and/or closed-celled. The structural characteristics of the wound filler are limited only by the capabilities of the 3D fabrication device, and thus all manner of structures and shapes suitable for wound treatment may be used.

In some embodiments, the wound filler is tailored for the application of negative pressure. As described above in relation to FIG. 4, and elsewhere in the specification, the wound filler may be designed to have various levels of porosity. In some embodiments, the porosity may be varied to promote liquid flow from portions of the wound via the application of negative pressure. To better control the application of negative pressure, portions of the bespoke wound filler may be made to cover portions of the anatomy from which minimal or no fluid removal is desired. For example, some tissue types, such as exposed bone or tendon, may dry out or be adversely impacted due to the application of negative pressure therapy. Manufacturing a bespoke wound filler that has minimal or no pores when placed over such tissue anatomy may thus be advantageous. Preferably, the bespoke wound filler is manufactured so that other parts of the tissue anatomy in that same wound that would benefit from a porous wound filler (e.g., epithelial tissue) are in contact with a material that has increased porosity.

In addition to altering the porosity of the wound filler to accommodate the desired application of negative pressure, the wound filler may contain flow channels that direct wound exudate drawn via negative pressure. Such flow channels may be oriented horizontally through the wound filler and/or may be oriented vertically. Regions of the filler where limited or no negative pressure is desired may have few if any channels. In certain embodiments, the material characteristics of the wound filler may also be further tailored to accommodate negative pressure such as by using hydrophobic materials like hydrophobic foam to allow for the application of negative pressure without trapping fluid. In some embodiments, hydrophilic materials may be used to trap wound exudate drawn from the surrounding wound tissues. The hydrophilic materials may be superabsorbers. The various regions of the wound filler may be open celled, closed celled, or a combination of the two as is needed to apply desired levels of negative pressure. In some embodiments, particular regions of the wound filler may be constructed as wicking layers to wick fluid in a desirable manner. As described herein this section and elsewhere in the specification, different regions of the wound filler may have different functions and properties, such that the application of negative pressure to various areas of the wound can be well controlled.

In some embodiments, the bulk of the wound filler comprises open-celled hydrophobic material to allow for fluid flow via the application of negative pressure. In certain embodiments, this significant bulk of open-celled hydrophobic material may be surrounded by other materials suited for more direct contact with the wound tissues.

In particular embodiments, as will be described in much greater detail below in relation to FIGS. 6A-44B, the wound filler may be tailored to collapse more readily in one direction than in another direction. As described elsewhere in the specification, the wound filler may collapse more readily in a horizontal direction while remaining relatively rigid in the vertical direction. It will be recognized by one of skill in the art that "horizontal direction" may refer to a plane parallel to the plane of the wound, while vertical direction may refer to a plane perpendicular to the plane of the wound. It will further be recognized by one of skill in the art, that such a wound filler may collapse under negative pressure horizontally within the wound in a direction perpendicular to the longitudinal axis of the wound, while remaining substantially rigid in the vertical direction. In certain embodiments, particular regions of the wound filler may collapse, while other regions remain rigid.

In some embodiments, the 3D wound filler may be tailored for the application of irrigation to the wound. In certain embodiments, the wound filler is connected to one or more reservoirs containing irrigant fluid. Such irrigant fluid may contain antimicrobial molecules, anti-inflammatory molecules, marking molecules, or growth factors that promote wound healing. Irrigant fluid may be applied simultaneously with the application of negative pressure, such that simultaneous irrigation and aspiration is possible. In other embodiments, aspiration then irrigation or irrigation then aspiration are sequential.

The use of irrigation may be desirable for certain regions of the wound, thus the wound filler may be tailored to best apply irrigation to those regions of the wound. For example, in drier areas of the wound or in areas requiring debridement via irrigation, the wound filler may be configured to allow greater irrigant flow to the wound. Such an application may include wound filler regions comprising flow channels, such as those described above in relation to negative pressure, that direct fluid flow towards specific portions of the wound. In other embodiments, regions of the wound filler directed towards irrigant flow may be more porous or be open-celled, thus allowing for greater flow of irrigant fluid. In areas of the wound where irrigation is less desirable, portions of the wound filler may be made to be more occlusive, with smaller or nonexistent pores, or a closed-cell structure. Such features are applicable to any manifold disclosed herein this section or elsewhere in the specification.

In some embodiments, the 3D wound filler model may be constructed such that the filler has different layers of material and structure. For example, in a penetrating wound, the filler may have layers of softer material deeper in the wound, with layers of more rigid material closer to the uppermost surface of the wound, thus allowing for the deeper portions of the wound to close before the portions of the wound that are closer to the exterior. In some embodiments, the central portion of the filler may be comprised of one material and/or structure while an exterior portion is comprised of a different material and/or structure. In further embodiments, the wound filler may be layered similar to an onion, with various layers with differing material or structural properties surrounding one another. In further embodiments, the layers may be oriented in a vertical manner such that each layer comprised a flattened section in the horizontal plane.

Figure 5A:
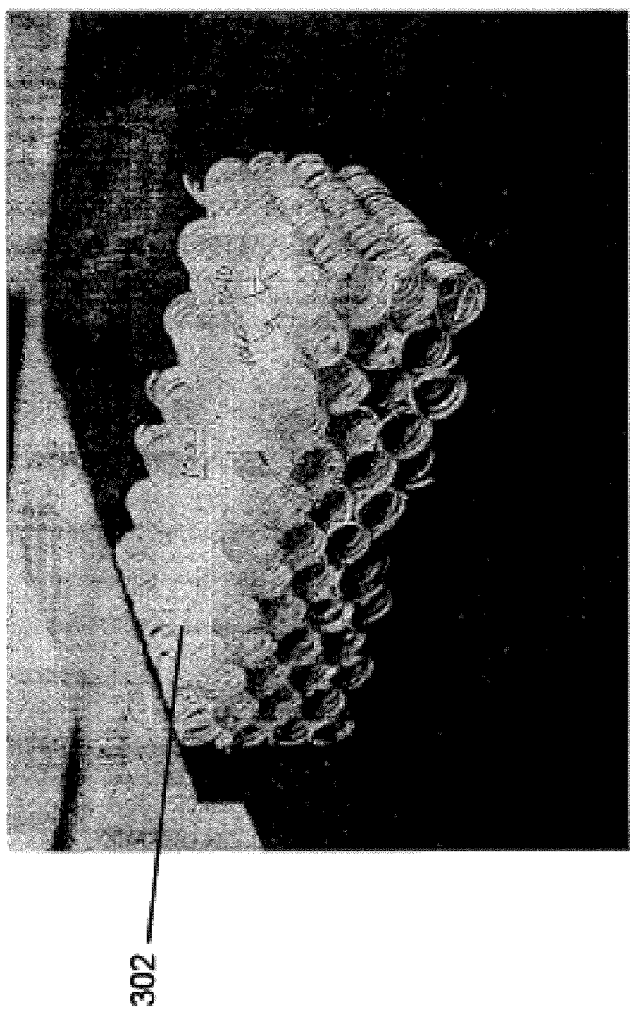
FIGS. 5A-C are photographs of an embodiment of a repeating building block that may be used as a bespoke wound filler system.
Figure 5B:
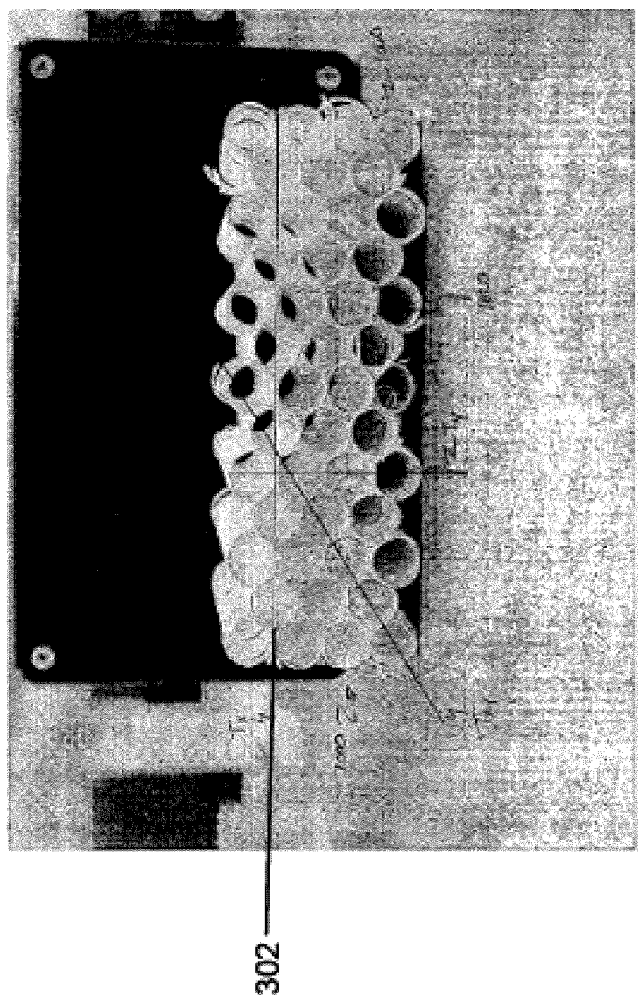
Figure 5C:
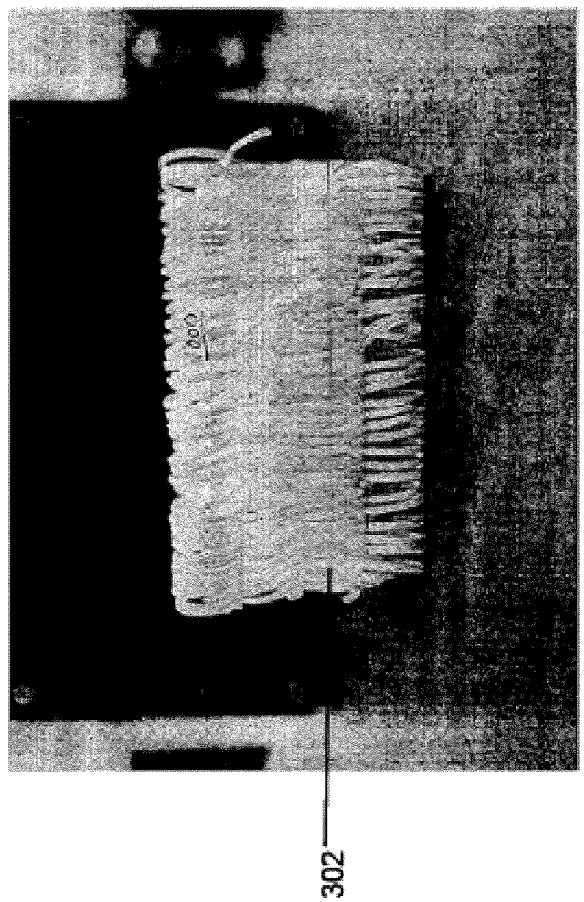

As described above in relation to the design of the wound filler, FIGS. 5A-C illustrate different views of a wound filler 302 which may comprise an anisotropic structure having a first compressive response along a first axis and a second compressive response along a second axis perpendicular to the first axis, the second compressive response being different from the first compressive response. In one embodiment, this structure may be nonabsorbent, and may comprise stacked, coil-like repeating units 302. This and other embodiments of wound fillers may be manufactured by the 3D printer with reference to a 3D model, and examples of such may be found in the '937 patent, incorporated into this application above. The materials described in the '937 patent have anisotropic properties, meaning that their material properties may be dimensionally dependent. For example, as described above, an anisotropic material may have increased stiffness in one direction versus another direction. Thus, a material with anisotropic properties such as those depicted in the '937 patent may collapse more readily in one direction rather than another. Such a material could be used within the wound to control the compression of the wound filler in particular directions and preferentially compress the filler to allow for improved wound closure. The material of the '937 patent is nonabsorbent, thus this material may allow for the passage of negative pressure. In some embodiments, the material of '937 may further be used in combination with negative pressure strategies to direct the application of negative pressure and wound closure, in a manner consistent with the embodiments described herein this section and elsewhere in this specification.

The materials that comprise the wound filler may be determined by the characteristics of a particular region of the 3D wound model or may be assigned. For example, an area of the wound that requires additional hydration could utilize a moist hydrophilic material such as a hydrogel. An area that is highly exudating may need to be highly absorbing and have a high water vapor evaporation. Areas with low levels of wound exudate may require a nonabsorptive material with low water vapor permeability so as to trap moisture.

Since a 3D printer is capable of printing a wide variety of shapes, in some embodiments, the 3D model may also include a port and/or tubing such that the wound filler may be connected to a source of negative pressure. In further embodiments, the 3D model includes additional suitable articles that may be useful for wound healing.

In some embodiments, the material may be configured as a scaffold material to promote tissue ingrowth and/or bioabsorption. For example, bioabsorption can be achieved by using polyglycolic or polylactic acids or co-polymers of these polymers, for the printing of the scaffold, and which then may be seeded with cells and/or cell growth promoters. Antibiotics, anti-inflammatory drugs, diagnostic agents such as radioopaque markers, and other such materials may also be incorporated therein. The scaffold material may be tailored to deliver a variety of molecules in the form of controlled delivery. For example, one region of the filler could deliver an antimicrobial molecule to an infected region of tissue, while another region of the filler delivers an anti-inflammatory molecule to an inflamed region of tissue. Various molecules may be released in to the surrounding tissue as is merited by the characteristics of the surrounding tissue. Released molecules are not limited only to locally acting molecules, in some embodiments systemically acting drugs may be released.

The wound filler is not limited to one continuous, intact structure. The wound filler can be constructed to be in separate pieces and applied separately to the wound rather than as a single unit. It should be understood that all embodiments described herein this section or elsewhere in the specification may be generated as a single continuous structure or as separate dividable portions. This approach is particularly useful for dealing with undetermined structures of wounds or tunneling wounds where it may not be possible to insert a single wound filler In some embodiments, the wound filler may be constructed as a rounded bowl-like shape, or may comprise a rounded bowl-like shape at the bottom of the filler. This bowl-like shape can be a comprised of a single material layer such as a foam bowl. In certain embodiments, the bowl comprises one material while a remainder of the wound filler positioned above or within the bowl comprises a different material. In some embodiments the bowl portion of the filler may be in the form of a divided separate section of the wound filler.

Fabrication of the 3D Wound Filler

Having generated the 3D model, the 3D model can be used by a 3D printing device to manufacture the bespoke wound filler. The 3D printing device may be any suitable 3D printer, including by means of example only the Objet Connex500™, the 3D Systems ZPrinter® 850, or the RepRap. In other embodiments, wound filler fabrication may be performed using any known wound dressing fabrication technique. The wound filler may be fabricated from any materials described herein this section or elsewhere within the specification, or any other type of suitable material. The wound filler may be fabricated to comprise any structure described herein this section or elsewhere within the specification, or any structure that may be suitable for the wound filler. The wound filler may be fabricated to comprise any characteristic described herein this section or elsewhere within the specification, or any characteristic that may be suitable for the wound filler.

In some embodiments, the wound filler may be fabricated separately from the wound and later placed within the wound. In other embodiments, the wound filler may be created directly in the wound. In still other embodiments, a portion or portions of the wound filler may be created separately from the wound, while a portion or portions of the wound filler may be created directly in the wound.

As described above, the wound filler may be fabricated via any known fabrication technique. In some embodiments, the wound filler may be fabricated via extrusion or via electrospinning techniques. The wound filler can also be fabricated via gas blowing or localized deposition directly into the wound or onto a substrate.

In some embodiments, the outermost or topmost layer of the wound filler can be comprised of a fluid impermeable polymer, such as silicone. This outermost or topmost layer can overlay the top of the wound filler and extend beyond the edges of the wound. This outermost or topmost layer can further comprise an adhesive or other means for sealing the outermost layer around the wound. In this manner, the outermost layer may function as a drape to contain the application of negative pressure. In some embodiments this outermost or topmost layer may be fabricated in combination with a biodegradable wound filler such that once the wound filler biodegrades, the outermost layer is still intact.

Similar to the above description of the materials utilized in the design of the wound filler, the 3D printer is configured to manufacture a bespoke filler from soft, conformable, and preferably resiliently flexible materials such as polymers, including thermoplastics. Suitable polymers include ABS synthetic rubbers, polyurethanes for example Elastollan SP9109 from BASF, nylons for example Nylon 618 from Taulman3D Missouri, polyamides, ethylenevinyle acetates, and polyethylenes. The Tangoplus family of resins, e.g. Tangoplus FC930, from Stratsys have varying levels of hardness so that structures with different degrees of flexibility and compression can be fabricated. In further embodiments, the materials utilized to construct the wound filler and other components of the wound treatment system encompass all materials disclosed in this section and elsewhere in the specification.

As described above in relation to the design of the wound filler, in some embodiments, the 3D printer may be capable of depositing materials or using materials that form a porous configuration. In some embodiments, the materials may be harder, and may include porous scaffolding materials such as hydroxyapatite that promote tissue growth. The 3D printer may be configured to use multiple materials so as to form a bespoke wound filler composed of multiple devices. In some embodiments, the 3D printer is capable of manufacturing a bespoke wound filler consisting of a repeating building block, for example the building blocks described herein this section and elsewhere in the specification.

Some embodiments may also provide for regions of the wound filler to be constructed from repeating building blocks. The use of repeating building blocks may be advantageous during manufacture because these building blocks could be replicated over and over again within the model allowing for an easier and more efficient creation of structures within the filler. Further, the use of building blocks may allow for the 3D fabrication device and/or the associated software to operate more efficiently. For example, the use of building blocks may allow the fabrication device to move through tight, specified patterns and limit the required movement and energy consumption of the device. In some embodiments, the repeating unit may be comprised of any physical, chemical, or structural characteristics as described herein this section or elsewhere in the specification. Different regions of the wound filler may be comprised of different building blocks, allowing for a complex construction of layered and/or stacked building blocks of different types. For example, one region comprising a repeating building block may utilize building blocks of foam having a desired porosity, structure or other characteristics. A second region may comprise repeating building blocks made from a different material such as the coil-like material described in '937 patent and depicted as 302 in FIGS. 5A-C. Based on the 3D model, repeating blocks may have different characteristics for positioning in different parts of the wound. The software for the 3D printer or other fabrication device may set the contours of the 3D model as the limits for a repeating building block and repeat the building block in three dimensions until it reaches the limit of a contour.

Preferably, for small details, the 3D printer can manufacture details in a range of at least about: 0.1 µm, 0.5 µm, 1 µm, 2 µm, 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm or 100 µm. Details between 30-50 µm may be conducive to obtaining good tissue growth. In some embodiments, the 3D printer is configured to manufacture bespoke wound fillers as detailed in PCT Application PCT/GB2012/000489, filed Jun. 7, 2012, titled "WOUND CONTACTING MEMBERS AND METHODS, APPARATUSES, SYSTEMS AND KITS INCORPORATING THE SAME," published as WO20122168678 and which is hereby incorporated by reference in its entirety.

Figure 47:
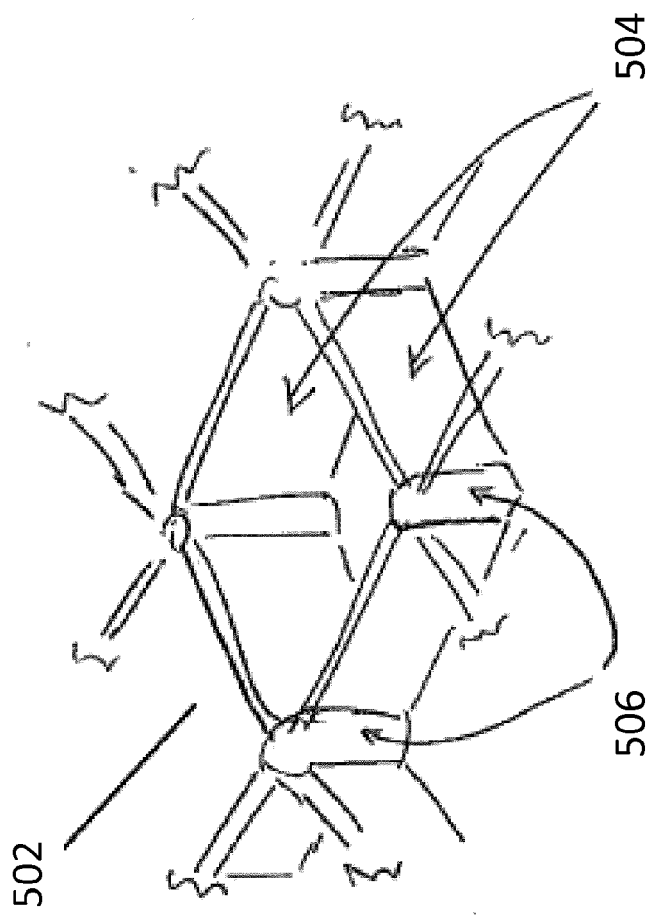
FIG. 47 illustrates an embodiment of a repeating building block that may be part of a bespoke wound.

With reference to FIG. 47, some embodiments may also provide for the wound filler to be constructed from a repeating building block or identical cells, for example the building block 502. The 3D fabrication software may thus set the contours of the 3D model as the limits for a repeating building block and repeat the building block in three dimensions until it reaches the limit of a contour. In some embodiments, the repeating building block may be the building block 502, which preferably comprises straight sections or walls 504, preferably constructed from a rigid polymer, joined together by hinged sections 506, preferably constructed from a flexible or soft polymer. Other embodiments of repeating building blocks or cells may be of any of the structures wound filler structures described herein this section or elsewhere in the specification. For example, the stabilizing structures, wound closure devices, or other structures described in relation to FIGS. 5A-44B may be used.

In certain embodiments, the wound filler may comprise a single horizontal layer of identical cells. In particular embodiments, the wound filler can comprise a plurality of horizontal layers, each layer comprising identical repeating cells. In some embodiments, repeating cells in a first horizontal layer are different from repeating cells in a second horizontal layer above the first horizontal layer. In some embodiments, the wound filler may comprise a first plurality of identical repeating cells and a second plurality of identical repeating cells, wherein the first plurality of identical repeating cells is different from the second plurality of identical repeating cells. At least some of the repeating cells may comprise side walls with an opening extending therethrough, such as shown in FIG. 47. In some embodiments, at least some of the repeating cells can comprise a first portion with a first stiffness and a second portion with a second stiffness different from the first stiffness. For example, the first portion may be an outer portion (such as formed by the walls 504 in FIG. 47) surrounding a second portion within the walls 504.

Some embodiments, may call for the bespoke wound filler to comprise a porous material. In any of the embodiments described herein, the bespoke wound filler may comprise at least one region comprising a porous material suitable for channeling wound exudate from a wound site and negative pressure to the wound site, and a more rigid stabilizing structure at least partially embedded within the porous material.

In some embodiments, the bespoke wound filler may be fabricated from a polymer. In some embodiments, an apparatus such as those described previously, may further comprise a drape configured to be placed over the bespoke wound filler and be sealed to skin surrounding the wound. In embodiments, a port may be configured to connect the drape to a source of negative pressure. In certain embodiments, a source of negative pressure may be configured to apply negative pressure to the wound filler under the drape.

Examples of Wound Closure Devices and Stabilizing Structures that May be Utilized for Bespoke Wound Fillers Some embodiments may provide for the entirety of or regions of the bespoke wound filler to be constructed with a shape, configuration or including components of stabilizing structures and wound closure devices such as those described below in relation to FIGS. 6A-44B and 47. The stabilizing structures and wound closure devices, as described herein this section or elsewhere in the specification, may therefore be made as bespoke wound fillers utilizing the methods and apparatuses described herein. Many of these stabilizing structures and wound closure devices include identical repeating units or cells that may constitute the entirety of or a portion of a desired bespoke wound filler. In at least some of these embodiments, the repeating units or cells are configured to collapse in a desired direction or in a desired manner to facilitate closure of a wound under negative pressure. The bespoke wound filler may be designed based on a 3D scan of the wound, the properties of the wound, the negative pressure treatment modality, and/or the manner in which the wound is expected or intended to close, to provide for a plurality of repeating cells in certain regions and in a certain orientation within the wound filler.

A bespoke wound filler may also incorporate any of the stabilizing structures or wound closure devices as described herein, and include other structures. For example, one region of a bespoke wound filler may comprise a stabilizing structure and/or wound closure device as described in relation to FIGS. 6A-44B and 47 while another region may comprise a biodegradable scaffold such as those described above. The stabilizing structures and wound closure devices described herein this section or elsewhere in the specification may be incorporated into the bespoke wound filler much like any other region, such as those described in relation to FIGS. 3-5C. In certain embodiments, different variations of stabilizing structures and/or wound closure devices may be incorporated within different regions of the same bespoke wound filler.

Some embodiments may call for the entirety of the fabricated wound filler to be in the form of stabilizing structures and/or wound closure devices. In particular embodiments, stabilizing structures and/or wound closure devices may encompass at least about 10% of the total volume of the bespoke wound filler, at least about 20%, at least about 30%, at least about 40%, at least about 50%, at least about 60%, at least about 70%, at least about 80%, at least about 90%, or about 100% as described above.

Accordingly, in the following description, embodiments of stabilizing structures and wound closure devices are described, wherein it will be understood that such structures and wound closure devices may be utilized or modified to create the entirety of or portions of a bespoke wound filler.

Stabilizing Structures and Wound Closure Devices of FIGS. 6A-7E

FIGS. 6A-D illustrate different views of an embodiment of a wound closure device comprising a stabilizing structure 1701. Here, the stabilizing structure 1701 comprises a first set of beams 1703 that are rigidly or semi-rigidly attached or bonded to a second set of intersecting beams 1705. These beams 1703, 1705 form a planar support structure 1702 that is preferably substantially rigid within a plane. The beams 1703, 1705 may meet at right angles to each other (although other configurations, e.g., honeycombs are possible). Two or more planar support structures 1702 may be joined together to form the stabilizing structure 1701, and each planar support structure 1702 is preferably separated from the other by spring elements 1711 and 1713, described in further detail below. The number of planar support structures 1702 used in the stabilizing structure may be tailored in relation to the size of the wound. For example, there may be 2, 3, 4, 5 or more planar support structures 1702 arranged parallel or substantially parallel to one another. The spring elements 1711, 1713 are preferably arranged so as to allow for compression of the stabilizing structure 1701 in one direction so as to bring the planar support structures 1702 closer together. In a preferred embodiment, the stabilizing structure 1701 may collapse to 40% or less of its original size, preferably 30% or less of its original size; more preferably, 20% or less of its original size; even more preferably, 10% or less of its original size. In some embodiments, the stabilizing structure 1701 may collapse to 5% or less of its original size.

The spring elements 1711, 1713 are preferably resiliently flexible and biased to be resiliently collapsible along a direction perpendicular to the plane defined by the planar support structure 1702. In some embodiments, the elements 1711, 1713 may be inelastic, and retain their shape when collapsed. In such embodiments, the spring elements or the stabilizing structure may be constructed with a ratchet mechanism that maintains the spring elements 1711, 1713 in their collapsed configuration.

Figure 6A:
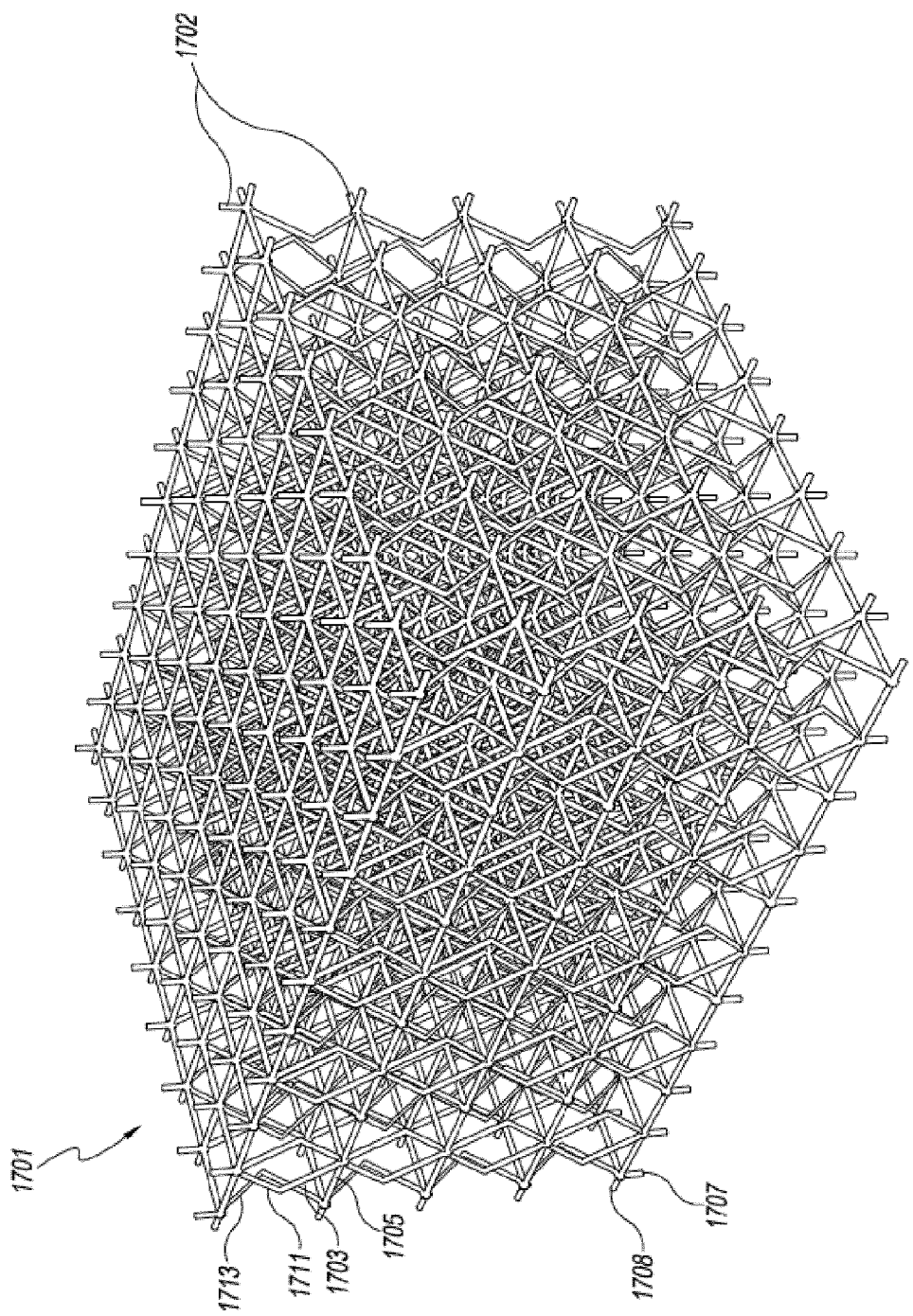
FIGS. 6A-D illustrate different views of embodiments of a wound closure device comprising a stabilizing structure.
Figure 6B:
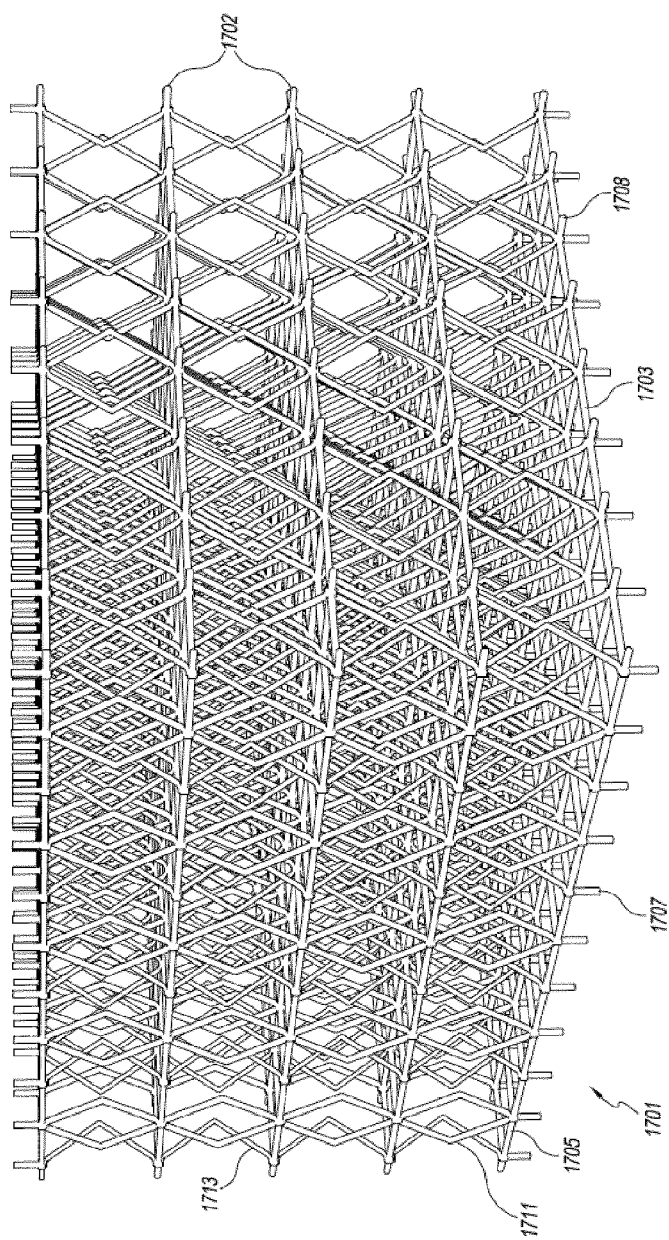
Figure 6C:
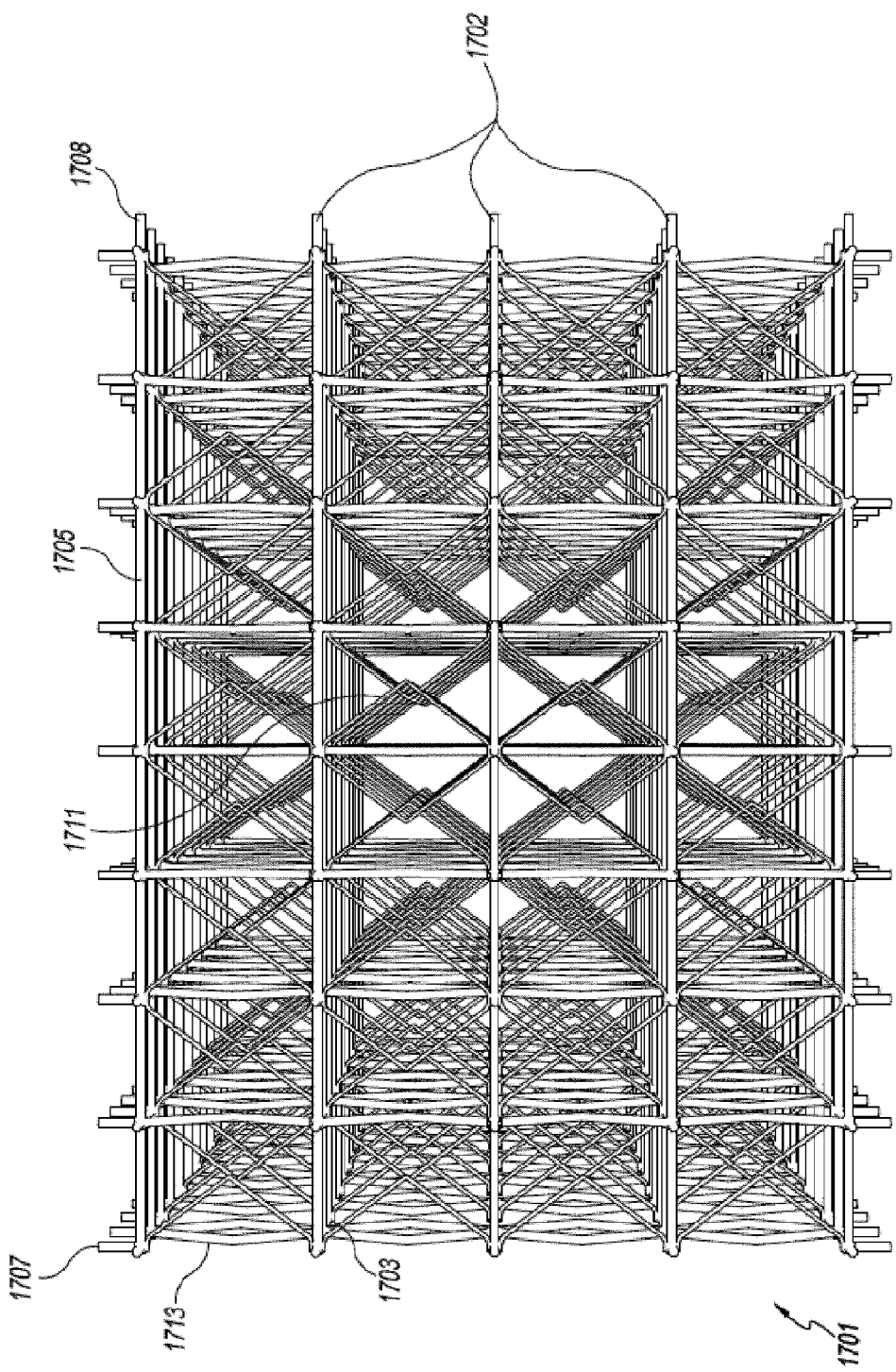
Figure 6D:
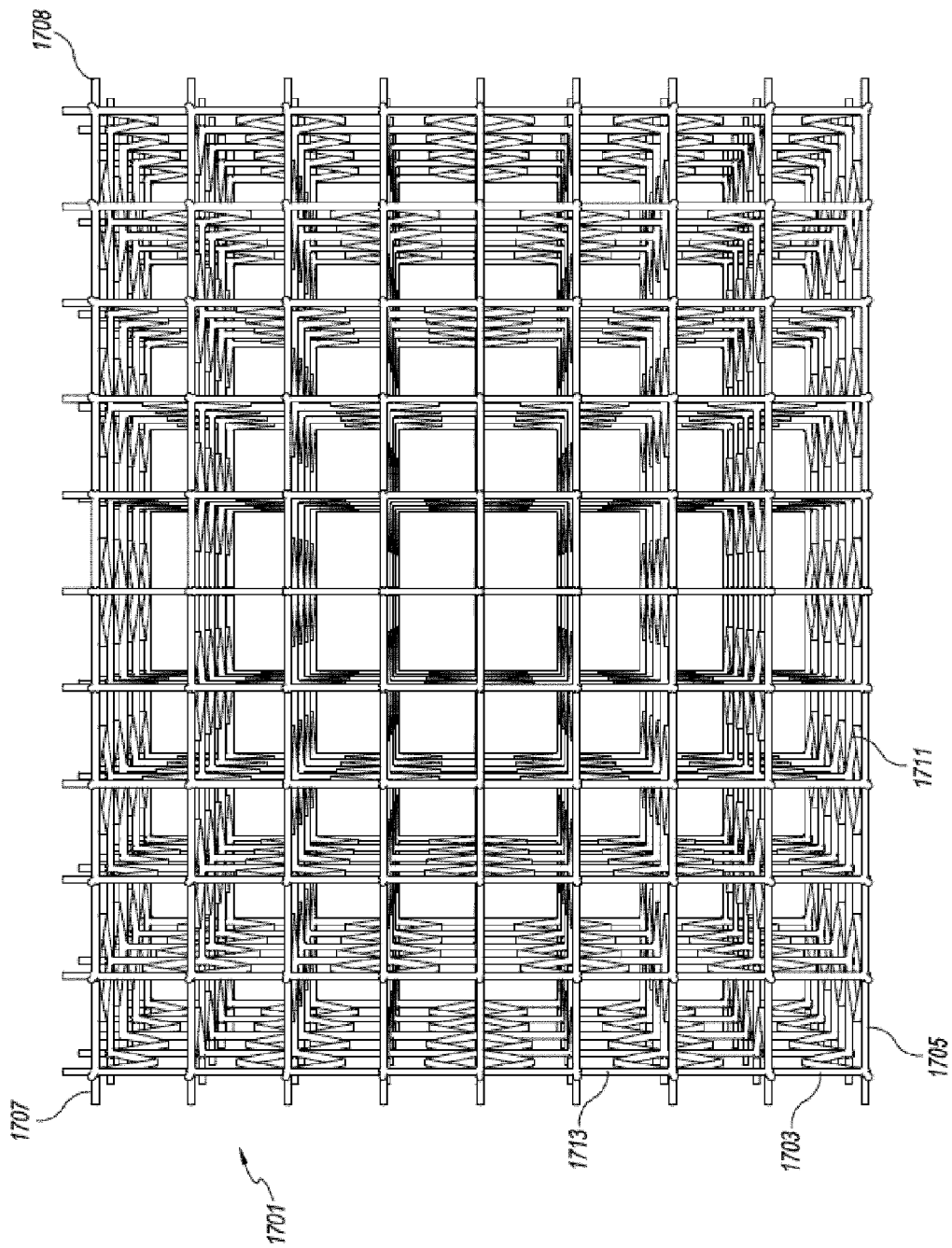
Figure 7A:
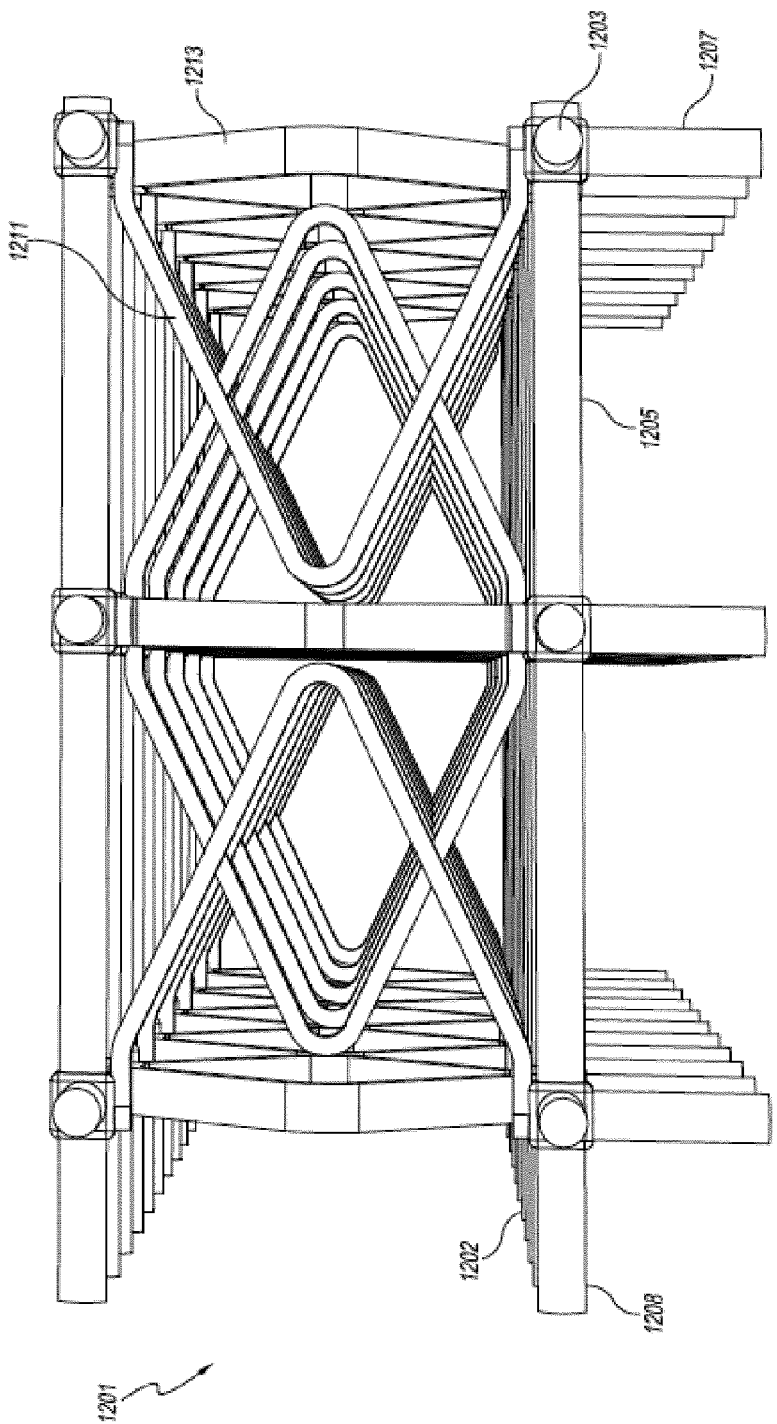
FIGS. 7A-E illustrate different views and photographs of embodiments of a wound closure device comprising a stabilizing structure.
Figure 7B:
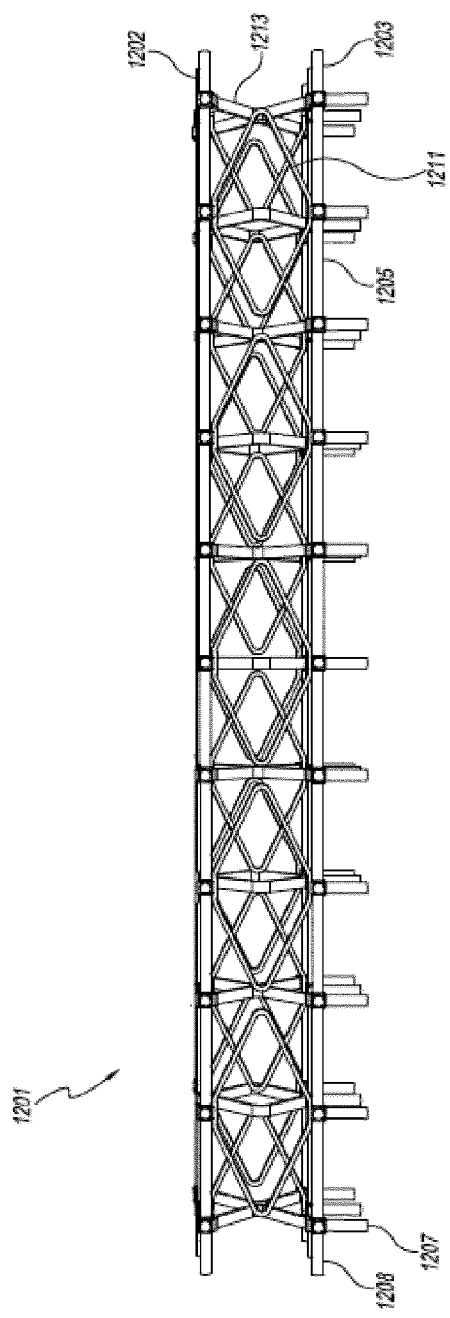
Figure 7C:
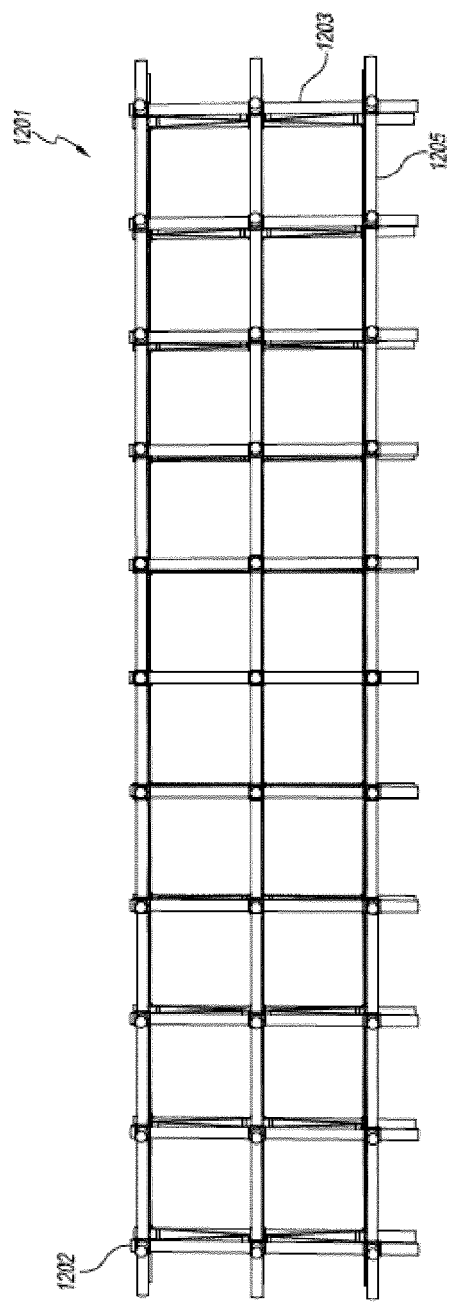
Figure 7D:
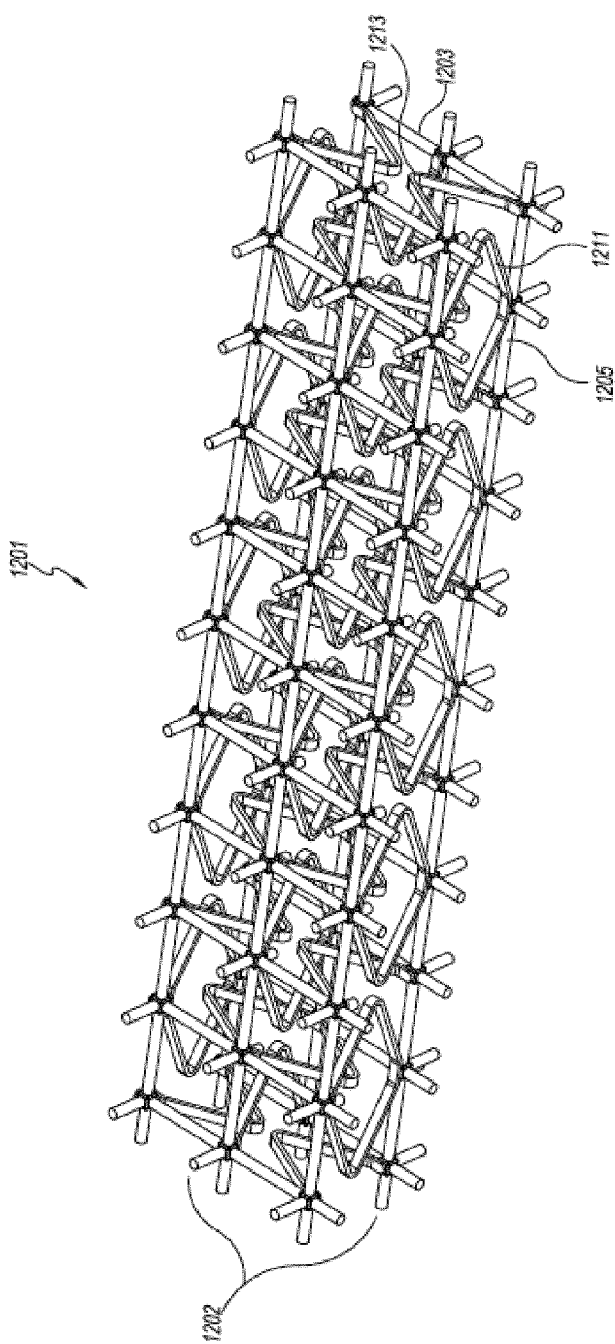
Figure 7E:
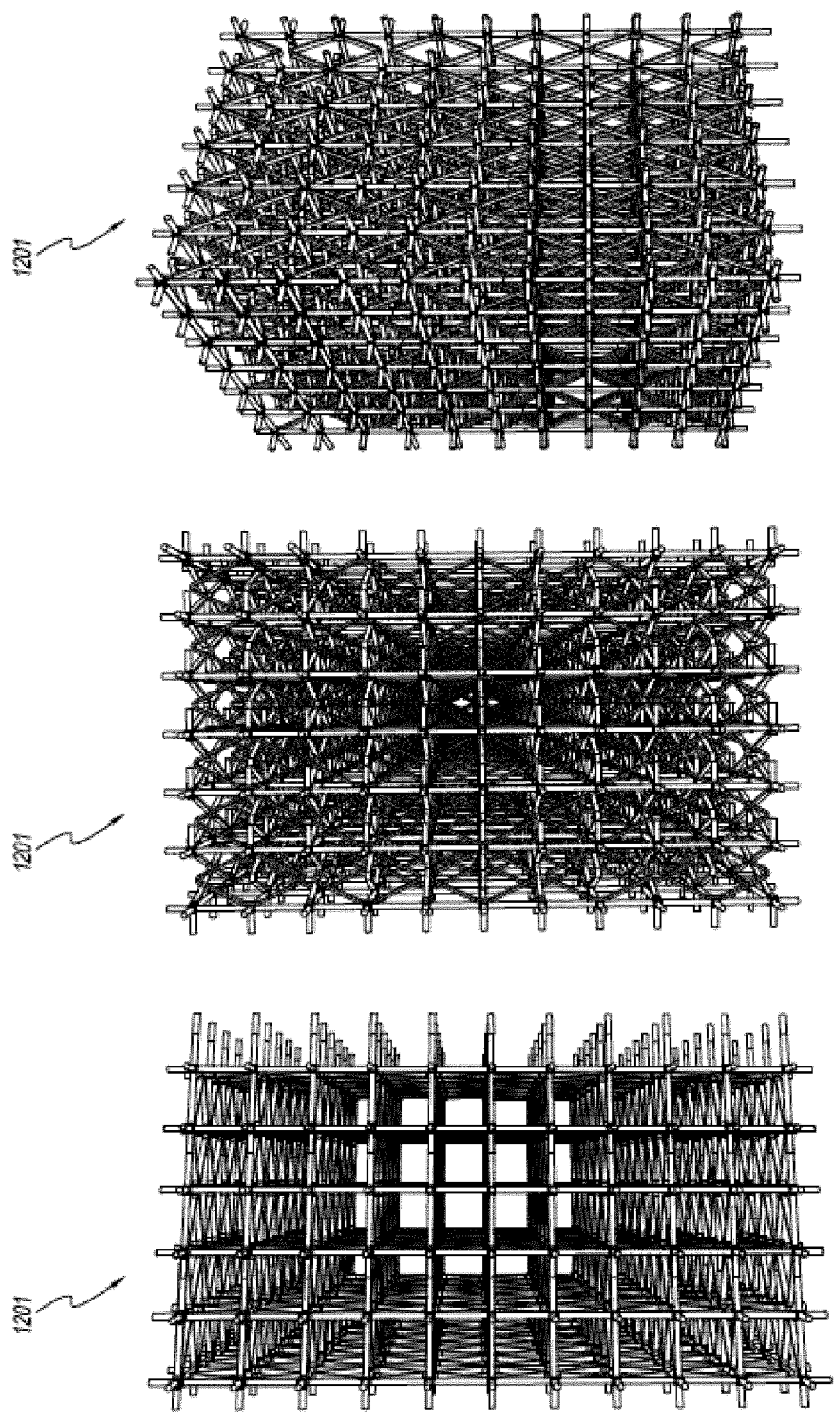

In a preferred embodiment, these spring elements 1711, 1713 may be V- or U-shaped. Each spring element may comprise two elongated portions that are bent relative to each other and form an obtuse angle (as shown in FIGS. 6A-C), or an acute angle (as shown in FIG. 7A). Spring elements 1711 preferably run in a plane parallel to beam 1705, and may be attached to either the beam 1703 or 1705. Similarly, spring elements 1713 preferably run in a plane parallel to beam 1703, and may be attached to either the beam 1703 or 1705. For both spring elements 1711, 1713, a preferred attachment point is at the junction between beams 1703 and 1705. Preferably, the spring elements 1711 are arranged in a first plurality of parallel planes, which run parallel to the direction of the beam 1705, and the spring elements 1713 are arranged in a second plurality of parallel planes which run parallel to the direction of the beam 1703. The spring elements 1711 located between two adjacent planar support structures 1702 may be arranged in a repeating pattern within the first plurality of parallel planes. The spring elements 1713 located between two adjacent planar support structures 1702 may be arranged in a repeating pattern within the second plurality of parallel planes. In one embodiment as illustrated in FIGS. 6A and 6C, adjacent spring elements 1711 and 1713 form a diamond shape. However, different patterns, arrangements and numbers of spring elements may be employed. In some embodiments, the spring elements 1711, 1713 may have a spring constant ranging between 10 and 30 N/m, more preferably between 15 and 25 N/m, and even more preferably 23 N/m. In some preferred embodiments, the force required to compress seven spring elements by 15 mm equals 250 g. In some embodiments, the force required to compress the same seven springs by the same distance ranges between 180 and 230 g. In some embodiments, there are a total of four spring elements 1711, 1713 per 10 $cm^3$. Of course, one will recognize that factors such as the spring constants and/or number of springs may be tailored to the particular tissue type and wound closure desired, and that higher or lower spring constants or numbers of springs may be used.

Standoffs 1707 and 1708 may be provided at the edges or along the outer faces of the structure 1701, and which may be configured to contact the wound. In some embodiments, the standoffs 1707, 1708 may be extensions of the beams 1703, 1705, or may be provided separately. In some embodiments, the standoffs 1707, 1708 may be provided with hook or anchor elements configured to anchor tissue placed into contact with them. Additionally or alternatively, hook or anchor elements attached to the structure 1701 may be provided separately from or instead of the standoffs 1707, 1708. Such hook or anchor elements may be useful to enhance fascial tissue closure by ensuring that different tissue layers (e.g., muscle tissue, fat tissue) are closed at approximately the same rate. Preferably, the hook or anchor elements are configured so as to be have a release force (once engaged into tissue) that causes no or minimal pain to the patient while permitting sufficient pulling force to be applied thereto so as to allow for wound closure. In some embodiments, different anchor elements may be used to engage different types of tissue. For example, the release force to release an anchor element from subcutaneous fatty tissue may be lower than the force needed to release another anchor element from muscle tissue.

Further, the anchor elements, by virtue of their attachment to the surrounding tissue, may be useful in helping prevent a drape or other materials placed over the wound from going into the edges between the skin and the structure 1701. In some embodiments, the anchor elements may be broken off, which may aid in sizing the device as described below so as to fit into a wound. Additionally, all or part of the structure 1701 may be covered or embedded within a porous wound filler material. In such configurations, the standoffs 1707, 1708 may be used to provide additional securement to any such wound filler material.

In use, the stabilizing structure 1701 may be constructed and/or modified as appropriate to fit the wound. Foam may also be added into the entire structure 1701, including its interior portions, and if this is done during manufacturing, the structure 1701 is preferably capable of withstanding a reticulation process. Such a device comprising foam will have composite tensile structures that are to be considered when inserting the device into the wound. When inserting the device into the wound as part of a bespoke wound filler, the stabilizing structure 1701 is preferably oriented such that the planar support structures 1702 are aligned such that they are perpendicular or substantially perpendicular to the general direction of wound closure, or perpendicular or substantially perpendicular to the patient's skin. Optionally, an organ protection layer, which may comprise a polymer sheet or other flexible material, optionally provided with apertures, may be placed into contact with at least the bottom portion of the wound and the wound filler. FIGS. 7A-E illustrate different views and photographs of embodiments of a wound closure device comprising a stabilizing structure 1201. This embodiment is similar in some respects and in function to the embodiment described above in relation to FIGS. 6A-D, and shares similar elements. The device comprises beams 1203 and 1205 that form a planar support structure 1202 separated by spring elements 1211 and 1213. Standoffs 1207 and 1208 may also be provided. Here, however, the spring elements 1211 and 1213 are thicker and have portions that are bent relative to each other at acute angles. Additionally, compared to FIGS. 6A-D, the structure 1201 has a greater volume and greater number of spring elements 1211, 1213. As illustrated best in FIG. 7D, the spring elements 1211 form a repeating diamond pattern within a first plurality of parallel planes, with the diamond location being staggered between adjacent parallel planes. A corresponding pattern is employed for spring elements 1213 with a second plurality of parallel planes. A similar configuration may be seen in FIGS. 6A-6D.

Example 1

Figure 8A:
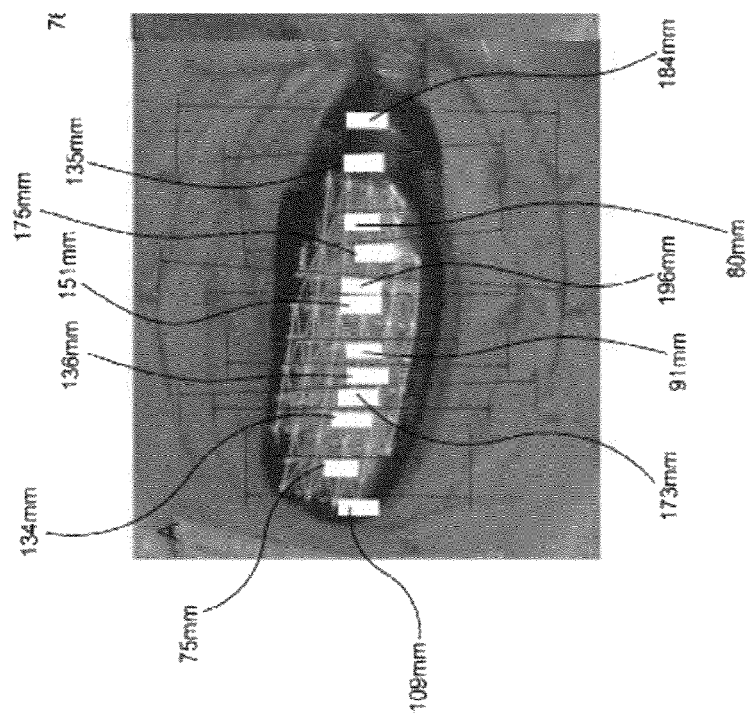
FIGS. 8A-B are before and after photographs of experiments performed to determine the efficacy of certain embodiments of wound closure devices.
Figure 8B:
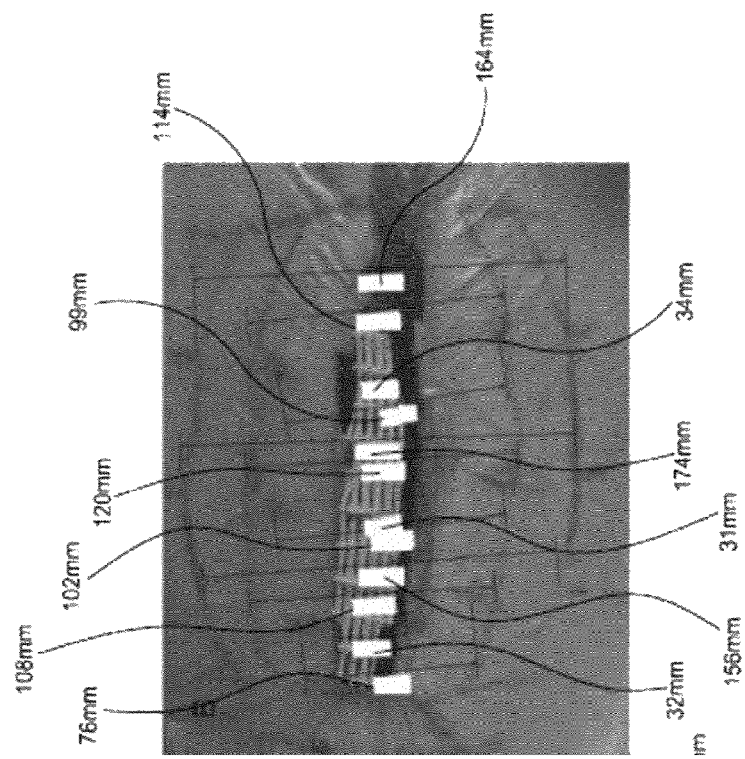

By means of a non-limiting example, an experiment was conducted to determine the effectiveness of an embodiment of the wound closure devices described above, with testing being performed on a cadaveric model. In this particular example experiment and in other examples, the stabilizing structure encompasses the majority of the wound filler, however as described elsewhere, stabilizing structures may encompass the majority of volume of a wound filler or only a small portion. FIGS. 8A-B illustrate the results where a structure with foam, similar to the embodiments of FIGS. 7A-E, was placed into a wound. The perimeter of the structure was wrapped in a layer of foam.

Wound area measurements before and after application of negative pressure indicated that the wound area decreased by 64%, from 152 mm$^2$ to 55 mm$^2$.

Example 2

Figure 9A:
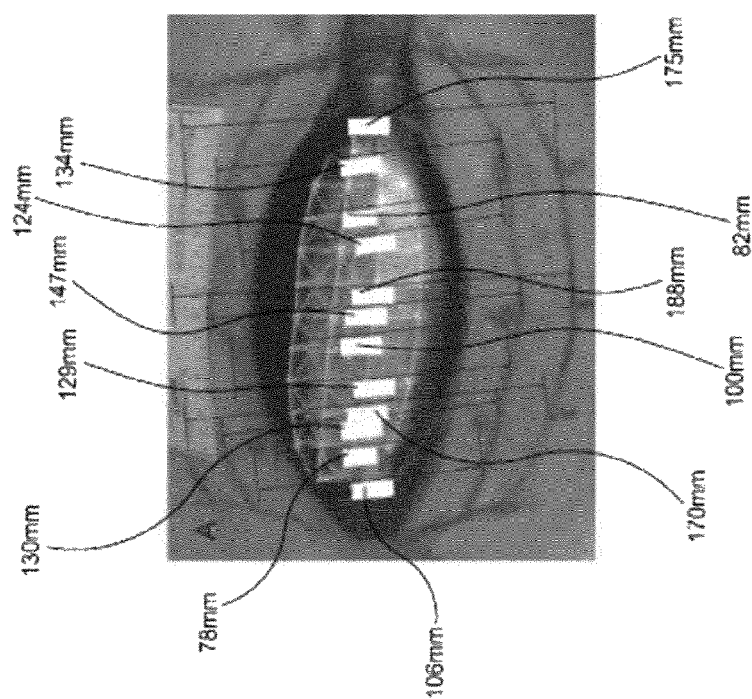
FIGS. 9A-B are before and after photographs of experiments performed to determine the efficacy of certain embodiments of wound closure devices.
Figure 9B:
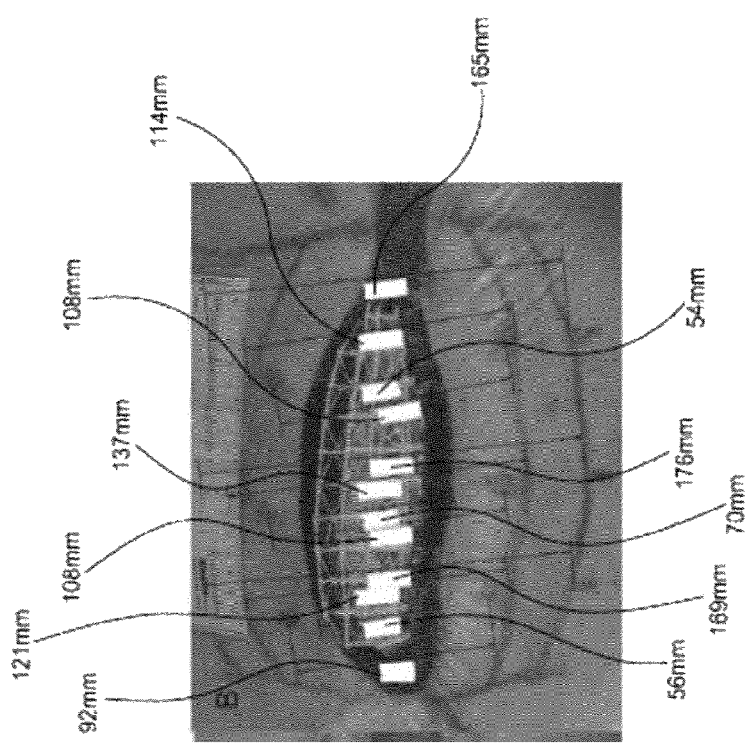

This non-limiting experiment tested a structure wrapped in foam and prestretched along its width and held in place by bendable plastic strips, but otherwise similar to the embodiments of FIGS. 7A-E. FIGS. 9A-B illustrate the wound size before and after application of negative pressure. Here, the wound area measured 154 mm$^2$ before the application of negative pressure, and 101 mm$^2$ afterwards, for a 34% reduction in wound area.

Example 3

Figure 10A:
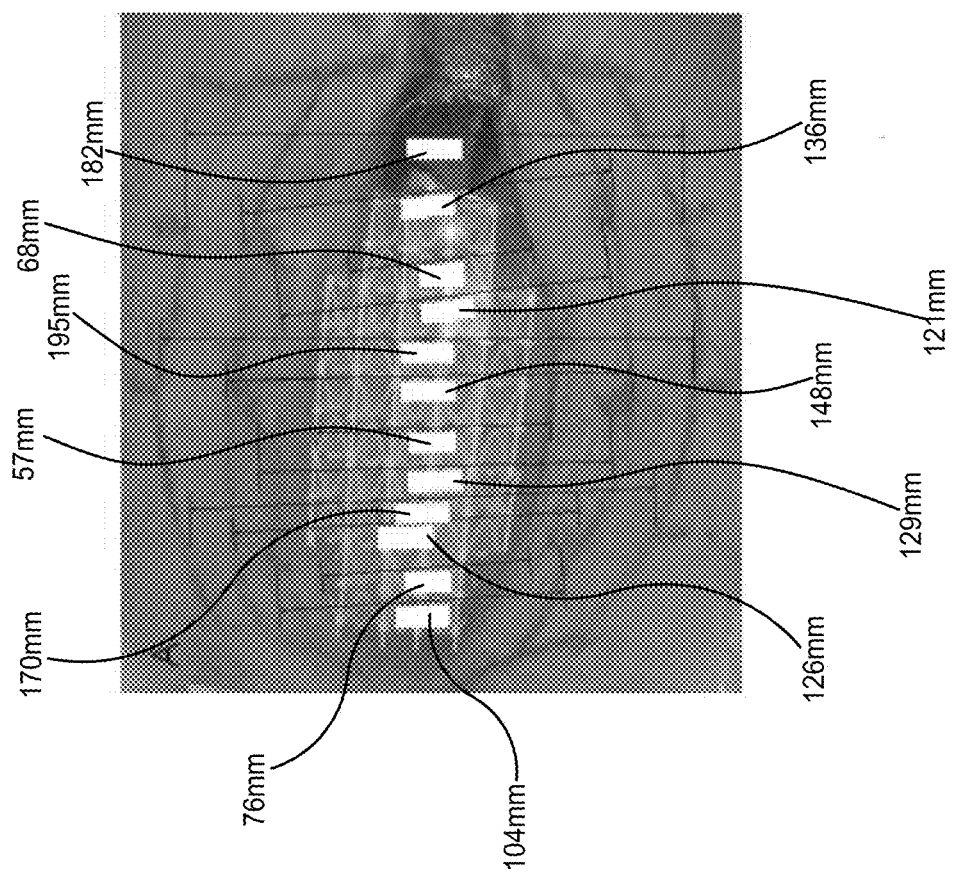
FIGS. 10A-B are before and after photographs of experiments performed to determine the efficacy of certain embodiments of wound closure devices.
Figure 10B:
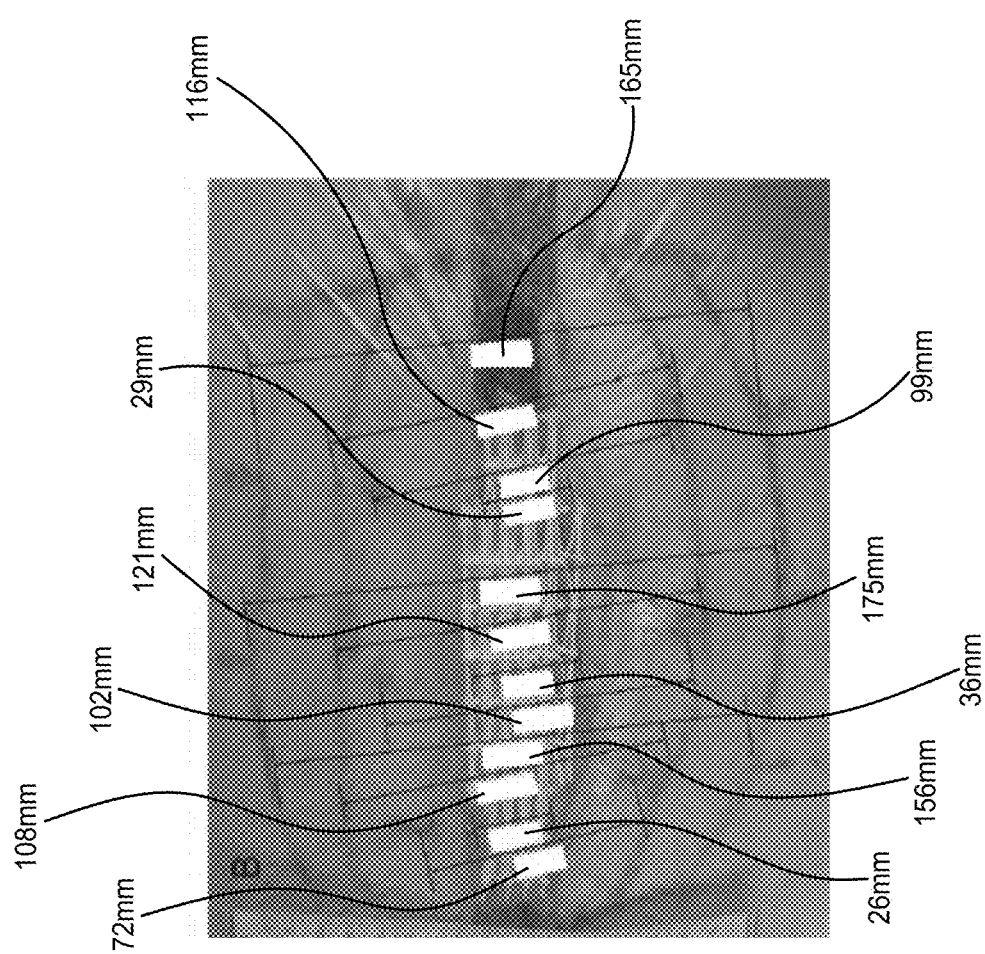

FIGS. 10A-B illustrate the non-limiting results of an experiment where a structure similar to the embodiment of FIGS. 7A-E was placed into a wound without any foam wrapping. The experiment was performed similarly to the other examples described in this section or elsewhere in this specification, and here, the wound area measured 126 mm$^2$ before application of negative pressure, and 53 mm$^2$ afterwards, for a 58% reduction in wound area.

Stabilizing Structures and Wound Closure Devices of FIGS. 11A-19B, 22-23B and 35

Figure 11A:
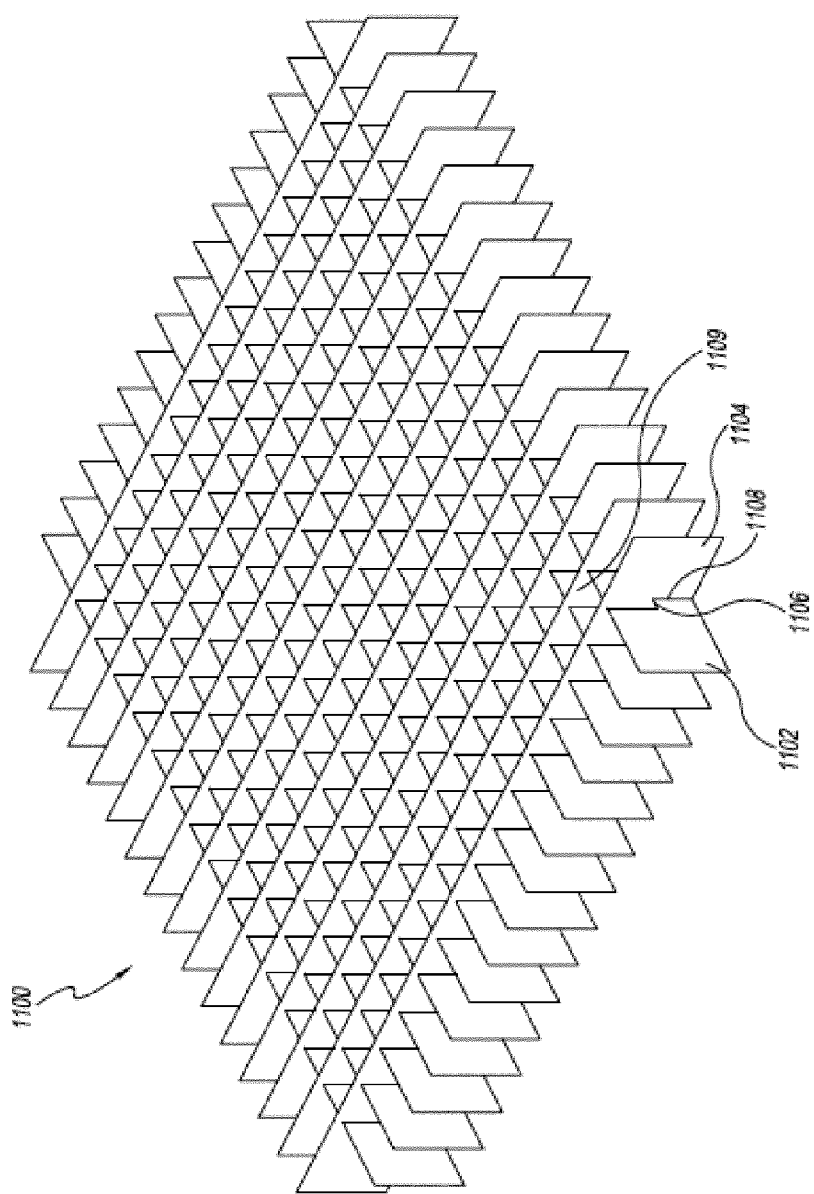
FIGS. 11A-E illustrate additional embodiments of a wound closure device comprising a stabilizing structure.

FIGS. 11A-E illustrate additional embodiments of a wound closure device comprising a stabilizing structure 1100. FIG. 11A shows a perspective view of an embodiment of a stabilizing structure 1100. Here, the stabilizing structure 1100 is preferably comprised of two or more interlocking strips (described below in more detail with relation to FIG. 8B) that extend in directions approximately perpendicular to each other when in a substantially uncollapsed configuration. The stabilizing structure is preferably configured to collapse in one direction or along a first plane while remaining relatively rigid and collapse-resistant in a direction perpendicular to the first direction or plane.

Figure 11B:
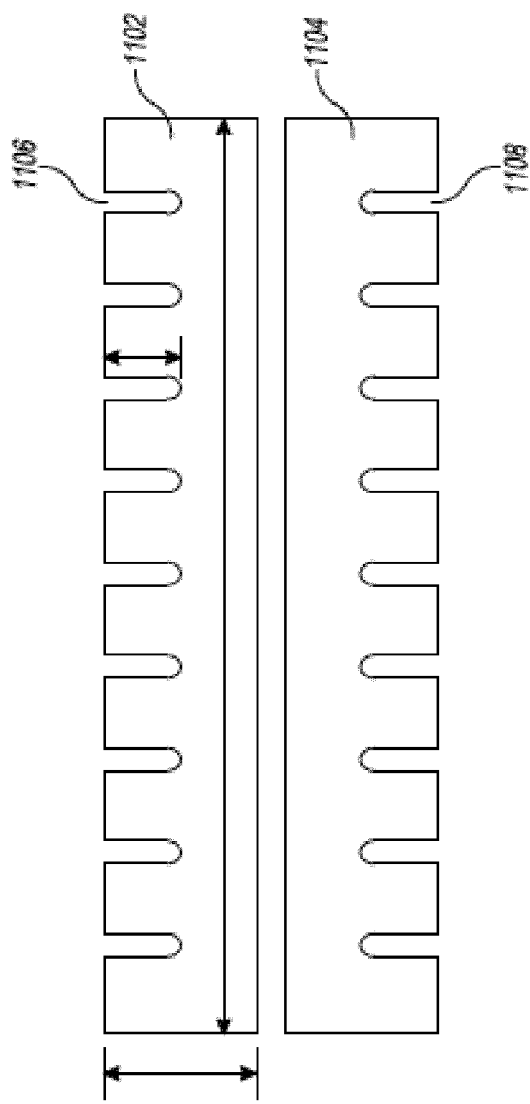

FIG. 11B illustrates side views of a bottom strip 1102 and a top strip 1104 that may be used to make a stabilizing structure 1100 such as the embodiment illustrated in FIG. 11A. Each of the top and bottom strips 1102, 1104 are preferably configured to movably interlock with each other, for example via matching notches 1106 and 1108. One or more notches 1106 may be provided on a top side of bottom strip 1102, and similarly, one or more notches 1108 may be provided on a bottom side of top strip 1104. When assembled together, the one or more top and bottom strips 1102, 1104 may be positioned so that the notches 1106, 1108 line up. Preferably, the top and bottom strips 1102, 1104 are positioned at substantially perpendicular angles to each other, thereby permitting the notches 1106, 1108 to slot together so as to create a movably interlocking structure. Typically, the number of notches 1106 on the bottom strip 1102 will equal the number of top strips 1108 that will form the stabilizing structure 1100, and vice versa. The notches 1106, 1108 are preferably shaped with a width that permits the strips 1102, 1104 to move from approximately perpendicular angles to angles far from perpendicular (i.e., close to parallel) to each other, thus permitting the stabilizing structure 1100 to articulate and collapse along one direction or plane.

In a preferred embodiment, the strips 1102, 1104 are constructed from a rigid or semi-rigid material, such as a polymer. Examples of suitable polymers include polyethylene, polypropylene, polyurethane, polyvinyl chloride, polystyrene, polyacrylate, polymethyl methacrylate, PEEK, silicone, polyurethane, polycarbonate, composites and laminates, or combinations thereof. In some embodiments, the material may include compressed or "felted" reticulated foam. Of course, other materials, such as cardboard or metal may be used. Preferably, the materials may be at least partially porous so as to permit fluid to flow through the material. Further, such properties may aid in distributing negative pressure through the device and to the wound, and may aid in removing fluid from the wound dressing. Such materials may include, for example, low density polypropylene, foamed material, or sintered material. The material used does not necessarily need to be strong along the length of the strips 1102, 1104, but should preferably be able to withstand pressure applied to a top or bottom edge. Preferably, the material is capable of withstanding the pressure from atmospheric pressure exerted on a drape when up to 200 mmHg negative pressure is applied to the wound. In some embodiments, the material can withstand a force of 5 psi applied to a top or bottom edge.

In a preferred embodiment, each strip 1102, 1104 measures 180 mm long by 30 mm high. The thickness of the strips 1102, 1104 may range, for example, between 1.50 to 2.40 mm, although the thickness will be selected at least partly based on the ability of the material to withstand pressure being applied along its edge. The thickness is preferably balanced between keeping the material thin enough to minimize the compressed thickness of the stabilizing structure 1000, while keeping the material thick enough to avoid causing excessive localized pressure upon the wound bed. The notches 1106, 1108 may measure approximately 15 mm in height, and may be spaced apart from other notches by 18 mm. Although the notches 1106, 1108 are shown with rounded bottoms, these may also be cut with squared-off or triangular bottoms. In some embodiments, the rounded edges reduce stresses onto the strips 1102, 1104 so as to prevent fracture and crack propagation, and may also increase the springiness of the stabilizing structure 1100.

It will be understood that the interlocking strips 1102, 1104 may not necessarily need to be joined together via notches. Hinges or other devices could be used to provide the articulation or movable interlocking ability illustrated above. In some embodiments, hinges may be constructed from thinner areas of the same material used to construct the strips 1102, 1104, and are configured to flex or bend to a predetermined position. The stabilizing structure 1100 could also be molded as a single piece such that the interlocking strips 1102, 1104 form a single unit.

Returning to FIG. 11A, the perspective view illustrates an example of a stabilizing structure 1100 configuration with multiple interlocking top and bottom strips 1102, 1104 movably interlocked via multiple notches 1106, 1108. The intersections of two top strips 1102 and two bottom strips 1104 form a quadrilateral-shaped boundary space 1109. When the top and bottom strips 1102, 1104 are at perpendicular angles to each other, the space 1109 will be square or rectangular. However, as the stabilizing structure 1100 collapses along a direction or plane, the space 1109 will become more diamond- or parallelogram-shaped. The stabilizing structure 1100 will preferably comprise multiple spaces 1109, which form cells defined by the walls of the top and bottom strips and with openings on top and bottom ends.

Figure 11C:
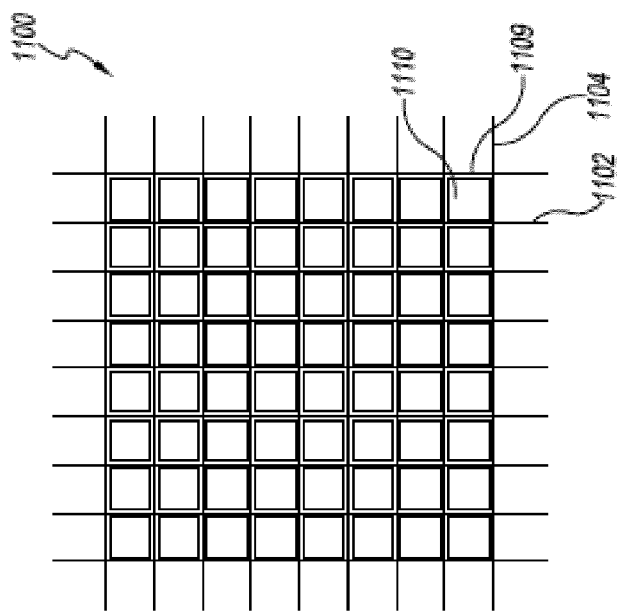

FIG. 11C illustrates a top view of an embodiment of the stabilizing structure 1100 where a porous wound filler material 1110 has been fabricated into the quadrilateral-shaped boundary space 1109. Here, the porous wound filler material 1110 used is preferably soft and conformable so as to be able to adapt to the any change in the configuration of the stabilizing structure 1100 if it collapses. Preferably, the porous wound filler material is a foam, such as a polyurethane foam. This porous wound filler material may be fabricated around the stabilizing structure 1100 so as to completely encapsulate it. When used, the resulting stabilizing structure 1100 may be cut to size so as to fit into a wound. Such porous wound filler material 1110 may be used to aid in the fluid transmission or wicking of fluid from within a wound, and may also, when in contact with the wound (e.g., when used in negative pressure wound therapy), aid in the healing of the wound.

Figure 11D:
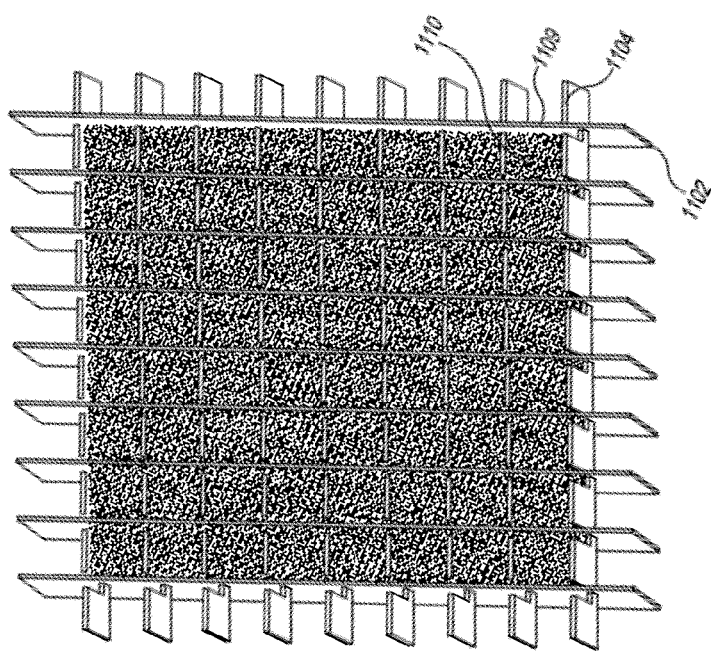

FIG. 11D illustrates a perspective photograph of an embodiment of the stabilizing structure 1100 with a porous wound filler material 1110 fabricated into the spaces 1109. In some embodiments, additional porous wound filler material may also be used to encapsulate or surround the structure 1100. For example, a sock or wrap may be fabricated around the structure 1100, and may for example be constructed from foam or gauze. When inserted into a wound as part of a fabricated wound filler, the stabilizing structure 1100 may be preferably oriented so as to collapse in a direction generally parallel with the orientation of collagen and other fibrous tissue fibers in the body. This orientation is sometimes referred to as Langer's lines or Kraissl's lines, and closing a wound in a direction coinciding with (and preferably parallel to) these lines may heal faster and more easily than attempting to close a wound in a direction perpendicular or opposed to these lines. It will be appreciated that the other embodiments of stabilizing structures described in this specification may also be oriented in the same manner with respect to Langer's lines or Kraissl's lines, or other landmarks.

Advantageously for some types of wounds, the stabilizing structure of FIG. 11A may elongate in a direction perpendicular to the primary direction of closure, but still within the horizontal plane. Such elongation can be beneficial to wound healing as the physiology of the wound may dictate that it should lengthen as it closes.

In use, the stabilizing structure 1100 may be placed into a wound such that the upward facing portion of the structure 1100 is substantially rigid and resists collapse in the vertical direction once negative pressure is applied to the wound (e.g., once covered by a drape as described previously). A porous material such as foam may be fabricated around, into, and/or so as to surround or encapsulate the stabilizing structure 1100. In some embodiments, an organ protection layer as described previously may be placed into contact with at least the bottom portion of the wound or may be fabricated as part of the wound filler. As negative pressure is applied, the structure 1100 will then preferably collapse in the plane perpendicular to the vertical direction, aiding in wound closure. Due to the relative incompressibility of the vertical dimension of the device, the pressure on the drape transmitted from the greater atmospheric pressure onto the wound will reduce the pressure applied to the stabilizing structure 1100 onto the wound margins in comparison to existing prior art devices (such as those illustrated in FIGS. 5A-B). Optionally, in this and other embodiments described in this section or elsewhere in this specification, negative pressure may be applied so as to increase transmission of negative pressure to the sides of the wound rather than the bottom portions thereof. This may be accomplished, for example, by providing an organ protection layer that at least partially shields the bottom of the wound from negative pressure. In a preferred embodiment, the sides of the wound would be provided with negative pressure of at least 100 mmHg, preferably 120 mmHg, 140 mmHg, 180 mmHg, or 200 mmHg, while the bottom of the wound would be provided with at most 120 mmHg, more preferably 80 mmHg, 40 mmHg, 20 mmHg, or 10 mmHg.

Figure 11E:
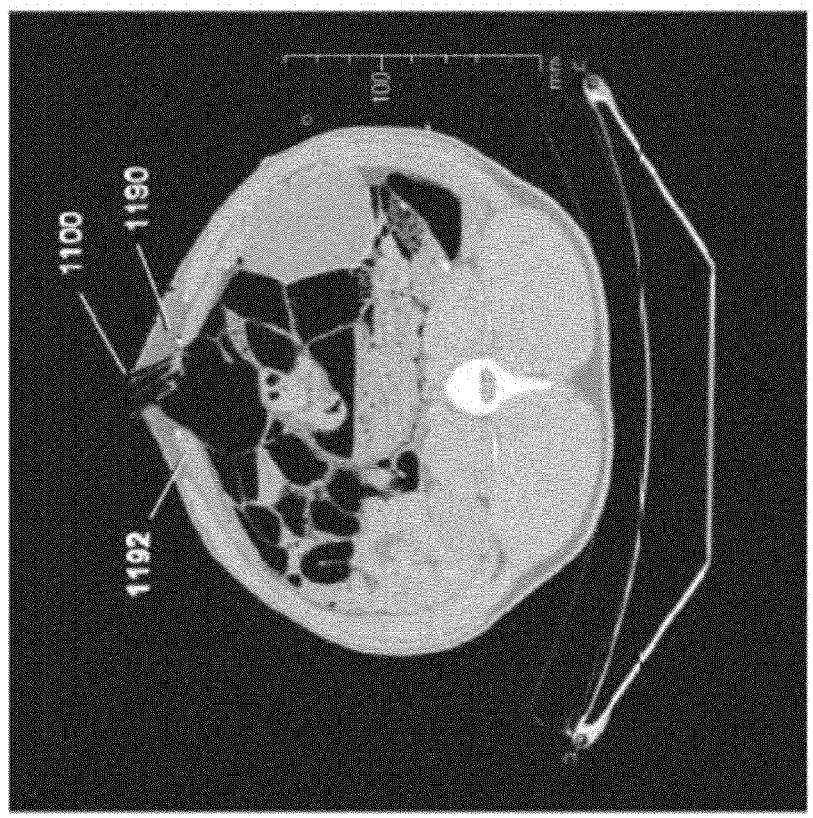

FIG. 11E illustrates a CT image of an embodiment of a stabilizing structure 1100 described in FIGS. 11A-D inserted into an abdominal wound. The tissue fascia layers are also visible, with a subcutaneous fat layer 1190 above a layer of muscle tissue 1192. With the application of negative pressure (as illustrated), improved fascial reapproximation and wound closure may be observed. In particular, the muscle tissue layers 1192 on opposite sides of the wound have been moved much closer together, while remaining attached to the other fascial layers. In measurements, the width of the wound along the view illustrated reduced from approximately 82 mm to 28 mm, a reduction of 65%.

Figure 12A:
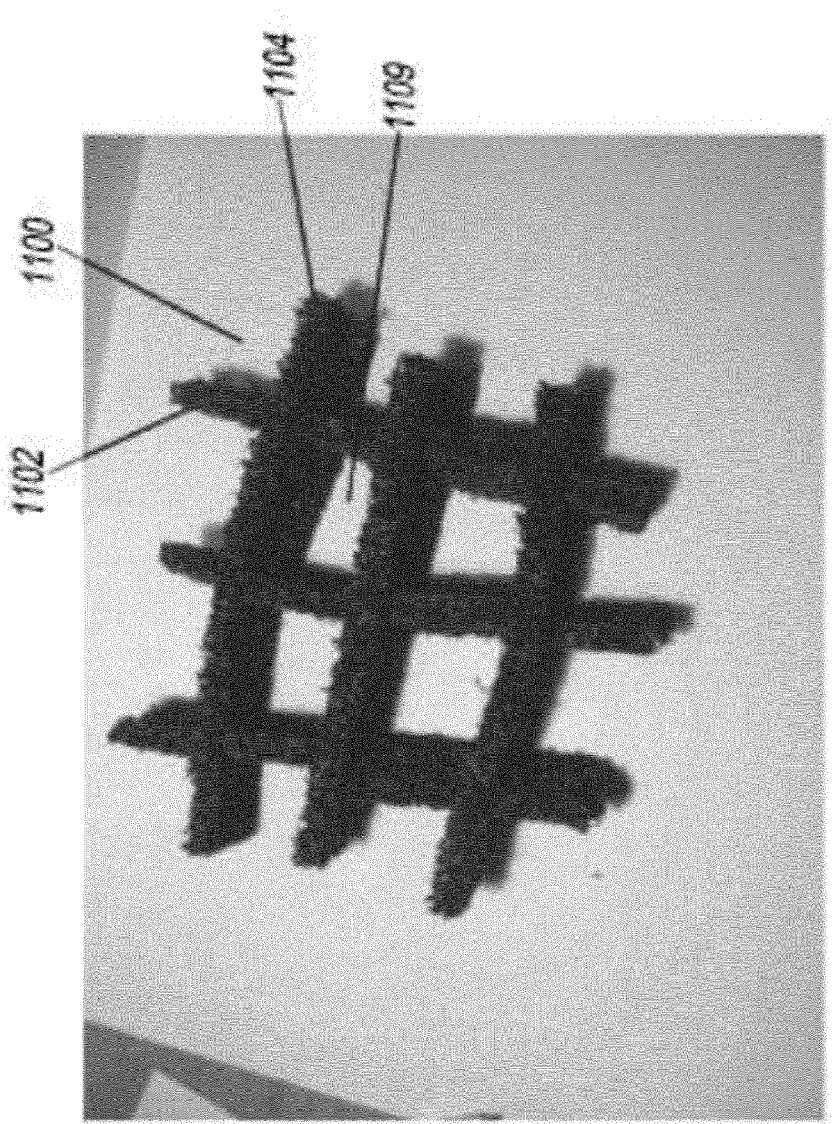
FIGS. 12A-C illustrate an embodiment of a stabilizing structure manufactured from felted foam.
Figure 12B:
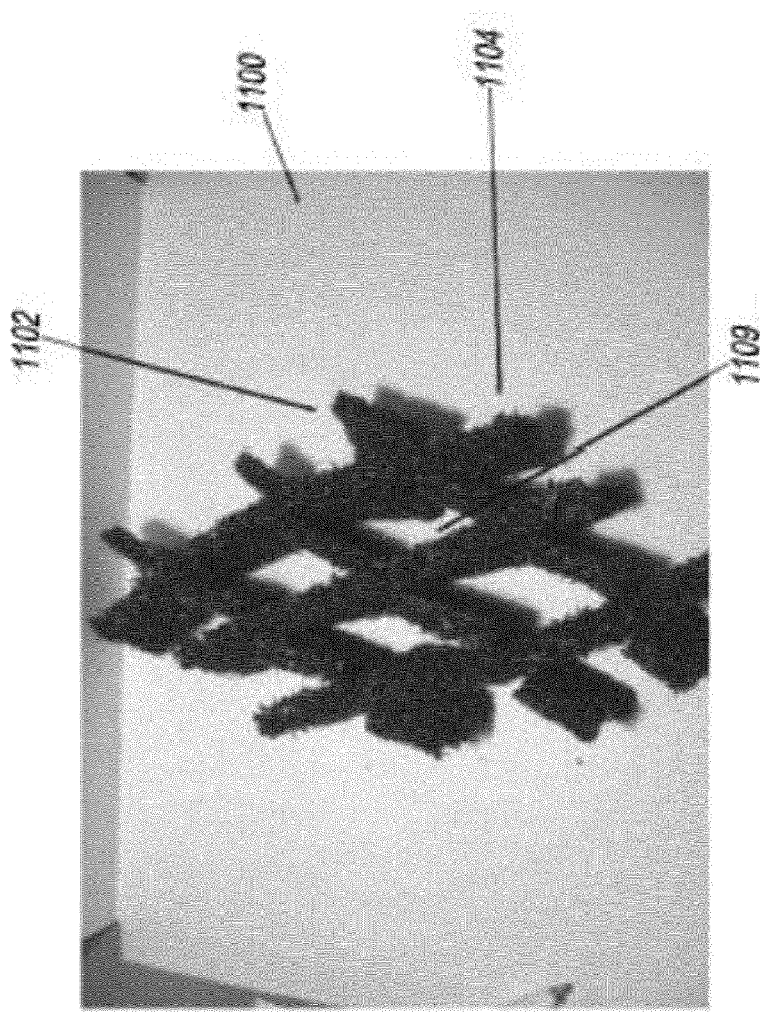
Figure 12C:
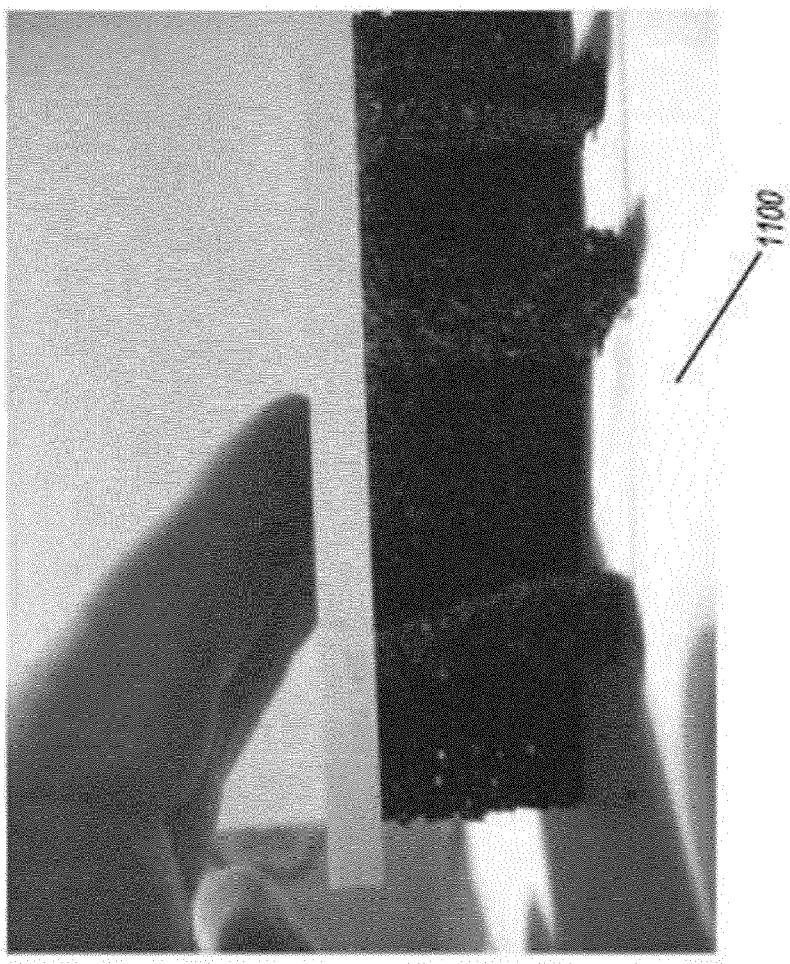

FIGS. 12A-C illustrate an embodiment of a wound closure device comprising a stabilizing structure 1100 similar to that described above in relation to FIGS. 11A-E. Here, the stabilizing structure 1100 is constructed from interlocking strips constructed from felted foam. The physical relationship between and the mechanism for the interlocking top and bottom strips 1102 and 1104 are substantially similar to what was discussed previously above, and will not be repeated here. Felted foam, however, is foam (e.g., polyurethane foam) that has been treated with heat and compressed. After this procedure, the foam will be stiffer and less compressible, while still remaining porous. Such a material may be produced via a 3D fabrication device. Additionally, such a material may be advantageously used in a stabilizing structure 1100 used for a wound closure device, as the material may be compressible in a plane defined by the top and bottom strips 1102, 1104, as shown in FIG. 12B. However, the material is substantially rigid in the vertical direction, as illustrated in FIG. 12C, where a weight has been placed over the foam without substantial buckling. Here, the foam can support approximately 6 kg of weight, and embodiments of the device have been measured to support at least 3 psi of applied pressure without collapse. Further, while such material is substantially rigid, the porous nature of the material permits negative pressure to be transmitted to the wound and for wound exudate to be removed.

Figure 13A:
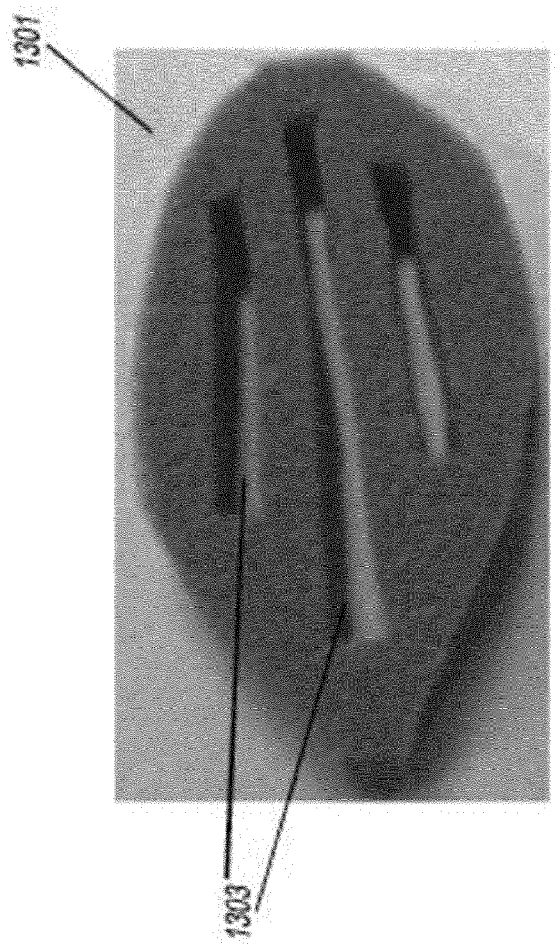
FIGS. 13A-B are photographs of further embodiments of wound closure devices comprising a porous wound filler material.
Figure 13B:
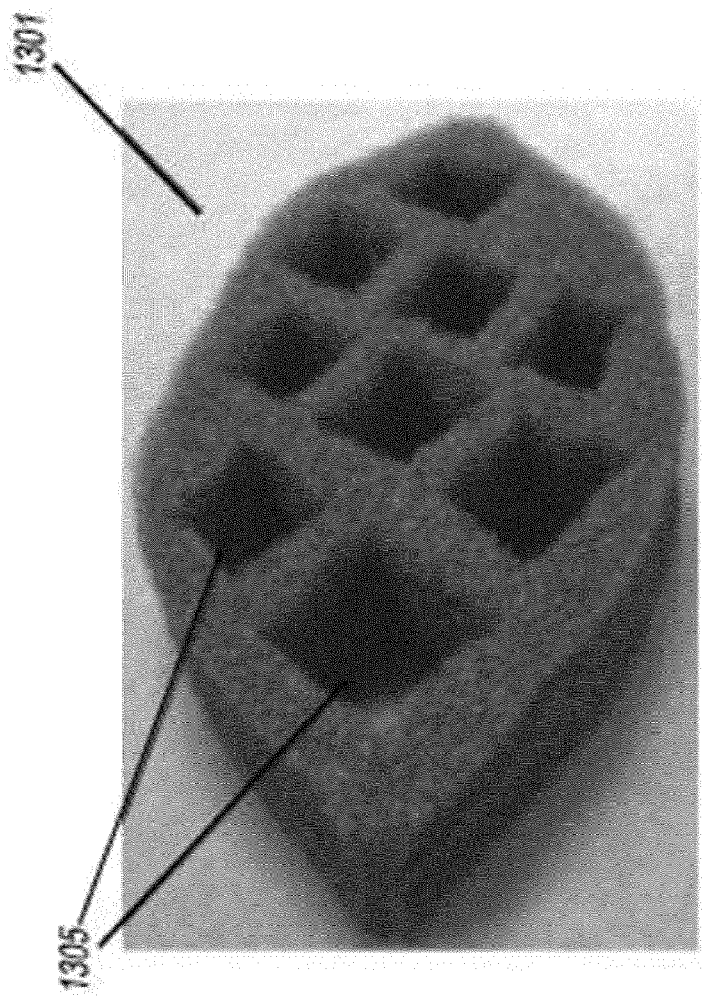

FIGS. 13A-B are photographs of further embodiments of wound closure devices. FIG. 13A illustrates an embodiment of a wound closure device 1301 that preferentially collapses along one direction. Here, the wound closure device 1301 comprises a porous wound filler material (e.g., foam) into which one or more slots 1303 have been fabricated. These slots 1303 preferably extend longitudinally through the thickness of the wound closure device 1301. Accordingly, the empty space will permit the wound closure device to preferentially collapse in a direction when a force is applied in a direction perpendicular to the slots 1303. Because the empty space is easier to compress than the remainder of the foam, the width and thickness of the foam will preferably not (or minimally) compress compared to the resulting compression perpendicular to the length of the wound closure device 1301.

As illustrated in FIG. 13B, the wound closure device 1301 may also be provided with holes or cells 1305 in other configurations, such as diamond-shaped holes forming a lattice. This configuration permits compression along the length and width of the wound closure device due to the compressible holes 1305, while the comparatively more rigid thickness of the foam resists compression to a greater extent.

In some embodiments, as described above with respect to 3D fabrication, stabilizing structures similar to those illustrated above in FIGS. 11A-E may be fabricated as a single unit. As with the previously-described embodiments, the stabilizing structures are configured to form an array of one or more cells defined by one or more walls and forming a plane, with each cell having a top and bottom end with an opening extending through the top and bottom ends in a direction perpendicular to the plane. In some embodiments, the stabilizing structures may have cells that are square, diamond, oblong, oval, lozenge, and/or parallelepiped, and non-limiting examples of the same are illustrated in FIGS. 14-23. While some embodiments may have cells that are all the same shape, the cells may also be tailored to be larger, smaller, or differently-shaped than other cells in the structure. The shape and size of the cells may be tailored to the desired characteristics (e.g., resilience and ease of collapse) for optimal wound closure and healing.

Construction of a single unit stabilizing structure may be advantageous in terms of ease of use and cost. For example, single unit stabilizing structures may be trimmed post fabrication as necessary to fit into a wound site, although as described elsewhere in the specification, 3D fabrication techniques allow a wound filler to be formed to the shape of a wound during fabrication. The material used is preferably biocompatible, and even more preferably nonadherent to the wound site. Suitable materials are preferably chosen to be soft while remaining sufficiently strong to resist collapse in a vertical direction, and may include polymers, such as polyethylene, polypropylene, polyurethane, silicone (including siloxanes), ethyl vinyl acetate, and copolymers and blends thereof. The hardness of the material may affect the thickness of the resulting stabilizing structure, and may be selected based upon the desired thickness of the stabilizing structure components (including hinges and other joints thereof) and the ability of the stabilizing structure to resist collapse, e.g., due to the atmospheric pressure acting upon a drape placed over the stabilizing structure. Suitable durometer hardnesses of materials used range from about 30 shore to 120 shore (as measured on the Shore durometer type A scale), preferably from about 40 shore to 60 shore, and even more preferably about 42 shore. Generally, the material chosen is preferably softer (while still satisfactorily meeting other material requirements), as harder materials may provide reduced levels of closure as the hardness increases.

Figure 22:
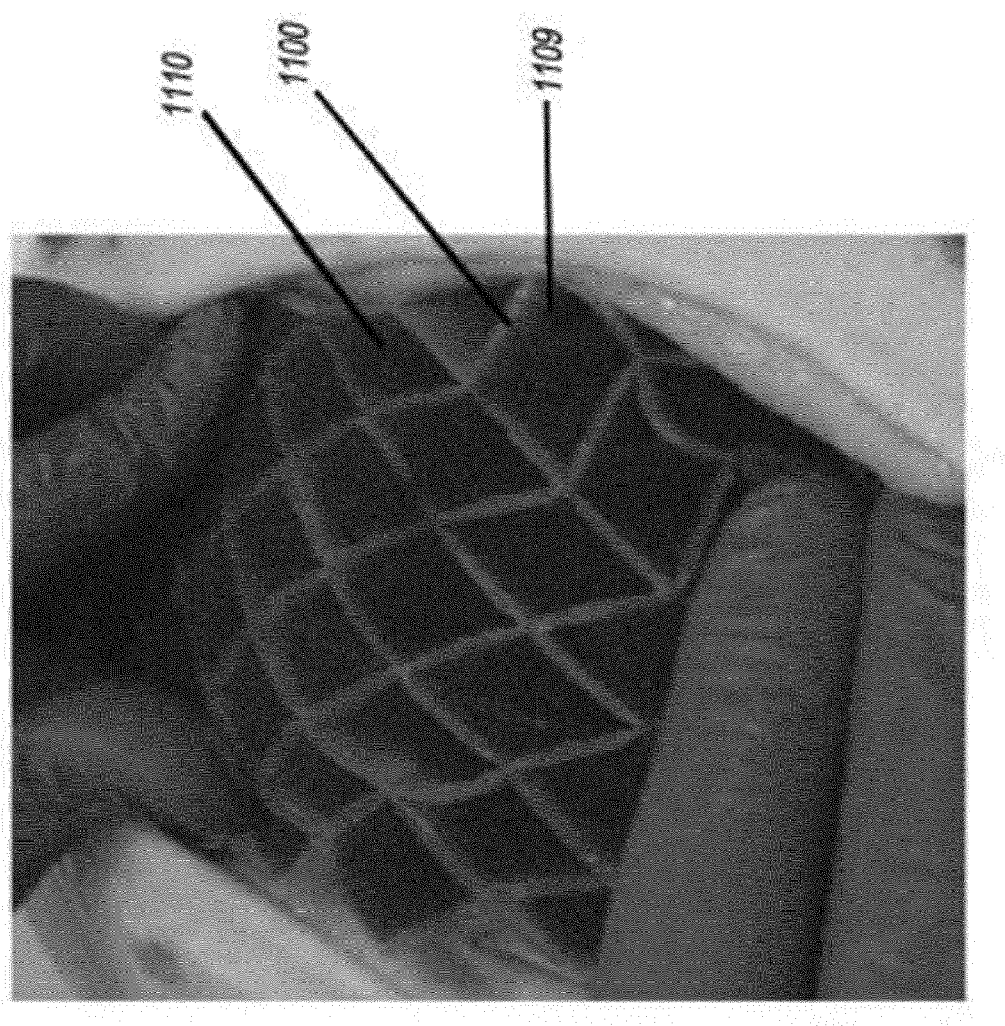
FIG. 22 is a photograph of an experiment performed to determine the efficacy of certain embodiments of wound closure devices.

FIG. 22 is a photograph of an embodiment of such device 1100 constructed as a single unit. The apertures 1109 are fabricated to be filled with a porous material 1110, which in some embodiments may comprise foam. Here, the fabricated wound filler 1100 is inserted into a wound.

Figure 14A:
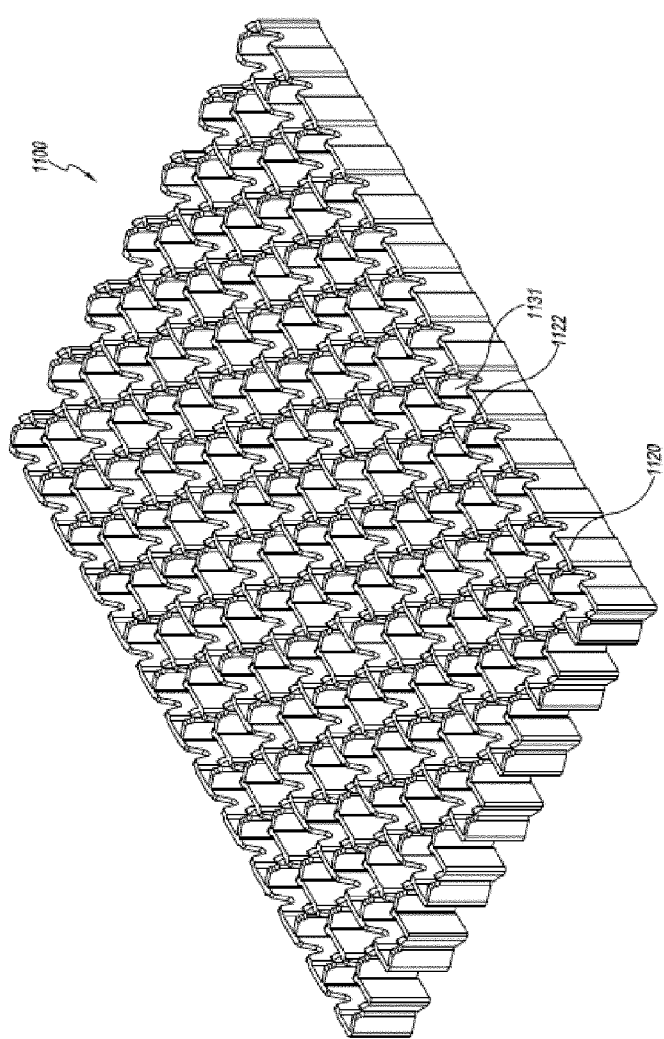
FIGS. 14A-B illustrates an additional embodiment of a wound closure device comprising a stabilizing structure.
Figure 14B:
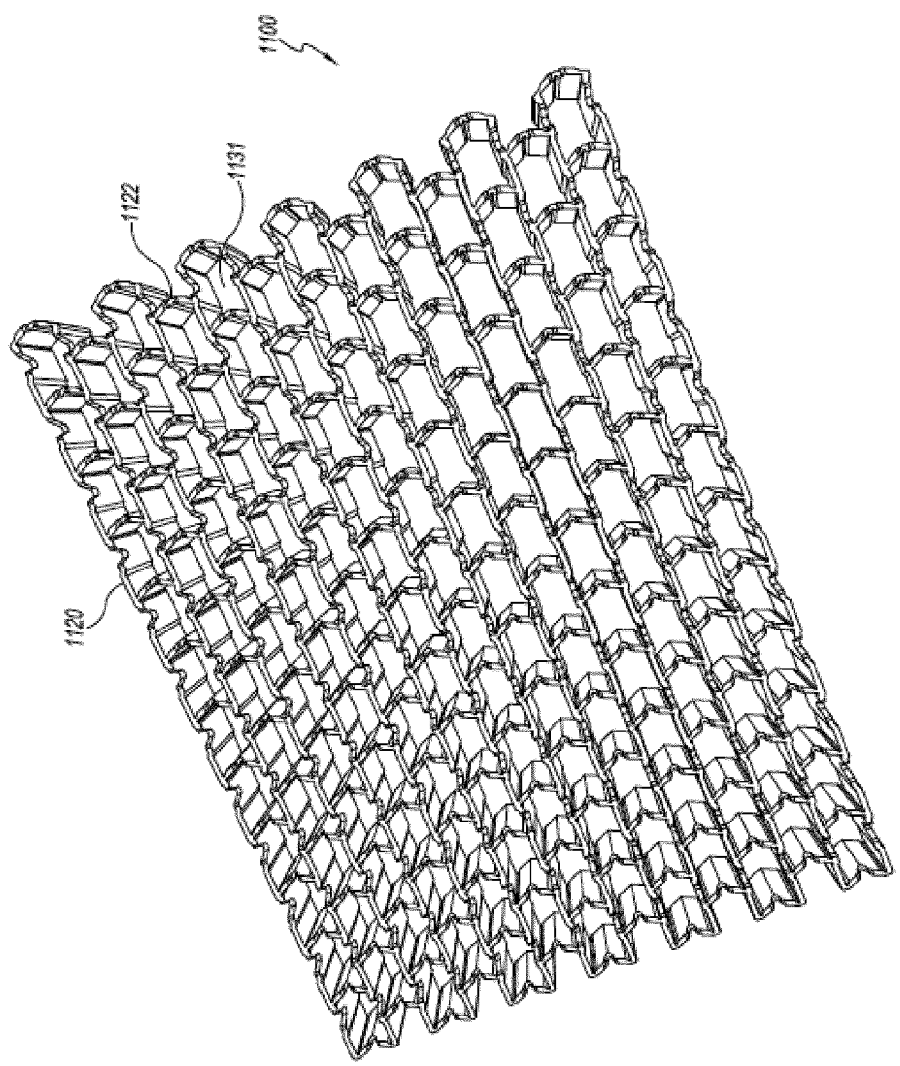

FIGS. 14A-B illustrate an embodiment of a stabilizing structure 1100 configured to preferentially collapse in only one horizontal direction while remaining substantially rigid or uncollapsed when force is applied in a vertical direction. Preferably, the stabilizing structure 1100 is constructed as a single unit as illustrated so as to form one or more cells 1131. Here, two or more longitudinal strips 1120 (which form the walls of the cells) may have relatively straight configurations, and are connected together via one or more collapsible cross strips 1122. It will be appreciated that in a single unit embodiment, the strips are merely portions of the same material that may have been formed together to form the entire single unit structure. The collapsible cross strips 1122 may be angled or indented so as to make them more likely to collapse in a direction generally parallel to their length. In this embodiment illustrated in this section or elsewhere in this specification, the collapsible cross strip 1122 is more likely to collapse at the apex of the angled portion and at the junctions to the longitudinal strips 1120 when a force is applied in a direction approximately parallel to the general length of the collapsible cross strip 1122. In some embodiments, the collapsible cross strip is configured to fold into a portion (which may be thinner) of the longitudinal cross strip 1120.

In some configurations, one or both of the longitudinal strips 1120 and/or collapsible cross strips 1122 may comprise one or more notches positioned along a length thereof. These notches promote fluid transfer across the structure, and aid in distributing negative pressure. In some embodiments, notches may be used in conjunction with a porous material so as to enhance fluid transfer. In relation to the longitudinal strips 1120, the collapsible cross strips 1122 may be positioned alternately along the length of the longitudinal strips 1120, as best illustrated in FIG. 14B, to form a configuration somewhat analogous to a "stretcher bond" used in bricklaying. Of course, other configurations are possible. Further, although this embodiment is illustrated as being formed as a single unit, those of skill in the art will recognize that this embodiment (and the others described below) may be constructed from multiple pieces joined or connected together.

Figure 23A:
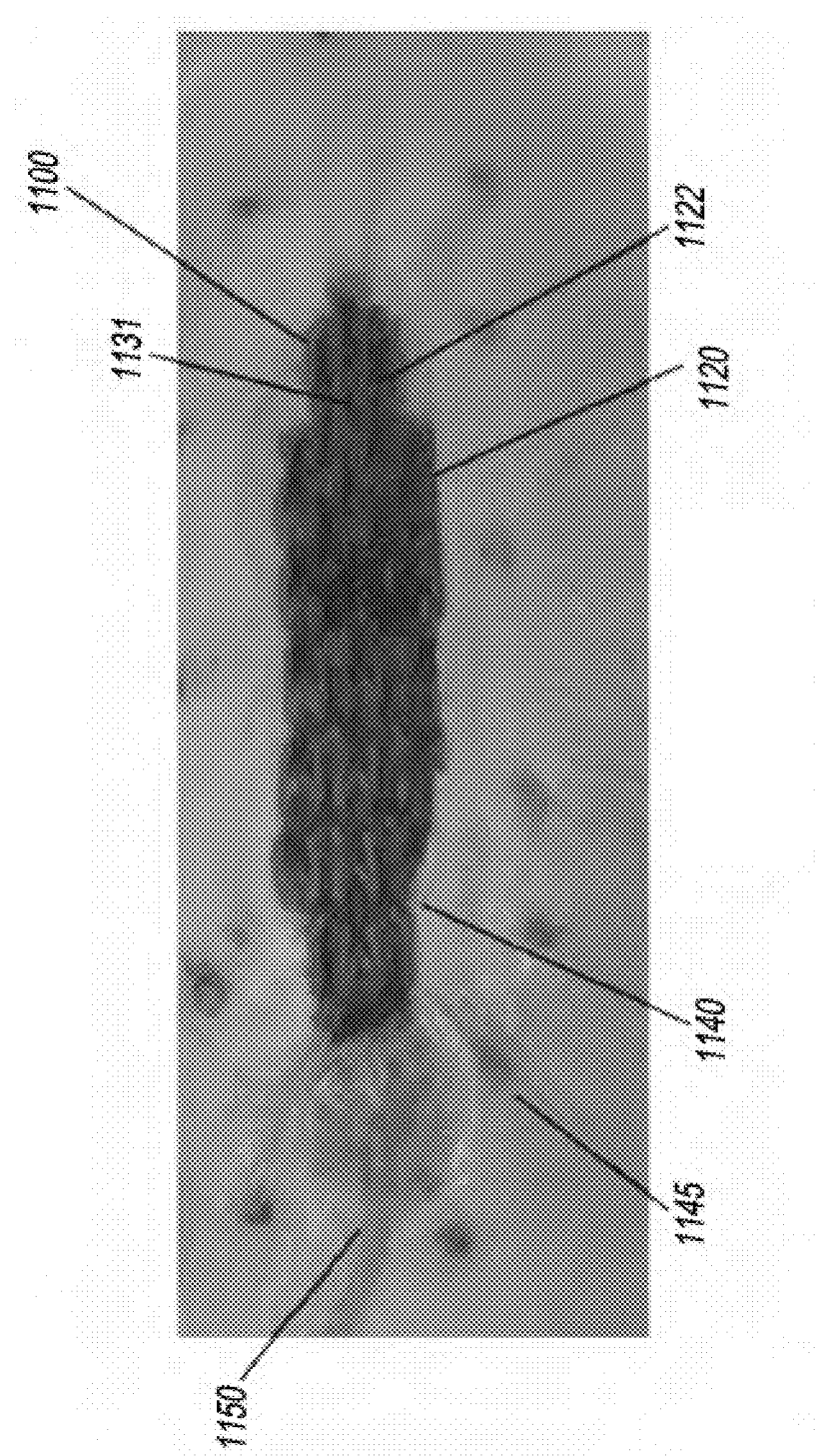
FIGS. 23A-B are photographs of experiments performed to determine the efficacy of certain embodiments of wound closure devices.
Figure 23B:
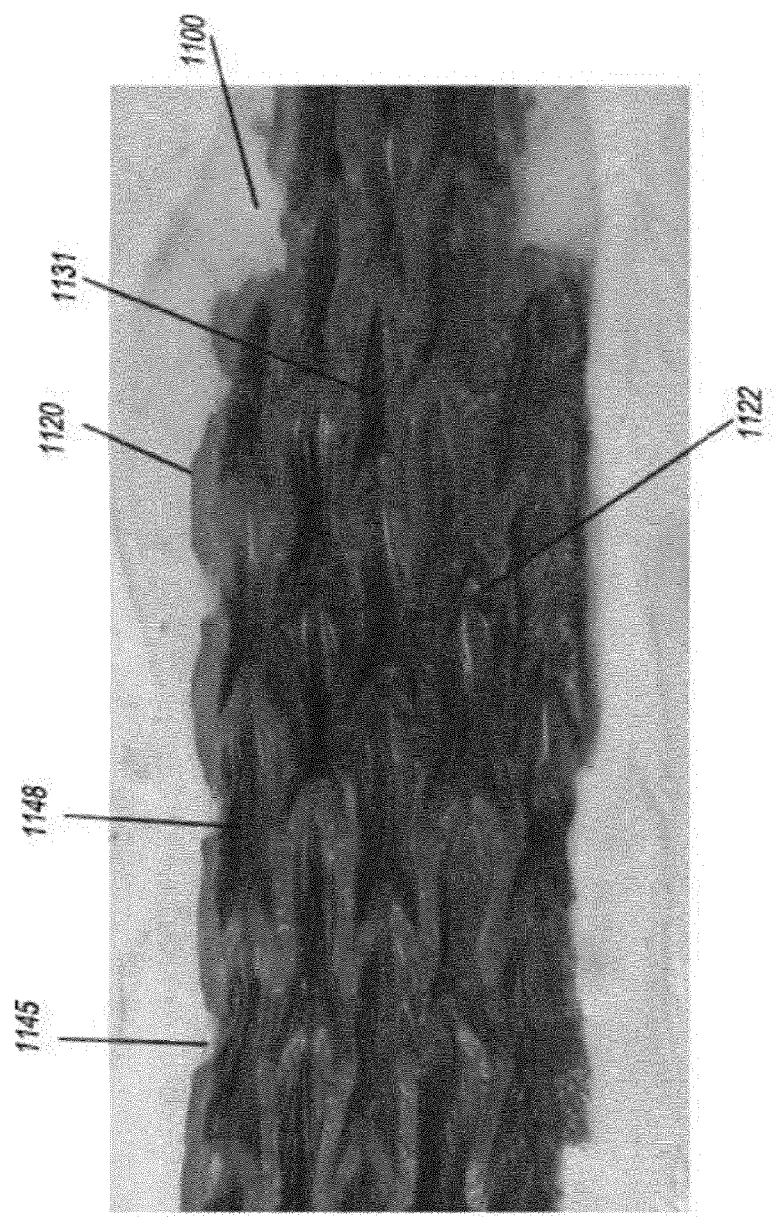

FIGS. 23A-B are photographs of an embodiment of a stabilizing structure 1100 similar to the one described above in relation to FIGS. 14A-B. Here, the structure 1100 is inserted into a wound 1140 and placed under a drape 1145. A source of negative pressure is connected via a fluidic connector 1150. FIG. 23B is a closeup view of the stabilizing structure 1100 photographed in FIG. 23A, which illustrates how the cells 1131 collapse upon the application of negative pressure while under the drape 1145. An optional porous wound filler 1148 is also illustrated. As with the other stabilizing structures and/or wound closure devices described elsewhere in the specification, the stabilizing structure of FIGS. 23A-B may be incorporated as a region or regions of a fabricated wound filler.

Figure 15:
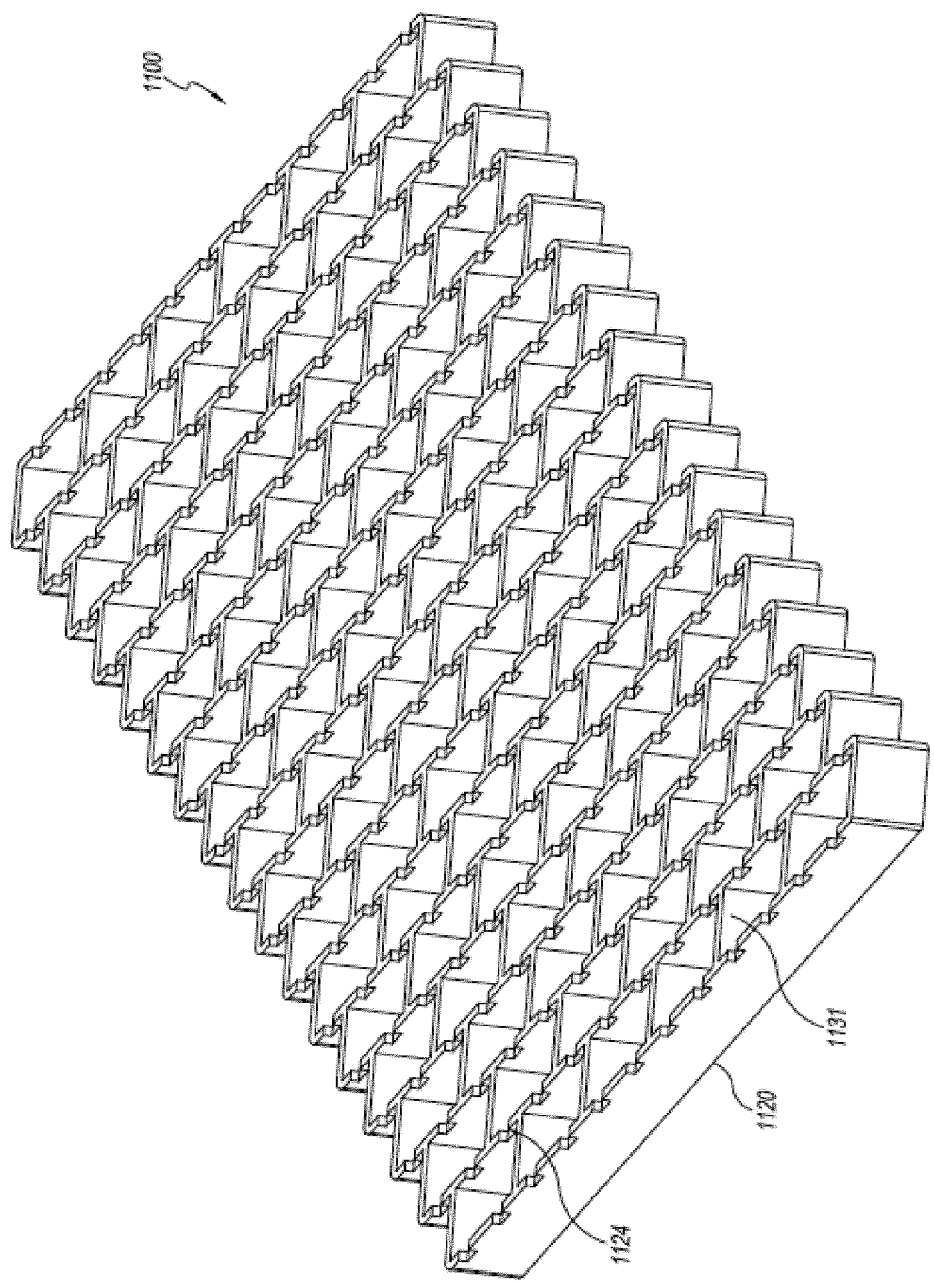
FIG. 15 illustrates an additional embodiment of a wound closure device comprising a stabilizing structure.

FIG. 15 illustrates another embodiment of a stabilizing structure 1100, here comprising two or more longitudinal strips 1120 attached to each other via one or more angled cross strips 1124 so as to form cells 1131. As with the embodiment illustrated in the preceding figure, the stabilizing structure 1100 is configured to collapse when pushed in a direction perpendicular to the length of the longitudinal strips 1120, while remaining substantially rigid or uncollapsed when force is applied in a vertical direction. The angled cross strips 1124 are preferably attached to the longitudinal strips 1120 so as to form a non-perpendicular angle so as to promote collapse of the stabilizing structure 1100 in the direction perpendicular to the length of the longitudinal strips 1120. As with FIGS. 11A-B, one or more notches may be formed on either or both of the longitudinal strips 1120 and/or angled cross strips 1124.

Figure 16:
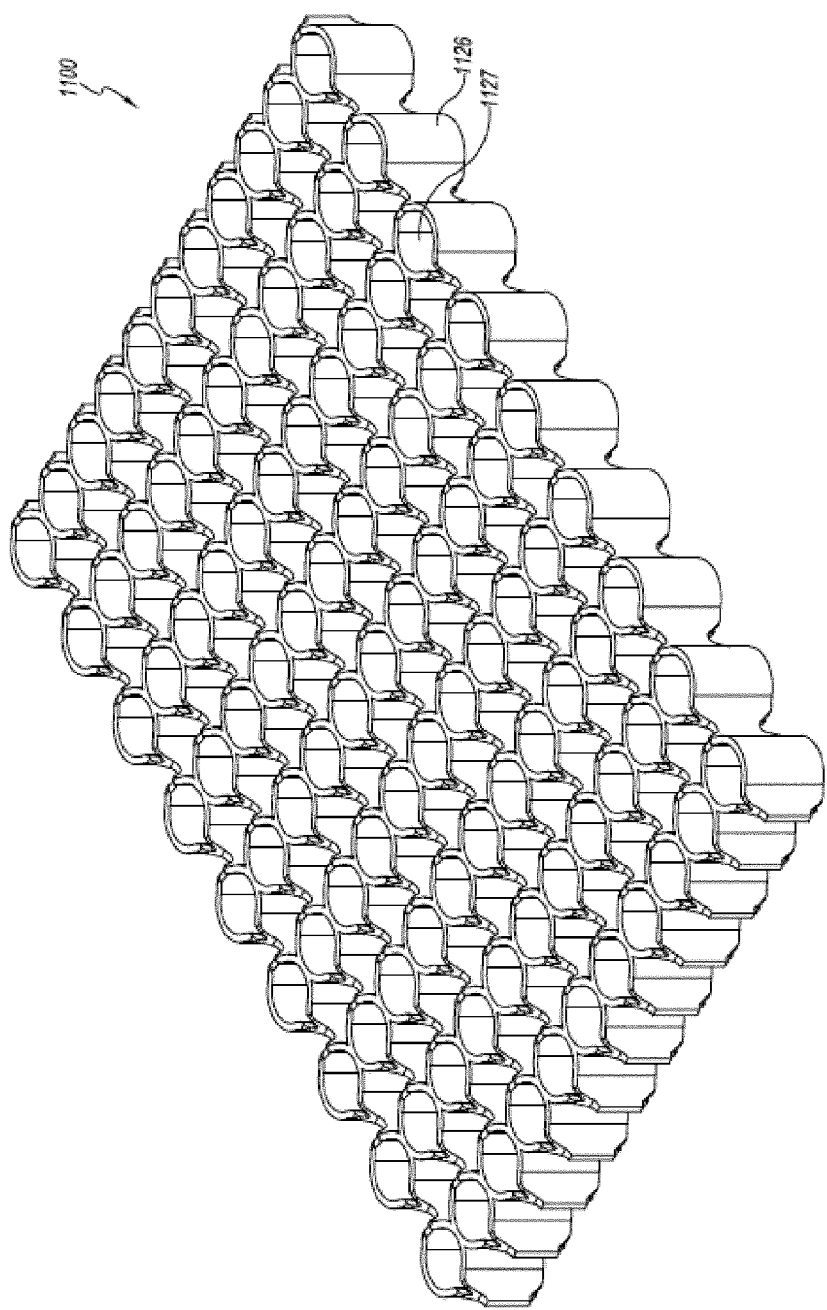
FIG. 16 illustrates an additional embodiment of a wound closure device comprising a stabilizing structure.

FIG. 16 illustrates a single unit stabilizing structure 1100 comprising one or more pairs of curved longitudinal strips 1126. Each individual longitudinal strip 1126 may be formed as a "wavy" strip (when seen from a vertical orientation) that, when joined face-to-face, form a one or more circular or ovoid cells 1127. As with the other stabilizing structures illustrated in this section or elsewhere in this specification, this structure 1100 is configured to preferably collapse along a horizontal plane or direction while remaining substantially rigid or uncollapsed when force is applied in a vertical direction. Although the structure 1100 is illustrated here as being formed from a single unit, the structure may be constructed from two or more curved longitudinal strips 1126 welded or attached together at the points shown. As with several other embodiments described in this section or elsewhere in this specification, one or more notches may be made onto the walls so as to aid in fluid transfer across and through the structure 1100.

Figure 17:
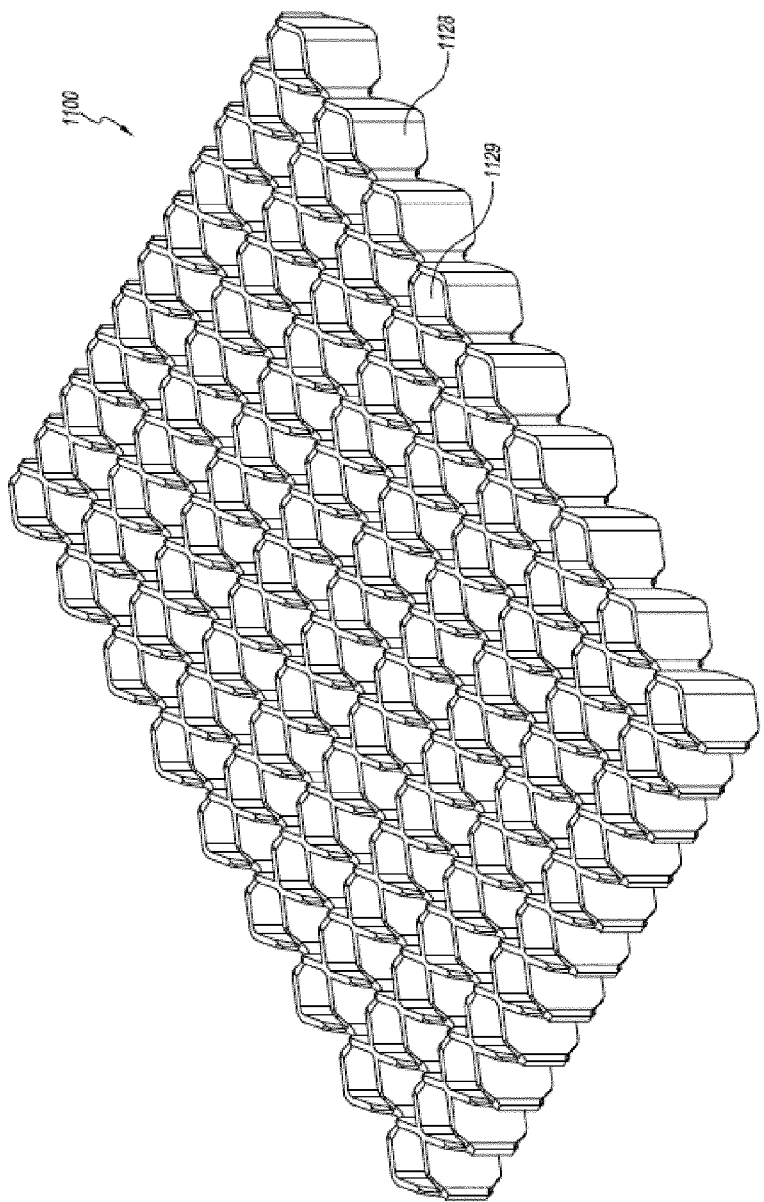
FIG. 17 illustrates an additional embodiment of a wound closure device comprising a stabilizing structure.

FIG. 17 illustrates a stabilizing structure 1100 similar to the one illustrated in FIG. 16. Here, however, zigzag longitudinal strips 1128 are joined to form diamond-shaped (rather than circular or ovoid) cells 1129. It will be of course appreciated that this embodiment may also be fabricated using substantially straight strips in a style similar to the embodiments illustrated in FIGS. 11A-D.

Figure 18:
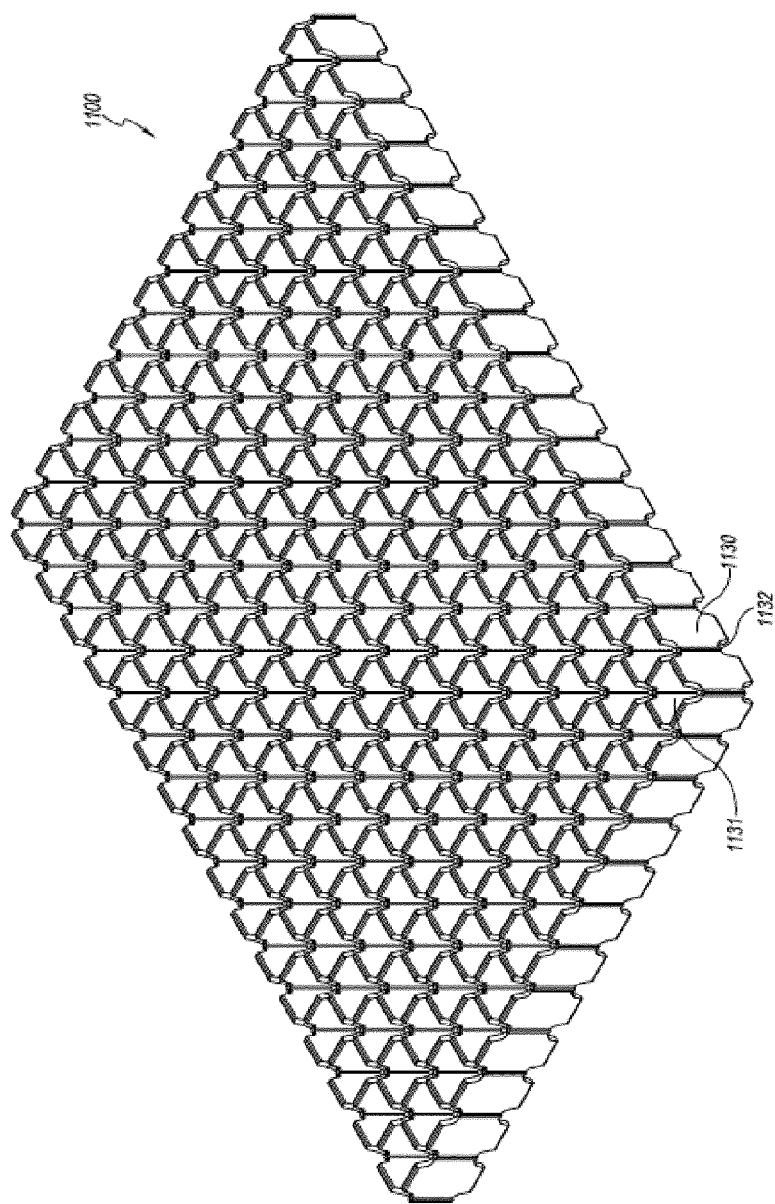
FIG. 18 illustrates an additional embodiment of a wound closure device comprising a stabilizing structure.

FIG. 18 illustrates a stabilizing structure 1100 comprising vertical segments 1130 joined together at approximately perpendicular angles so as to form quadrilateral or square cells 1131. Preferably, the vertical segments 1130 are of a square or rectangular shape, with tapers 1132 that join the segments together in a movable and flexible configuration. As with the other embodiments described in this section or elsewhere in this specification, this stabilizing structure 1100 may be fabricated as a single unit, and is preferably configured to collapse in a horizontal plane or direction while remaining substantially uncollapsed in a vertical direction.

Figure 19A:
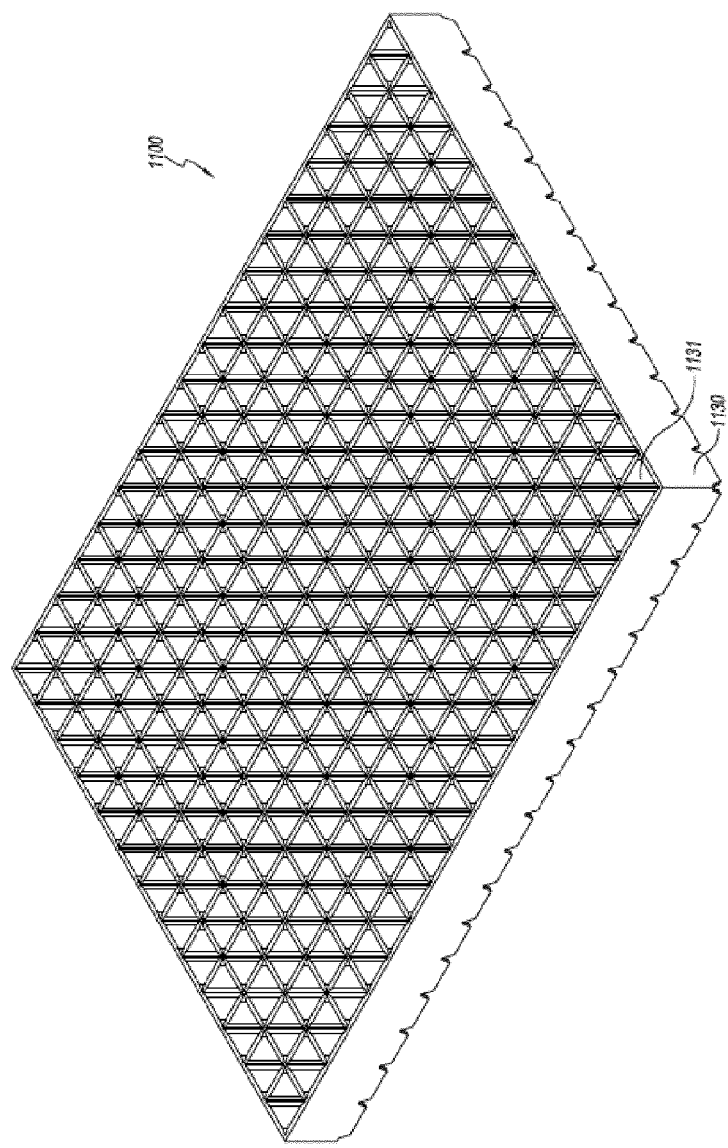
FIGS. 19A-B illustrate additional embodiments of wound closure devices comprising a stabilizing structure.
Figure 19B:
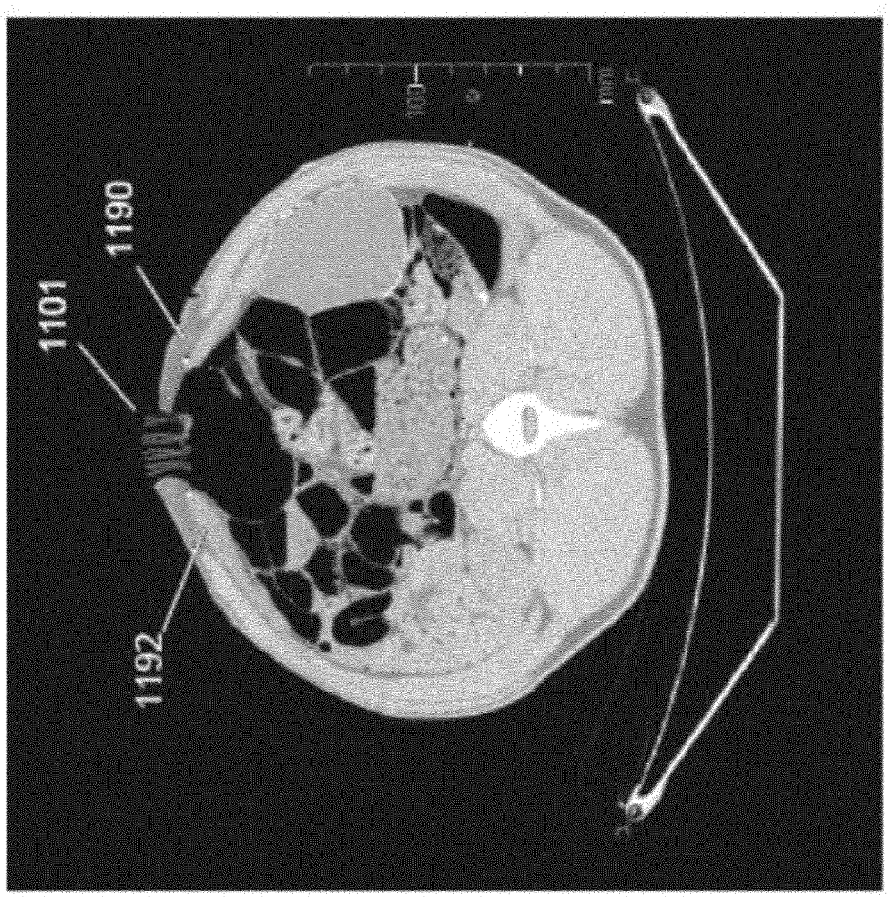
Figure 20:
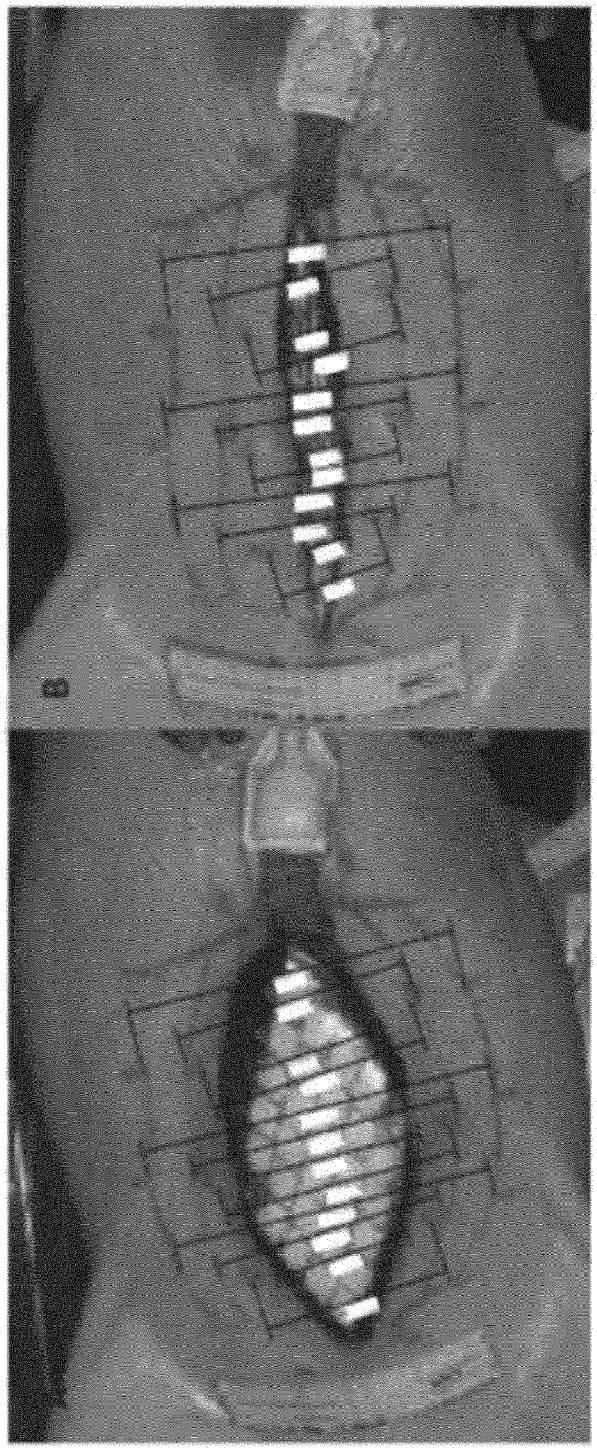
FIGS. 20A-B are before and after photographs of experiments performed to determine the efficacy of certain embodiments of wound closure devices.
Figure 21:
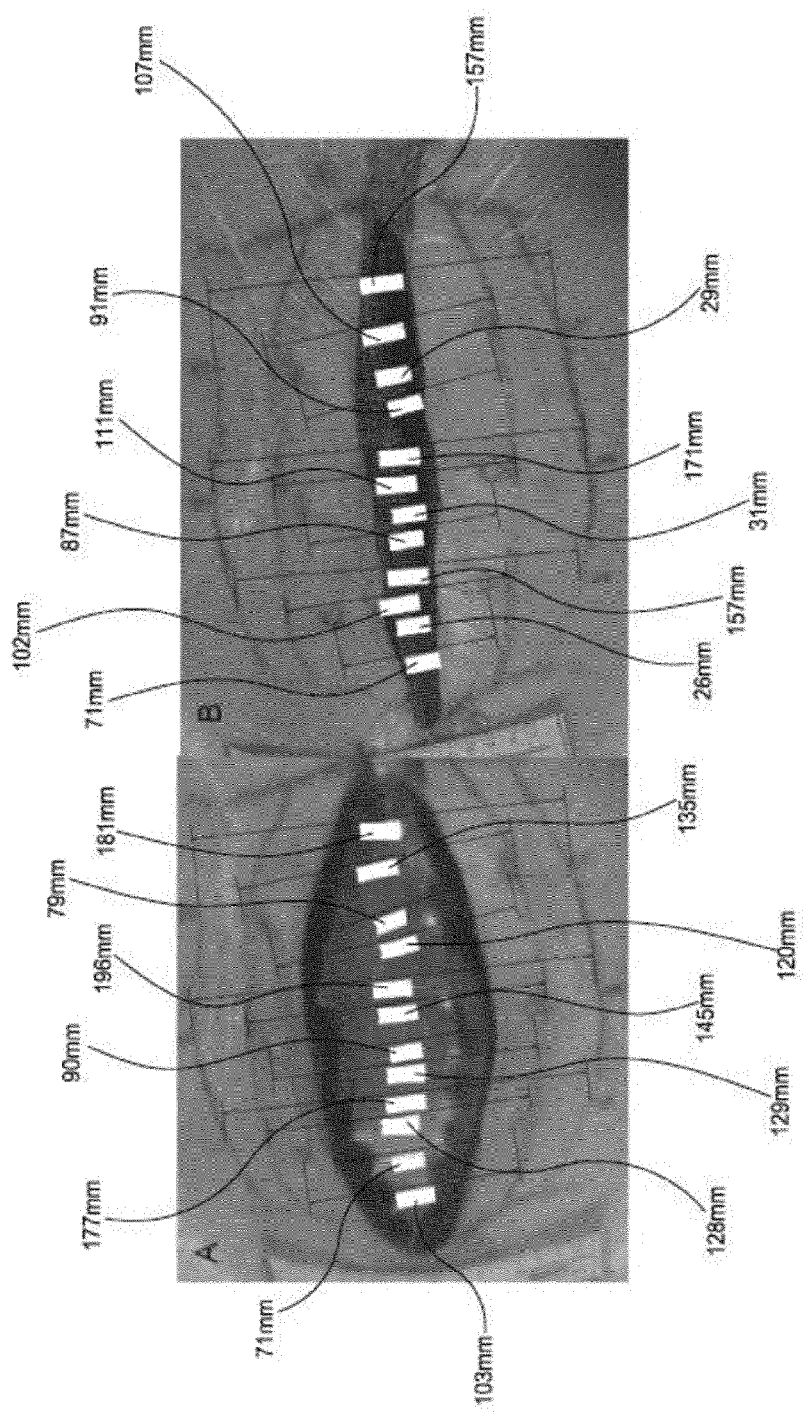
FIGS. 21A-B are before and after photographs of experiments performed to determine the efficacy of certain embodiments of wound closure devices.

FIG. 19A-B illustrates another stabilizing structure 1100 similar to the embodiment illustrated above in FIG. 18. The vertical segments 1130 are preferably joined together so as to form one or more quadrilateral or square cells 1131. Here, however, the vertical segments 1130 do not comprise a tapered portion 1132. However, one or more notches may be present on the underside (wound-facing side) of the structure 1100, and which function as described in preceding embodiments. Although this embodiment may be manufactured from multiple vertical segments 1130, it is preferably molded as a single unit.

FIG. 19B illustrates a CT image of an embodiment of a stabilizing structure 1100 as described above in relation to FIG. 19A, and which has been inserted into an abdominal wound. Subcutaneous fat layers 1190 are bilateral and present over muscle tissue layer 1192. Upon application of negative pressure (as illustrated), improved fascial re-approximation and wound closure may be observed. Here, the width of the wound along the view illustrated reduced from approximately 82 mm to 52 mm, a reduction of 37%. As with the other stabilizing structures and/or wound closure devices described elsewhere in the specification, the stabilizing structure of FIGS. 19A-B may be incorporated as a region or regions of a fabricated wound filler.

In some embodiments, the stabilizing structures described in this section or elsewhere in this specification (such as those described in FIGS. 14A-19B) may be fabricated from a single type of material, such as a plastic. In other embodiments, the stabilizing structures described in this section or elsewhere in this specification may be fabricated via a process whereby the more rigid portions of the structure are fabricated first and the hinges or flexible portions are fabricated second. In further embodiments of the stabilizing structure described in this section or elsewhere in this specification, a soft polymer could be fabricated over the entire structure to soften the feel of the device, thereby protecting the surrounding organs and/or other tissues. In other embodiments, the soft polymer could be fabricated only on the bottom portion of the stabilizing device, while in some embodiments the softer polymer can be fabricated over the top and/or the sides of the device. In some embodiments, the soft polymer could be fabricated over particular edges of the stabilizing structure, such as those on the bottom, sides, and/or top. In certain embodiments, the soft polymer could be fabricated over any side or combination of sides of the stabilizing device. The soft polymer may act like a softened rim surrounding the hard edges of the stabilizing structure.

Figure 35:
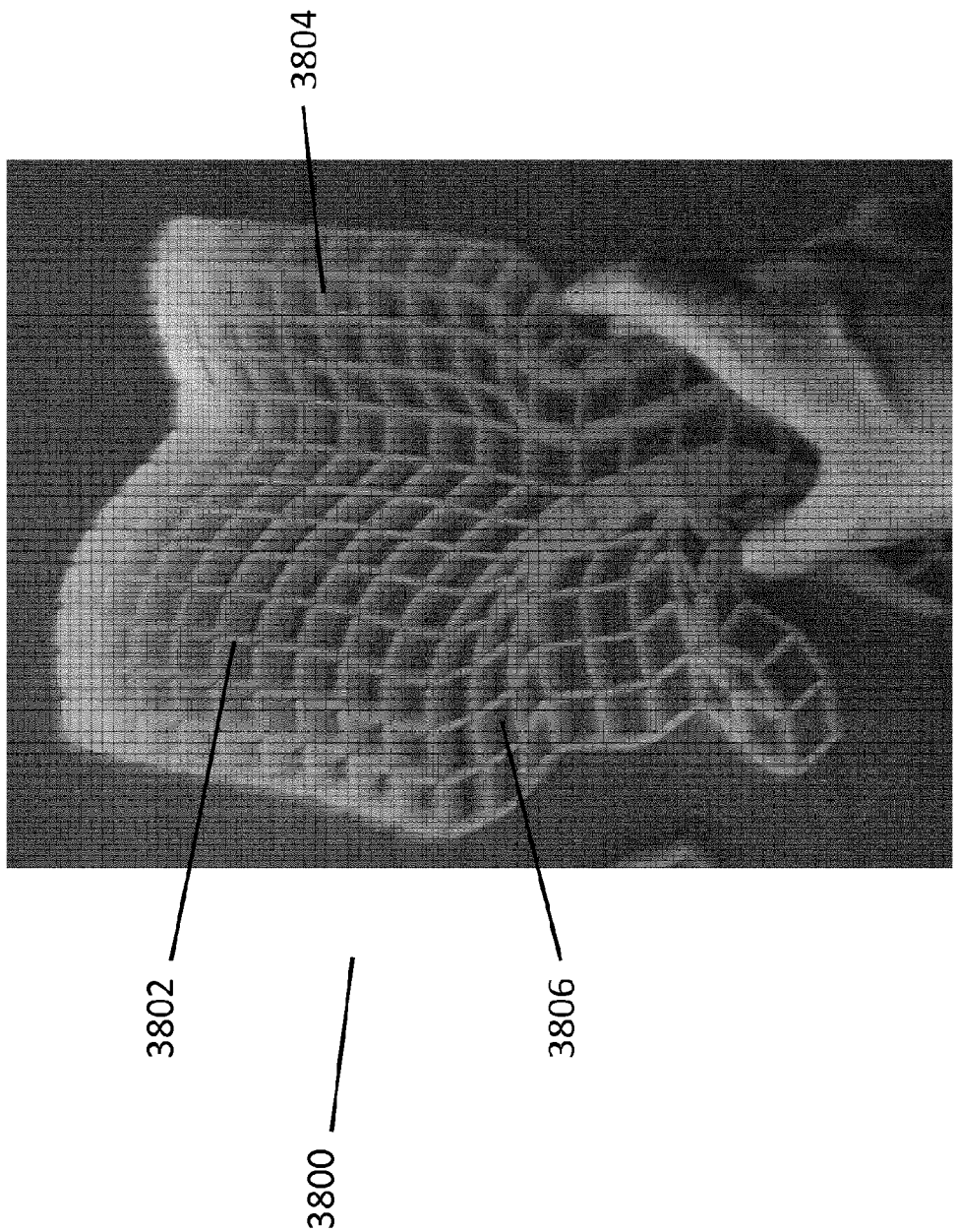
FIG. 35 illustrates an embodiment of a fully flexible stabilizing structure.

FIG. 35 illustrates an embodiment of a stabilizing structure 3800 similar to the structures described in FIGS. 14-19A. In this embodiment, the longitudinal strips 3802 and cross strips 3804 form rows of flexible cells 3806 that are configured to collapse in a horizontal plane. Because each of the longitudinal and cross strips are formed from the same flexible material, applying a lateral force to the structure causes the cells to collapse generally independently of each other. In other words, the collapse of one or more cells in a row does not necessarily cause the collapse of other cells in the same row.

Example 4

In this next example of a non-limiting experiment involving structures for use in regions of a fabricated wound filler, an embodiment of a stabilizing structure such as those described above in relation to FIGS. 11A-E was inserted into an abdominal wound. In this experiment, and as illustrated in FIG. 20A, white foam inserts were placed into the quadrilateral openings of the stabilizing structure, and the outer edges (in contact with the wound) were wrapped in black foam. The wound and stabilizing structure were then sealed with a drape and connected to a source of negative pressure as described previously.

Wound area measurements were taken before and after activation of the negative pressure source. Here, the size of the wound before application of negative pressure was measured as 171 mm$^2$. Upon the application of negative pressure, as illustrated in FIG. 20B, the area of the wound was greatly reduced to 55 mm$^2$, a reduction of 68%. It is noted that here and in the following examples, as the wound area contracts along its width, the length of the wound increases slightly, indicating that the tissue margins are returning to their original anatomical position.

Example 5

FIGS. 21A-B illustrate the results of a non-limiting experiment similar to those illustrated above, where a stabilizing structure similar to the embodiments of FIGS. 11A-E was inserted into the abdominal cavity. Here, the spaces in the quadrilateral openings of the stabilizing structure were empty, and a layer of foam was wrapped around the outer edges of the structure.

Wound area measurements before and after application of negative pressure indicated that the wound area decreased by 63%, from 155 mm$^2$ to 58 mm$^2$.

Without wishing to be bound by theory, the improved reduction in wound area in the preceding examples as compared to more commonly utilized pure foam dressings, is believed to be due to the fact that the wound devices used therein do not significantly compress in a vertical direction when negative pressure is applied. This is different from traditional foam dressings, where the application of negative pressure causes downward pressure on the foam due to the air pressure pressing onto the drape, [thus causing the foam to collapse towards the wound bed, creating a concave shape to the drape. The atmosphere acts predominantly in a perpendicular direction to the surface of the drape. Thus, on the periphery of the concave shape, closest to the wound edge or where the drape approaches an angle perpendicular to the plane of the wound, the atmosphere now creates a force in a direction that pushes the wound apart.] Similarly, pressure is transmitted along the foam dressing into a horizontal force that pushes the wound margins outward. Traditional negative pressure wound treatment typically uses foam (or other porous materials) placed into a wound underneath a drape, to which negative pressure is applied to the wound. In such situations, the application of negative pressure may cause downward pressure on the foam due to the air pressure pressing onto the drape, which is then transmitted along the foam dressing into a horizontal force that pushes the wound margins outward. Without wishing to be bound by theory, it is believed that some of the embodiments of stabilizing structures, wound closure devices, and wound treatment devices, methods, and systems described in this specification are able to cause a greater reduction in wound area as compared to traditional negative pressure treatment. One of these factors is believed to be because embodiments of the stabilizing structures and wound closure devices described in this section or elsewhere in this specification do not significantly compress in a vertical direction when negative pressure is applied. With the use of certain embodiments described in this section or elsewhere in this specification, foam and other dressing components are not pushed outward due to negative pressure, and thus the wound margins may be approximated more easily so as to achieve faster wound closure and better wound healing.

Stabilizing Structures and Wound Closure Devices of FIGS. 24A-30B

Figure 24A:
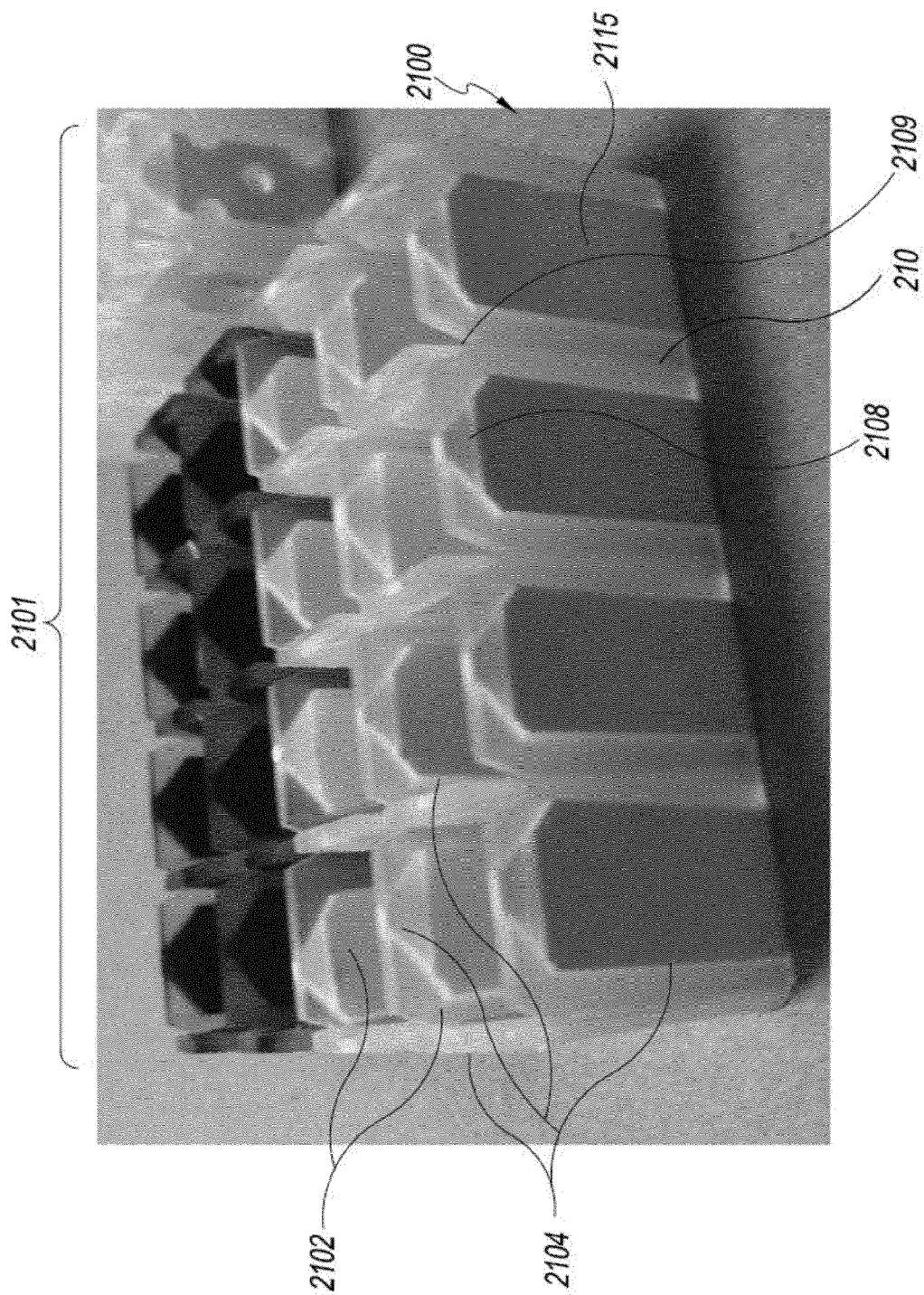
FIGS. 24A-E are photographs of various embodiments of stabilizing structures comprising inserts disposed therein.

FIG. 24A is a photograph of an embodiment of a wound closure device comprising a stabilizing structure 2100 that may be placed or inserted into a wound. Here, the device comprises a plurality of cells 2102 provided side-by-side in a generally planar configuration. Preferably, the stabilizing structure 2100 is configured to collapse in a direction along a plane 2101 defined by the width of the device, without significantly collapsing in a direction perpendicular to the plane 2101. That is, when viewed in the figure, the stabilizing structure 2100 will collapse in the horizontal direction, but will not compress in the vertical direction. In some embodiments, the stabilizing structure collapses in conjunction with the movement of tissue. Here, the cells 2102 are preferably open at both ends in a direction perpendicular to the plane 2101.

Each of the cells 2102 is preferably formed with four walls 2104, each wall 2104 being joined to the next by a flexible joint 2106. The joints 2106 are preferably designed so as to be more flexible than the walls 2104, and promote collapse of the stabilizing structure 2100 in the direction of the plane. Of course, it will be understood that other configurations are possible, and in some embodiments each cell 2102 may be defined by less than or greater than four walls 2104, for example five walls or six walls, thus forming pentagonal or hexagonal cells. The cells 2102 may not necessarily be symmetric, and can form rectangular, diamond, rhomboidal, trapezoidal, parallelepiped, oblong, oval, lozenge and other such shapes in addition to the square-walled embodiment illustrated in this section or elsewhere in this specification.

One or more of the walls 2104 defining the one or more cells 2102 may further comprise an insert 2115 fabricated and disposed therein, and described in greater detail below in FIGS. 25A-F. Preferably, the insert 2115 will be fabricated from a material more rigid than the material used to construct the remainder of the wall 2104. Some suitable materials may include metals such as titanium, stainless steel, and largely inert alloys (such as monel and hastelloy), and/or polymers such as polyurethane, silicone, rubber, isoprene, polyethylene, polypropylene, nylon, polyacrylate, polycarbonate, and PEEK. Some embodiments may also comprise composite materials, including resin-reinforced fiber composites where the resin may be, for example, various types of epoxies. Suitable fibers may include glass, carbon, carbon nanotubes, graphene, and aramids (e.g., Kevlar). Preferably, the material chosen for the insert 2115 is not only sufficiently rigid, but also able to adhere to the material used in the wall 2104. For example, the insert material is preferably able to adhere to softer polymers such as silicones or polyurethanes used in the wall 2104. The more rigid materials used in the insert 2115 may provide for additional collapse resistance in the direction perpendicular to the plane for the stabilizing structure 2100.

In some embodiments, one or more notches 2109 may be provided between multiple walls 2104, and which may further aid in permitting the flexible joints 2106 to move. Without wishing to be bound by theory, the notches 2109 may also aid in distributing negative pressure and transmitting fluid throughout the stabilizing structure 2100 when negative pressure is applied, for example in a clinical care setting. Some embodiments may also comprises holes in the walls 2104 or joints 2106, or be constructed from porous materials.

Preferably, a cavity 2108 is provided within each wall 2104 for the insert 2110 to be fabricated within the cavity. In some embodiments, the walls 2104 may be fabricated around each insert 2115. An insert 2115 may also be inserted into the cavity 2108 after the wall 2104 is fabricated. For example, the insert and wall could be fabricated separately via 3D fabrication techniques, and then the insert later inserted into the cavity via suitable means. While the embodiment illustrated here and in the subsequent images shows a single insert 2115 in each wall 2104, some embodiments may be provided with one or more inserts 2115 disposed therein.

Figure 24B:
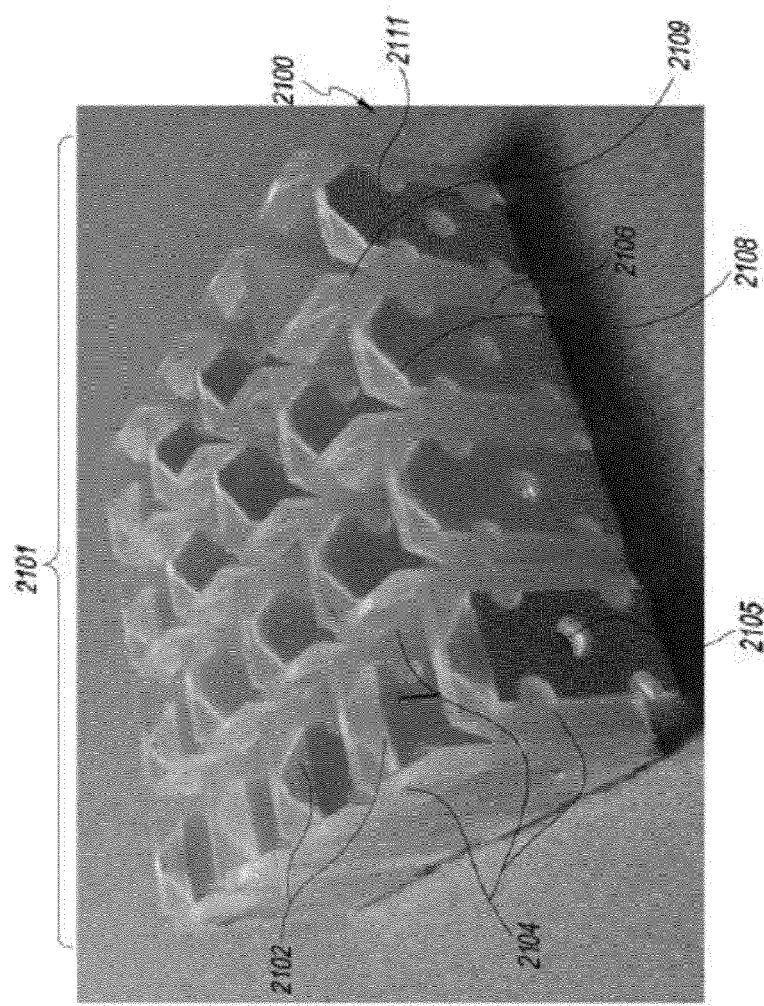

FIG. 24B illustrates an embodiment of a stabilizing structure 2100 with many similar features to FIG. 24A. Here, an insert 2111 comprises structural differences compared to the insert 2110, and is discussed in more detail below in relation to FIG. 24E. When inserted or fabricated within the cavity 2108, one or more of the walls 2104 may comprise a hole 2105 communicating through at least one aperture in the insert 2111. In addition to any notches 2109, the one or more holes 2105 may permit additional displacement of wound exudate and distribution of negative pressure within the stabilizing structure 2100.

Figure 24C:
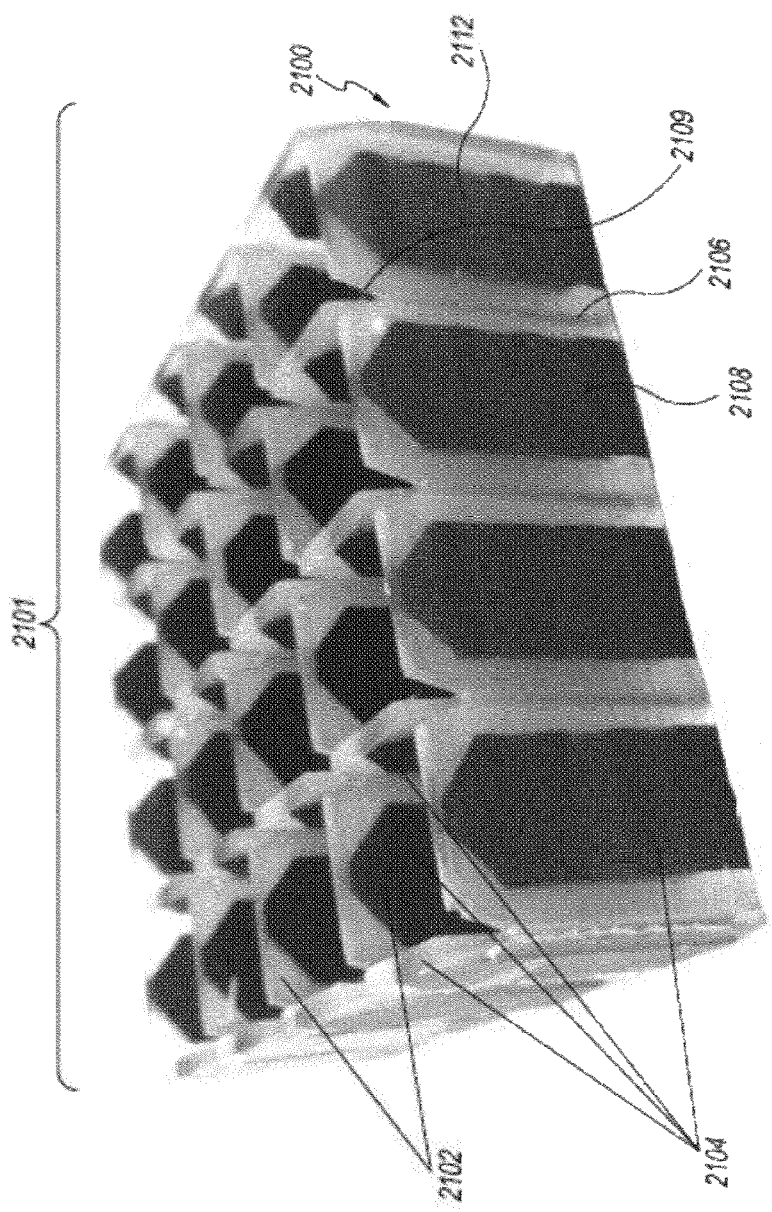

FIG. 24C illustrates an embodiment of a stabilizing structure 2100 with similar features as the other embodiments described previously. In this embodiment, the stabilizing structure 2100 comprises an insert 2112 described in greater detail below in FIG. 25F.

Figure 24D:
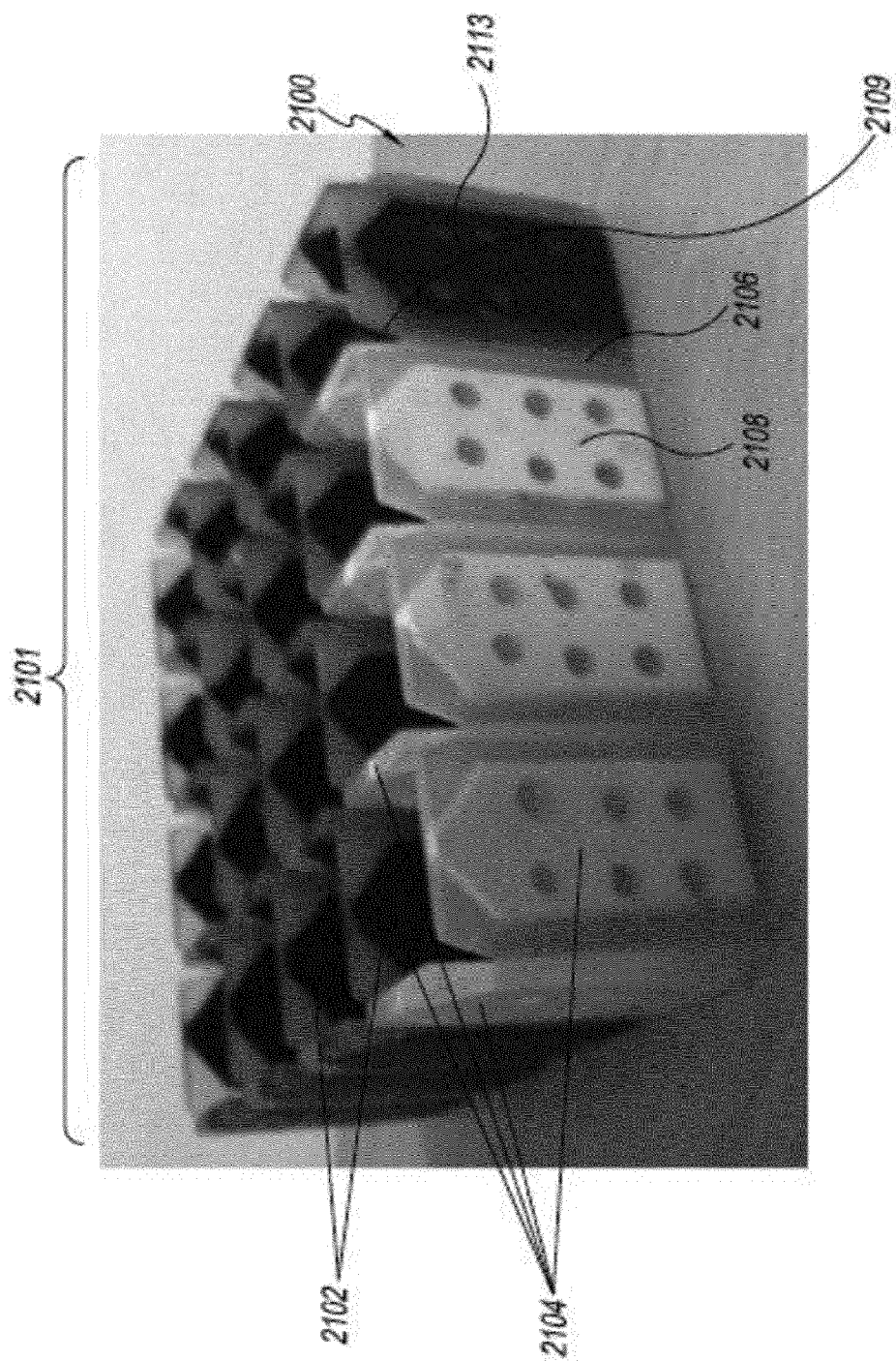
Figure 24E:
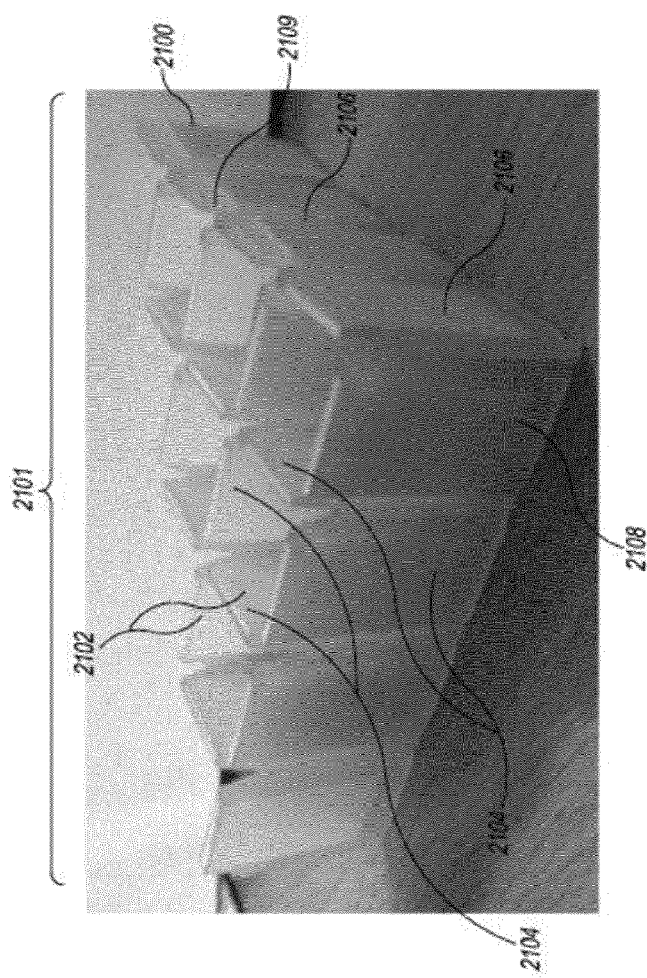
Figure 25:
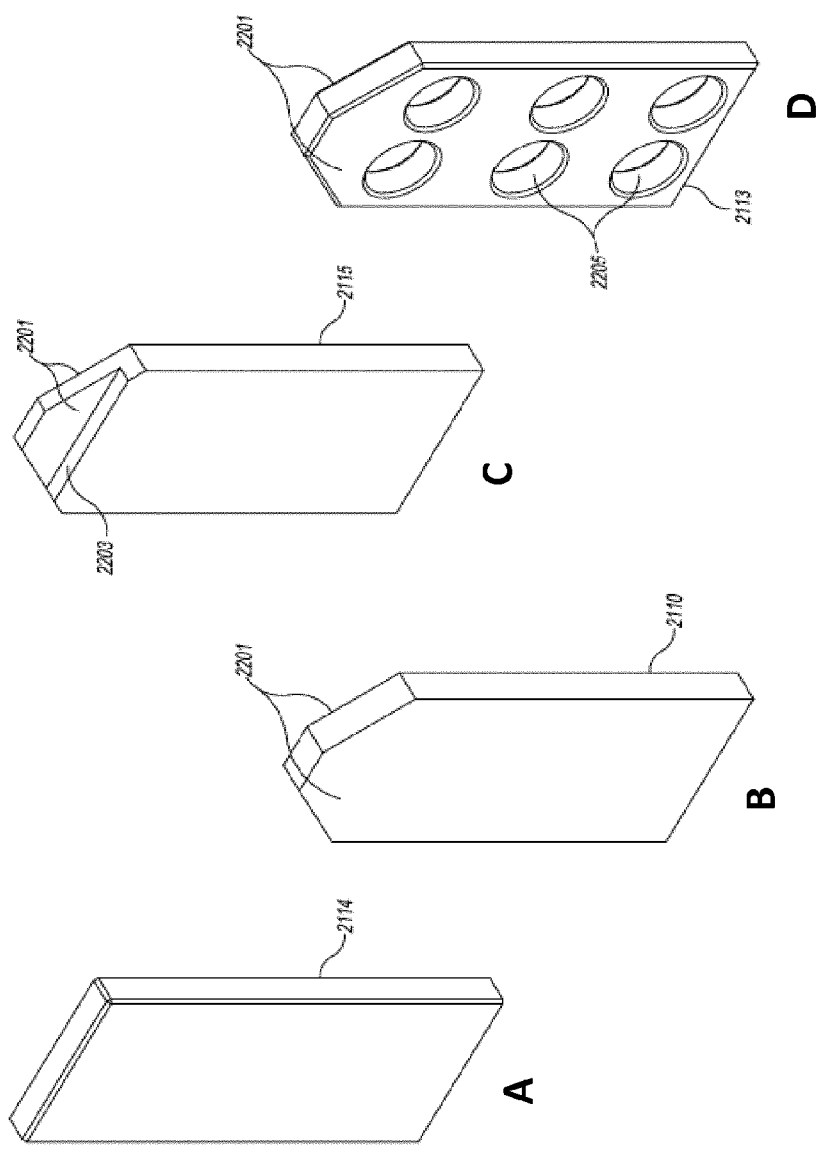
FIGS. 25A-F illustrate various embodiments of inserts that may be used in stabilizing structures.

Similarly, FIG. 24D illustrates an embodiment of a stabilizing structure 2100 comprising an insert 2113 described in greater detail below in FIG. 25D. FIG. 24E illustrates an embodiment of a stabilizing structure 2100 comprising an insert 2114 described in greater detail in relation to FIG. 25A.

In the preceding embodiments of stabilizing structures 2100 comprising various inserts 2110, 2111, 2112, 2113, 2114, and 2115, it will of course be understood that embodiments of the stabilizing structure 2100 do not need to contain only one type of insert. Likewise, each cell 2102 or wall 2104 may comprise one or more different types of inserts, or no inserts at all. Varying the different inserts and other properties of the cells 2102 and walls 2104 may thus permit the stabilizing structure 2100 to be tailored to the appropriate wound type so as to effect optimal wound closure and/or treatment.

FIGS. 25A-F illustrate examples of different inserts that may be used as part of a stabilizing structure 2100. Preferably, these inserts may be placed, molded into, or formed as part of a wall 2104 in a stabilizing structure 2100 (e.g., of the types illustrated above in FIG. 24A-E). Various modifications may be made, as described below, that may improve or alter characteristics of the inserts.

Turning now to FIG. 25A, the embodiment of the insert 2114 illustrated here is approximately rectangular in shape, and is adapted to be inserted or formed into one or more of the walls 2104 of an embodiment of the stabilizing structure 2100. In some embodiments, one or more of the inserts 2114 may have a height greater than the width, and the wall 2104 may have a height of at least about 1 mm, at least about 5 mm, at least about 10 mm, at least about 15 mm, at least about 20 mm, at least about 25 mm, at least about 30 mm, at least about 35 mm, at least about 40 mm, at least about 50 mm, at least about 75 mm, at least about 100 mm, at least about 150 mm, at least about 200 mm, at least about 250 mm, at least about 300 mm, at least about 350 mm, at least about 400 mm, or more than 400 mm, particularly in extremely obese patients. Preferably, in average patients, the heights may range from about 10 mm to 40 mm. These measurements may apply to any stabilizing structure described in this section or elsewhere in this specification.

In some embodiments of any stabilizing structure described in this section or elsewhere in this specification, the width may be between about 1 mm to 30 mm, 2 mm to 25 mm, 4 mm to 20 mm, 6 mm to 18 mm, 8 mm to 16 mm, or 10 mm to 14 mm, preferably about 10.8 mm. These measurements may apply to any stabilizing structure described in this section or elsewhere in this specification.

The insert 2114 is preferably thin but with enough structural strength to resist collapse, and in some embodiments of any stabilizing structure described in this section or elsewhere in this specification, the thickness may be at least about 0.01 mm to 10 mm, 0.2 mm to 8 mm, 0.4 mm to 6 mm, 0.5 mm to 4 mm, 0.75 mm to 3 mm, or 1-2 mm. These measurements may apply to any stabilizing structure and/or wound closure device described in this section or elsewhere in this specification.

In some embodiments of any stabilizing structure described in this section or elsewhere in this specification, multiple discrete stabilizing structures may be stacked on top of one another to form the wound closure device, to extend the height of the device to any of the dimensions described in this section or elsewhere in this specification (including the dimensions provided for the inserts above). The stacking of multiple stabilizing structures may allow the clinician to have further flexibility in their treatment strategies when fabricating a wound filler via 3d fabrication techniques.

FIG. 25B illustrates an embodiment of the insert 2110 with a generally rectangular configuration, but provided with two notches 2201 cut diagonally across a top end of the insert 2100. The notches 2201 may facilitate clearance of the insert 2100 from any notches 2109 that may be provided in the walls 2104. Further, the notches 2201 may also aid in the insertion of the insert 2100 into the cavity 2108 of the wall 2104. The notches 2201 may also be helpful in conjunction with the notches 2109 in further defining a channel or other opening for fluid to be transmitted or transferred between and through each cell 2102. The notches 2201 may also aid in ensuring that the entire stabilizing structure is able to more easily collapse.

FIG. 25C illustrates an embodiment of an insert 2115 provided with two notches 2201 as well as a horizontal lip 2203. The horizontal lip 2203 may aid in inserting the insert 2115 into the cavity 2108 of the wall 2104, or may aid in fixing the wall 2104 around the insert 2115 when the wall is fabricated around it. The horizontal lip 2203 may be beneficial in effectively reducing the bulk of the insert at one end of the wall 2104, and in conjunction with a softer material used in the wall 2104, may thereby increase comfort due to the correspondingly greater amount of wall material. In some embodiments, the horizontal lip 2203 and/or notches 2201 may be present on both ends of the insert 2115 or other inserts described in this section or elsewhere in this specification. In some embodiments, the horizontal lip 2203 is approximately half the thickness of the overall insert 2115. For example, the insert 2115 may be between 0.5 mm and 4 mm in thickness, preferably 2 mm. If the insert 2115 measures 2 mm in thickness, the thickness of horizontal lip 2203 may be 1 mm.

FIG. 25D illustrates an embodiment of the insert 2113, and which is similar to the embodiment used in the stabilizing structure 2100 illustrated in FIG. 24D. This insert 2113 may comprise one or more apertures 2205, which in some embodiments may communicate with one or more holes 2105 that may be formed through one or more walls 2104. In some embodiments, the apertures 2205 are arranged in a 2×3 pattern illustrated here, although other arrangements are possible. Notches 2201 may also be present.

FIG. 25E illustrates an embodiment of the insert 2111, which is similar to the embodiment used in the stabilizing structure 2100 illustrated in FIG. 24B. The insert 2111 preferably comprises two notches 2201. A horizontal lip 2203 may also be provided. Preferably, one or more apertures 2205 may be formed therein. In some embodiments, one or more of the apertures 2205 may extend to the edge of the insert 2111 as illustrated. In some embodiments, the apertures 2205 may be configured to have four apertures arranged around a central aperture, although other configurations are of course possible. In some embodiments, the reduced amount of insert material at the locations of the apertures may be advantageous to provide a greater amount of softer wall material at a hinge point, where this may consequently increase flexibility. In a preferred embodiment, the insert 2111 has a height of 25 mm and a width of 10.8 mm, with a thickness of 2 mm. The first set of apertures may be centered approximately 5 mm from the bottom edge of the insert 2111, the central aperture may then be centered approximately 11 mm from the bottom, and the top set of apertures may be centered 17 mm from the bottom.

FIG. 25F illustrates an embodiment of the insert 2112, which shares some similarities to the embodiment used in the stabilizing structure 2100 illustrated above in FIG. 24C. The insert 2112 preferably may comprise one or more channels 2207 formed therein. Preferably, the one or more channels 2207 are disposed in a horizontal configuration across the width of the insert 2112. While the insert 2112 is preferably configured, like several other embodiments described in this section or elsewhere in this specification, to remain substantially uncompressed in the vertical direction, the inclusion of one or more horizontal channels 2207 may aid in providing additional rigidity in the direction of the plane defined by the cells 2102. In such a case, the rigidity of the one or more walls 2104 may be enhanced, and may thus control the compression of the stabilizing structure 2100 such that any collapse or bending occurs substantially only at the one or more joints 2106.

FIGS. 26A-F illustrate an embodiment of a stabilizing structure 3001 configured to be inserted into a wound, acting alone as a wound filler or as a region or regions within a larger fabricated wound filler. The stabilizing structure 3001 preferably comprises at least one top strip 3002 extending in a first direction (e.g., along an x axis) and at least one bottom strip 3004 extending in a second direction (e.g., along a y axis perpendicular to the x axis), these being preferably arranged into an array comprising multiple strips 3002, 3004. The strips 3002, 3004 are preferably connected together in a movably interlocking configuration, which preferably comprises an interlock mechanism 3006. The strips 3002, 3004 are preferably arranged in an un-collapsed configuration wherein the strips 3002 and 3004 are disposed at angles approximately perpendicular to each other. This arrangement forms a first plane that the stabilizing structure 3001 preferably adopts. Preferably, the stabilizing structure 3001 is more rigid in the direction perpendicular to the plane (i.e., in the vertical direction or along a z axis), and thereby substantially resists compression or deformation in that direction.

Figure 26A:
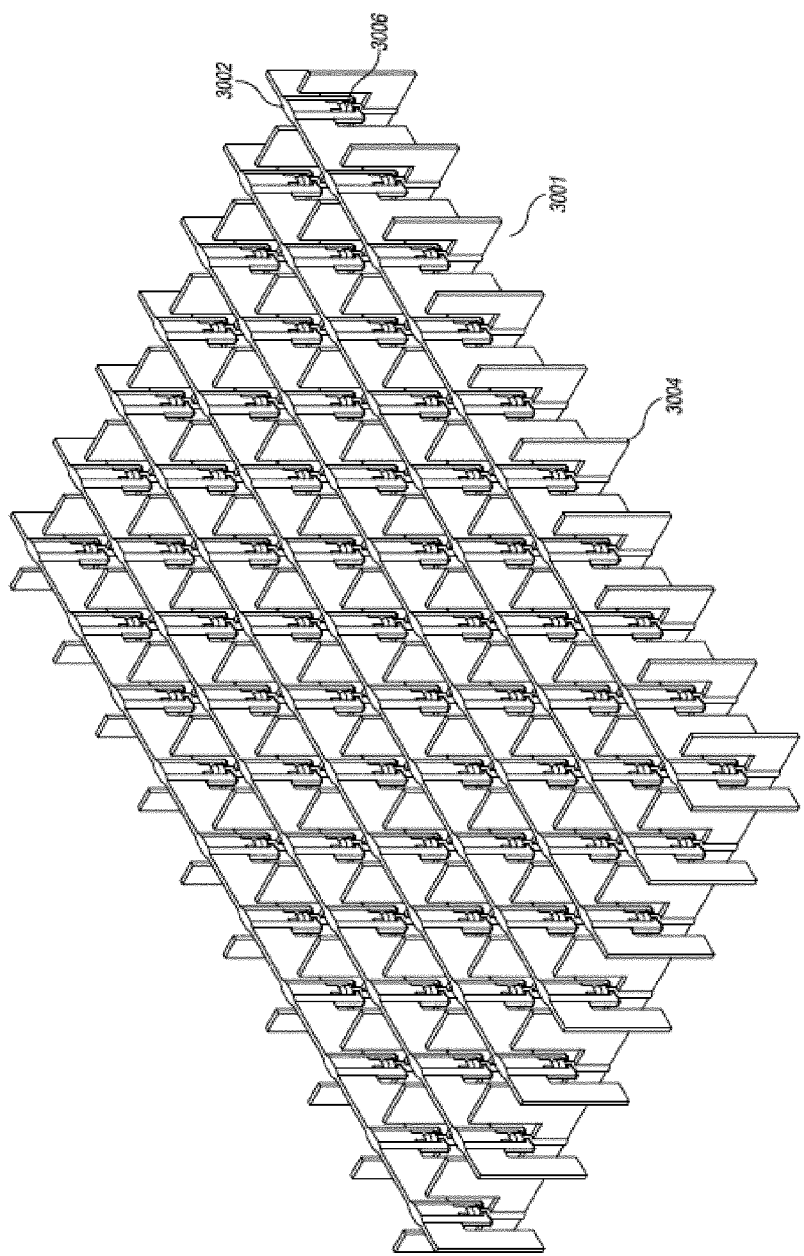
FIGS. 26A-F illustrate multiple views of an embodiment of a stabilizing structure.
Figure 26B:
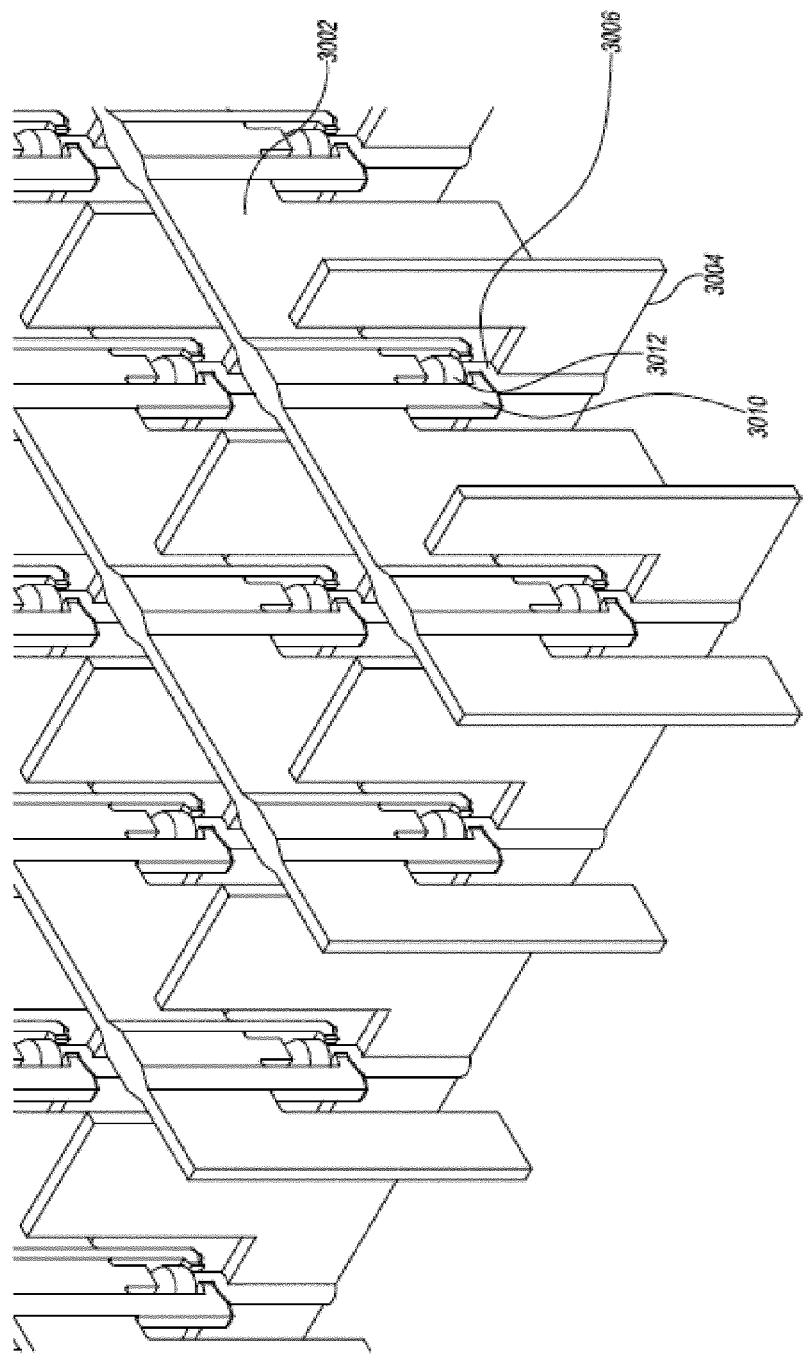
Figure 26C:
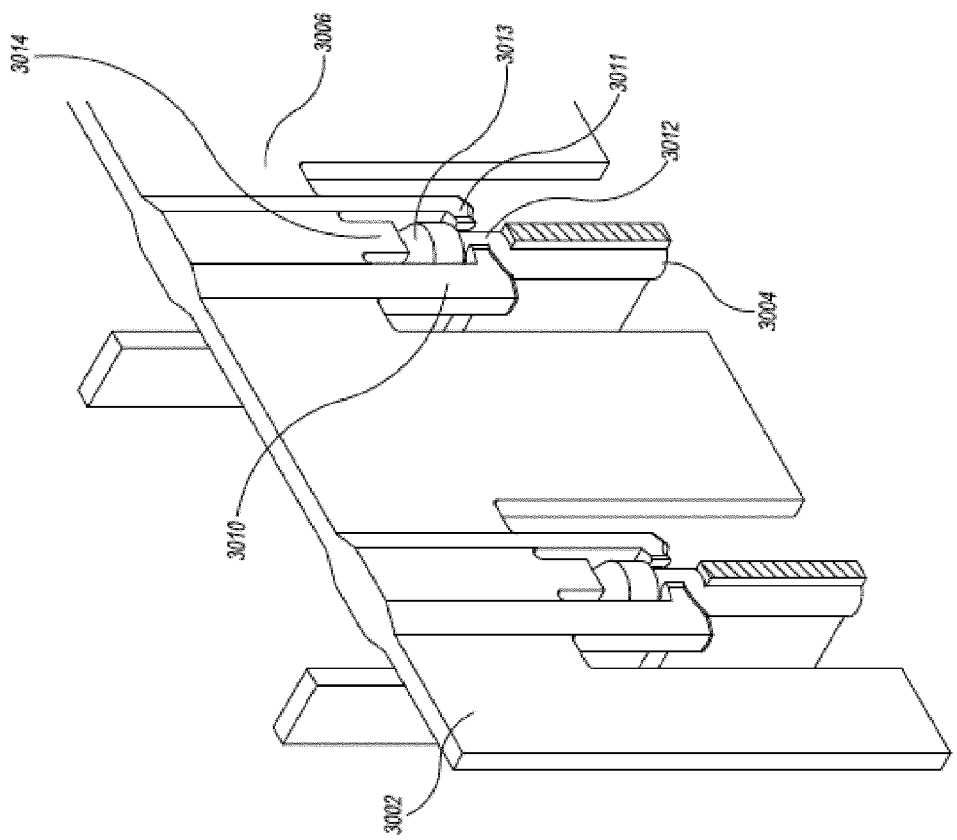
Figure 26D:
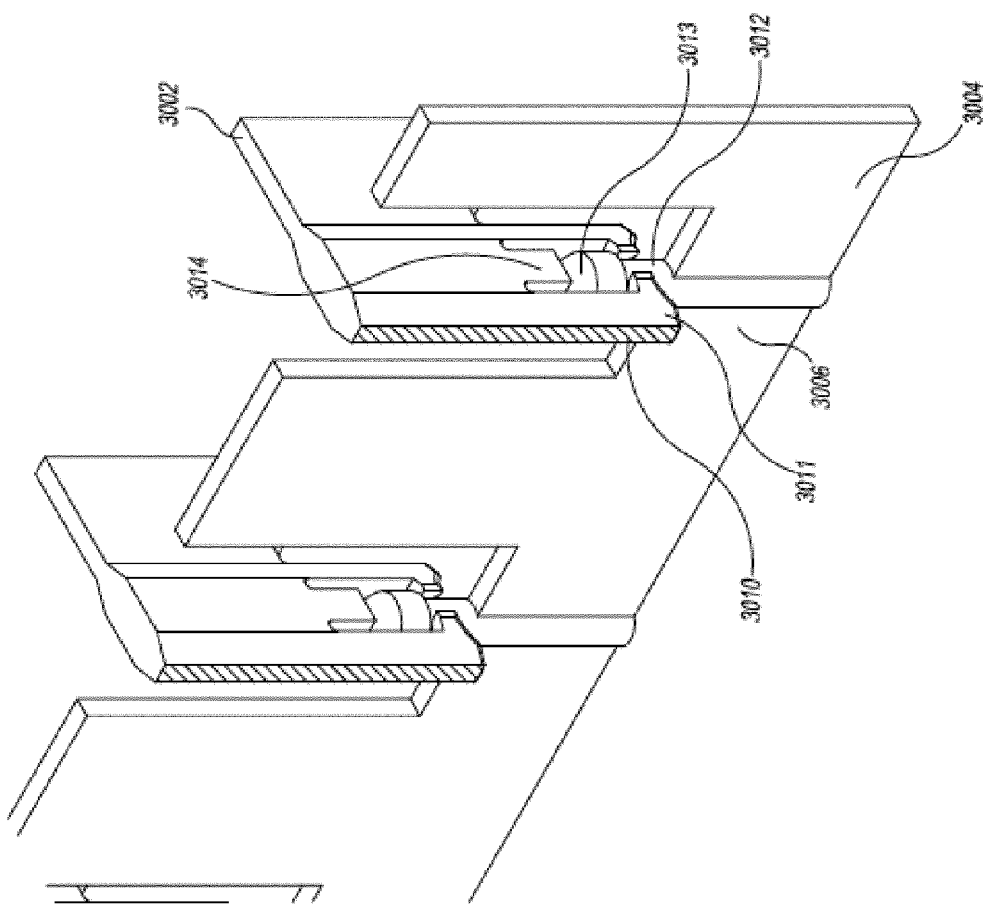
Figure 26E:
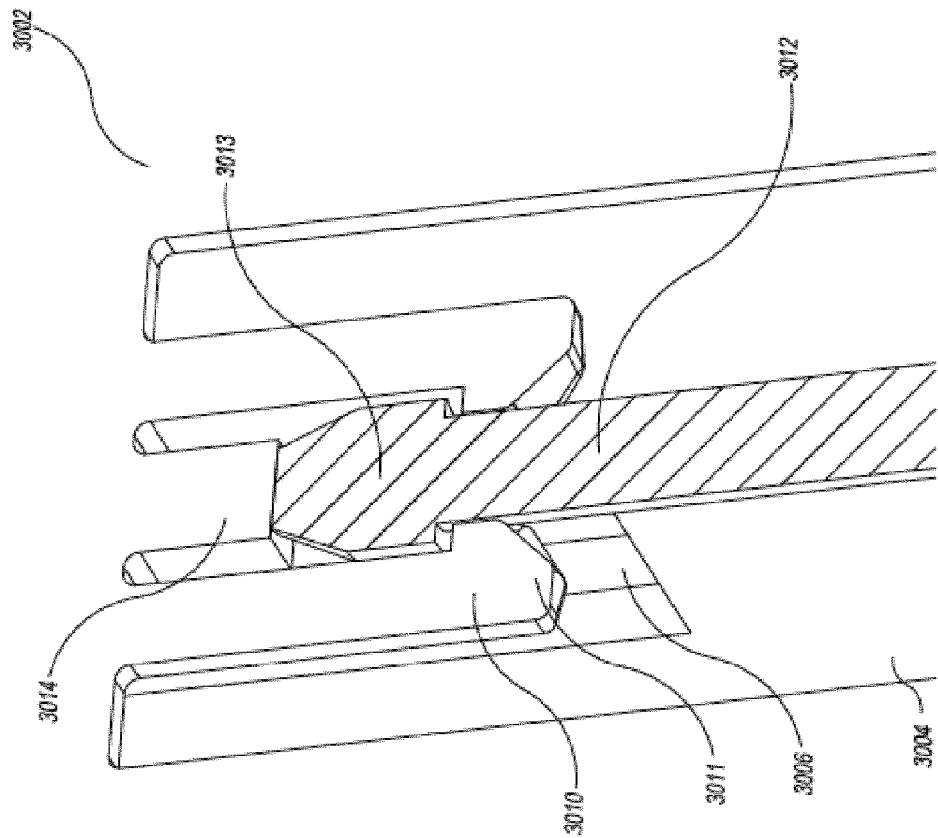
Figure 26F:
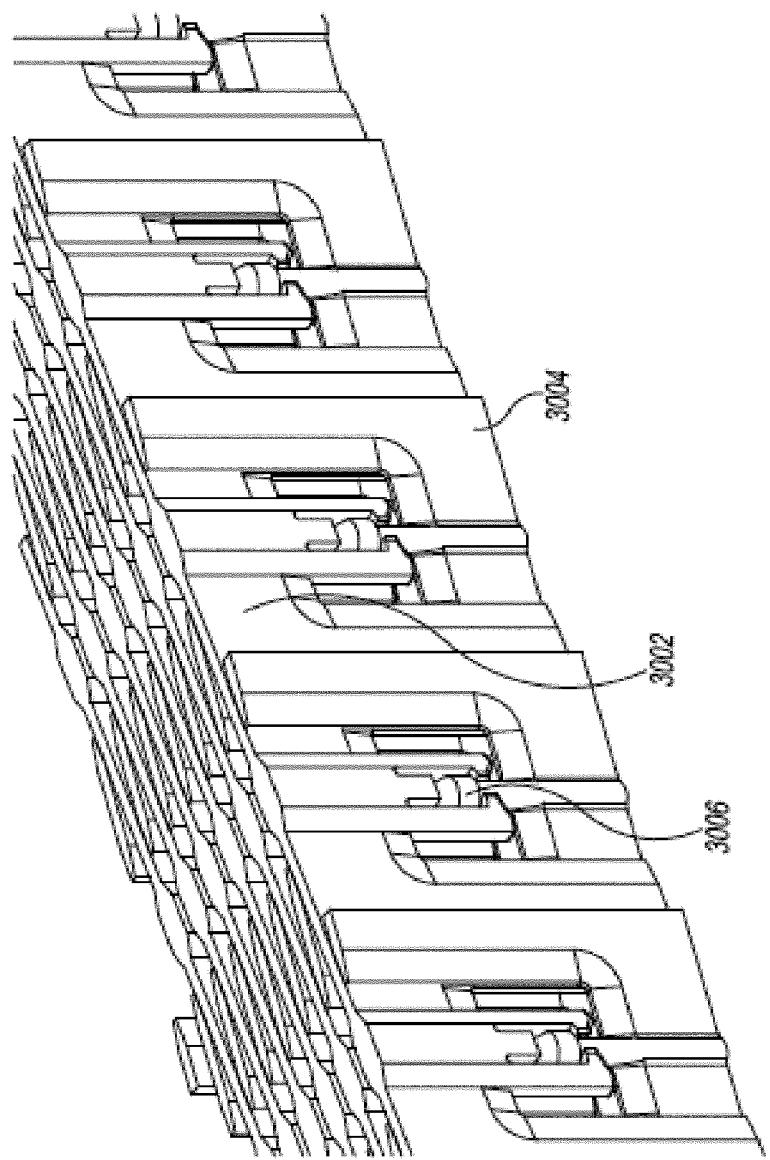

To aid in the closure of a wound, the stabilizing structure 3001 is preferably movable from the substantially un-collapsed configuration to a collapsed configuration, as illustrated in FIG. 26F. This may be beneficial for wound closure and healing, as described previously. In use, negative pressure may apply a closing force across the margins of the wound containing a wound filler comprising the stabilizing structure 3001. As the structure 3001 is preferably configured to be substantially rigid in the vertical direction (i.e., perpendicular to the plane defined by the structure 3001), pressure resulting from atmospheric pressure exerted onto the structure 3001 via the drape is focused substantially downward rather than outward, such that the wound margins are no longer pushed outward as in conventional negative pressure dressings.

Preferably, the structure 3001 adopts a smaller area in the first plane as a result of moving to the compressed configuration. As such, the structure 3001 aids in wound closure by aiding re-approximation of the wound margins. In some embodiments, the stabilizing structures described in this section or elsewhere in this specification are able to reduce their captured volume when in a collapsed configuration (i.e., the volume change between an uncompressed and compressed stabilizing structure) by at least 10%, preferably at least 15%, and even more preferably at least 25%.

FIGS. 26C-E illustrate close-ups of the interlock mechanism 3006. It is to be noted that although reference may be made to various parts of the interlock mechanism 3006 being present on either the top strip 3002 or bottom strip 3004, this description should not be considered as limiting in terms of orientation, and the same interlock mechanism 3006 may be constructed with the top or bottom strips 3002, 3004 reversed.

In a preferred embodiment, the interlock mechanism 3006 preferably comprises two clasps 3010 extending downward from the top strip 3002. Preferably, the clasps 3010 are parallel to each other so as to be on opposite sides of a projection 3012 extending upward from the bottom strip 3004. The clasps 3010 preferably comprise a lip or hook 3011 that may secure themselves under an end 3013 located at the distal end of the projection 3012. In a preferred configuration, the enlarged end 3013 is arranged such that all or a portion of the lip 3011 engages with the enlarged end 3013. The combination of the lip 3011 and enlarged end 3012 may aid in preventing the top strip 3002 from disengaging in a vertical direction away from the bottom strip 3004. In some embodiments, the projection 3012 may abut on the bottom edge of the top strip 3002. In some embodiments, however, and as illustrated here, a stabilizing post 3014 may be present to locate the distal side of the projection 3012 and enlarged end 3013.

FIGS. 27A-D illustrate an embodiment of a stabilizing structure 3201 assembled in a similar manner to the embodiment illustrated above in FIGS. 26A-F. Here, the interlock mechanism 3006 comprises four clasps 3010 surrounding the projection 3012 and the enlarged end 3013 of the projection 3012. Preferably, the clasps 3010 are arranged in a mutually orthogonal configuration, although different orientations are contemplated as well. It will be understood that any number of clasps 3010 may be used to secure the projection 3012, for example three or five clasps 3010.

Figure 27A:
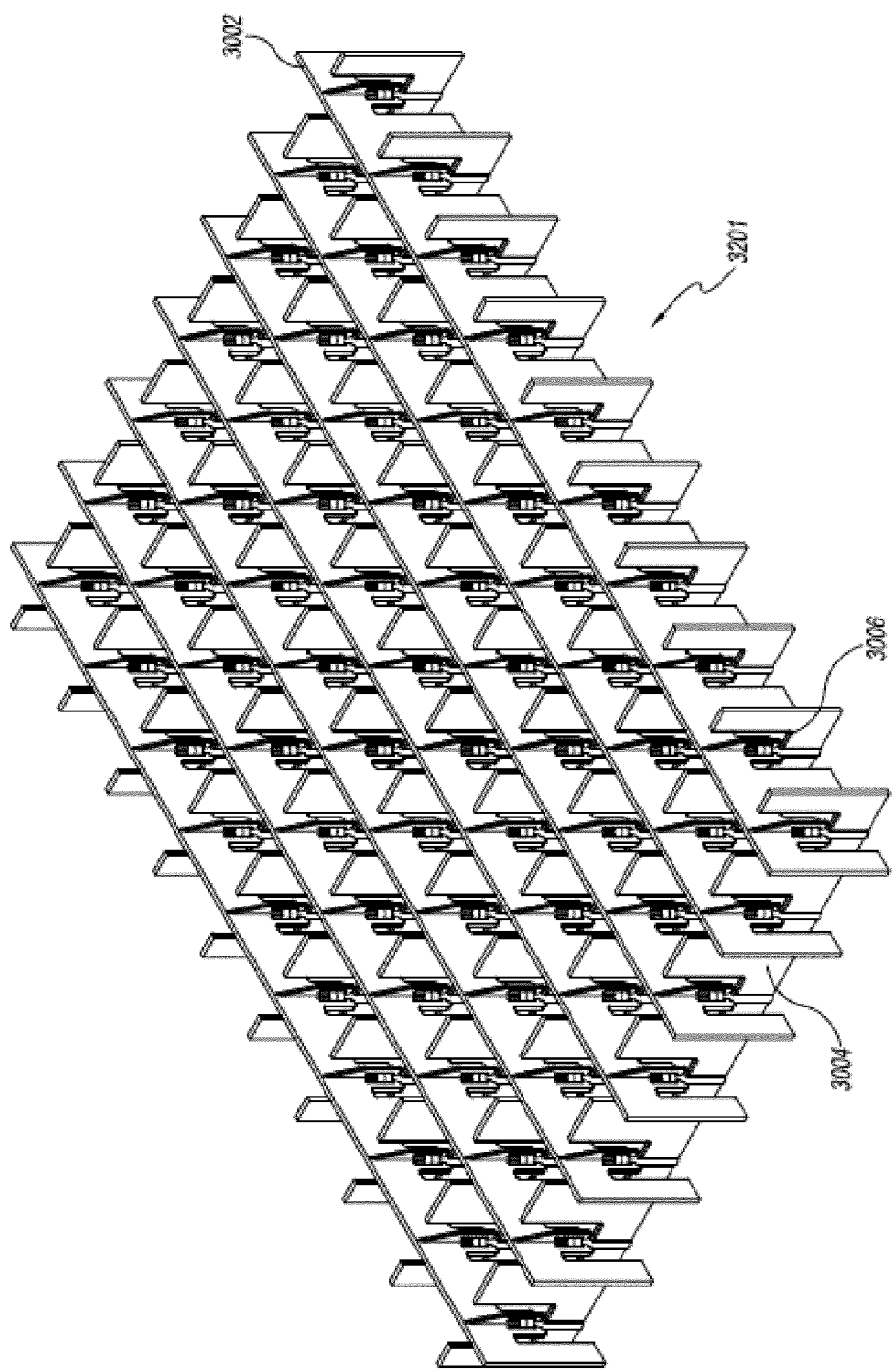
FIGS. 27A-D illustrate multiple views of an embodiment of a stabilizing structure.
Figure 27B:
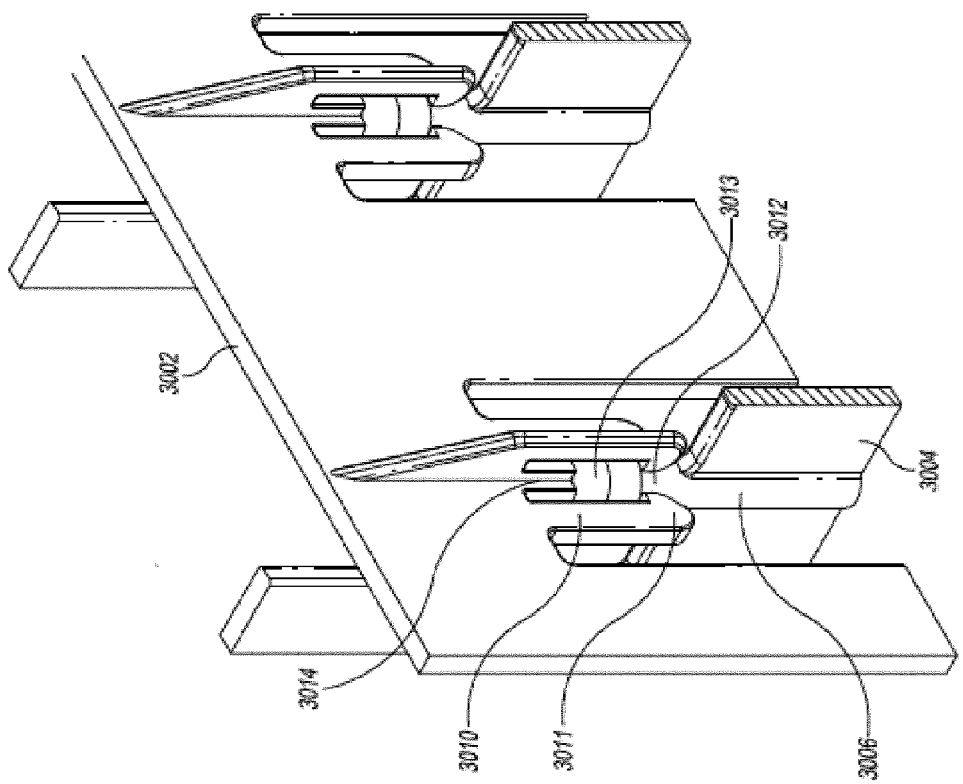
Figure 27C:
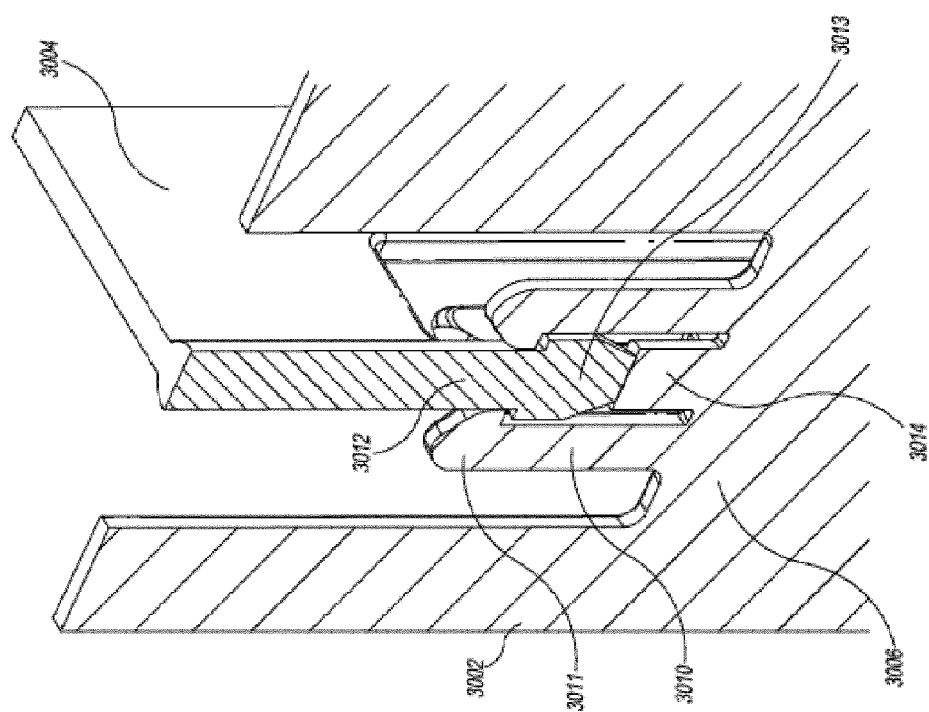
Figure 27D:
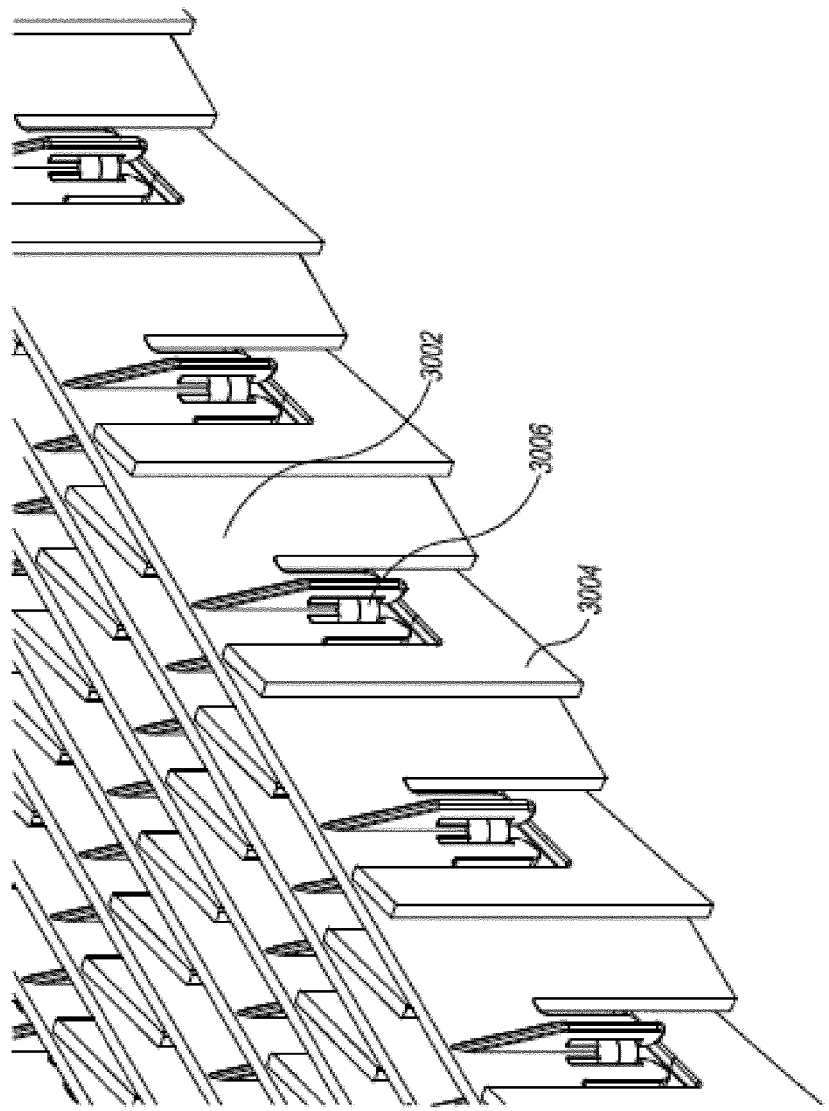

It will be noted that due to the addition of additional clasps 3010 in comparison to the embodiment illustrated in FIGS. 26A-F, the embodiment illustrated here will have a compressed configuration that is slightly larger, as illustrated in FIG. 27D. This may be useful in some situations; for example, some wounds may require a more gradual closure of the wound margins, and the embodiment described here may be well adapted for this purpose. For example, in clinical situations involving compartment syndrome, especially in the abdomen, application of full wound closure may not be appropriate or desirable, as wound closure may cause complications such as excessive pressure on organs and underlying tissue structures and/or reduction of blood flow to distal anatomical structures. Additionally, in some cases a too rapid or complete wound closure may be too painful for a patient. Accordingly, limiting the amount of closure may therefore be beneficial in such types of wounds. Limiting the amount of closure may also be beneficial in cases of compartment syndrome in the lower limbs.

FIGS. 28A-E illustrate an embodiment of a stabilizing structure 3301 comprising an interlock mechanism 3006 arranged in a tubular conformation. In this embodiment, a cup-shaped member 3020 is preferably configured to receive the enlarged end 3013 of the projection 3012. The projection 3012 may extend vertically from the top strip 3002. The cup-shaped member 3020 is preferably cylindrical or tubular in shape, and may extend vertically from the bottom strip 3004, although it will be understood that the cup-shaped member 3020 and projection 3012 may be located on opposite strips.

Preferably, one or more slits 3021 are formed into the cup-shaped member 3020 so as to permit some "give" to permit the projection 3012 to be received into the cup-shaped member. A lip or hook 3022 may also aid in securing the enlarged end 3013 of the projection 3012. A stabilizing post 3014 may also be present to prevent the projection 3012 from extending too deeply into the cup-shaped member 3020.

Figure 28A:
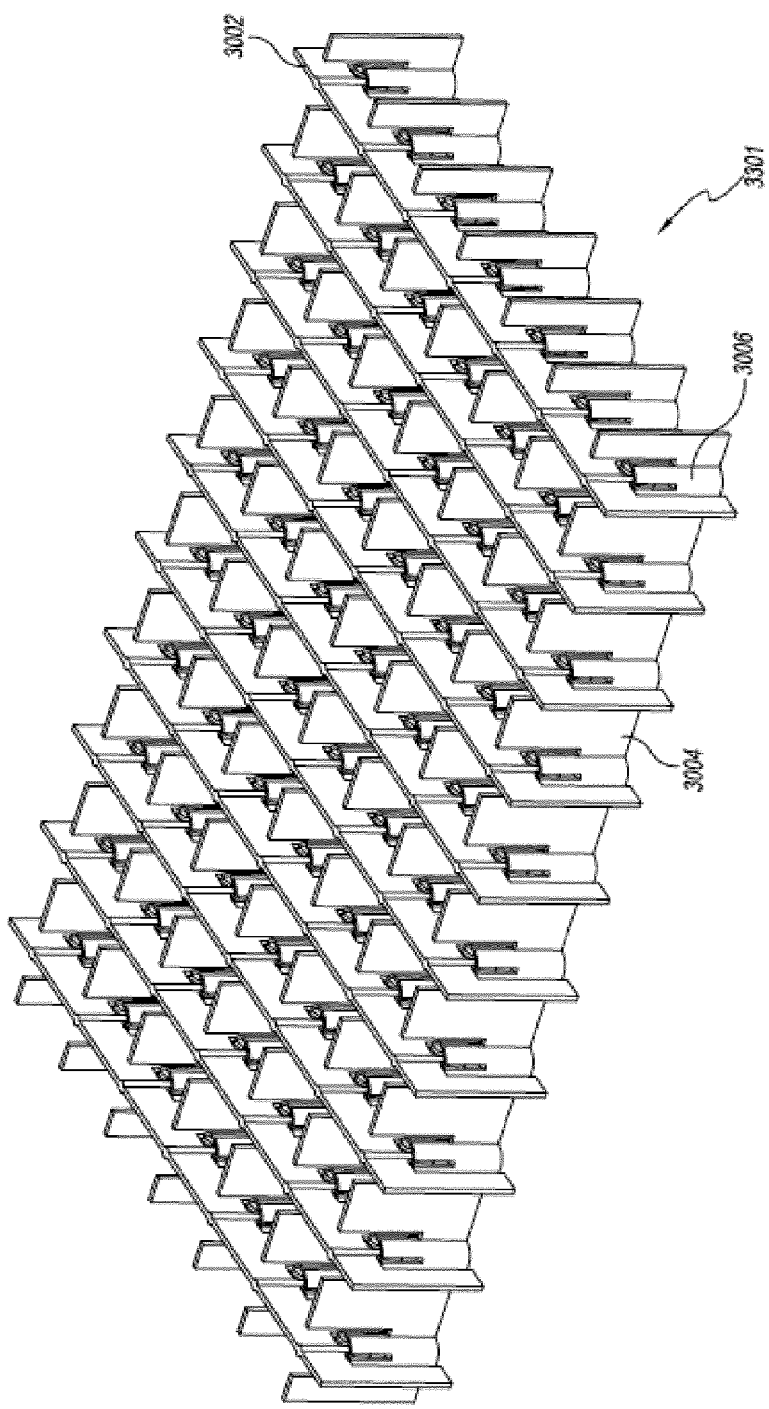
FIGS. 28A-E illustrate multiple views of an embodiment of a stabilizing structure.
Figure 28B:
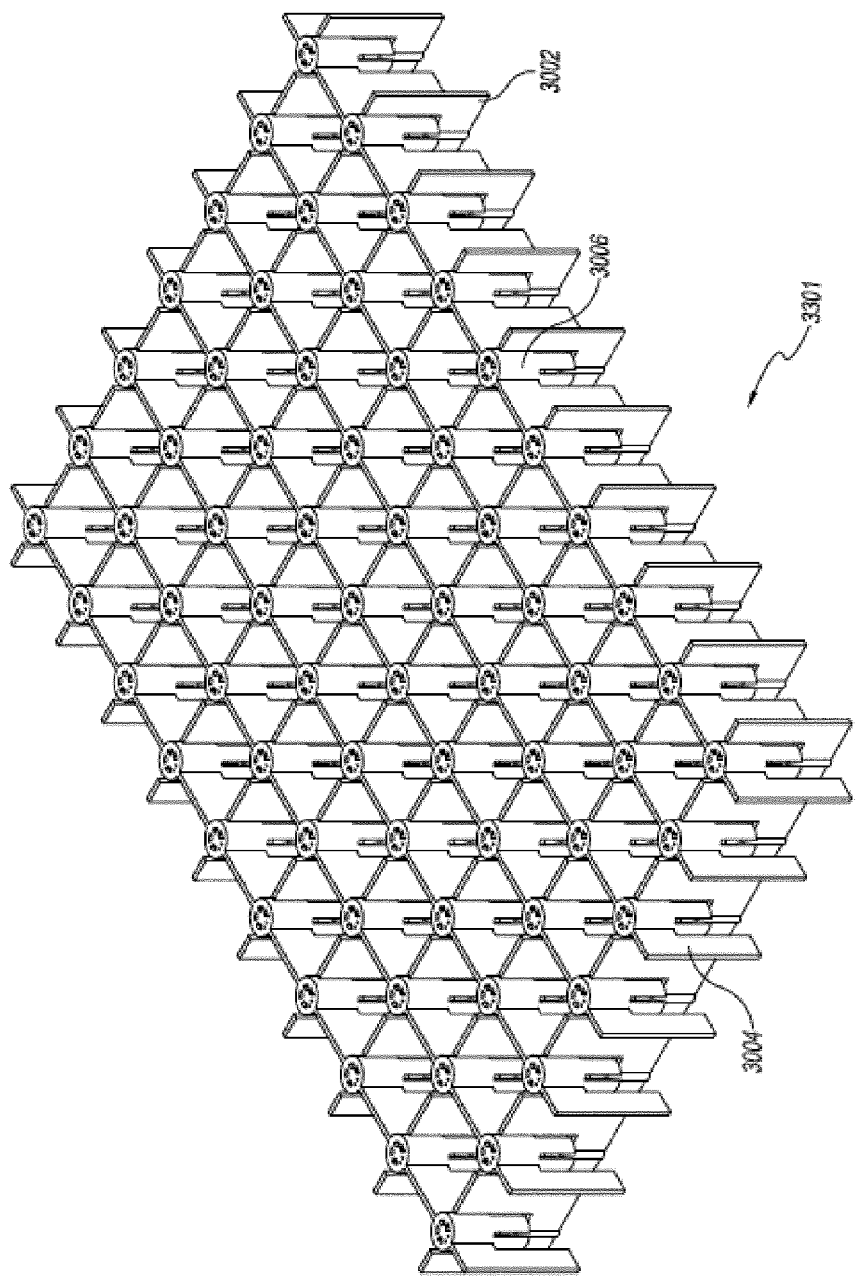
Figure 28C:
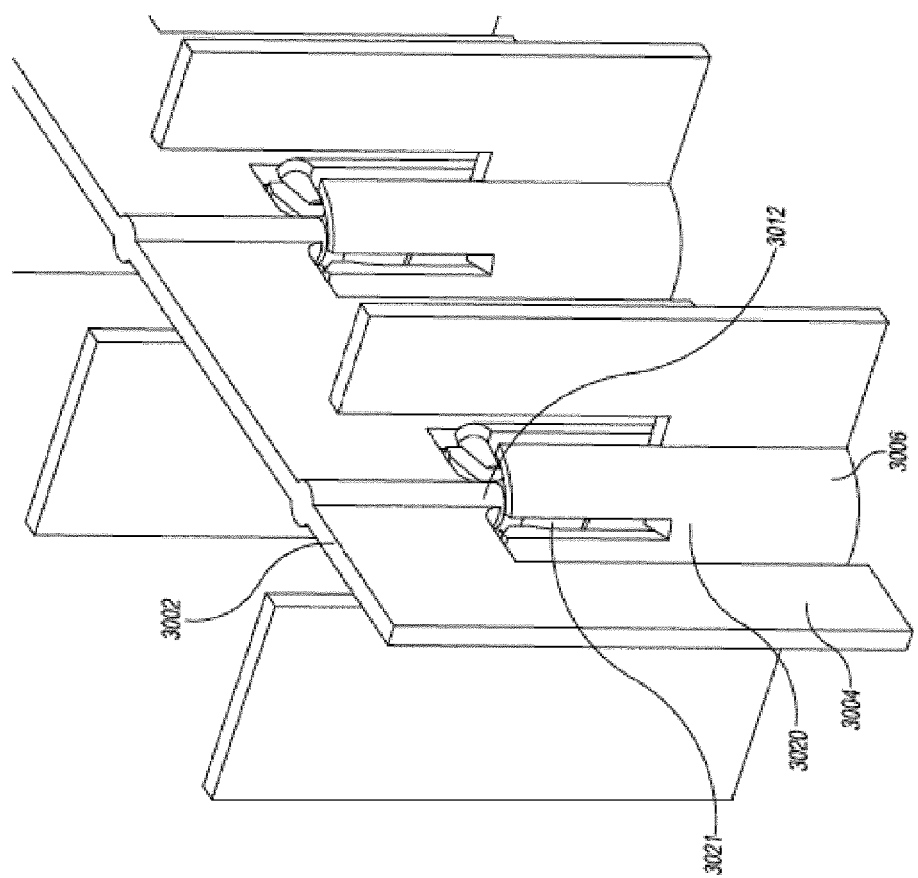
Figure 28D:
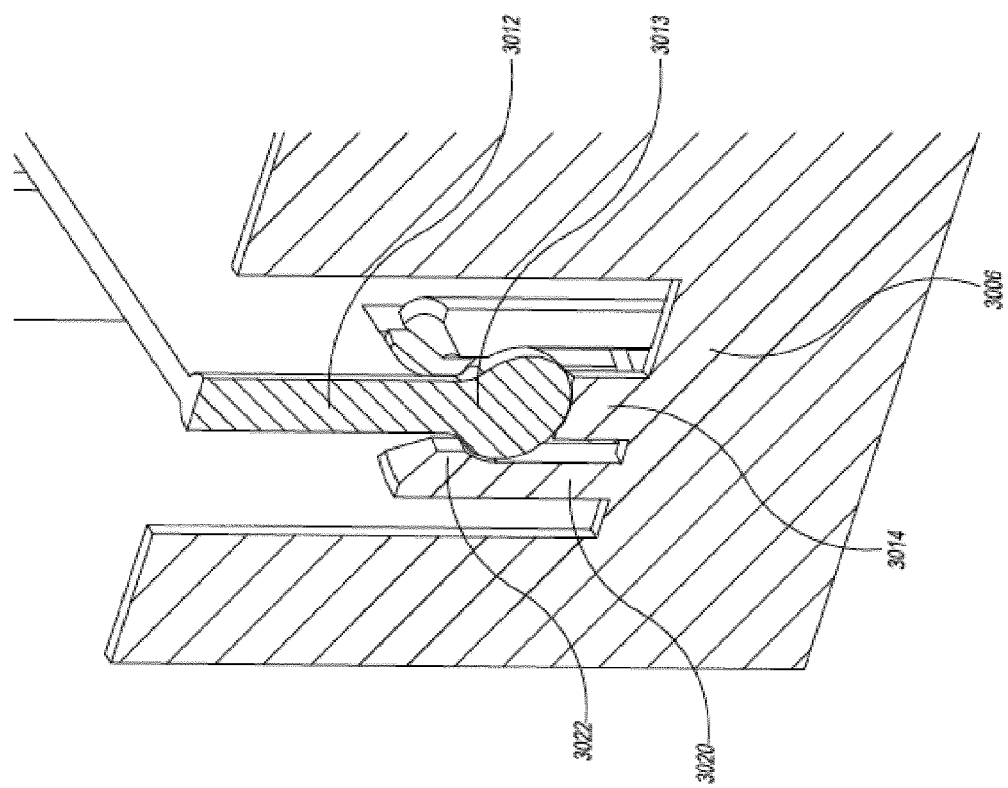
Figure 28E:
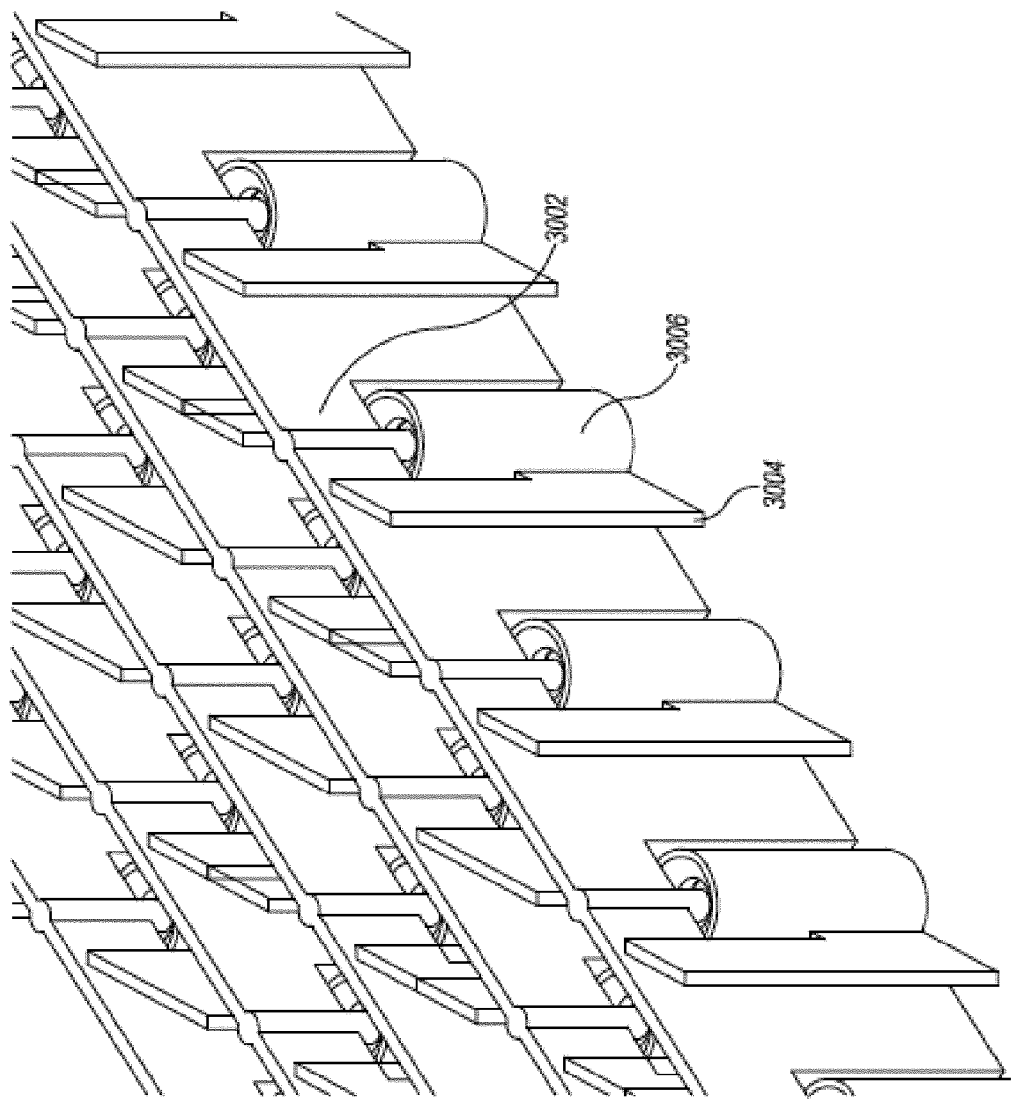

FIG. 28E illustrates a compressed view of an embodiment of the stabilizing structure 3301. Compared to FIG. 26F, this embodiment has a slightly larger compressed configuration.

FIG. 29 schematically illustrates an embodiment of a stabilizing structure 3400 configured to be inserted into a wound. Here, the stabilizing structure 3400 is shown inserted into a wound 3405. Preferably, the stabilizing structure 3400 preferably comprises at least one, and more preferably at least two, long strips 3402 whose longitudinal length may be oriented along a longitudinal axis of the wound 3405, or along a direction along which closure is sought. Each of the one or more long strips 3402 are preferably substantially rigid and extend substantially along the entire length of the wound 3405. In a preferred embodiment, the long strip 3402 is continuous and does not have any breaks or hinges along its length. This is in contrast to certain other embodiments described above.

One or more struts 3404 are preferably attached at one or more points to the long strip 3402. Preferably, these struts 3404 are movably attached, for example via a hinge-like attachment or flexible joint, such that these may collapse in a direction perpendicular to a longitudinal length defined by the length of the one or more long strips 3402. In some embodiments, the struts 3404 may be angled at a non-perpendicular angle with respect to the long strip 3402 so as to collapse more readily. In embodiments comprising two or more long strips 3402, the struts 3404 may be hinged between two parallel long strips 3402.

It will be recognized that while these struts 3404 may be configured to collapse along a direction perpendicular to the longitudinal length of the one or more long strips 3402, the struts 3404 are preferably rigid in a vertical direction (i.e., in the direction extending upward from a plane defined by the wound 3405). As such, a combination of the struts 3404 and the long strips 3402 may thus form a stabilizing structure 3400 that is substantially rigid in a vertical direction while being collapsible in a horizontal direction perpendicular to the longitudinal axis of the long strips 3402 (i.e., in the plane of the wound 3405).

FIG. 30A illustrates a top view of an embodiment of stabilizing structure 3400 cut into an oval shape and inserted into a wound 3405. Preferably, the stabilizing structure 3400 comprises a plurality of elongate strips 3402 whose longitudinal length may be oriented along a longitudinal axis of the wound 3405, or along a direction along which closure is sought. Each of the plurality of elongate strips 3402 is preferably substantially rigid and extends substantially along the entire length of the wound 3405. A plurality of intervening members are positioned between adjacent elongate strips 3402. These intervening members may be struts 3404 as described with respect to FIG. 29, preferably attached at one or more points to the elongate strips 3402. The intervening members may also be portions of elongate strips such as described with respect to FIGS. 26A-28E above, extending perpendicular or at an angle to elongate strips 3402. The stabilizing structure of FIG. 30A may also comprise the embodiments described with respect to FIGS. 24A-25F.

FIG. 30B illustrates a top view of an embodiment of an oval shaped stabilizing structure 3400 inserted into a wound 3405. This embodiment may have the same configuration as described above with respect to FIG. 30A. Additionally, foam 3406 can be fabricated between and around the stabilizing structure.

Stabilizing Structures and Wound Closure Devices of FIGS. 31A-34 and 36-38

Figure 31A:
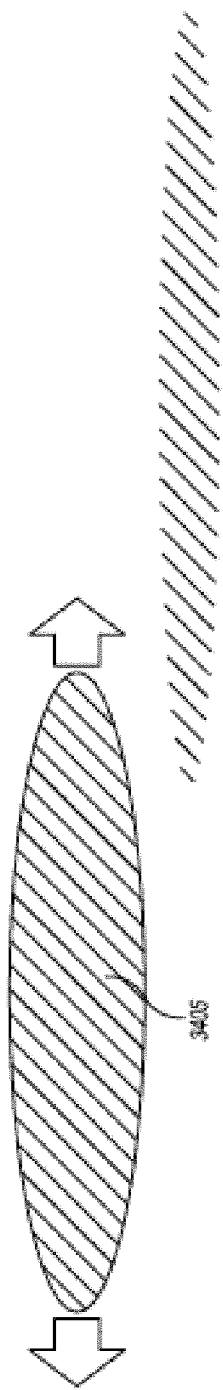
FIGS. 31A-B illustrate embodiments of methods for closing a wound.

FIG. 31A illustrates an embodiment of a method for the closure of a wound using any of the stabilizing structures described in this section or elsewhere in this specification before or as hereafter described, through the application of tension along an axis of wound 3405. As described previously, such stabilizing structures may be incorporated as various regions within a fabricated wound filler. In this example, when the wound is viewed from above, tension is applied along the longitundinal axis of the wound, generally represented by arrows 3407. Tension along the longitudinal axis prevents contraction of the wound along the longitudinal axis, however the tension along the longitudinal axis can cause the lateral edges of the wound to be drawn together, promoting wound closure. In some embodiments, additional inward tension can be applied to the lateral edges of the wound, thereby providing additional wound closing force.

Figure 31B:
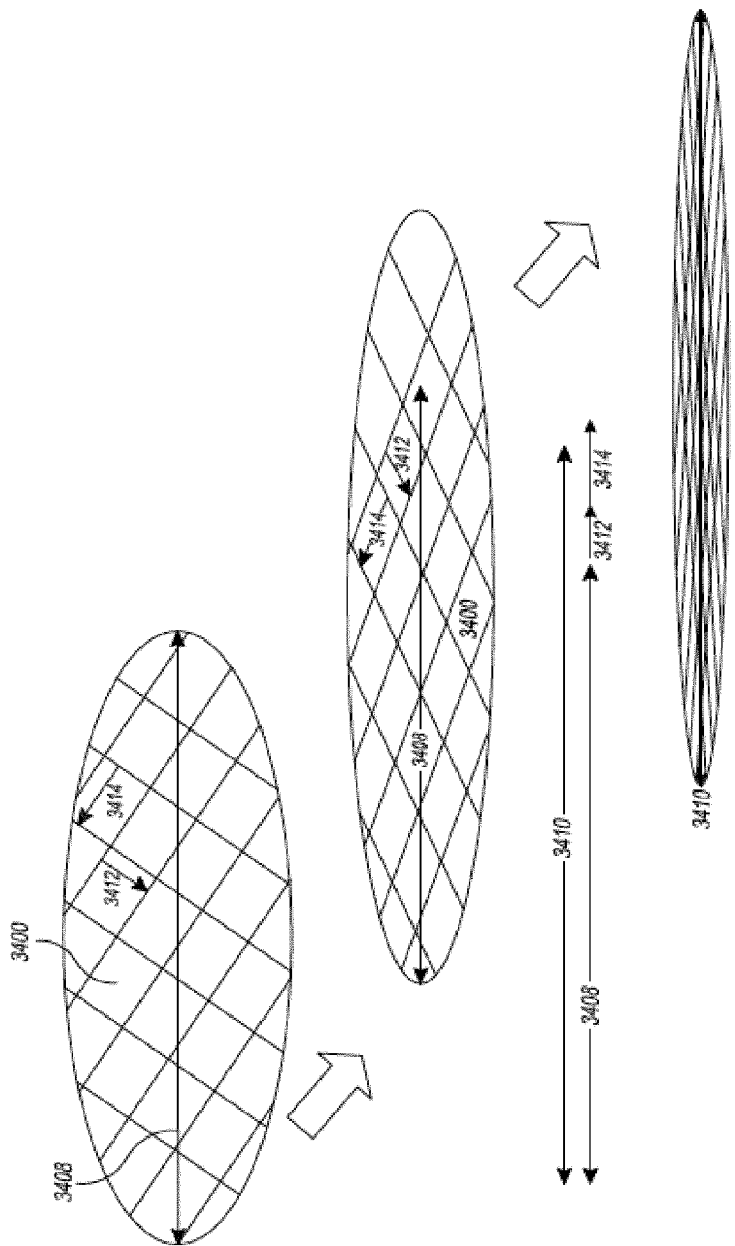

FIG. 31B illustrates an embodiment of a method for the closure of a wound through the use of a stabilizing structure 3400 that collapses and lengthens when a wound is treated under negative pressure. As illustrated, the stabilizing structure 3400 may be cut to an appropriate size to approximate the shape of the wound (e.g., in an oval shape), and the stabilizing structure is placed in the wound 3405. In some embodiments as described above, the stabilizing structure may have a plurality of diamond-shaped cells, and the cells are arranged in the wound in an orientation that causes the cells to be flattened as the lateral edges of the wound come closer together, while becoming longer along the longitudinal axis of the wound. It will be recognized that while this structure is configured to collapse under negative pressure horizontally within the wound in a direction perpendicular to the longitudinal axis of the wound, the structure is substantially rigid in the vertical direction. Line 3408 represents the length of the structure prior to lengthening under negative pressure, while line 3410 represents the final length of the structure after collapsing and lengthening under negative pressure. Lines 3412 and 3414 represent the lengths of particular sections within the stabilizing structure. In certain embodiments, when a wound is treated with application of negative pressure, the structure will collapse inward on one axis, thereby lengthening the structure by some additional amount in another axis that can be the sum of the lengths of lines 3412 and 3414. In some embodiments, the structure can lengthen by amounts other than the sum of lines 3410 and 3412.

In some embodiments, the collapse can occur slowly, thereby applying increasing longitudinal tension over a long period of time. In certain embodiments, the collapse and lengthening of the structure can occur immediately upon application of negative pressure. In further embodiments, the collapse can occur at any rate.

Figure 32A:
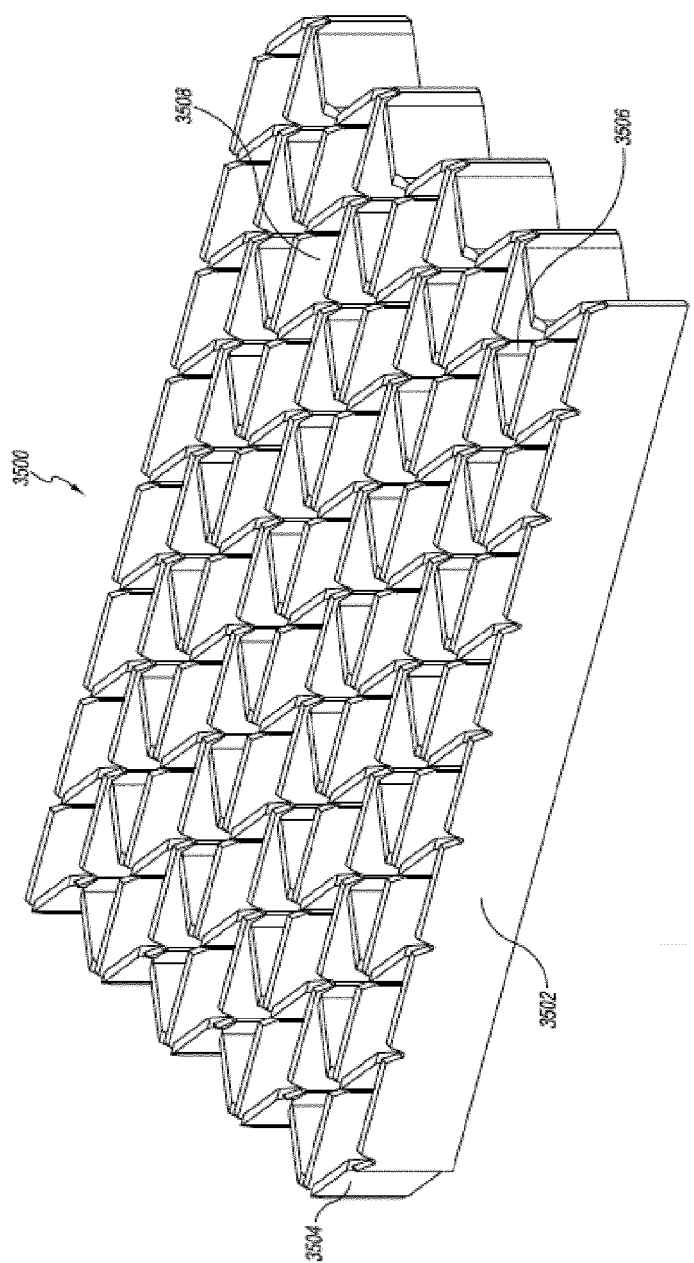
FIGS. 32A-C illustrate multiple views of an embodiment of a stabilizing structure.
Figure 32B:
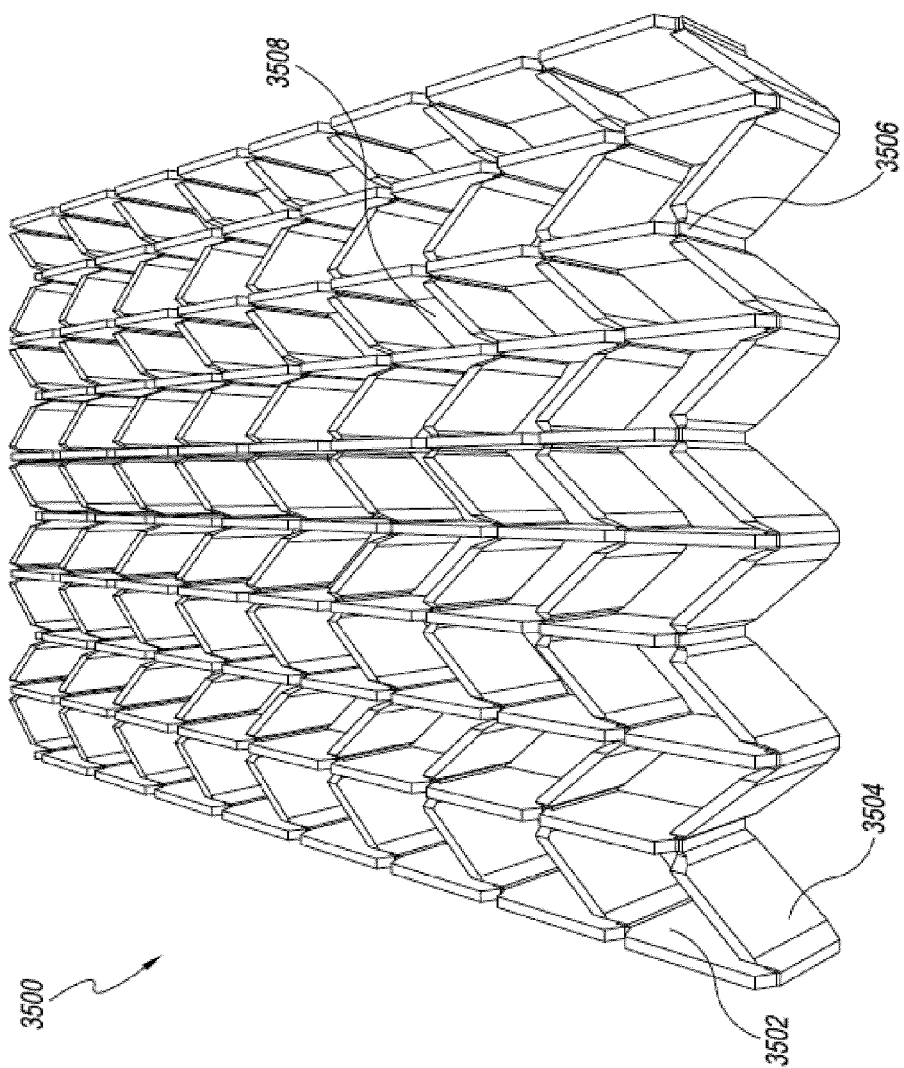
Figure 32C:
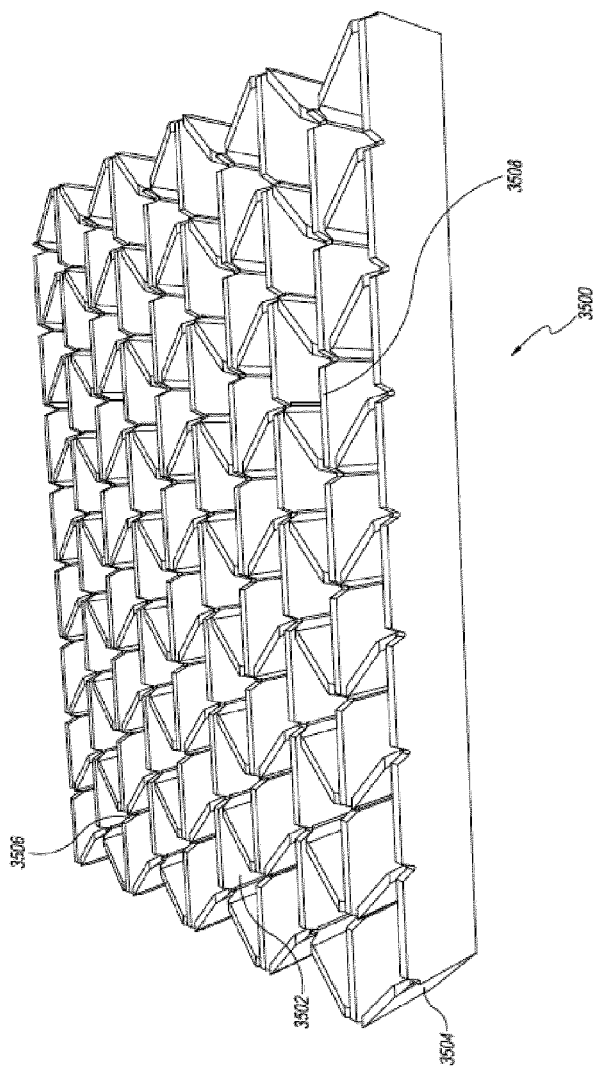

FIGS. 32A-C illustrate another embodiment of a stabilizing structure 3500. The stabilizing structure 3500 comprises a plurality of elongate strips 3502 arranged in parallel, and whose longitudinal length can be aligned with the longitudinal axis of a wound when placed in a wound. The stabilizing structure further comprises a plurality of intervening members 3504 connected to the elongate strips 3502 by a plurality of joints 3506. As illustrated, the plurality of intervening members 3504 between adjacent elongate strips 3502 define a row of cells 3508 between each pair of adjacent elongate strips.

In some embodiments, the elongate strips 3502 may be rigid, semi-rigid, and/or flexible. In some embodiments, the elongate strips 3502 are compressible. As illustrated in FIGS. 32A-32C, one embodiment comprises a plurality of strips that are rigid in a vertical dimension but also are flexible and capable of bending along their length.

In some embodiments, the intervening members 3504 may be rigid, semi-rigid, and/or flexible. In some embodiments, the intervening members 3504 are compressible. As illustrated in FIG. 32A-32C, one embodiment comprises intervening members in the form of panels equally spaced apart between adjacent strips, to define a plurality of similar-shaped (e.g., diamond-shaped) cells. In other embodiments, the intervening members need not be equally spaced. The intervening members may be attached to the strips by joints 3506 in the form of a hinge (e.g., a living hinge or a more flexible piece of material between the strips and the intervening members).

In some embodiments, the plurality of intervening members 3504 are configured to pivot relative to the elongate strips 3502 and to collapse so as to allow the elongate strips to collapse relative to one another and come closer together. In some embodiments, the joints 3506 are configured to pivot and collapse in only one direction. In certain embodiments, the joints 3506 are configured to pivot and collapse in both directions, comprising a full 180 degrees of rotation relative to the elongate strips 3502. In certain embodiments, when the joints pivot, they pivot completely so as to rest the intervening members 3504 against the elongate strips 3502. In some embodiments, the joints do not pivot completely and the intervening members do not come to rest against the elongate strips 3502.

Preferentially, in certain embodiments, by controlling the direction in which the pivoting occurs, the collapsed length of the stabilizing structure 3500 can be controlled. In particular embodiments, because of the rigidity of the elongate strips, the cells 3508 in a row between adjacent elongate strips are configured to collapse together as the adjacent elongate strips 3502 collapse relative to one another. In some embodiments, one or more rows of cells 3508 between adjacent strips 3502 are configured to collapse in a first direction, and one or more rows of cells between adjacent strips 3502 are configured to collapse in a second direction opposite the first direction. As illustrated in FIGS. 32A-32C, the orientation of cells in adjacent rows alternates so that cells of a first row collapse in a first direction, and cells of a next row collapse in an opposite second direction. Joints 3506 may be configured so that joints 3506 in adjacent rows collapse in different directions.

By configuring the joints 3506 and/or cells of the stabilizing structure to pivot and collapse in preferred directions, the length of the collapsed structure can be modified. The embodiment shown in FIGS. 32A-32C will have a shorter collapsed length than a structure where all the rows of cells 3508 are configured to collapse in the same direction. Thus, the collapsed length of the structure can be controlled depending on the orientation of the cells and the direction in which the intervening members collapse between adjacent rows. In some embodiments as described above with respect to FIGS. 31A-31B, the stabilizing structure preferably lengthens after collapse under negative pressure. In other embodiments, it may be preferred that the stabilizing structure not lengthen after collapse under negative pressure.

In FIGS. 32A-32C, the intervening members 3504 in adjacent rows are generally aligned so that the intervening members connect to the elongate strips at approximately the same location on opposite sides of the strip and share the same joint 3506 location. In other embodiments, the intervening members 3504 between a first elongate strip 3502 and a second elongate strip 3502 are offset relative to intervening members 3504 between the second 3502 and a third adjacent strip 3502. In these embodiments, the intervening members 3504 are staggered such that they do not share the same joint 3506 location.

As shown in FIGS. 32A-32C, the enclosed cell 3508 formed by two intervening members and two sections of the elongate strips is a quadrilateral. In some preferred embodiments, the enclosed shape can be a square, rectangle, diamond, oblong, oval, and/or parallelepiped. In some embodiments, the enclosed shape is a rhomboid. In certain embodiments the enclosed shape is a trapezoid.

In certain preferred embodiments, the joint 3506 may be configured to limit the range of motion of the intervening member 3504, and may be used to prevent the intervening members 3504 from becoming fully perpendicular to the adjacent strips. Thus, the joint may be configured to pre-set the intervening members 3504 in a partially collapsed position. For example, a lip or other portion of material at the joint may be used to limit the angular motion of the intervening members. The lip or other portion of material may also prevent the joint from collapsing completely flat. In some embodiments, the joint may be configured to prevent the intervening members from rotating in 180 degrees along the plane formed by the strips.

In some embodiments, when the stabilizing structure 3500 is placed in a wound as part of a fabricated wound filler, the elongate strips 3502 are positioned generally parallel to the lateral edges of the wound. Preferably, the stabilizing structure is configured in the wound such that the elongate strips are positioned parallel to the longitudinal axis of the wound, as described with respect to FIGS. 31A-31B above. The strips may also bend along their length and bow outwardly to fit within the wound. The stabilizing structure may be cut to an appropriate size to fit the structure in the wound. In other embodiments, the elongate strips 3502 are positioned perpendicular to the edge of the wound, or may not be oriented along any edge of the wound.

In the embodiments of FIGS. 32A-32C, as well as in other embodiments of stabilizing structures described in this section or elsewhere in this specification, the strips can be constructed from a material selected from the group consisting of silicone, polyurethane rigid plastics, semi-rigid plastics, flexible plastic materials, composite materials, biocompatible materials and foam. In some embodiments, the intervening members can be constructed from a material selected from the group consisting of silicone, polyurethane, rigid plastics, semi-rigid plastics, flexible plastic materials, composite materials, biocompatible materials and foam. In some embodiments, the stabilizing structure is surrounded by absorbent materials. In certain embodiments the stabilizing structure is surrounded by non-absorbent materials. In some embodiments the material surrounding the stabilizing structure is foam. In particular embodiments, the spaces between the intervening members 3504 and the elongate strips 3502 are filled with foam.

Figure 33A:
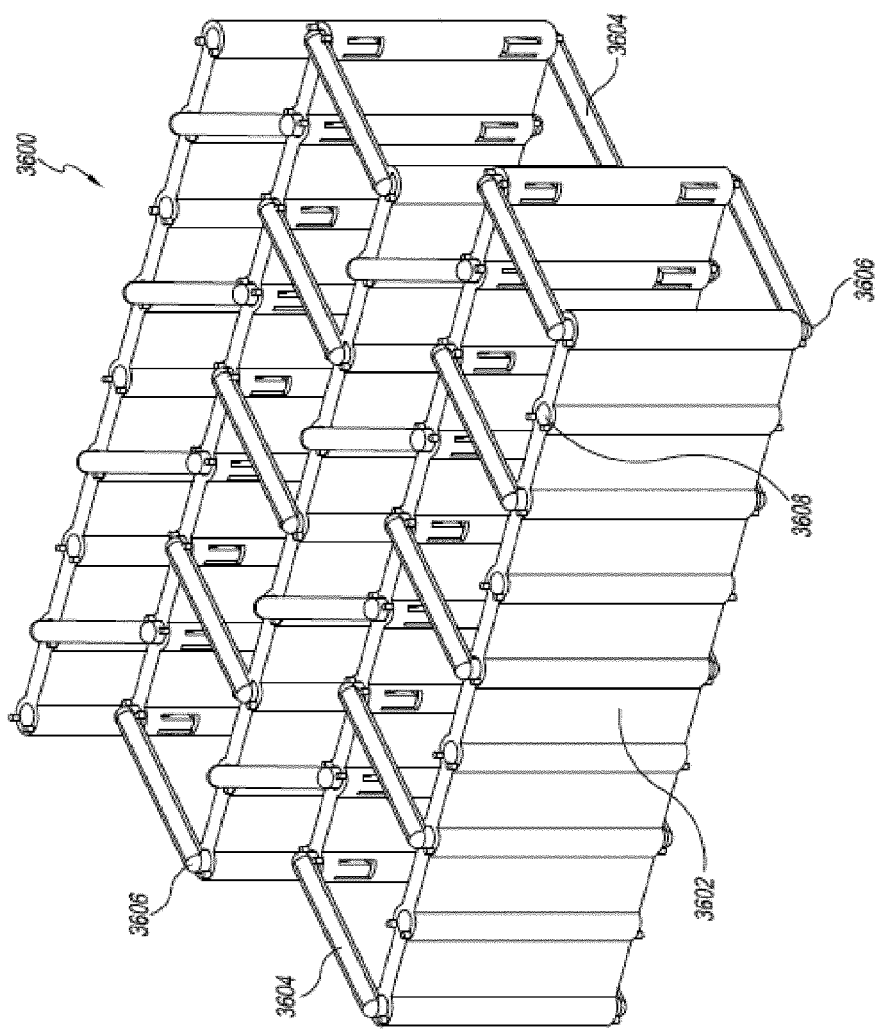
FIGS. 33A-G illustrate multiple views of an embodiment of a stabilizing structure.

FIGS. 33A-G illustrate an embodiment of a stabilizing structure 3600 that is similar to the ones described above in relation to FIGS. 32A-C and FIG. 31B. As illustrated in FIG. 33A, in some embodiments, the stabilizing structure 3600 comprises a plurality of elongate strips 3602 connected by a plurality of intervening members 3604 at a plurality of joints 3606. As illustrated in FIGS. 33A-G, the plurality of intervening members comprise a plurality of bars 3604 connecting adjacent elongate strips and connected to the elongate strips at upper and lower joint locations. The plurality of joints in one embodiment comprise a plurality of pins 3606 connected to the bars and received in upper and lower vertical openings in the strips 3602. Other types of joints are also contemplated, including ball joints. The bars are preferably equally spaced within a row between adjacent elongate strips, and may be offset or staggered in an adjacent row, such that in an adjacent row, the bars connect to the elongate strip at a location between the bars of the first row. In other embodiments, the intervening member can comprise a wire or other elongate structure configured to extend between adjacent elongate strips.

Figure 33B:
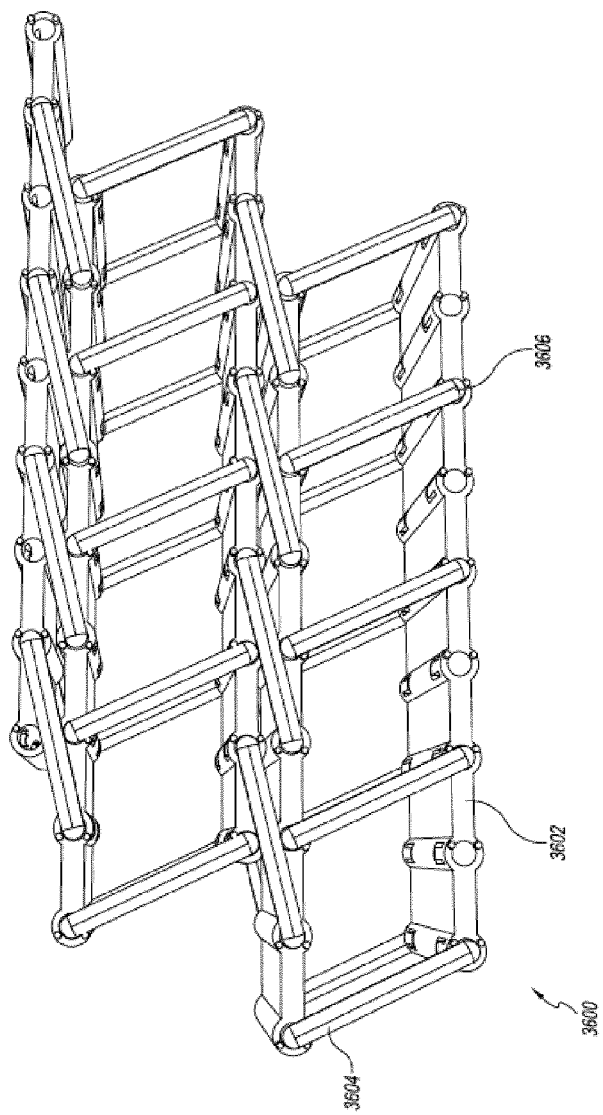
Figure 33C:
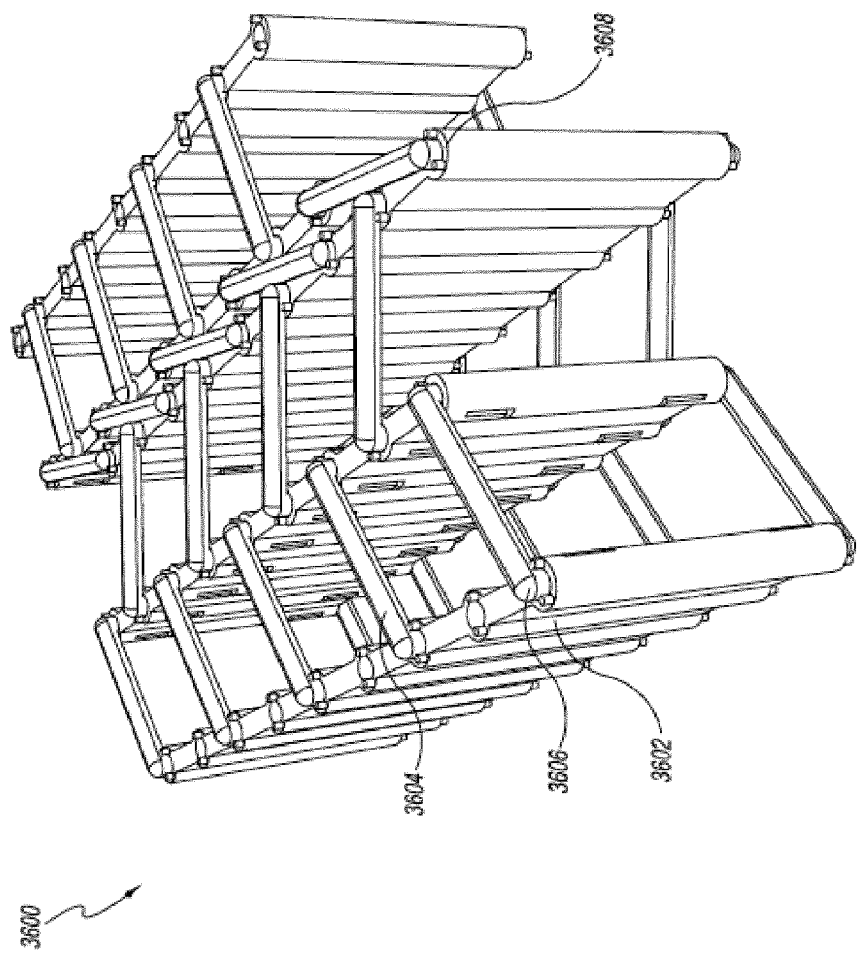
Figure 33D:
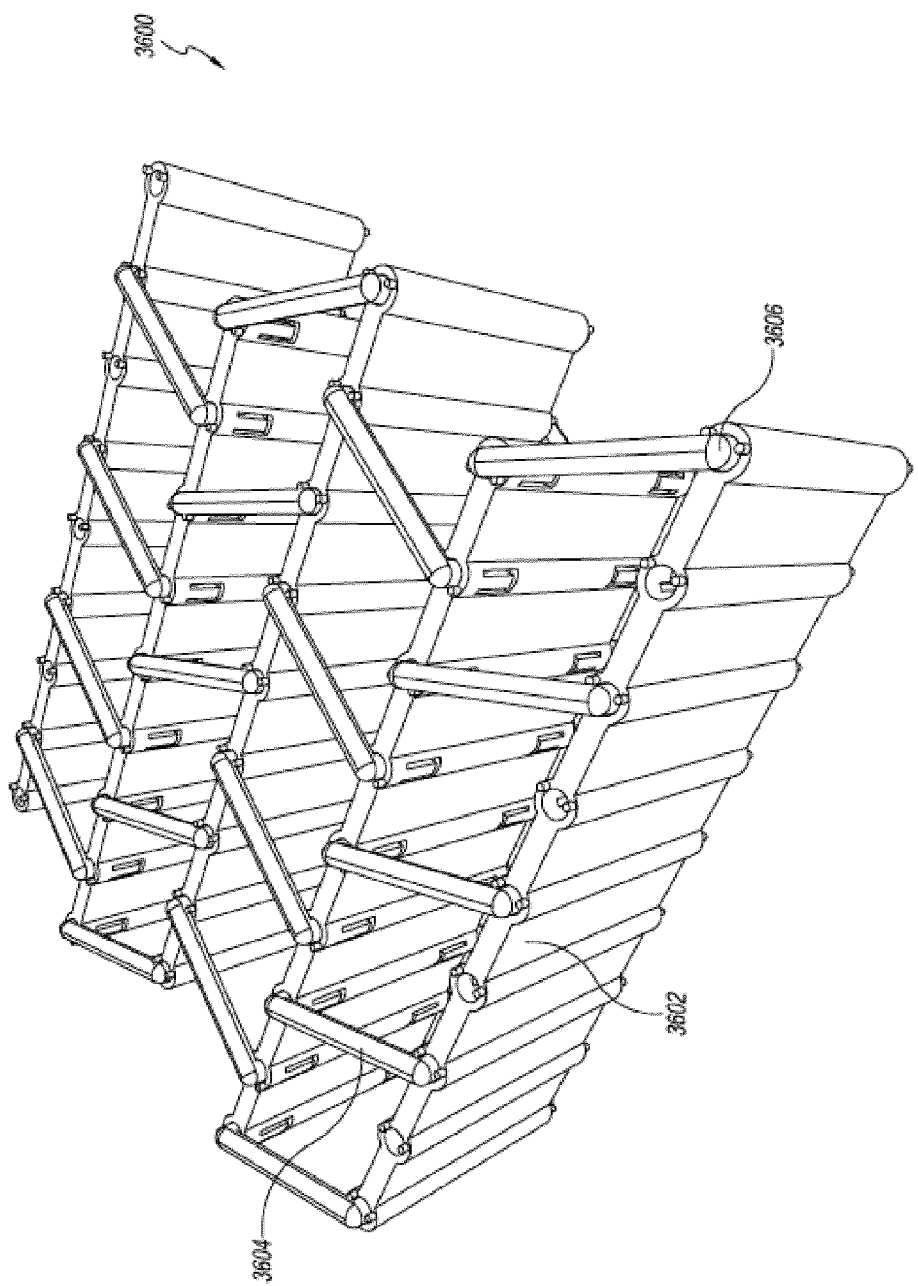

Preferably, as illustrated in the top view of FIG. 33B and the front view of FIG. 33C, in certain embodiments the pins cause the bars to protrude above the vertical top and the vertical bottom of the elongate strips 3602. In other embodiments, the bars 3604 may be connected to the elongate strips so that they are located flush with the vertical top and vertical bottom of the elongate strips 3602. In further other embodiments, the bars 3604 may be connected so that they are located below the vertical top of the elongate strips 3602 and above the vertical bottom of the elongate strip.

As illustrated in FIGS. 33A and 33C, the joints 3606 can preferably comprise a plurality of stops 3608 configured to limit the rotation of the bars relative to the strips. The stops may protrude vertically from the strips to limit the movement of the bars. For example, these stops may be used to prevent the bars from becoming fully perpendicular with respect to the adjacent strips, and may be used to provide a preferential direction of collapse to adjacent rows. As shown in FIG. 33A, a first row may have bars angled in a first direction, and a second row may have bars angled in a second direction. In some embodiments, there are two stops per bar on a given strip, to restrict motion in two directions. In other embodiments, there is one stop or three or more stops per bar on a given strip.

Figure 33E:
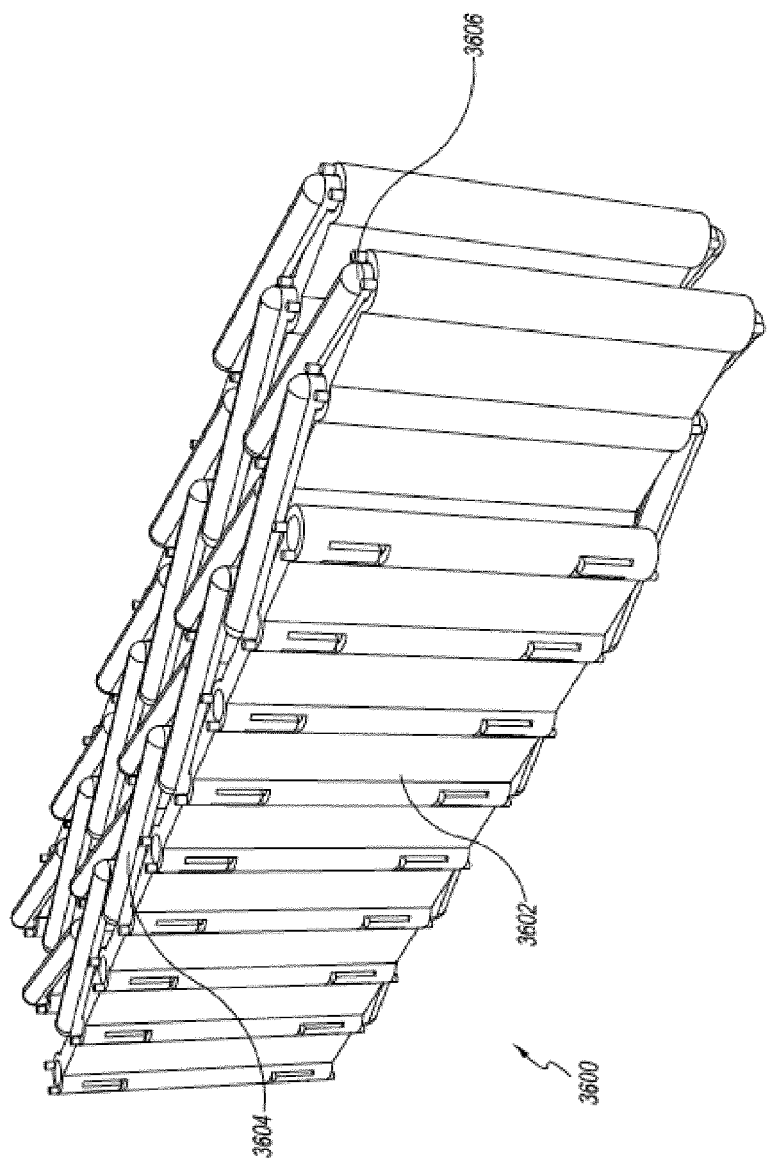
Figure 33F:
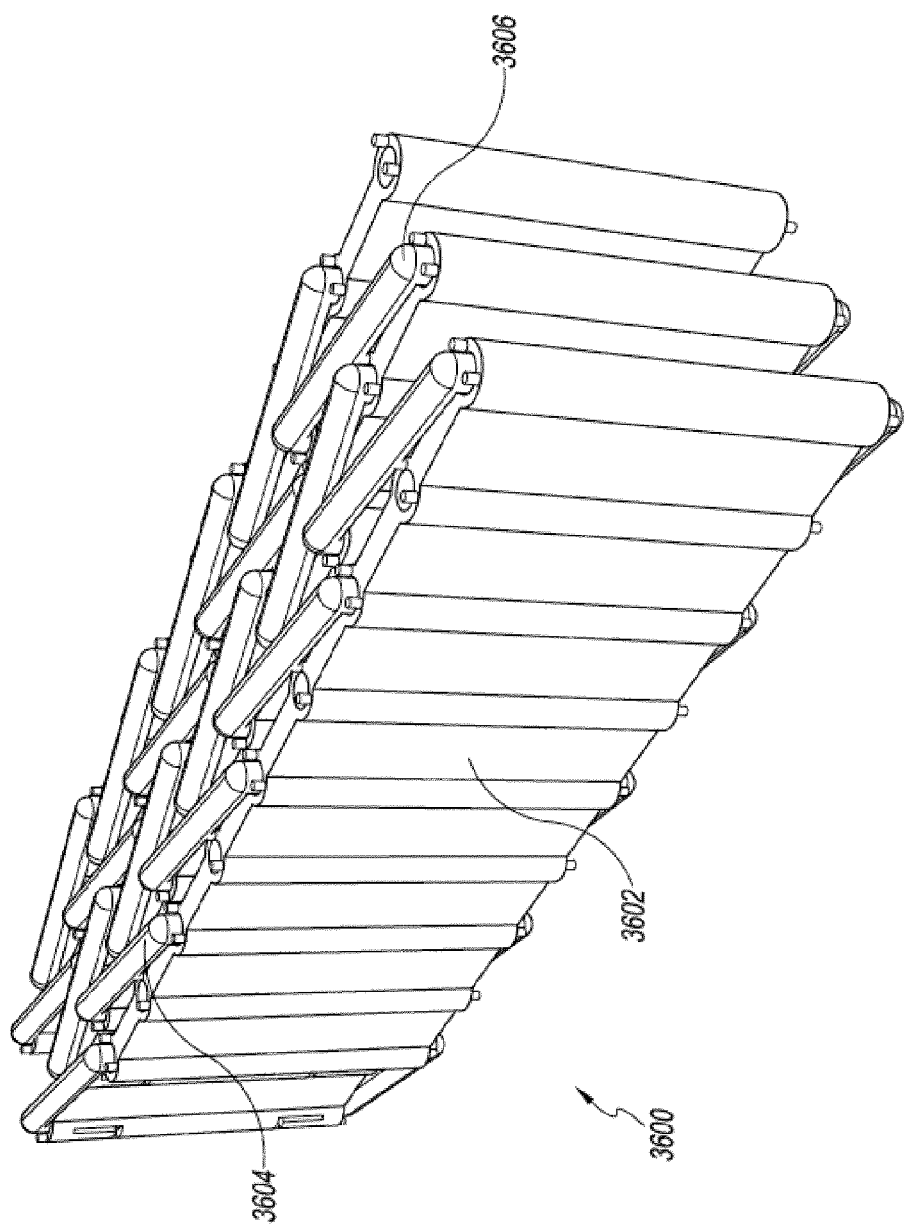
Figure 33G:
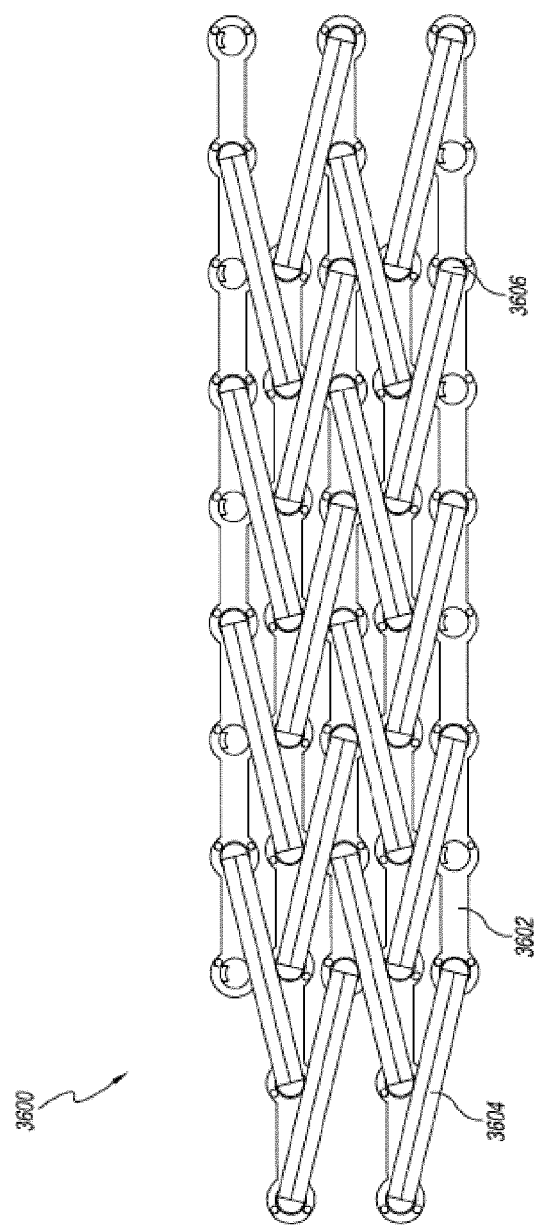

FIGS. 33E-G illustrate the stabilizing structure 3600 in a collapsed configuration. Similar to the structures of FIGS. 32A-C and FIG. 31B, the structure 3600 may be positioned in a wound in an orientation configured to collapse in a direction perpendicular to the longitudinal axis of the wound. As described above, the stabilizing structure may be surrounded by or filled with absorbent material such as foam. In one embodiment, because the vertical space between the upper and lower bars of the structure 3600 are open (as best shown in FIG. 33C), elongate blocks of foam or other compressible material may be placed in between adjacent strips to provide a desired compressibility as the structure collapses.

Figure 34:
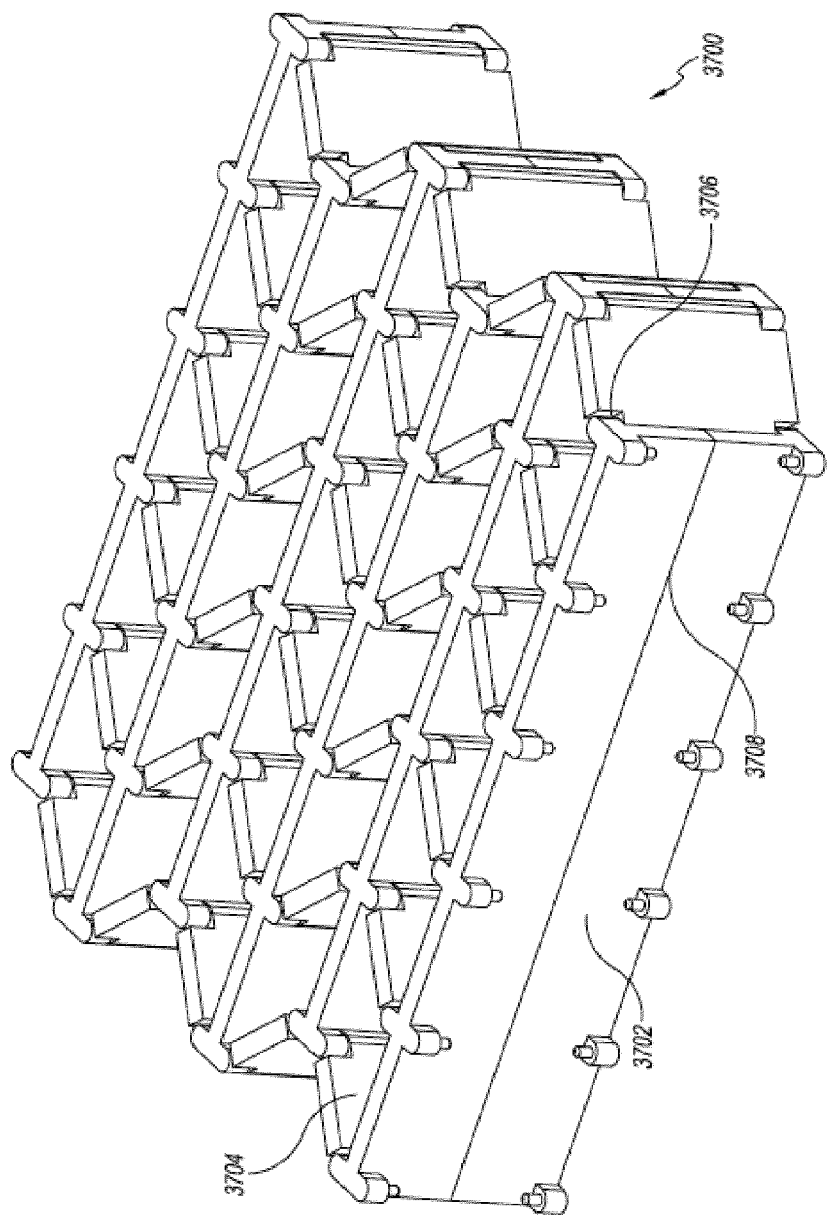
FIG. 34 illustrates one embodiment of a hinged stabilizing structure for closing a wound.

FIG. 34 illustrates an embodiment of a stabilizing structure 3700 that is similar to the structures described above in relation to FIG. 31B, FIGS. 32A-C and FIGS. 33A-G. In certain embodiments, the stabilizing structure 3700 can collapse in any manner described above. The elongate strip 3702 as illustrated is formed in two halves, and can be separated along line 3708. The intervening members 3704 can be in the form of panels as described above. The joints 3706 on the upper half of an elongate strip may comprise pins located on opposite sides of the strip extending downward from the top of the upper half of the strip. The joints 3706 on the lower half of an elongate strip may comprise pins located on opposite sides of the strip extending upward from the bottom of the lower half of the strip. These pins may engage vertical openings located at the four corners of the intervening member 3704. As the upper and lower halves are brought together, the pins may engage the openings in the panels. The upper and lower halves may be secured by any number of mechanisms, such as with adhesive and mechanical connections.

In the FIG. 34 embodiment, with the ability to separate the two halves of 3702 along line 3708, intervening members 3704 may be easily removed or replaced. In some embodiments, only some of the intervening members 3704 are removed. In certain embodiments, alternating intervening members 3704 are removed. In certain preferred embodiments, intervening members are removed in a preferential manner so as to allow the stabilizing structure 3700 to collapse in a controlled manner most appropriate for a particular wound. For example, the joints 3706 may have variable levels of resistance to rotation, thus allowing for control over the collapse of the structure by adding or removing the intervening members 3704. Additionally, stops such as those described in relation to FIG. 33A, could be incorporated into the structure or any other structure described in this section or elsewhere in this specification to further control collapse. In some embodiments, the intervening members are replaced or removed to maximize the collapsed length of the structure 3700. In certain embodiments, intervening members are replaced or removed to minimize the collapsed length of structure 3700. In some embodiments, intervening members are replaced or removed to attain a desired length for the collapsed structure.

Figure 36:
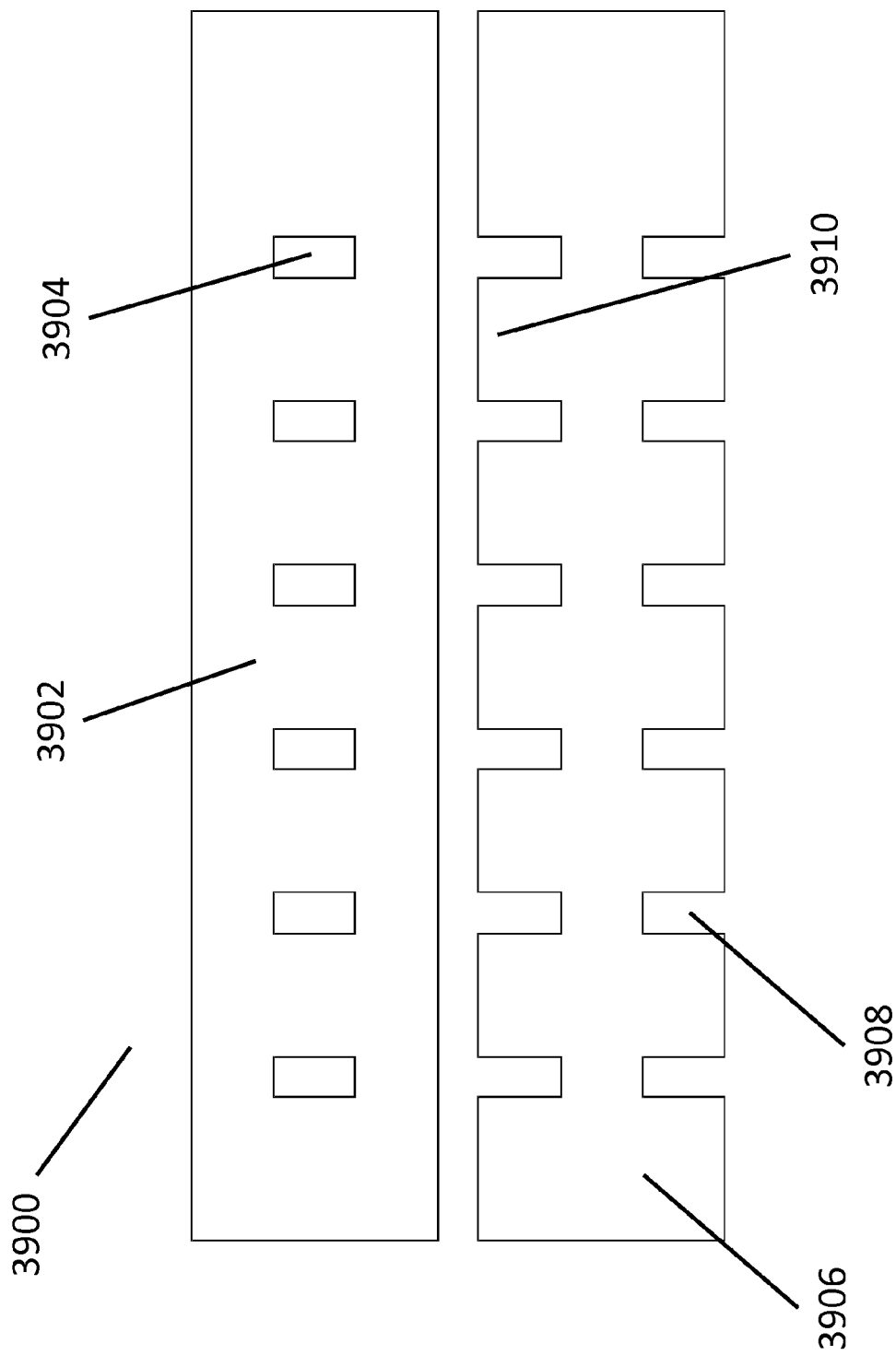
FIG. 36 illustrates one embodiment of a stabilizing structure for a wound.

FIG. 36 illustrates another embodiment of elongate strips 3900 that may be used to form a stabilizing structure, similar to that described in FIGS. 11A-D. The first strip 3902 illustrated in the upper portion of FIG. 36 may be an elongate strip having a plurality of spaced apart openings 3904 extending along a central axis of the strip. The second strip 3906 illustrated in the lower portion of FIG. 36 may have a plurality of spaced apart notches 3908 extending from the upper and lower edges of the second strip and separate by a middle portion. A plurality of the first strips 3902 and a plurality of the second strips 3906 can be assembled into a stabilizing structure similar to what is shown in FIGS. 11A, 11C and 11D, wherein the plurality of first strips 3902 are arranged in parallel to each other, and the plurality of second strips 3906 are arranged in parallel to each other. The plurality of first 3902 and second strips 3906 engage one another by the middle portions 3910 of the second strips positioned through the openings 3904 in the first strips, to place the plurality of first strips at an angle to the plurality of second strips. This structure is configured to collapse in a horizontal plane while remaining rigid in the vertical plane.

Figure 37:
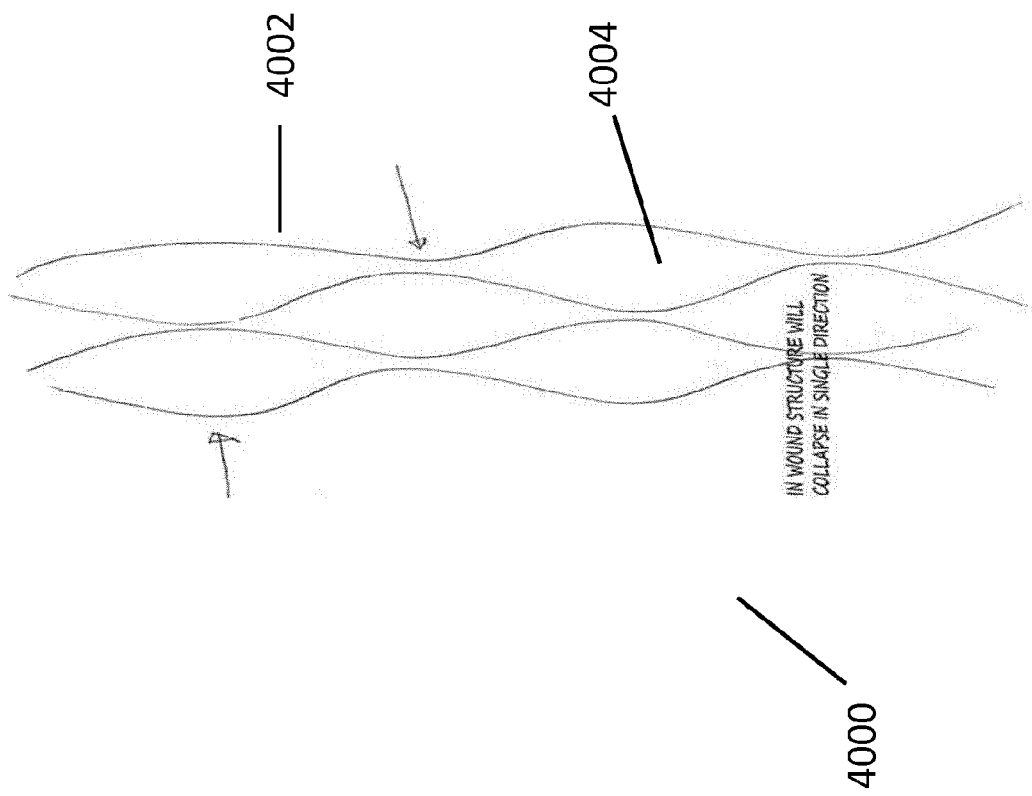
FIG. 37 illustrates an embodiment of a stabilizing structure for a wound cut from a roll.
Figure 38:
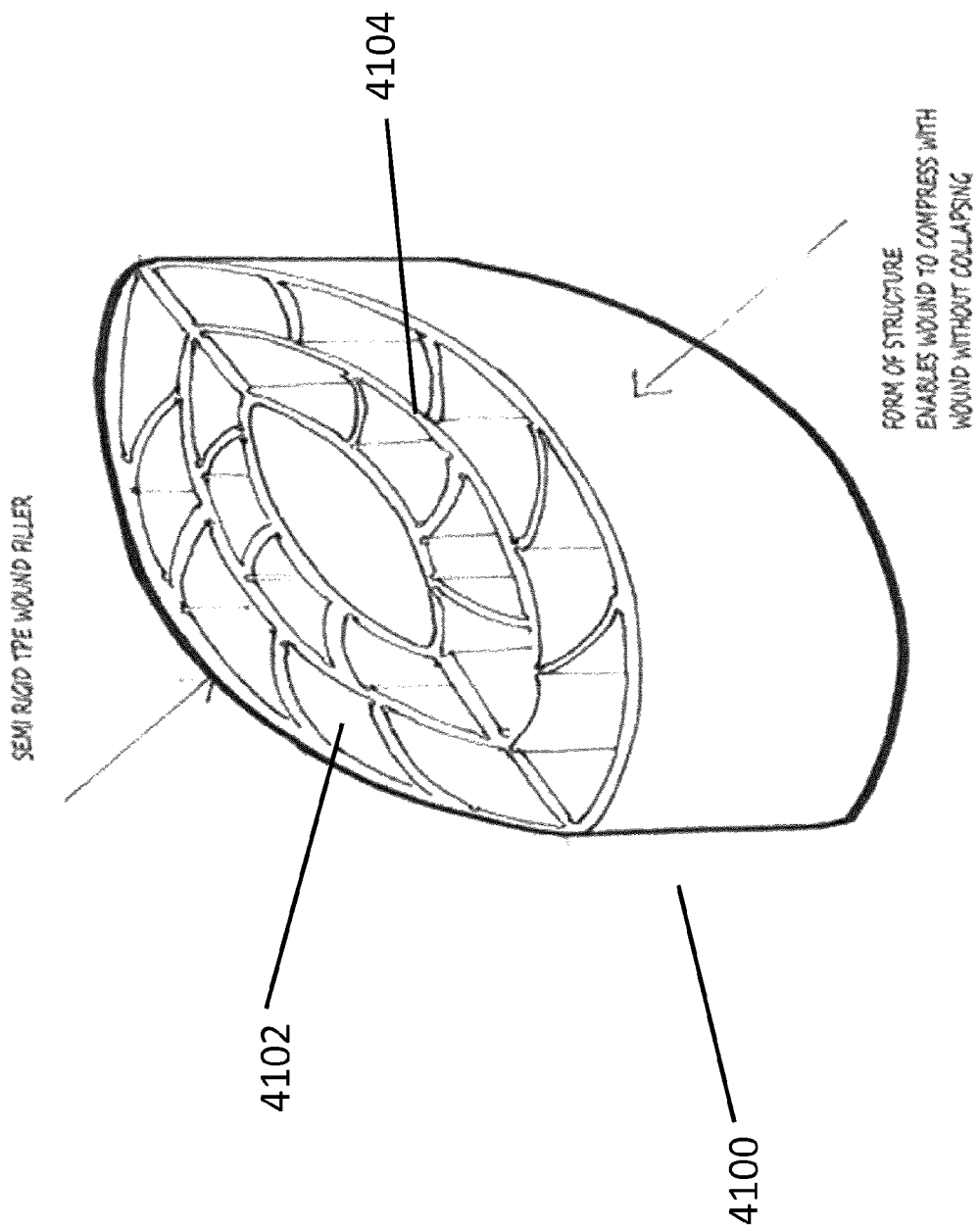
FIG. 38 illustrates an embodiment of a stabilizing structure having an oval shape.

FIG. 37 illustrates an embodiment of a stabilizing structure 4000 similar to the embodiment of FIG. 16 described above. A plurality of longitudinal strips 4002 can be provided each in the form of a wavy strip that, when joined face-to-face, form one or more circular or ovoid cells 4004. FIG. 38 illustrates another embodiment of a stabilizing structure. In this embodiment, the stabilizing structure 4100 has an elongate, preferably oval shape, wherein cells 4102 within the oval shape have a plurality of cells arranged in a plurality of concentric rings 4104. In the embodiment illustrated, a central oval cell is surrounded by two oval-shaped rings. Other embodiments can include more than two oval-shaped rings.

Stabilizing Structures and Wound Closure Devices of FIGS. 39A-43

FIGS. 39A-F illustrate embodiments of a stabilizing structure 4200 that are similar to the embodiments described above in relation to FIGS. 32A-35. The stabilizing structure may comprise a plurality of elongate strips 4202 arranged in parallel, whose longitudinal length can be aligned with the longitudinal axis when placed in a wound. The stabilizing structure can further comprise a plurality of intervening members 4204 connected to the elongate strips 4202 via joints 4206. In certain embodiments, the stabilizing structure 4200 can collapse in any manner described in this section or elsewhere in this specification with or without the application of negative pressure. For example, the stabilizing structure may collapse significantly more in one plane than in another plane. In some embodiments, the stabilizing structure can be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

The stabilizing structure 4200 and all stabilizing structures and wound closure devices described in this section or elsewhere in this specification can collapse on a variety of timescales in a dynamic fashion. As described elsewhere in the specification, the stabilizing structures and/or wound closure devices may be incorporated as various regions within a fabricated wound filler, thus the fabricated wound filler can collapse in any manner described herein this section or elsewhere in the specification. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can placed into a wound as part of a fabricated wound filler for a period of time and then removed or replaced with another fabricated wound filler comprising a stabilizing structure. For example, a fabricated wound filler comprising a stabilizing structure could be inserted into a wound for a period of time, promoting closure of the wound by drawing the edges closer together. After a period of time has passed, the fabricated wound filler comprising a stabilizing structure can be replaced by a fabricated wound filler comprising a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue.

In some embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate.

In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 39A:
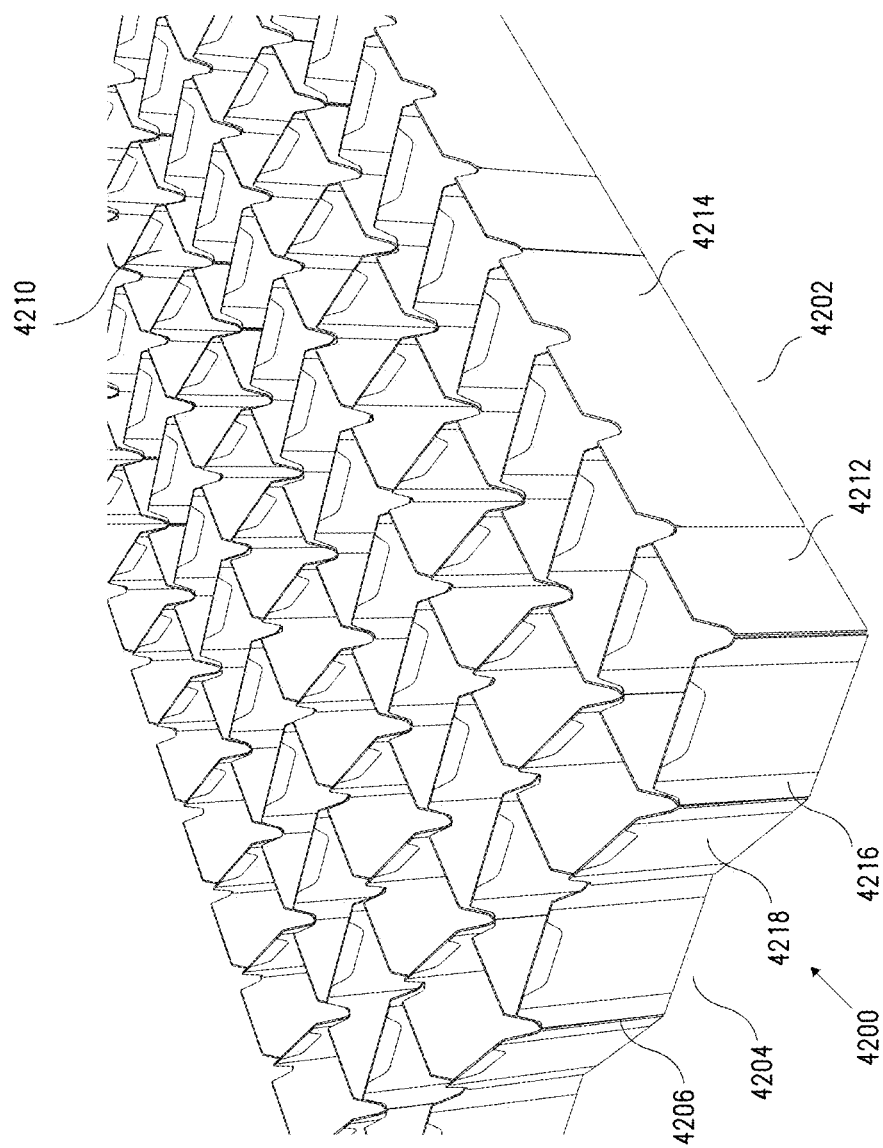
FIGS. 39A-F illustrate multiple views of an embodiment of a stabilizing structure.
Figure 39B:
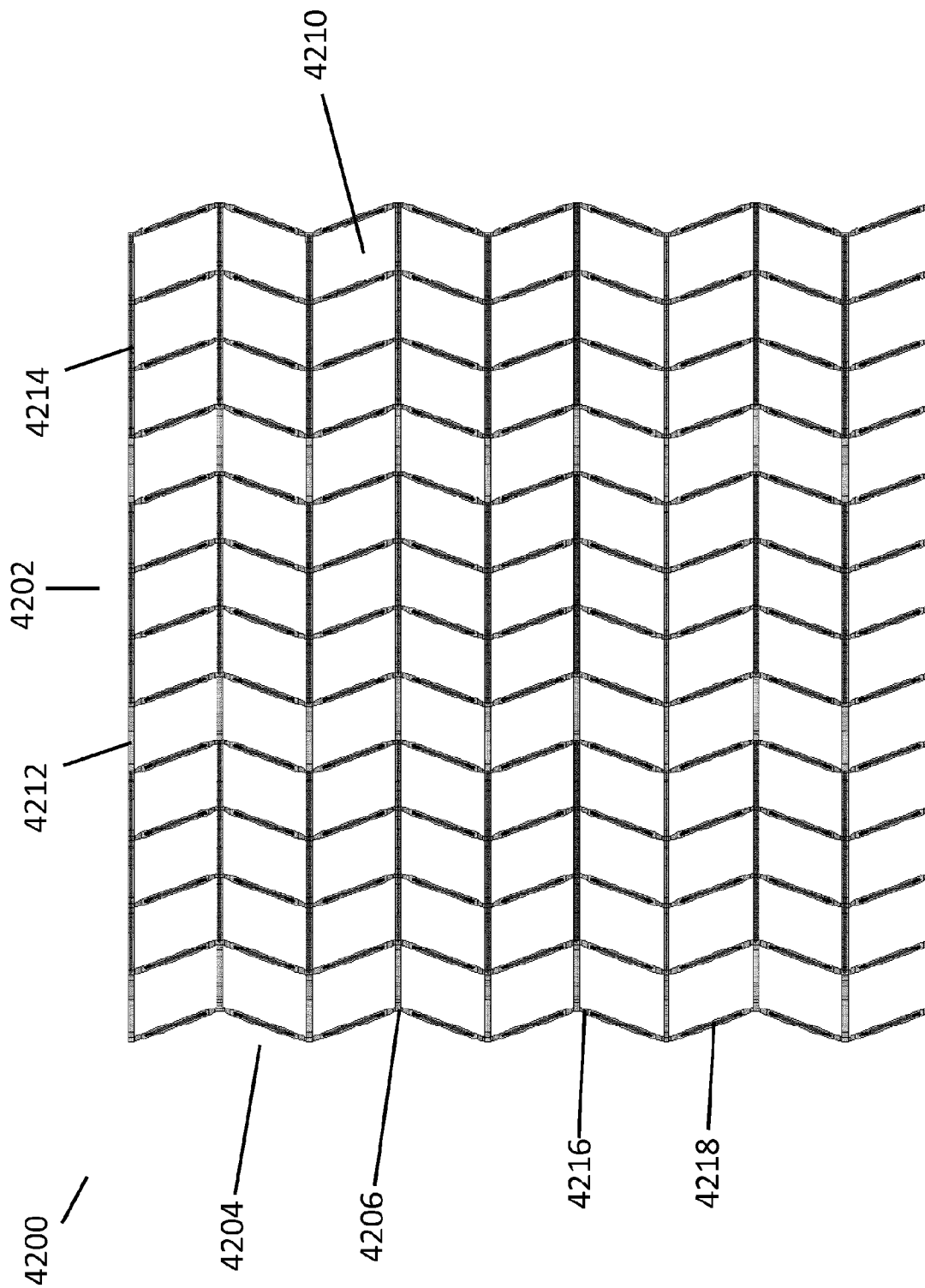

As illustrated in the perspective view of FIG. 39A and the top view of FIG. 39B, the intersection of the intervening members 4204 and the elongate strips 4202 may define a plurality of cells 4210. In certain embodiments, the cells 4210 may be of any of the shapes and sizes described in this section or elsewhere in this specification, such as those described in relation to FIGS. 32A-32C. For instance, a cell may be in the shape of a square, a diamond, an oblong, an oval, and/or a parallelepiped.

The joints 4206 are configured to allow the intervening members 4204 to collapse, similar to the joints described in FIGS. 32A-C and FIG. 34. The joints 4206 can be configured to allow the intervening members to collapse in any manner as described in this section or elsewhere in this specification in relation to other embodiments, such as those described in relation to FIGS. 32A-C. For example, the joints 4206 may be configured to allow or preferentially cause a first row of intervening members 4204 to collapse in one direction, while allowing or preferentially causing an adjacent row to collapse in another direction.

The elongate strips 4202 may comprise alternating flexing segments 4212 and supporting segments 4214. In a preferred embodiment, the flexing segments 4212 can be constructed from a flexible or semi-flexible material such as silicone and/or polyurethane. However, any flexible or semi-flexible material may be suitable. The flexing segments 4212 can flex in any direction, allowing the stabilizing structure to collapse more readily in any direction, but particularly in the horizontal plane. In a preferred embodiment, the supporting segments 4214 can be constructed from a rigid or semi-rigid material such as polyvinyl chloride (PVC). However, any rigid or semi-rigid material may be suitable. In the embodiment illustrated, the elongate strips 4202 comprise elongate strips of a first material such as silicone and/or polyurethane, with a plurality of elongate inserts of a second, more rigid material 4214 embedded into the first material. Thus, the flexing segments 4212 are the areas in the elongate strips 4202 where the more rigid inserts are not located.

As illustrated in FIGS. 39A-D, the supporting segments 4214 may be larger than the flexing segments 4212. In one embodiment, the supporting segments 4214 can be approximately three times as large as the flexing segments 4212 (such as by spanning three cells 4210). In other embodiments, the supporting segments 4214 may be the same size as the flexing segments 4212. In further embodiments, the flexing segments 4212 can be larger than the supporting segments 4214. Alternatively, the lengths and widths of the individual segments of the elongate strips 4202 can be variable. For example, the height of the supporting segments 4214 can be reduced, such that they do not extend from approximately the top to approximately the bottom of the stabilizing structure 4200. In some embodiments a smaller supporting segment could encompass approximately half the height of the elongate strip 4202. In certain embodiments, the supporting segment 4214 could be located in the upper or in the lower portion of the elongate strip. Such embodiments may be accomplished by utilizing an insert of a second material that has a smaller height than the height of the first material forming the elongate strip 4202.

In some embodiments, the supporting segment does not alternate with the flexing segment 4212 and instead, the elongate strips 4202 are comprised entirely of supporting segments 4214 (e.g., a silicone strip or other material with an embedded more rigid insert extending the entire length thereof, or simply a more rigid material by itself). Alternatively, the entirety of the elongate strip 4202 can be comprised only of flexing segments 4212 (e.g., a strip made only of silicone or other more flexible material).

In further embodiments, the supporting segments 4214 are insertable and/or removable from the elongate strips 4202, and may be inserted and/or removed to alter the collapsibility of the stabilizing structure 4200. Supporting segments 4214 can be inserted and/or removed from the stabilizing structure 4200 after it has been placed in a wound to variably control the collapse of the stabilizing structure 4200. In such embodiments, the elongate strips 4202 may form pockets that are open from one side (e.g., from the top) to allow insertion and removal of the supporting segments 4214.

Figure 39C:
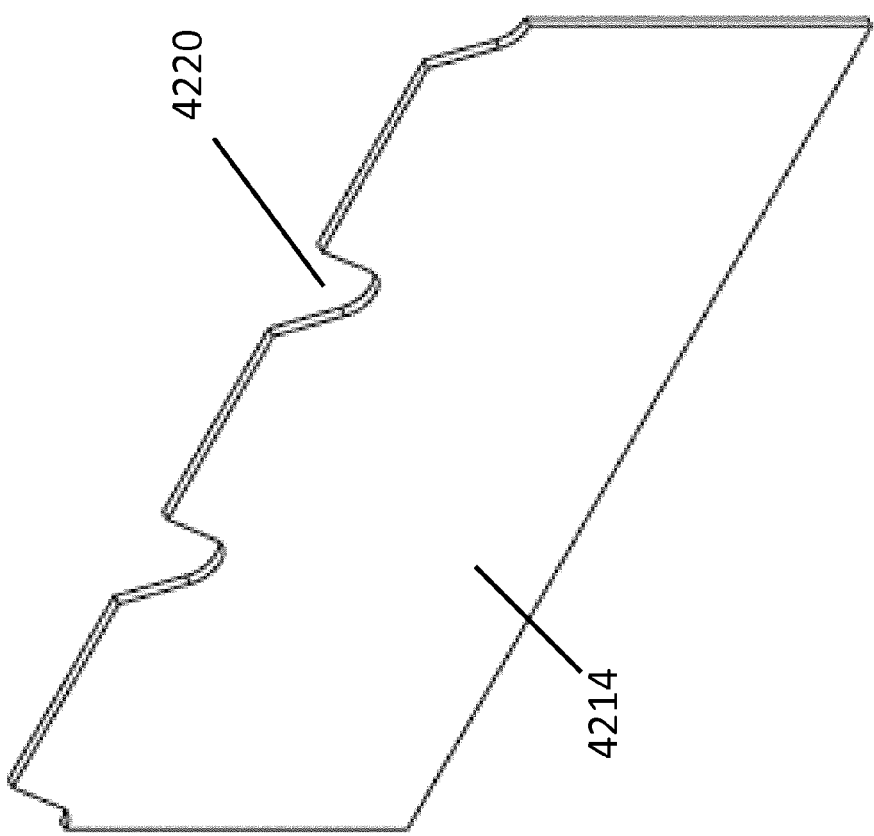
Figure 39D:
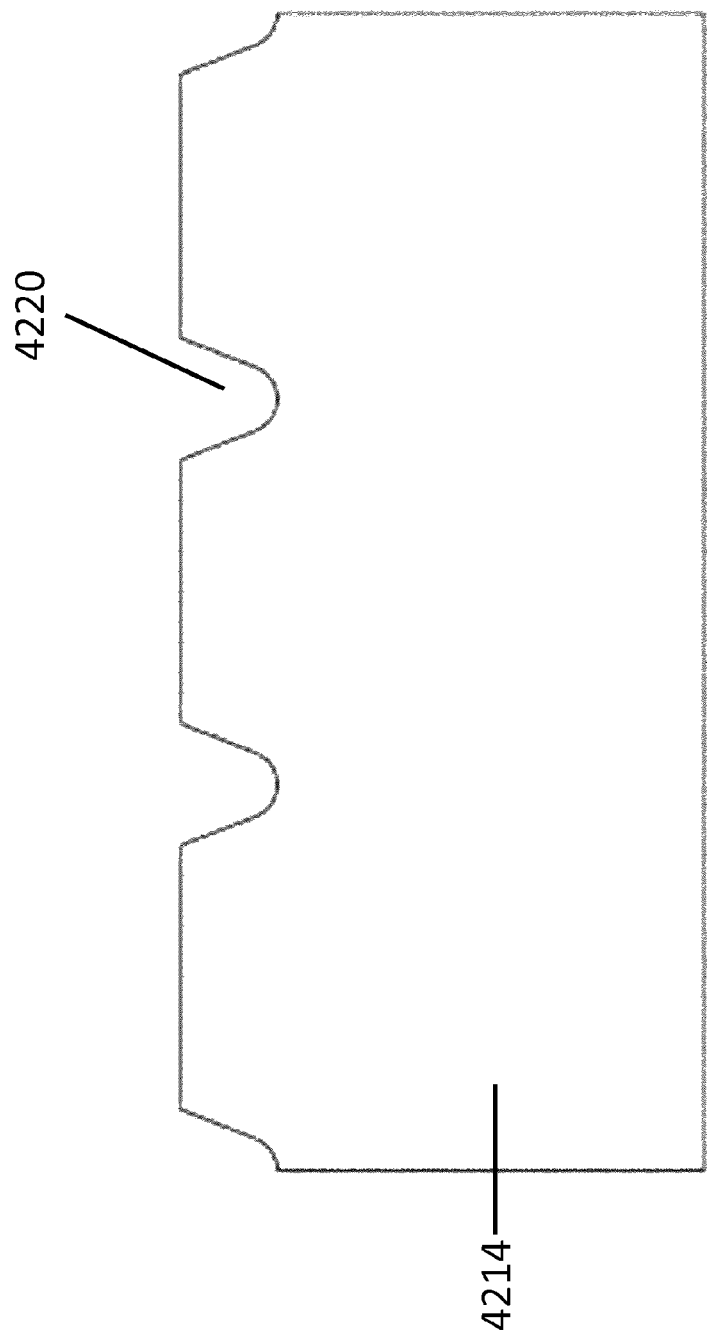

FIGS. 39C-D illustrate in greater detail an embodiment of an individual supporting segment 4214. The supporting member 4214 may be a flat, plate-like structure having a rectangular shape, with a length greater than its height, and two parallel surfaces. The supporting segment can comprise at least one notch 4220, preferably located on the upper edge of the supporting segment. In other embodiments, the notch or notches can be located on the bottom or the sides of the supporting segment. In further embodiments, the top notch could have a corresponding bottom notch. In certain embodiments, the notch could be configured so as to allow tearing of the supporting segment in a transecting line across the supporting segment. The notch or notches 4220 may advantageously provide flexibility to the structure. The notches 4220 may allow the stabilizing structure to flex more easily in the horizontal plane or in the vertical plane. The notches 4220 may further allow the stabilizing structure to twist in multiple planes. The notches 4220 may also improve fluid flow within the stabilizing structure 4200. In some embodiments, the supporting segment does not contain a notch and the uppermost edge is flat. The notch 4220 can be located at other locations on the supporting segment, for example the bottom edge or the sides. The shape of the notch can be a rounded triangle as in FIGS. 39C-D or any other similar shape.

Figure 39E:
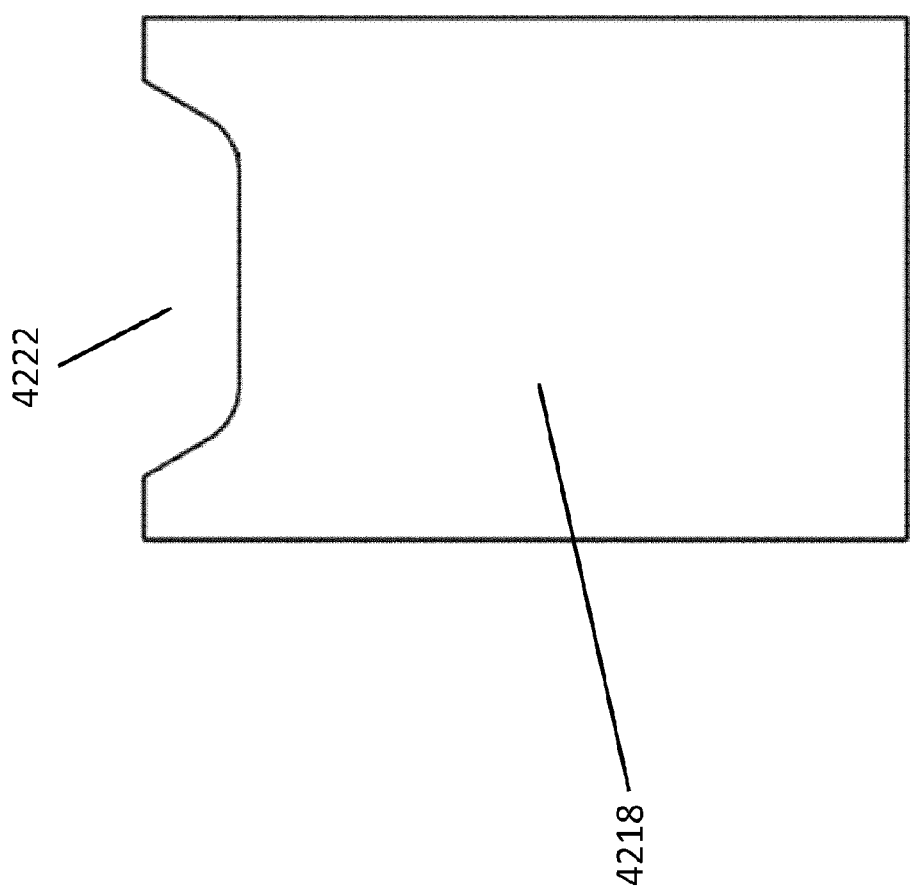
Figure 39F:
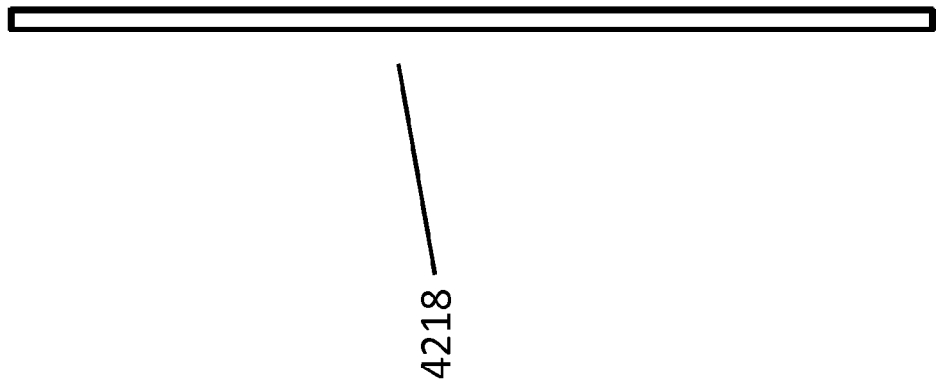
Figure 40A:
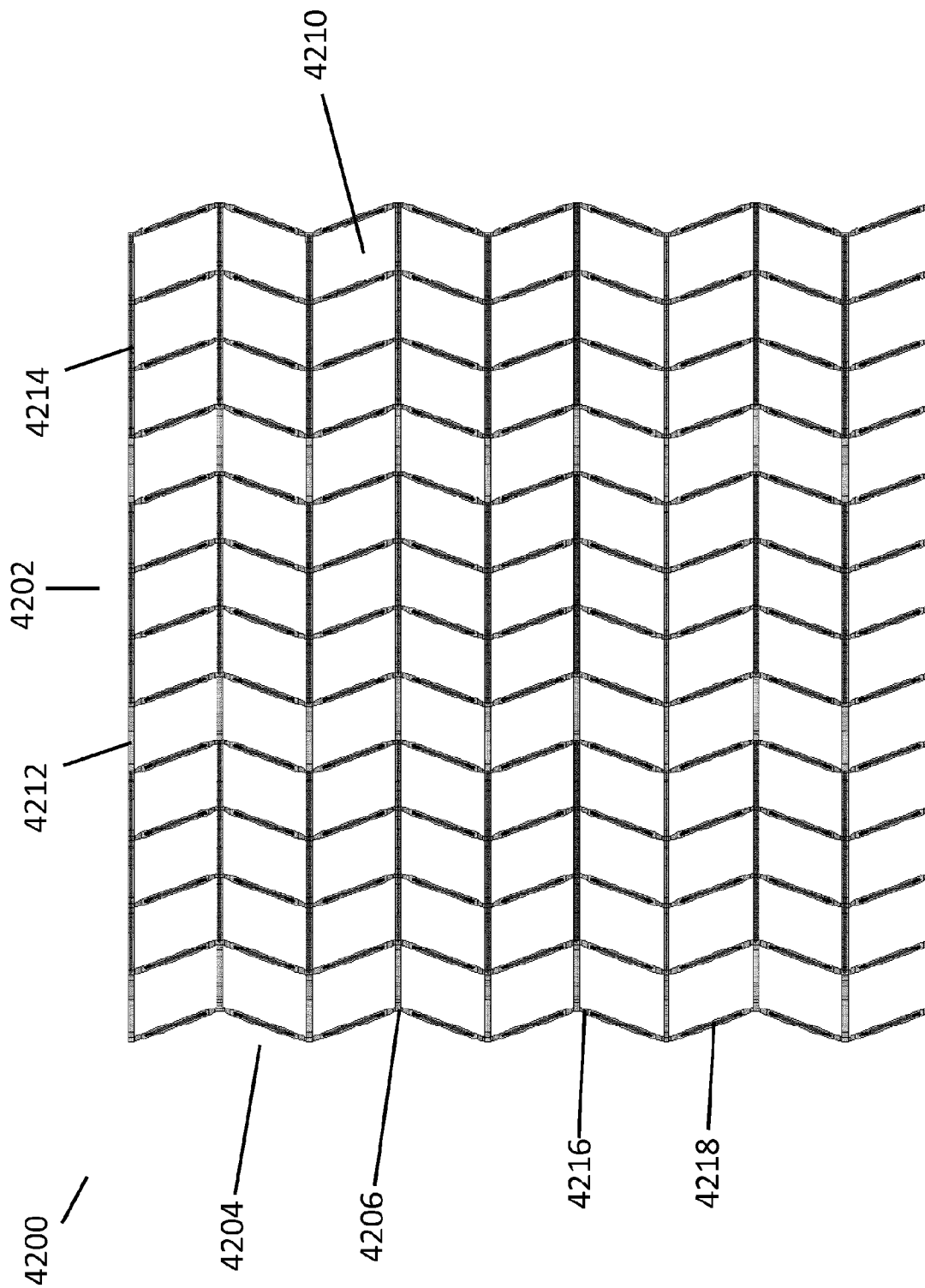
FIGS. 40A-D illustrate multiple views of an embodiment of a stabilizing structure comprising openings for fluid passage.
Figure 40B:
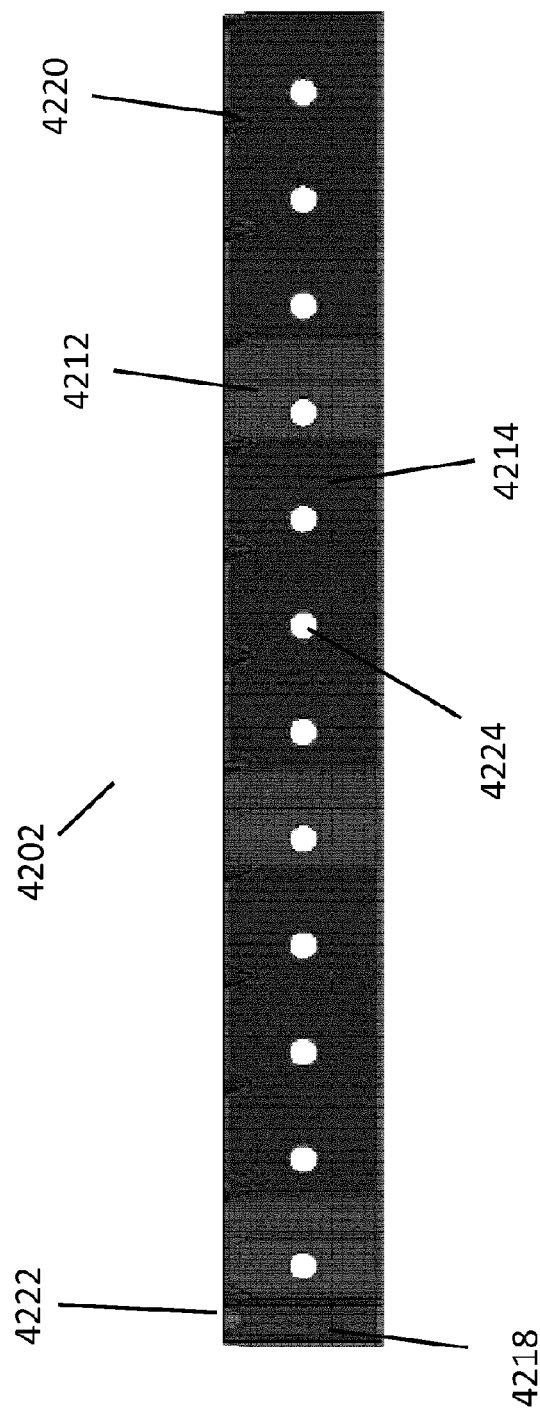
Figure 40C:
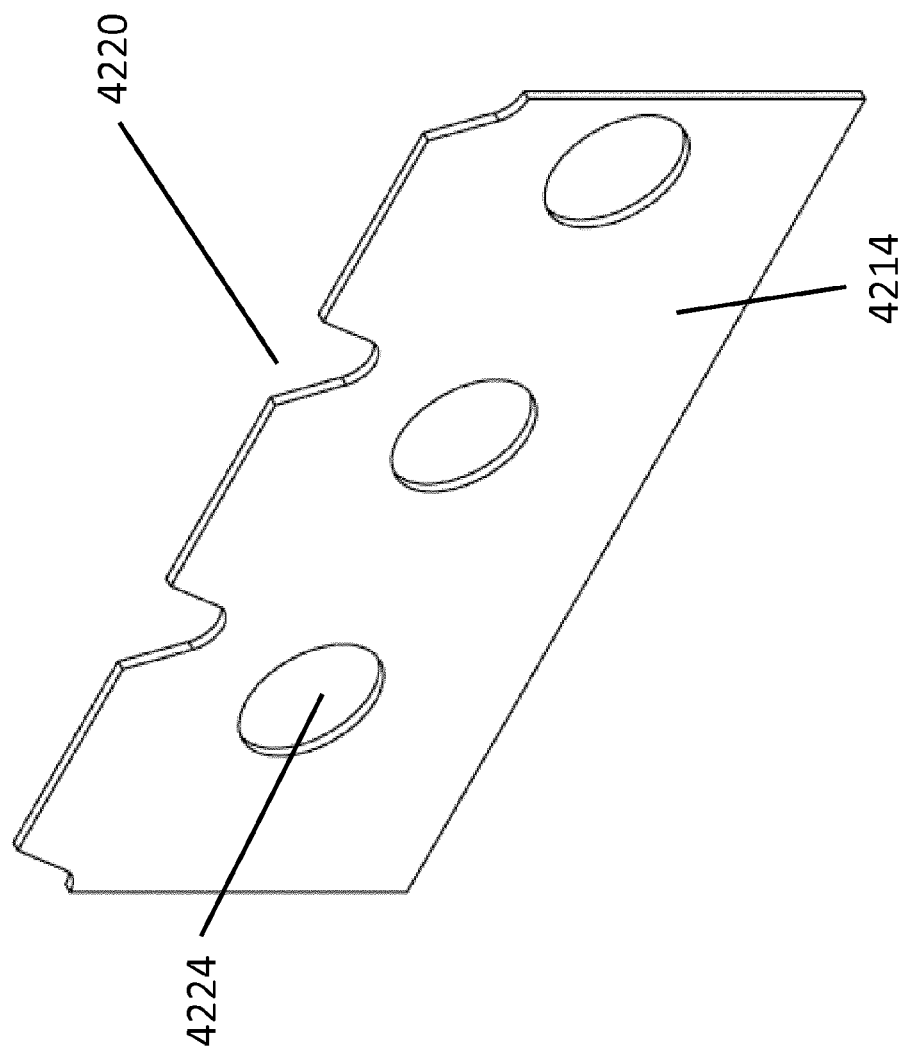
Figure 40D:
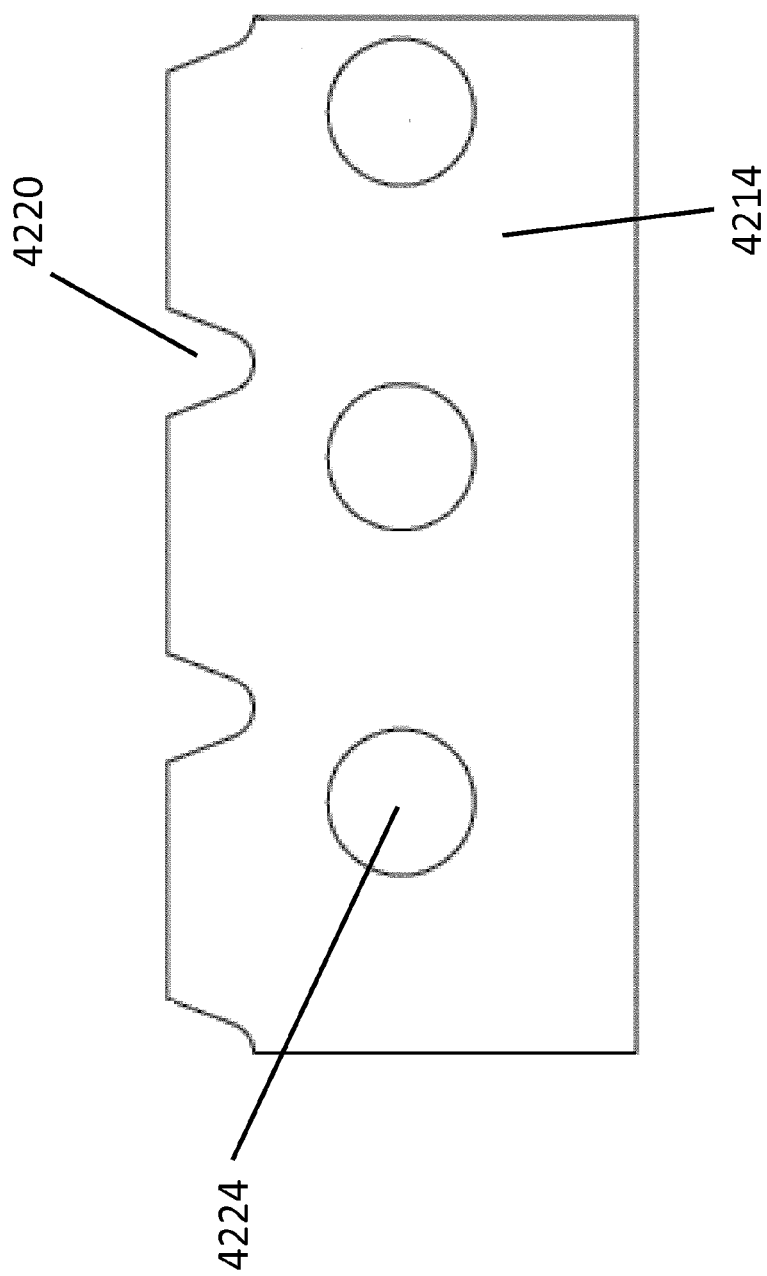

The intervening members 4204 in some embodiments may comprise a first material 4216 with an embedded insert 4218 made of a more rigid material. One embodiment of the embedded insert is illustrated in FIGS. 39E-F. In other embodiments, the first material 4216 may be in the form of a sleeve configured to receive the insert 4218. Further, the sleeve 4216 may be configured to allow for the removal of an insert 4218, such as by providing an opening in the top of the sleeve. In a preferred embodiment, the first material 4216 is constructed from a flexible or semi-flexible material such as silicone and/or polyurethane. However, any flexible or semi-flexible material may be suitable. In a preferred embodiment, the insert 4218 is constructed from a rigid or semi-rigid material such as polyvinyl chloride. However, any rigid or semi-rigid material may be suitable.

FIG. 39E illustrates a front view of insert 4218, while FIG. 39F illustrates a side view of insert 4218. The insert in one embodiment may be a flat, plate-like structure having a rectangular shape, with a height greater than its width, and two parallel surfaces. The insert can comprise an indent 4222. The indent is preferably located at the upper portion of the insert, however, the indent 4222 can be positioned on either side of the insert, or on the bottom. The indent 4222 can be configured such that it aids in allowing fluid to flow through the stabilizing structure by providing a flow path. The indent 4222 can improve flexibility of the stabilizing structure 4200 and be configured to allow for a more efficient collapse of the stabilizing structure 4200.

In some embodiments, the stabilizing structure 4200 of FIGS. 39A-B can be configured to include perforations or detachable sections that allow portions of the device to separate from the remainder of the device. For example, perforations may be incorporated into the joints 4206 between various cells contained within the stabilizing structure 4200, allowing for the removal of individual rows or cells to alter the shape of the stabilizing structure 4200. In some embodiments, as described above in relation to FIGS. 39C-D, the sections may be detached along perforations or lines in the elongate strips corresponding to the notches 4220.

In some embodiments, the inserts 4218 may be entombed within first material 4216 in a variable number of intervening members 4204 to control the shape and collapse of the stabilizing structure 4200. In other embodiments, the inserts 4218 may be fabricated separately and inserted directly into sleeves comprised of first material 4216 within the intervening members 4204 to control the shape and collapse of the stabilizing structure 4200.

For example, the inserts 4218 can be present in at least about 5% of the intervening members, at least about 10% of the intervening members, at least about 15% of the intervening members, at least about 20% of the intervening members, at least about 25% of the intervening members, at least about 30% of the intervening members, at least about 35% of the intervening members, at least about 40% of the intervening members, at least about 45% of the intervening members, at least about 50% of the intervening members, at least about 55% of the intervening members, at least about 60% of the intervening members, at least about 65% of the intervening members, at least about 70% of the intervening members, at least about 75% of the intervening members, at least about 80% of the intervening members, at least about 85% of the intervening members, at least about 90% of the intervening members, at least about 95% of the intervening members, or about 100% of the intervening members.

In certain embodiments, a variable number of supporting segments 4214 may be entombed within elongate strips 4202 to control the collapsibility of the stabilizing structure 4200. In other embodiments, a variable number of supporting segments may be inserted into a pocket contained within the elongate strips 4202 to control the collapsibility of the stabilizing structure. For example, the supporting segments 4214 can be present in at least about 5% of the total length of the elongate strips, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the total length of the elongate strips.

In certain embodiments, the inserts 4218 or supporting segments 4214 may be inserted and/or removed over time to variably control the collapse of the stabilizing structure 4200. For example, although initially all the available sleeves 4216 of the stabilizing structure may contain an insert, after the initial placement of the wound filler comprising a stabilizing structure into a wound, additional inserts 4218 may be removed over time, thus causing the stabilizing structure 4200 to collapse even further. Inserts can also be added to the stabilizing structure after it is inserted into a wound, thereby decreasing the collapsibility of the stabilizing structure 4200. Thus, the addition and/or removal of the inserts 4216 or supporting segments 4214 allows for variable control of the collapse of the stabilizing structure 4200. In similar fashion, supporting segments 4214 can be inserted and removed from the elongated strips over time to provide variable control over the collapse of the stabilizing structure 4200.

In certain embodiments of the stabilizing structures described in this section or elsewhere in this specification, such as in stabilizing structure 4200 as described in FIG. 39A, the flexibility of various sections of the stabilizing structure is enhanced by thinning of that section. For example, in certain embodiments, rather than using a flexible material for a flexing segment 4212 of elongate strip 4202, instead the flexing segment 4212 can be constructed of a similar material to that used to construct supporting segment 4214. In this embodiment, since supporting segment 4212 is thicker than flexing segment 4212 it will not flex to the degree of flexion that may be experienced by flexing segment 4212. In certain embodiments, the entire stabilizing structure 4200 may be constructed from a single rigid or semi-rigid material, but made to have different rigid and flexible portions by thinning certain areas of the stabilizing structure 4200. In further embodiments, the joints 4206 may be thinned to allow for greater flexibility as compared to the surrounding sections. In certain embodiments, thinning of a section of the stabilizing structure 4200, may allow the thinner portion to be more readily detached from the structure.

As described above in relation to FIGS. 14A-19B and applicable to all stabilizing structures or wound closure devices described in this section or elsewhere in the specification, a soft polymer could be fabricated over the entire stabilizing structure 4200 to soften the feel of the device, thereby protecting the surrounding organs and/or other tissues. In other embodiments, the soft polymer could be fabricated only over the bottom portion of the stabilizing device 4200, while in some embodiments the softer polymer can be molded over the top and/or the sides of the device. In some embodiments, the soft polymer could be fabricated over particular edges of the stabilizing structure 4200, such as those on the bottom, sides, and/or top. In certain embodiments, the soft polymer could be fabricated over any side or combination of sides of the stabilizing structure 4200. The soft polymer may act like a softened rim surrounding the hard edges of the stabilizing structure 4200.

FIGS. 40A-D illustrate multiple views of another embodiment of the stabilizing structure 4200, similar to the stabilizing structures depicted in FIGS. 32A-C and 39A-E. As in the stabilizing structure embodiment depicted in FIGS. 39A-F, the stabilizing structure 4200 comprises elongate strips 4202 and intervening members 4204. The elongate strips 4202 may comprise openings 4224 configured to allow the passage of fluid through the elongate strips 4202. To construct the openings, holes or other shapes may be fabricated directly through the elongate strips 4202. In the embodiment illustrated and as further shown in FIGS. 40C and 40D, the elongate strips 4202 further comprise more rigid inserts 4214 as described above. In such embodiments, the openings 4224 may be fabricated through the rigid inserts 4214 in locations of the strip where the inserts are located, as well as through flexing segments 4212 where the inserts are not located. The openings can be configured to evenly distribute fluid throughout the stabilizing device and/or direct fluid flow along a particular passage or direction. In other embodiments, the intervening members comprise openings, similar to the openings described in relation to the elongate strips.

Figure 41A:
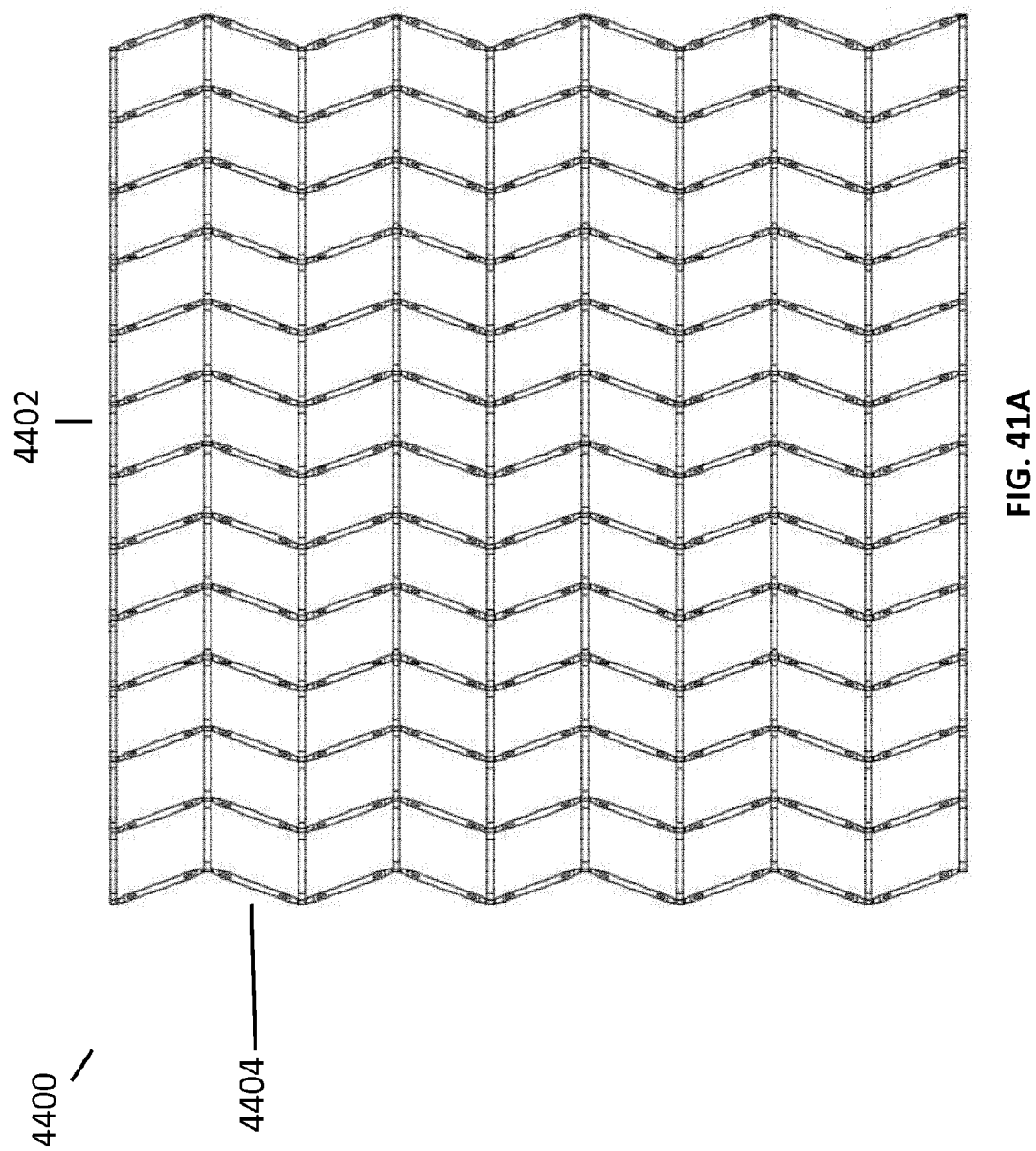
FIGS. 41A-C illustrate multiple embodiments of a stabilizing structure.
Figure 41B:
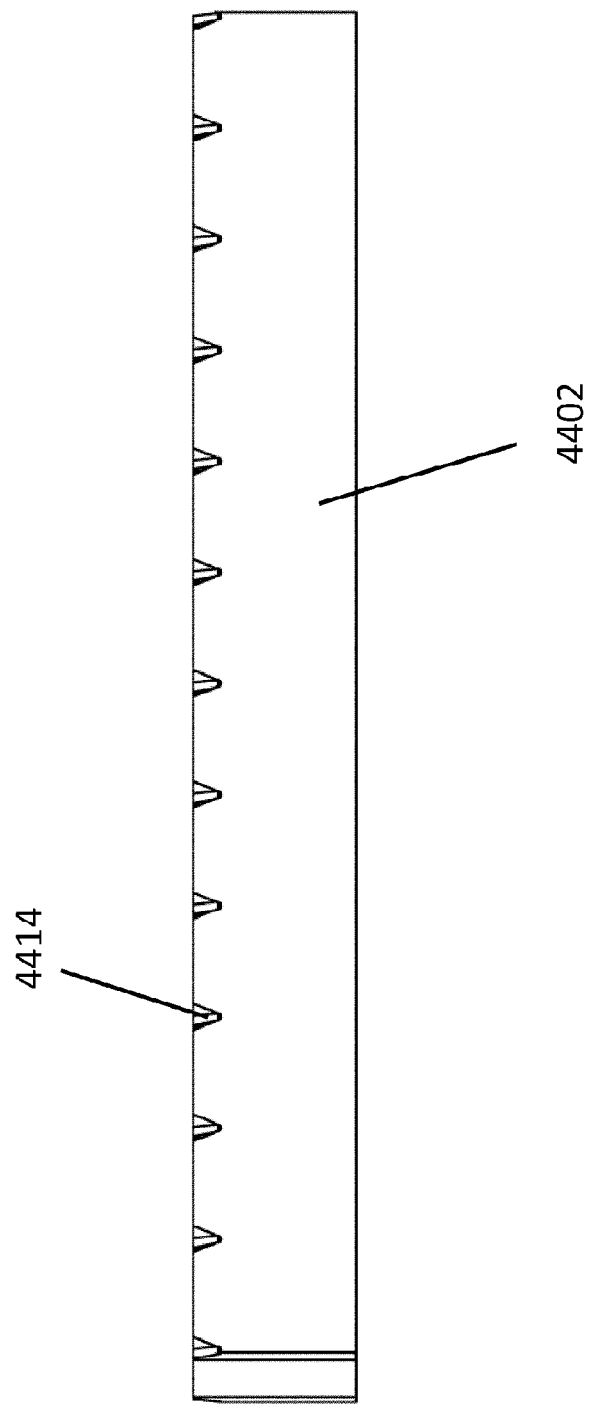
Figure 41C:
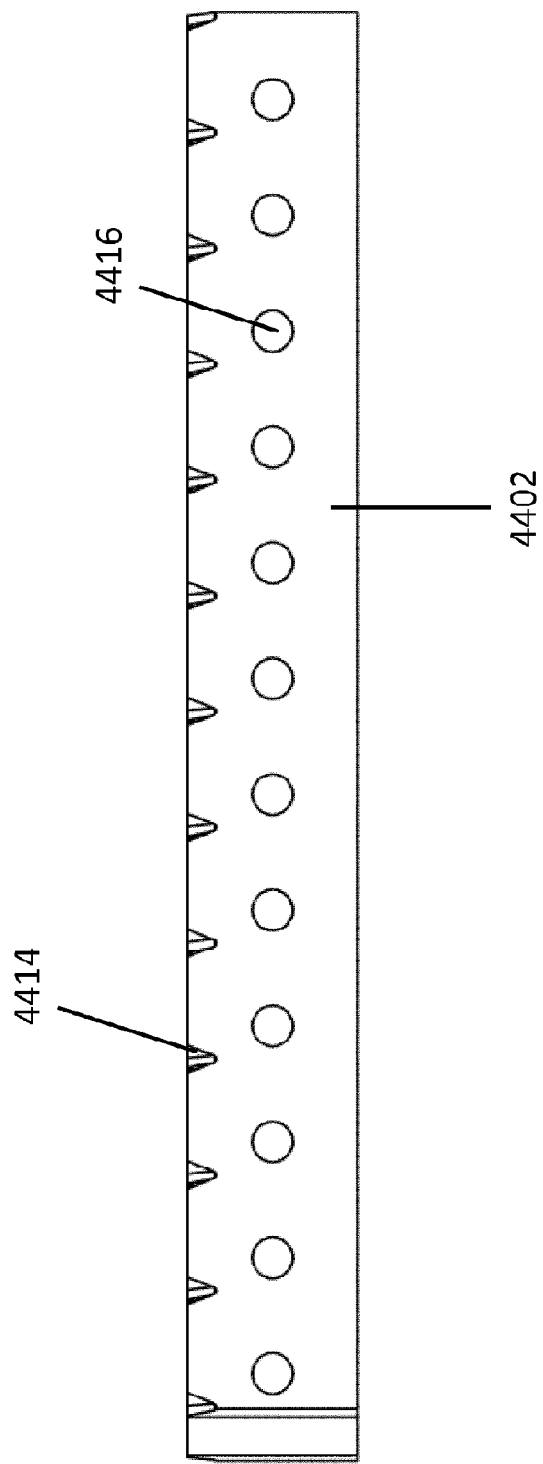

FIGS. 41A-B illustrate embodiments of a stabilizing structure 4400, with functional and structural elements similar to the embodiments of the stabilizing structure depicted in FIGS. 39A-F. Similar to the other stabilizing structures described previously, the stabilizing structure 4400 comprises elongate strips 4402 and intervening members 4404. The elongate strip 4402 may be a single unitary strip with no differing flexing segments or support segments. In certain embodiments, the elongate strip 4402 can be comprised entirely of rigid or semi-rigid materials such as polyvinyl chloride. In other embodiments, the elongate strip 4402 may be comprised entirely of flexible or semi-flexible material such as silicone and/or polyurethane. Similar to the embodiments described in FIGS. 39A-F, stabilizing structure 4400 may collapse in any manner described in this section or elsewhere in this specification within any timescale described in this section or elsewhere in this specification. FIG. 41C depicts an embodiment of the elongate strips 4402 comprising openings 4416 to allow the passage of fluid similar to the passage of fluid described in FIGS. 40A-E.

Figure 42A:
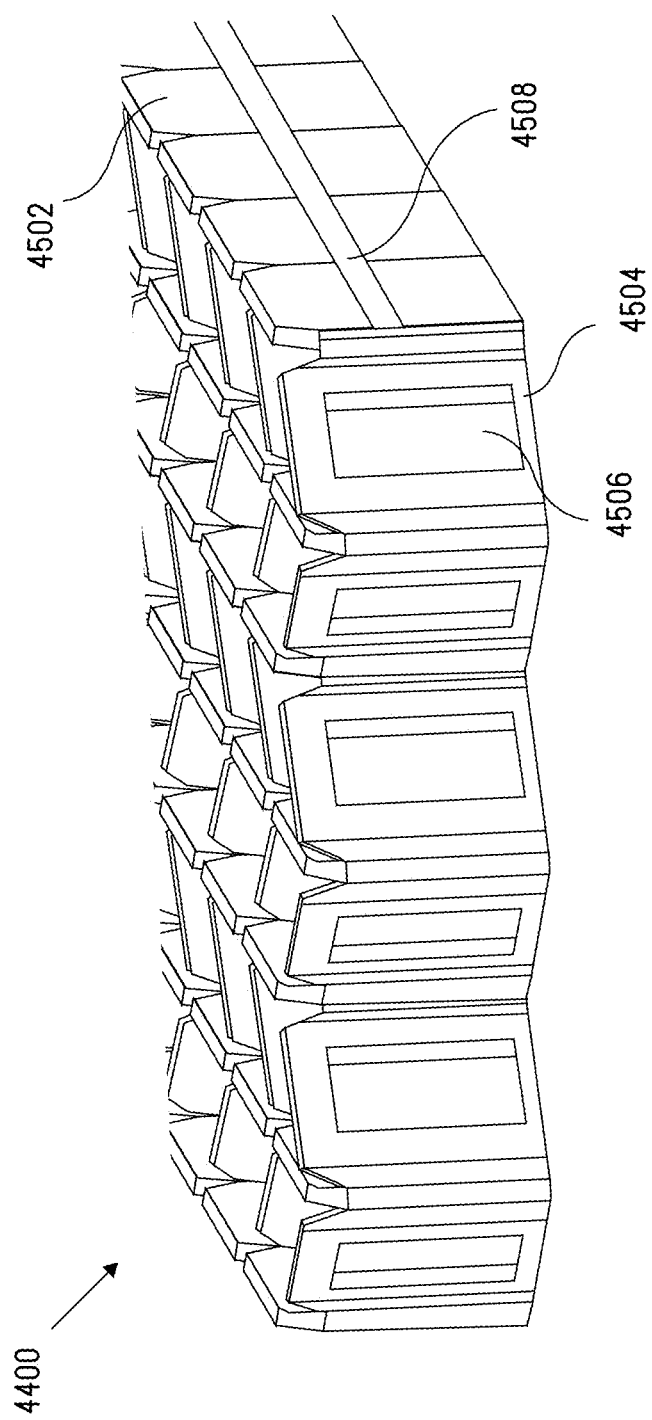
FIGS. 42A-B illustrate multiple embodiments of a stabilizing structure comprising windows.
Figure 42B:
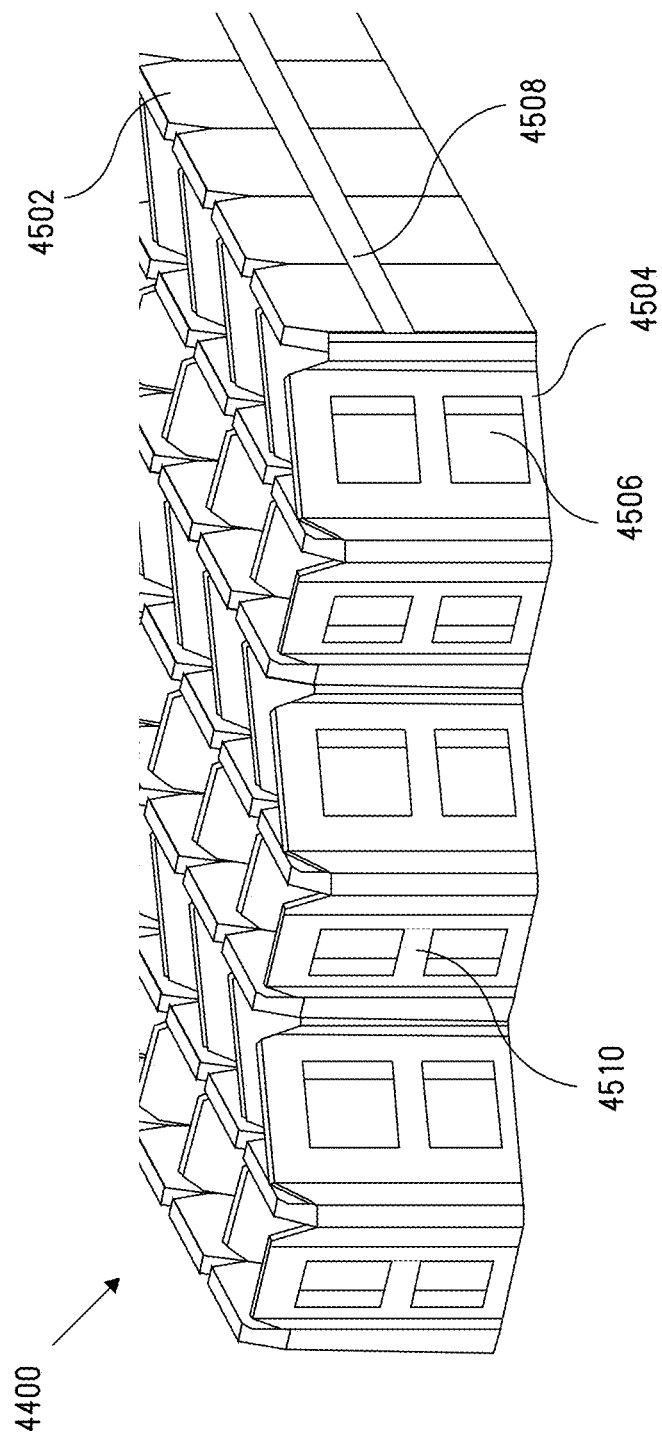

FIGS. 42A-B illustrate embodiments of stabilizing structure 4500 that are similar to the stabilizing structures described above in relation to FIGS. 32A-35. Stabilizing structure 4500 comprises elongate strips 4502 and intervening members 4504. Intervening members 4504 can further comprise windows 4506, configured to allow the passage of fluid. In some embodiments, all intervening members 4504 may comprise windows 4506, however in other embodiments only the horizontally outermost intervening members 4504 comprise windows 4506, while the inner intervening members are similar to other embodiments described in this section or elsewhere in this specification.

In certain embodiments, at least about 5% of the intervening members comprise windows, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the intervening members.

The elongate strip 4502 may further comprise a gap 4508, configured to allow the passage of fluid. The gap may extend nearly the entire length of the elongate strips 4502 or extend only a portion of the length of the elongate strip 4502.

FIG. 42B illustrates an embodiment of a stabilizing structure 4500, where the windows 4506 further comprise bars 4510. In certain embodiments, at least about 5% of the windows comprise bars, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the windows.

Figure 43A:
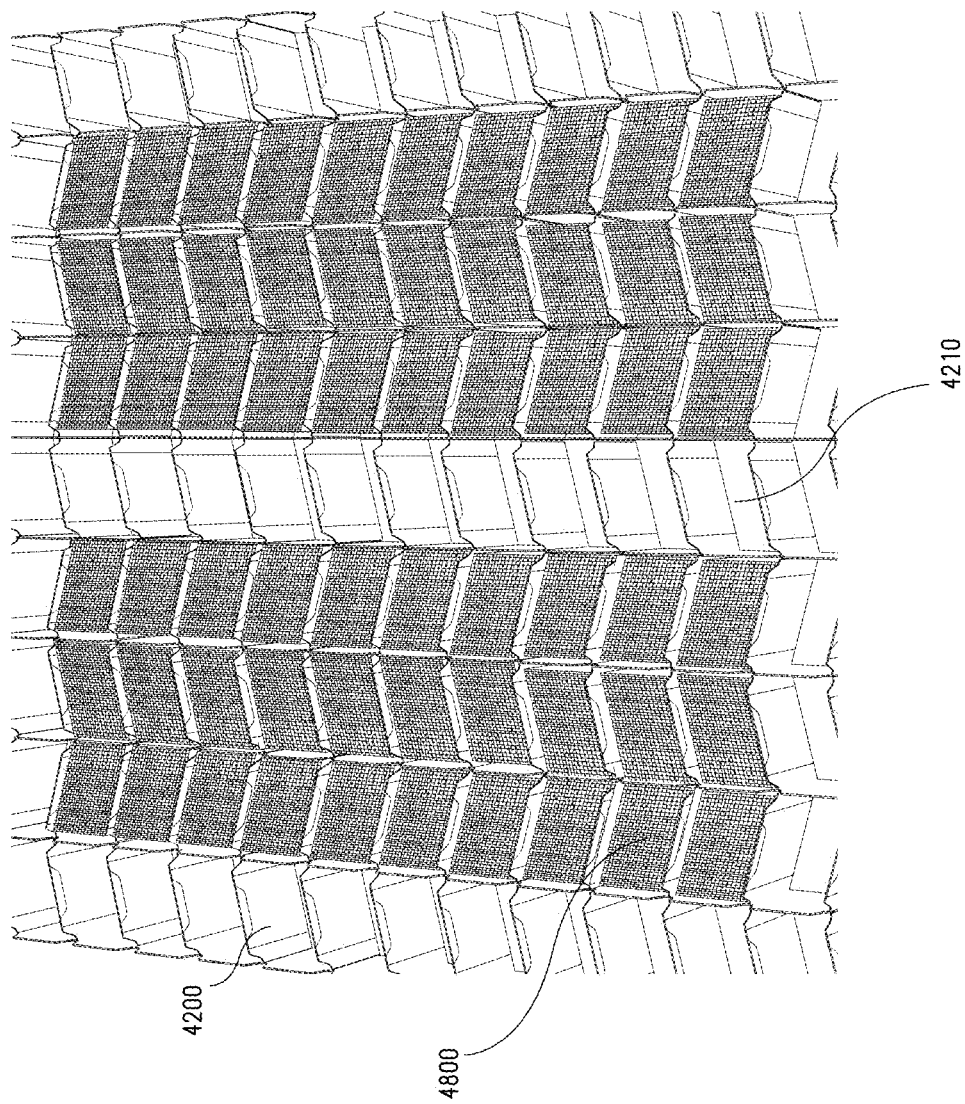
FIGS. 43A-C are photographs of various embodiments of a stabilizing structure comprising foam inserts.
Figure 43B:
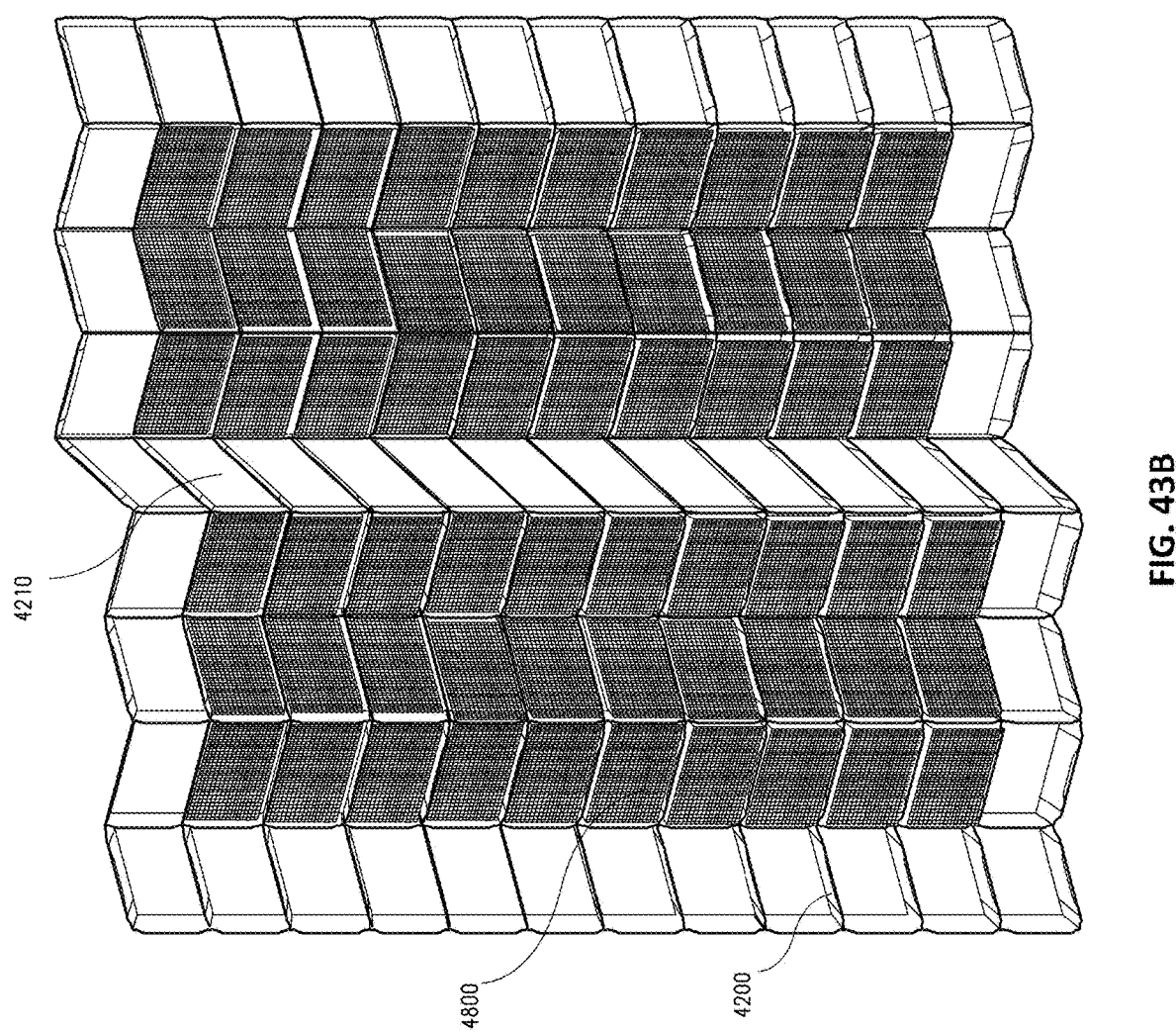
Figure 43C:
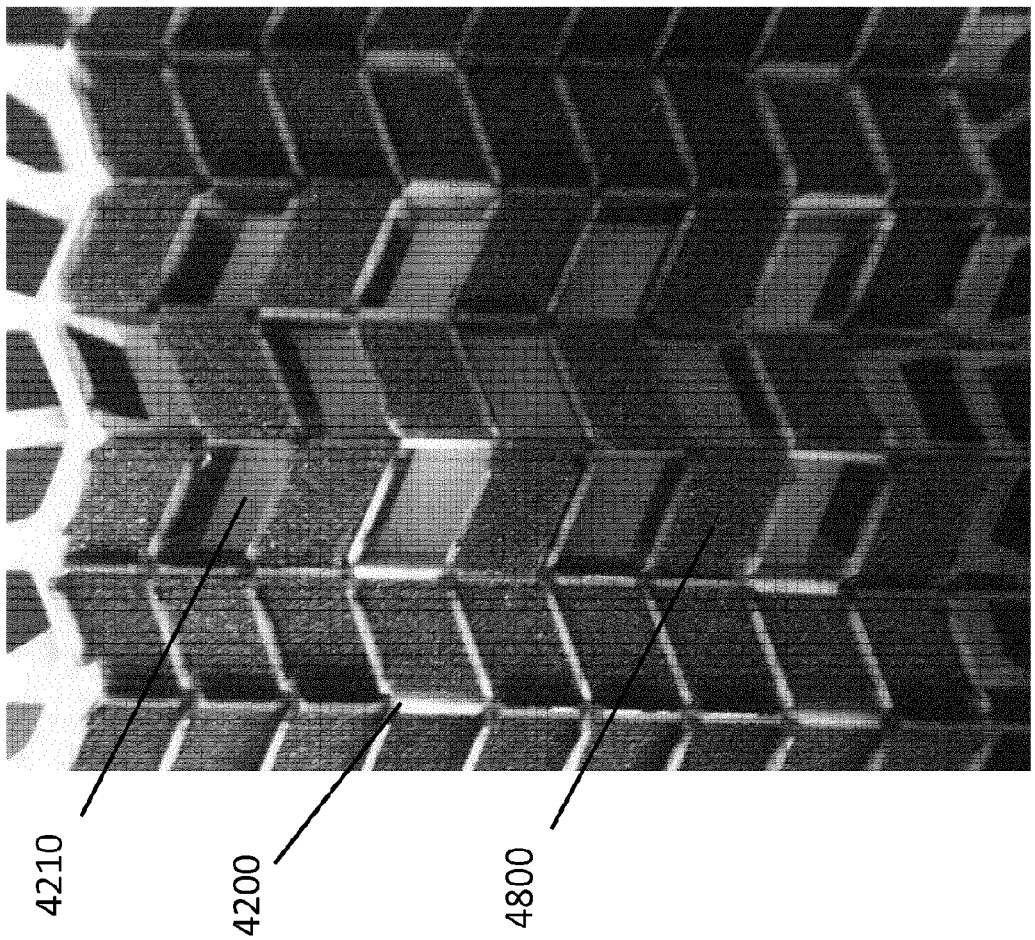

FIGS. 43A-C are photographs of embodiments of stabilizing structure 4200, similar to those embodiments of a stabilizing structure described in relation to FIGS. 39A-42B, further comprising foam inserts 4800. Similar to the fabrication techniques described elsewhere in the specification, the stabilizing structure and foam inserts may be fabricated together via 3D fabrication techniques to form a region of a wound filler such as those described in relation to FIGS. 2-4. As described previously, different types of structures and materials, including the stabilizing structures and wound closure devices described herein this specification, may be fabricated as various regions of a fabricated bespoke wound filler. The inserts 4800 may be constructed from any material described in this section or elsewhere in this specification, including flexible foams, semi-flexible foams, semi-rigid foams, and rigid foams and other porous or compressible materials. The stiffness of the foam inserts 4800 can be used to control the collapse of stabilizing structure 4200. For example, stiffer foams may impede the collapse of the stabilizing structure 4200, while flexible foams may allow the stabilizing structure to collapse more quickly and easily. Varying the flexibility/stiffness of the foams allows the structure to collapse at any rate as described in this section or elsewhere in this specification. In some embodiments, the overall density of the stabilizing structure and/or wound closure device may be altered by increasing or reducing the amount of foam within the structure 4200. By reducing the overall density, the structure will be more readily collapsible. Thus, the use of a lower density structure with less foam may allow for greater wound closure as such a structure is more readily collapsible. Conversely, the use of a higher density structure with more foam may be less collapsible. In other embodiments, the foam inserts only comprise a portion of the individual cells 4210.

In some embodiments, the foams may be configured to degrade or dissolve over time, thereby allowing foam inserts to prop the stabilizing structure open initially, before later degrading or dissolving in a controlled manner to control the rate of collapse of the stabilizing structure. In further embodiments, the foam inserts may be impregnated with biologically active materials that may promote wound healing. For example, the biologically active materials may be anti-inflammatory molecules, growth factors, or anti-microbials.

FIG. 43A is a photographic perspective view of the stabilizing structure 4200 in an open state whereby the cells 4210 that do not contain foam are not collapsed. FIG. 43B is a photographic of the top of stabilizing structure 4200 wherein the cells 4210 are in a collapsed state. FIG. 43C is a photograph of a top view of the stabilizing structure 4200 wherein some of the rows have alternating cells filled with foam inserts 4800 or without foam inserts 4210. In some embodiments, the foam inserts can be inserted into at least about 5% of the cells, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of cells.

Figure 44A:
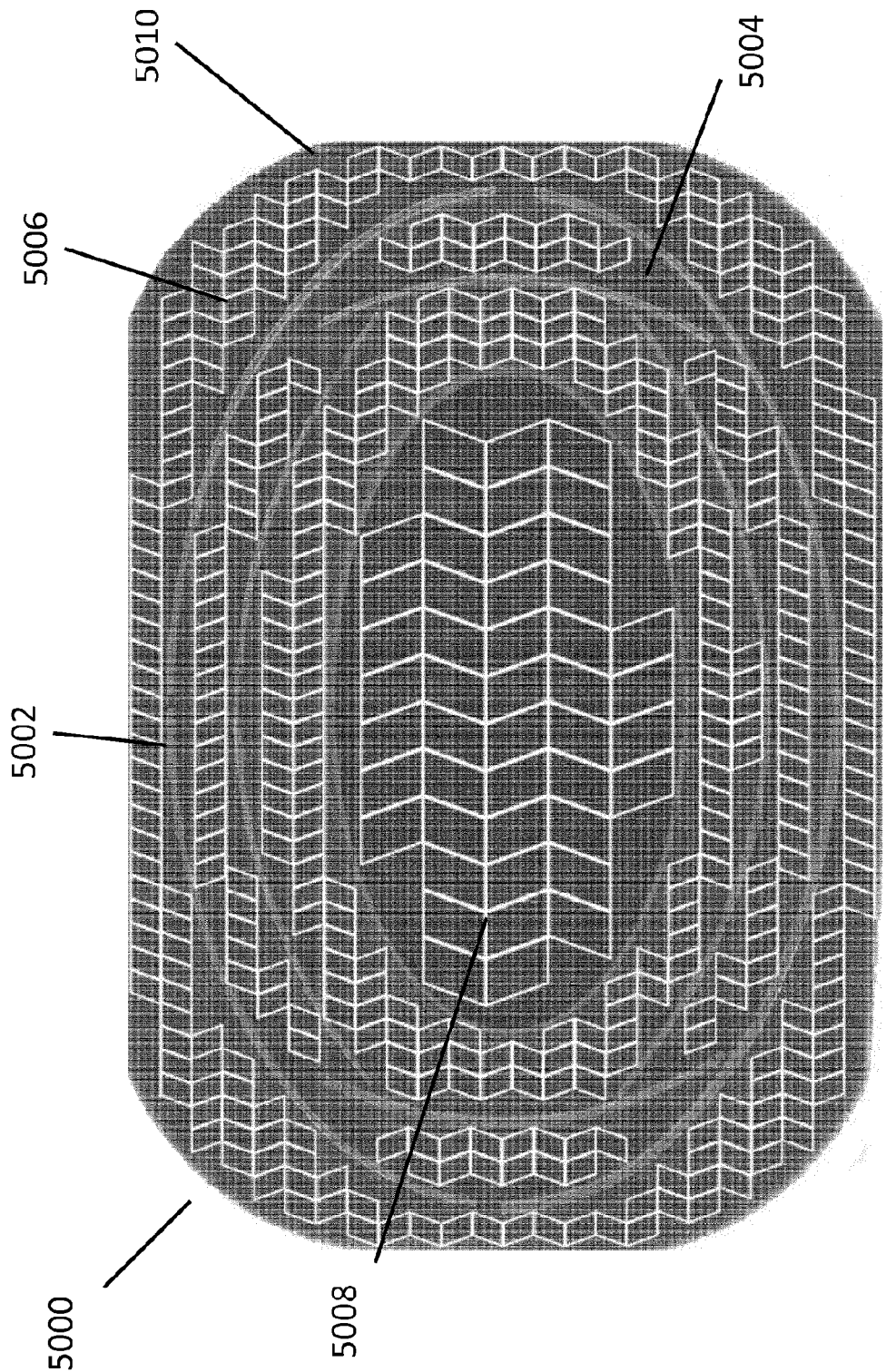
FIGS. 44A-B illustrate embodiments of a wound filler comprising stabilizing structures within a porous material.
Figure 44B:
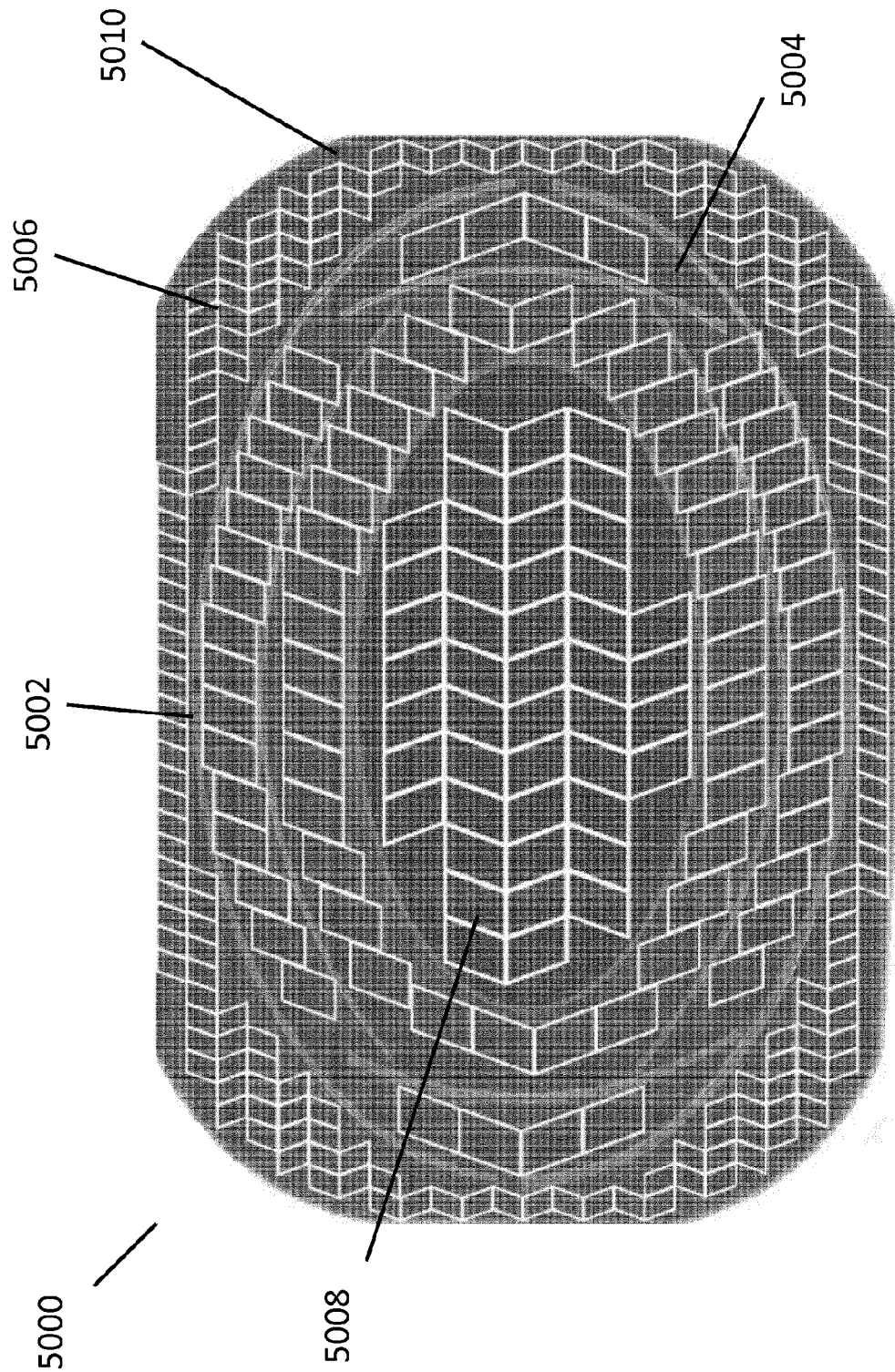

The Wound Fillers and Stabilizing Structures of FIGS. 44A-B

FIGS. 44A-B depict embodiments of a fabricated bespoke wound filler 5000 comprising stabilizing structures, such as those described previously in this specification, surrounded by a porous material 5004 such as foam.

In certain embodiments, the wound filler 5000 of FIGS. 44A-B may comprise a series of cuts or perforations 5002. The wound filler may be comprised of a porous material 5004, such as those described herein this section and elsewhere in this specification. The wound filler may further comprise one or more stabilizing structures 5006, 5008 embedded within the porous material 5004. The stabilizing structures may be completely encased within the surrounding porous material 5004, such that the stabilizing structures are completely surrounded by the porous material in all directions. In certain embodiments, portions of the stabilizing structures may protrude from the porous material. For example, the stabilizing structures may protrude from the top, bottom, or sides of the porous material.

As will be understood by one skilled in the art, the stabilizing structures are not limited to a side by side arrangement in a two-dimensional plane. Instead, with reference to the three-material structure embodiments described elsewhere, the stabilizing structures may also be arranged along the height of the structure in three dimensions.

In certain embodiments, the cuts or perforations 5002 in wound filler 5000 through porous material 5004 may be of any type described herein this section or elsewhere in the specification, The cuts or perforations may allow frangible regions of the pad 5000 or three-dimensional structure to be detached so as to shape the wound filler or three-dimensional structure to the shape of a wound. In certain embodiments, the stabilizing structures 5006 and 5008 are completely contained within the detachable regions. In other embodiments, the stabilizing structures may extend between frangible regions, and thus the stabilizing structures themselves may be separable. For example, the stabilizing structures may have cuts or perforations similar to those cuts or perforations in the porous material 5004. In particular embodiments, the frangible stabilizing structures may not be surrounded by any porous material, instead they may be shaped to the shape of a wound without the use of an encasing porous material. Further, any of the stabilizing structure embodiments described herein this section or elsewhere in the specification may be frangible and capable of being shaped even in the absence of an encasing porous material. In certain embodiments, frangible regions of the stabilizing structure may be adhered to one another via an adhesive.

The stabilizing structures may be of a variety of shapes and sizes such as those described herein this section or elsewhere in the specification. Further, different types of stabilizing structures may be incorporated into a single wound filler 5000. For example, as depicted in FIG. 44A, the wound filler 5000 may be comprised of two types of stabilizing structures, a smaller-celled stabilizing structure 5006, and a larger-celled stabilizing structure 5008. As illustrated in FIG. 44A, the larger-celled structure may be contained within the central portion of the wound filler 5000, while the smaller-celled stabilizing structure can be contained throughout the outer regions. In certain embodiments, the larger-celled structures may be contained within the outer regions of the wound filler 5000, while the smaller-celled structures may be contained within the central portions. The wound filler may be surrounded by a flexible annular outermost region 5010. In some embodiments, there may be additional similar regions, allowing for further frangible regions.

In particular embodiments, a portion of the wound filler containing only porous material may extend beyond the sections of the wound filler that comprise a stabilizing structure. This extending porous material-only portion of the wound filler may extend above, beneath or between layers of surrounding tissue, such as the skin, fatty tissue, fascia, muscle, or other suitable tissues. In some embodiments, this porous material-only portion of the wound filler may extend for less than one inch, at least 1 inch, at least 2 inches, at least 4 inches, at least 8 inches, at least 12 inches, at least 15 inches, or more than 15 inches.

As depicted in FIG. 44B, the wound filler 5000 may be comprised of larger-celled stabilizing structures 5008 within the central region and surrounding regions, while the smaller-celled stabilizing structures 5006 are contained only within the flexible outermost region 5010. In further embodiments, the wound filler may comprise more than two types of stabilizing structures. For example, the wound filler may comprise at least three types of stabilizing structures, at least four types of stabilizing structures, at least five types of stabilizing structures, at least six types of stabilizing structures, or more than six types of stabilizing structures. In certain embodiments, all of the stabilizing structures are of the same type, i.e. have cells of the same size.

The stabilizing structures 5006, 5008 may be configured to collapse in any manner described herein this section or elsewhere in the specification such as in relation to FIG. 32A-34, 39A-42B, or 43A-C. Briefly, as described in detail elsewhere, the stabilizing structures 5006 and 5008 can be configured to collapse more readily under negative pressure in a first direction, while not collapsing to a significant degree in a second direction. Further, various stabilizing structures may have different collapsibility properties as described herein this section or elsewhere in the specification.

In certain embodiments, the stabilizing structure may be of any type described herein this section or elsewhere in this specification. Further, the stabilizing structure may be comprised of any of the materials described herein this section or elsewhere in the specification. In some embodiments, the wound fillers 5000 depicted in FIGS. 44A-B may be surrounded by an anchoring layer such as those described in relation to FIG. 45. The anchoring layer may be attached to the wound filler in any manner described herein this section or elsewhere in the specification. For example, the anchoring layer may be attached by an adhesive and/or via tape. In some embodiments, the anchoring layer may be fabricated directly as part of the wound filler via 3D fabrication techniques.

Figure 45:
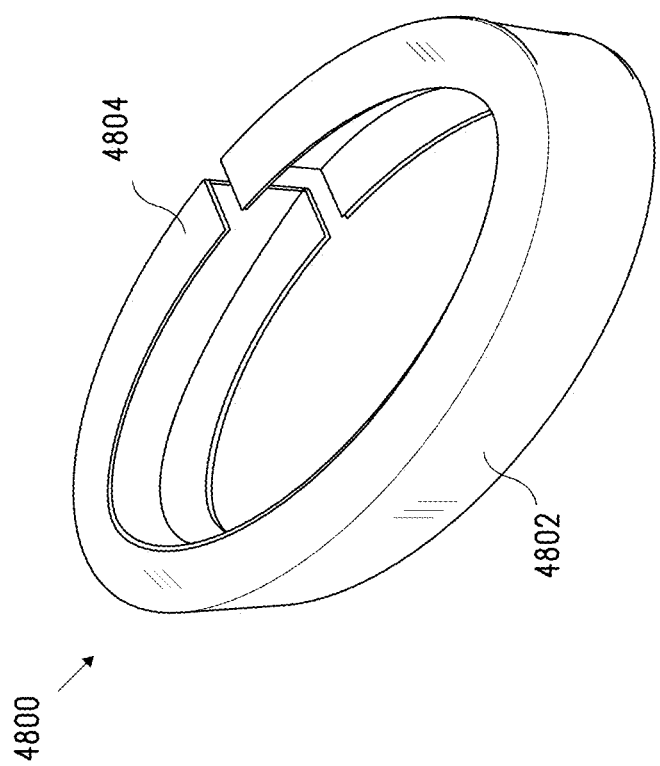
FIG. 45 illustrates an embodiment of a ring that can surround a stabilizing structure.

In some embodiments, the wound filler 5000 may further comprise tissue anchors similar to those described in relation to FIG. 45. The tissue anchors can be hooks, barbs, prongs, or other structures that serve to attach to the tissue of a wound. In some embodiments, the tissue anchors comprise hook and loop fasteners such as those used in Velcro technologies. The anchors may extend from the stabilizing structures or from the foam portions of the wound filler.

The Anchoring Layer of FIG. 45

FIG. 45 illustrates an embodiment of an anchoring layer 4800 that may surround the wound fillers described in this section or elsewhere in this specification. As described above, the anchoring layer or ring can be fabricated directly as part of the outside of the wound filler or may be added separately. The ring 4800 can comprise a layer of tissue anchors 4802 configured to grip the surrounding edges of a wound. For example, the tissue anchors can be hooks, barbs, prongs, or other structures that serve to attach to the tissue of a wound. In certain embodiments, the tissue anchors comprise hook and loop fasteners such as those used in Velcro technologies. In certain embodiments, the ring 4800 can be comprised of foam, such as those described previously or the ring can be comprised of a combination of a foam layer and a tissue anchor layer 4802. A lip 4804 may extend inward from the ring 4800 and serve to overlap the top and/or the bottom of a stabilizing structure as described in this section or elsewhere in this specification, thereby securing the ring 4800 around the stabilizing structure.

Applying the Bespoke Wound Filler

As is described herein this section and elsewhere in the specification, the bespoke wound filler may be applied to a wound in combination with other conventional wound healing related articles, such as a drape, vacuum source, foam, tubing, reservoir, bandage, adhesive, or any other articles suitable for the treatment of wound. In certain embodiments the bespoke wound filler may be combined with other wound fillers, such as a bowl-shaped foam that may be placed underneath the wound filler as described above. In some embodiments, these other wound healing articles may be constructed alongside the wound filler via suitable 3D fabrication equipment. In certain embodiments, these other wound care articles or components may be fabricated as attached to the bespoke wound filler to form a wound treatment apparatus.

Figure 46A:
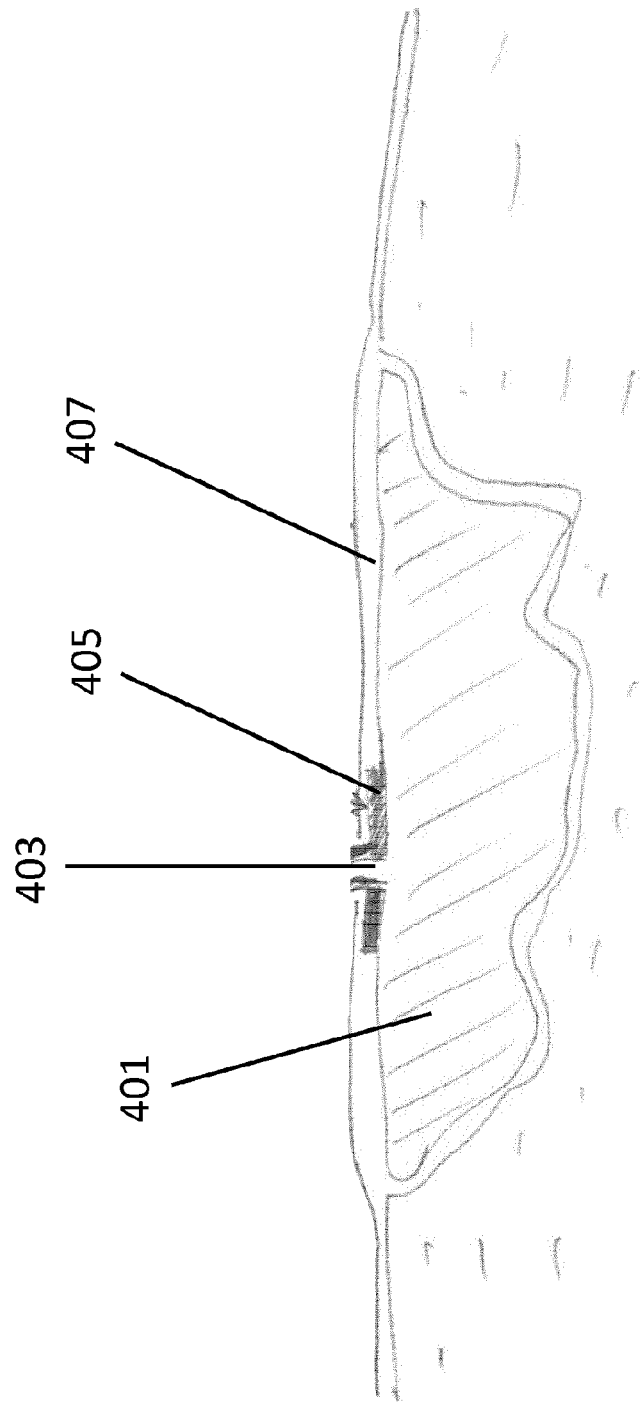
FIGS. 46A-B are schematic illustrations of embodiments of a wound treatment apparatus comprising a bespoke wound filler.
Figure 46B:
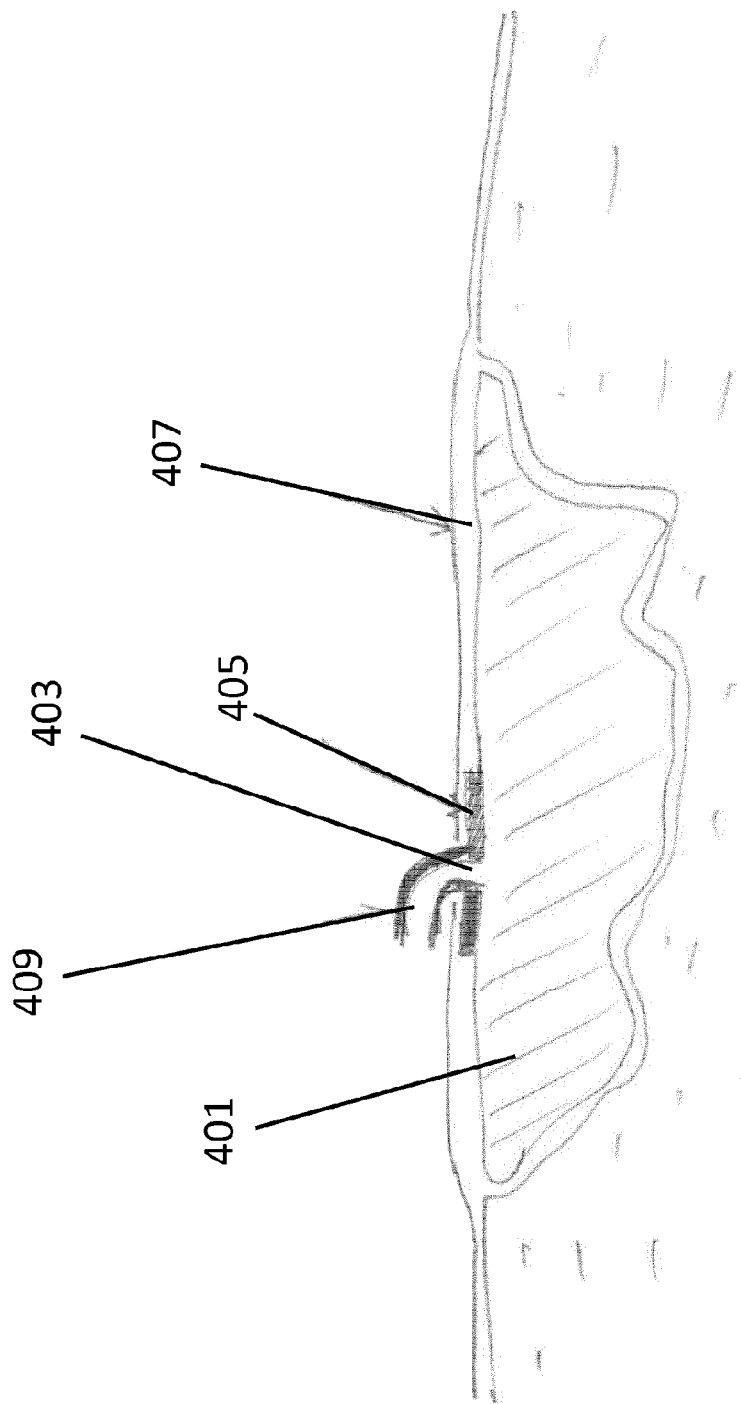

FIGS. 46A-B illustrate different views of a wound treatment apparatus comprising a wound filler, similar to the wound treatment apparatuses and wound fillers described herein this section and elsewhere in the specification. FIG. 46A illustrates a wound treatment apparatus comprising a bespoke wound filler 401 as described herein this section and elsewhere in the specification. The wound treatment apparatus further comprises an opening 403, which may be connected to a source of negative pressure such as a suitable pump or other related structures such as a port or filter. One example of a suitable pump is the Renasys EZ pump available from Smith & Nephew. The apparatus may further comprise a flat sealed surface 405 that allows for sealing of the drape 407. In some embodiments, the flat sealed surface immediately surrounds the opening 403, such that the drape 407 can seal around the opening 403. In certain embodiments, the flat sealed surface could be extended to the wound edge or beyond and sealing strips applied as is described in the PICO system available from Smith & Nephew. In some embodiments, the drape 407 may extend beyond the edges of the wound and may be sealed to the edges of the wound via any suitable means such as via an adhesive, or via sealing strips such as those disclosed above.

Similar to the apparatus described in FIG. 46A and elsewhere in the specification, FIG. 46B illustrates a wound treatment apparatus comprising a bespoke wound filler 401 as described herein this section and elsewhere in the specification. The wound treatment apparatus further comprises an opening 403, which may be connected to a source of negative pressure such as a suitable pump. The apparatus may further comprise a flat sealed surface 405 that allows for sealing of the drape 407. The apparatus also comprises an integral port 409 to allow for ease of connection to a source of negative pressure. The port, as with all of the components described in relation to FIGS. 46A-B, may be fabricated directly via 3D fabrication techniques. In some embodiments, the bespoke wound filler 401 is fabricated directly attached to the port 409.

In certain embodiments, to aid the clinician in the proper orientation of the bespoke wound filler, marks may be printed on the wound filler or dermis surface such that it allows the clinician to properly orient and place the filler within the wound. These marks may be arrows, lines, words, or any other marking that will aid in placement of the filler. In certain embodiments, anatomical terms or general terms may be used to mark the filler, for example, words such as "foot," "head," or "distal" may be used to direct the clinician in any desirable manner. In certain embodiments, marks are also made on the tissue surrounding the wound to allow for ease of orientation of the filler and wound treatment system In some embodiments, the bespoke wound filler may be replaced multiple times over the course of closure of a wound. The wound filler can be replaced with another fabricated wound filler that may be better suited to the wound at this later stage in the healing process. For example, a wound filler inserted earlier in the healing process may comprise bioactive molecules that are primarily directed towards the early inflammatory stages of the host response to a wound while a later wound filler may comprise bioactive molecules that are better suited to latter stage tissue repair. In other embodiments, wound fillers of various shapes may be used at different stages of the wound healing process. For example, a larger wound filler could be used earlier in the healing process before much closure of the wound has occurred. At a later time, once the wound has closed to some degree, a smaller wound filler may be used as it may be better suited to the wound. The wound filler could be replaced after at least about: 1 hour, 3 hours, 6 hours, 12 hours, 24 hours, 2 days, 4 days, 7 days, 14 days, 21 days, 28 days, or more than 28 days.

In some embodiments, the methods and apparatuses described above can be applied to create a 3D model for a wound dressing that need not fill a wound, but may be placed over a wound (such as with an incisional wound). For example, a 3D model for an entire or portion of a wound dressing may be constructed having multiple layers, each with discrete properties, such as described with respect to the multiple applications incorporated above regarding wound treatment apparatuses and methods incorporating absorbent materials. The layers may be customized by the model to optimize certain properties, such as absorbency, fluid transfer, etc., based on the type, size and characteristics of the wound being treated and the treatment modality (e.g., negative pressure wound therapy). The 3D printing methods or other techniques as described above may then be used to fabricate the wound dressing.

Figure 48:
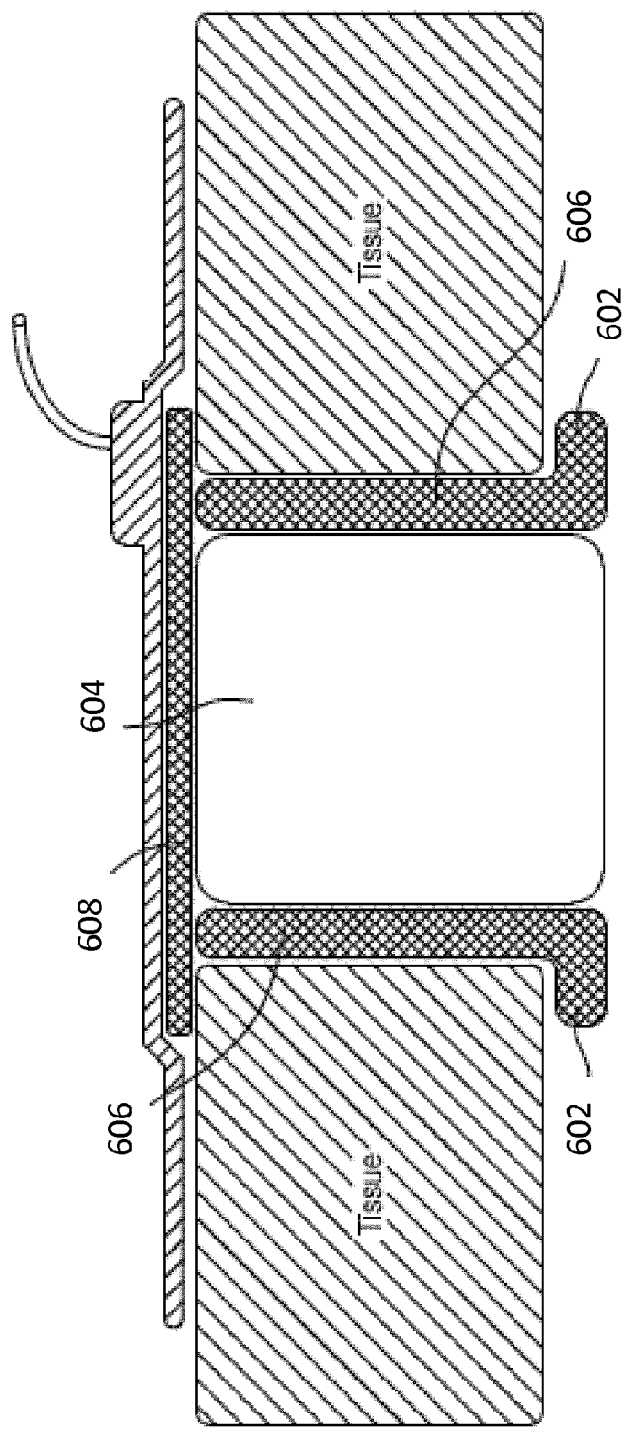
FIG. 48 illustrates an embodiment of a bespoke wound filler comprising a surrounding lip.
Figure 49A:
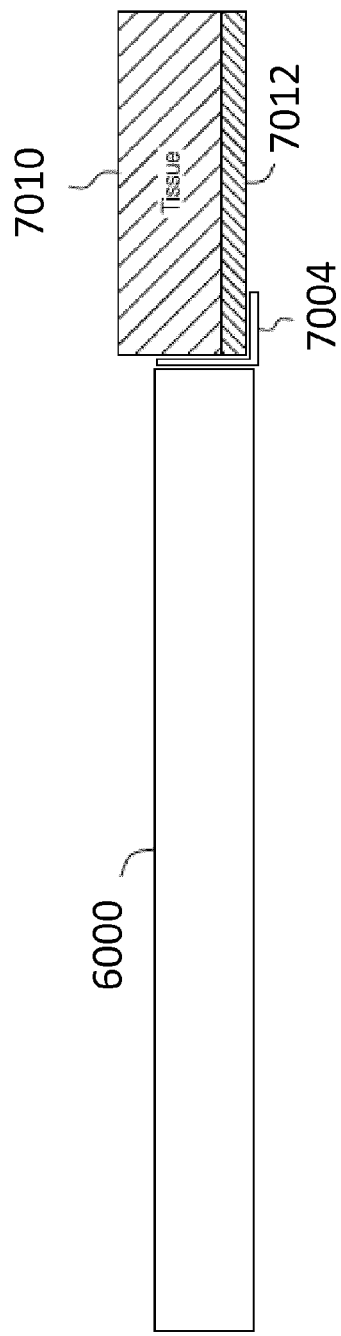
FIGS. 49A-49D illustrates embodiments of securing portions and clips that may be constructed as part of a bespoke wound filler.
Figure 49B:
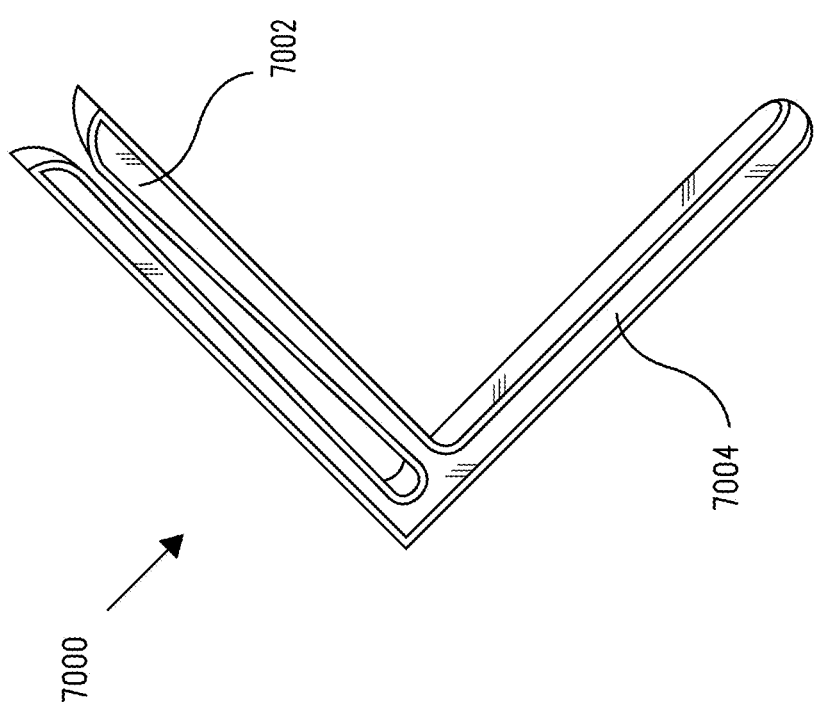
Figure 49C:
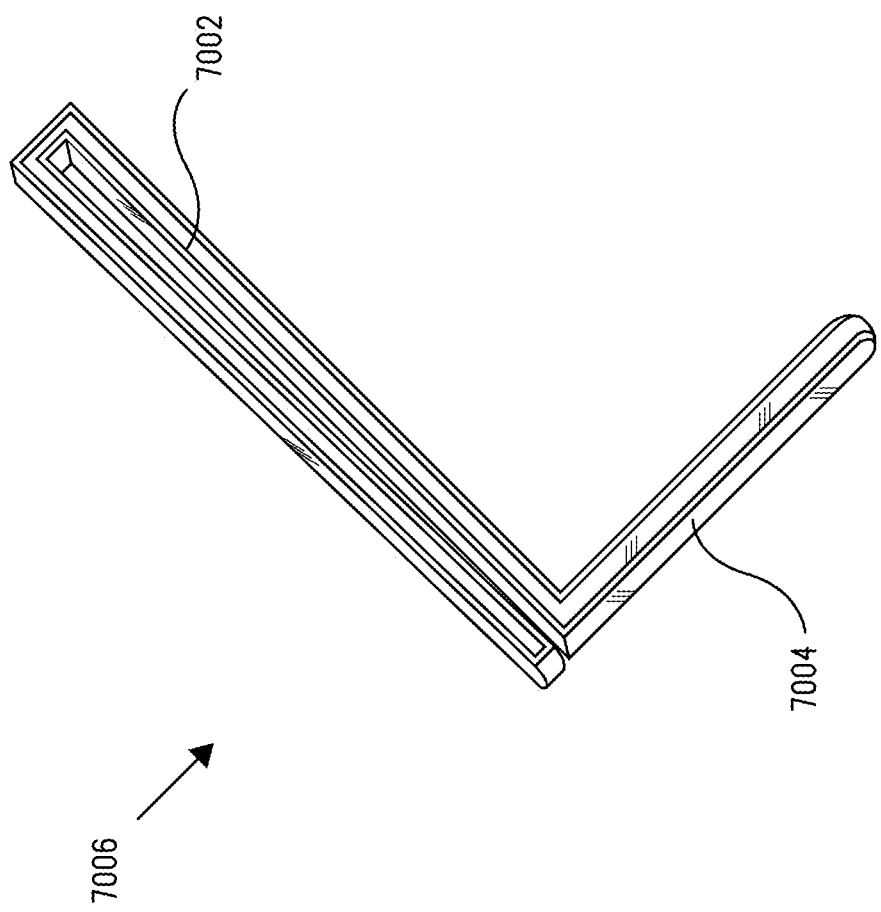
Figure 49D:
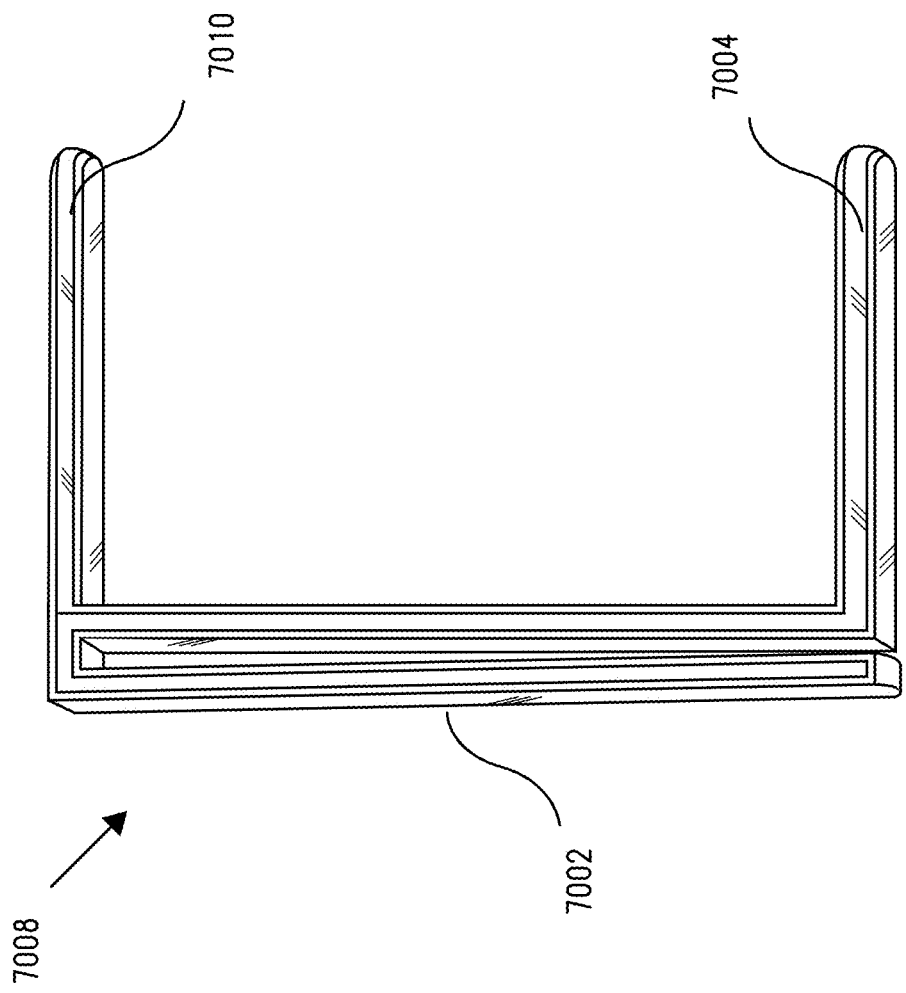

The Securing Mechanisms of FIGS. 48-49D

FIG. 48 illustrates an embodiment of a bespoke wound filler comprising a lip 602 and multiple regions 604, 606, and 608, all printed integrally as one wound filler. In certain embodiments, and as described elsewhere in the specification, the bespoke wound filler may be printed with a lip 602 around the periphery of the wound filler, to aid in securing the bespoke wound filler within the wound cavity. The lip may extend horizontally out from the bespoke wound filler, to secure the wound filler in place beneath a layer of tissue in an abdominal wound or elsewhere. For example, the lip may extend underneath the fascia or other tissue (represented here by "tissue"), thereby applying force through the fascia to maintain the bespoke wound filler in place while the wound filler is pushed upward by the underlying abdominal organs. In certain embodiments, the lip may comprise any material disclosed herein this section or elsewhere in the specification, for example, foam. Preferably, the lip is integral with the bespoke wound filler, meaning that the lip is printed while the remainder of the wound filler is printed. The lip may be constructed from the same materials as the remainder of the wound filler or the lip may be constructed from a different material.

The lip may comprise a variety of shapes and sizes, for example, the lip 602 can have a length in some embodiments between 5 mm and 60 mm (or about 5 mm and about 60 mm), for example 60 mm (or about 60 mm) or less, 50 mm (or about 50 mm) or less, 40 mm (or about 40 mm) or less, 30 mm (or about 30 mm) or less, or 10 mm (or about 10 mm)

or less. In certain embodiments, the lip may comprise tissue anchors such as any tissue anchor described herein this section or elsewhere in the specification. In some embodiments, the lip may comprise individual discrete fingers that extend outward to secure the bespoke wound filler within the wound cavity.

FIG. 49A illustrates an embodiment of a securing portion 7004 that may be printed integrally with the bespoke wound filler 6000 or may be printed separately and attached to the bespoke wound filler 6000. In some embodiments, the bespoke wound filler may be printed with securing portions 7004 that extend outward from the wound filler to aid in securing the wound filler within the wound cavity, similar to the lip described above in relation to FIG. 48. The securing portions will be described in more detail below. Although embodiments of the securing portion are described in two formats: 1. a format where they are printed integrally with the wound filler and 2. where the securing portions are 3D printed separately to be later attached to a bespoke wound filler, all the embodiments described herein this section or elsewhere in the specification may be printed integrally or separately from the bespoke wound filler. As illustrated in FIG. 49A, in some embodiments, a 3D printer such as disclosed herein this section or elsewhere in the specification may be used to construct a securing portion 7004 that can extend above or below tissue layers to aid in securing the bespoke wound filler 6000 to the surrounding tissue. For example, when a bespoke wound filler is placed into an abdominal wound, the underlying viscera may tend to expand and push the wound filler upwards and out of the abdominal wound. Such an occurrence is undesirable because, as described elsewhere in the specification, in some embodiments the wound filler is suited to be placed within a wound whereby the wound filler can advantageously draw the edges of the wound together. To alleviate the outward pressure of the expanding viscera, in some embodiments as illustrated by FIG. 49A, before placing the stabilizing structure within the wound, the securing portion 7000 may be printed directly as part of the 3D wound filler to extend outward under 6000. The securing portion 7004 of the bespoke wound filler 6000 may then extend outward from the stabilizing structure and under the surrounding tissue 7010, for example the fascia 7012.

In some embodiments, the securing portions are rigid, therefore once the securing portion 7004 is extended below the fascia 7012, the securing portion can absorb upward force from the swelling viscera while maintaining the bespoke wound filler 6000 in place within an abdominal or other type of wound. In further embodiments, the securing portion 7004 may be semi-rigid or soft. In some embodiments, the securing portion can be made from any suitable material including, for example, plastics, ABS, PU, PE, PP, PET, silicone, Nylon, or other suitable materials known in the art. Further, the securing portion can be made of metals including, for example, titanium, stainless steel, Inconel, or other suitable material known in the art. Additionally, the securing portion can be made of composites including, for example, carbon fiber, Kevlar, reinforced plastics, or other suitable material known in the art.

The securing portion may extend from the top or the bottom of the wound filler, thereby extending the securing portion over the top or below the surrounding tissue. In some embodiments, an anchoring layer such as those described elsewhere in the specification, may be attached to the securing portion. One of skill in the art with recognize that such an anchoring layer may be applied to the securing portion in any suitable manner, such as around or under the securing portion.

FIGS. 49B-D illustrates embodiments of stabilizing clips 7000, 7006, and 7008, which comprise an attachment portion 7002, such that these clips may be 3D printed separately from the bespoke wound filler and attached ("clipped") to the wound filler later. After attachment to the bespoke wound filler, the securing portion 7004 of stabilizing clip 7000 extends outward to secure the bespoke wound filler within the wound cavity. Stabilizing clip 7000 may comprise an attachment portion 7002 that allows the clip to attach to the underside or the top of a wound filler. In contrast, stabilizing clip 7006 may comprise an attachment portion 7002 that loops over the top of a wall of a bespoke wound filler. In this way, the stabilizing clip 7006 will be more difficult to dislodge from the bespoke wound filler. Similar to stabilizing clip 7000 described above, the stabilizing clip 7006 of FIG. 49C may comprise a securing portion 7004 that extends below a layer of tissue such as the fascia, to maintain the wound filler in place. The securing portion 7004 may extend from a lower end of the attachment portion 7002, however, in this instance the lower end of the attachment portion is the open end because the stabilizing clip "clips" onto the stabilizing structure from the top.

FIG. 49D depicts another embodiment of a stabilizing clip 7008, similar to the stabilizing clip embodiments of FIGS. 49B-C. Stabilizing clip 7008 has securing portions 7004, 7010 on both the upper and lower portions of the stabilizing clip. The stabilizing clip may have a first securing portion 7010 extending outward from an upper end of the attachment portion and a second securing portion 7004 extending outward from a lower end of the attachment portion. Therefore, once attached to a bespoke wound filler, stabilizing clip 7008 may more tightly secure the bespoke wound filler in place because the securing portions extend both above and below various tissue layers such as the fascia. Further examples of lips, securing portions, and bespoke wound fillers may be found in PCT Patent Application PCT/US2014/025059, filed Mar. 12, 2014 and published as WO 2014/165275, entitled NEGATIVE PRESSURE WOUND CLOSURE DEVICE AND SYSTEMS AND METHODS OF USE IN TREATING WOUNDS WITH NEGATIVE PRESSURE, PCT Patent Application PCT/US2014/061627, filed Oct. 12, 2014, entitled NEGATIVE PRESSURE WOUND CLOSURE DEVICE, and PCT Patent Application PCT/IB2013/002494, filed Aug. 8, 2013 and published as WO 2014/024048, entitled BESPOKE WOUND TREATMENT APPARATUSES AND METHODS FOR USE IN NEGATIVE PRESSURE WOUND THERAPY. The aforementioned applications are hereby incorporated by reference in their entireties.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A method of manufacturing a bespoke tissue engaging apparatus, the method comprising:
   creating a three-dimensional model of a bespoke tissue engaging apparatus using a repeating building block based on a three-dimensional model of an area to be treated; and
   fabricating a bespoke tissue engaging apparatus based on the created three-dimensional model of the area to be treated, wherein the bespoke tissue engaging apparatus comprises at least a first plurality of identical repeating sections configured to collapse in a manner determined by the three-dimensional model to account for attributes of the area to be treated.

2. The method of claim 1, wherein the bespoke tissue engaging apparatus is fabricated with a three-dimensional printer.

3. The method of claim 1, wherein the bespoke tissue engaging apparatus comprises a porous material.

4. The method of claim 1, wherein the three-dimensional model of an area to be treated comprises repeating blocks having different characteristics for positioning in different parts of the area to be treated.

5. The method of claim 1, wherein the area to be treated comprises bone.

6. The method of claim 1, wherein the bespoke tissue engaging apparatus is fabricated from two or more different materials.

7. The method of claim 1, wherein the bespoke tissue engaging apparatus comprises a plurality of elongate strips.

8. The method of claim 7, wherein the bespoke tissue engaging apparatus comprises a plurality of intervening members connecting the elongate strips, wherein the plurality of intervening members are configured to pivot relative to the strips to allow the plurality of elongate strips to collapse relative to one another.

9. The method of claim 8, wherein the intervening members between a first strip and a second strip are configured to pivot independently of the intervening members between a second strip and a third strip.

10. The method of claim 1, wherein the bespoke tissue engaging apparatus comprises a polymer.

11. The method of claim 1, wherein the bespoke tissue engaging apparatus is in the shape of an oval.

12. The method of claim 1, wherein the bespoke tissue engaging apparatus comprises tissue anchors, the tissue anchors configured to engage tissue.

13. The method of claim 8, wherein the plurality of intervening members between adjacent elongate strips define a row of cells between each pair of adjacent elongate strips.

14. The method of claim 13, wherein the cells in a row between adjacent elongate strips are configured to collapse together as the adjacent strips collapse relative to one another.

15. The method of claim 3, wherein the bespoke tissue engaging apparatus comprises foam.

* * * * *